United States Patent
Surleraux et al.

(10) Patent No.: US 11,236,093 B2
(45) Date of Patent: Feb. 1, 2022

(54) ADENINE DERIVATIVES AS PROTEIN KINASE INHIBITORS

(71) Applicant: B.C.I. PHARMA, Nivelles (BE)

(72) Inventors: Dominique Surleraux, Saint Gely du fesc (FR); Claire Amiable, Montpellier (FR); Rémi Guillon, Montarnaud (FR)

(73) Assignee: B.C.I. Pharma, Nivelles (BE)

( * ) Notice: Subject to any disclaimer, the term of this patent is extended or adjusted under 35 U.S.C. 154(b) by 0 days.

(21) Appl. No.: 16/097,805

(22) PCT Filed: May 4, 2017

(86) PCT No.: PCT/EP2017/060730
§ 371 (c)(1),
(2) Date: Oct. 30, 2018

(87) PCT Pub. No.: WO2017/191297
PCT Pub. Date: Nov. 9, 2017

(65) Prior Publication Data
US 2019/0127379 A1    May 2, 2019

(30) Foreign Application Priority Data

May 4, 2016 (EP) .................................. 16305530

(51) Int. Cl.
C07D 473/34 (2006.01)
(52) U.S. Cl.
CPC ................. *C07D 473/34* (2013.01)
(58) Field of Classification Search
CPC .................................................. C07D 473/34
See application file for complete search history.

(56) References Cited

U.S. PATENT DOCUMENTS

| | | |
|---|---|---|
| 5,994,361 A | 11/1999 | Penney et al. |
| 2003/0153752 A1 | 8/2003 | Hirst et al. |

FOREIGN PATENT DOCUMENTS

WO    2005/009348 A2    2/2005

OTHER PUBLICATIONS

Xu et al. Bioorganic & Medicinal Chemistry 23 4333-4343 (Year: 2015).*
Dayal et al. Future Med. Chem. 10(7), 823-835 (Year: 2018).*
Csuk, R., and Y. von Scholz, "Enantiomerically Pure Cyclopropanoid Nucleoside Analogues: Synthesis and Analysis," Tetrahedron 52(18):6383-6396, Apr. 1996.
International Search Report dated Aug. 3, 2017, issued in corresponding International Application Mo. PCT/EP2017/060730, filed May 4, 2017, 4 pages.

* cited by examiner

*Primary Examiner* — Emily A Bernhardt
(74) *Attorney, Agent, or Firm* — Christensen O'Connor Johnson Kindness PLLC

(57) ABSTRACT

The present invention relates to a compound suitable for use as a kinase inhibitor according to general formula (I) [compound (C), herein after], or the N-oxide, pharmaceutically acceptable salt, pharmaceutically acceptable solvate, or stereoisomer thereof, formula (I) wherein A, $R_1$, $R_2$, $R_3$, $R_{3'}$, $R_4$, $R_{4'}$, X, Y, Z, T are as defined in the claims. The invention further relates to an in vitro method of inhibiting protein kinase activity which comprises contacting a protein kinase with a compound of formula (I), or the N-oxide, pharmaceutically acceptable salt, pharmaceutically acceptable solvate, or stereoisomer thereof. The invention further relates to the compounds of formula (I) per se, as well as to their use as a medicament, and for use or in a method of treatment of a disease mediated by a protein kinase selected from cancer, inflammatory disorders, cardiovascular diseases, viral induced diseases, circulatory diseases, fibro-proliferative diseases and pain sensitization disorders.

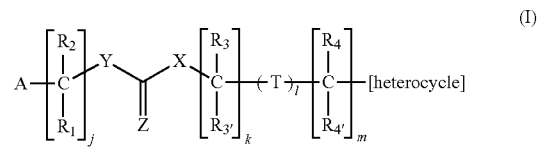

15 Claims, 8 Drawing Sheets

*NB: Inhibition are reported as follows:*

Table 2: Results biological assay

| N° | FLT3wt | FLT3ITD | FLT3D835Y | KIT | CSF1R (FMS) | PDGFR alpha | PDGFR beta | RET |
|---|---|---|---|---|---|---|---|---|
| 1 | | | | | | | | |
| 10 | | | | | | | | |
| 15 | | | | | | | | |
| 16 | | | | | | | | |
| 17 | | | | | | | | |
| 19 | | | | | | | | |
| 21 | | | | | | | | |
| 23 | | | | | | | | |
| 24 | | | | | | | | |
| 25 | | | | | | | | |
| 42 | | | | | | | | |
| 43 | | | | | | | | |
| 44 | | | | | | | | |
| 45 | | | | | | | | |
| 46 | | | | | | | | |
| 47 | | | | | | | | |
| 48 | | | | | | | | |
| 49 | | | | | | | | |
| 50 | | | | | | | | |
| 51 | | | | | | | | |
| 52 | | | | | | | | |
| 53 | | | | | | | | |
| 54 | | | | | | | | |
| 55 | | | | | | | | |
| 56 | | | | | | | | |
| 57 | | | | | | | | |
| 58 | | | | | | | | |
| 59 | | | | | | | | |
| 60 | | | | | | | | |
| 61 | | | | | | | | |
| 62 | | | | | | | | |

| N° | FLT3wt | FLT3ITD | FLT3D835Y | KIT | CSF1R (FMS) | PDGFR alpha | PDGFR beta | RET |
|---|---|---|---|---|---|---|---|---|
| 129 | | | | | | | | |
| 130 | | | | | | | | |
| 131 | | | | | | | | |
| 132 | | | | | | | | |
| 133 | | | | | | | | |
| 134 | | | | | | | | |
| 135 | | | | | | | | |
| 136 | | | | | | | | |
| 137 | | | | | | | | |
| 138 | | | | | | | | |
| 139 | | | | | | | | |
| 140 | | | | | | | | |
| 141 | | | | | | | | |
| 142 | | | | | | | | |
| 143 | | | | | | | | |
| 144 | | | | | | | | |
| 145 | | | | | | | | |
| 146 | | | | | | | | |
| 147 | | | | | | | | |
| 148 | | | | | | | | |
| 149 | | | | | | | | |
| 150 | | | | | | | | |
| 151 | | | | | | | | |
| 152 | | | | | | | | |
| 153 | | | | | | | | |
| 154 | | | | | | | | |
| 155 | | | | | | | | |
| 156 | | | | | | | | |
| 157 | | | | | | | | |
| 159 | | | | | | | | |
| 160 | | | | | | | | |
| 161 | | | | | | | | |
| 162 | | | | | | | | |

| N° | FLT3wt | FLT3ITD | FLT3D835Y | KIT | CSF1R (FMS) | PDGFR alpha | PDGFR beta | RET |
|---|---|---|---|---|---|---|---|---|
| 197 | | | | | | | | |
| 198 | | | | | | | | |
| 199 | | | | | | | | |
| 200 | | | | | | | | |
| 201 | | | | | | | | |
| 202 | | | | | | | | |
| 203 | | | | | | | | |
| 204 | | | | | | | | |
| 205 | | | | | | | | |
| 206 | | | | | | | | |
| 207 | | | | | | | | |
| 208 | | | | | | | | |
| 209 | | | | | | | | |
| 210 | | | | | | | | |
| 211 | | | | | | | | |
| 212 | | | | | | | | |
| 213 | | | | | | | | |
| 214 | | | | | | | | |
| 215 | | | | | | | | |
| 216 | | | | | | | | |
| 217 | | | | | | | | |
| 218 | | | | | | | | |
| 219 | | | | | | | | |
| 220 | | | | | | | | |
| 221 | | | | | | | | |
| 222 | | | | | | | | |
| 223 | | | | | | | | |
| 224 | | | | | | | | |
| 225 | | | | | | | | |
| 226 | | | | | | | | |
| 227 | | | | | | | | |
| 228 | | | | | | | | |
| 229 | | | | | | | | |

| N° | FLT3wt | FLT3ITD | FLT3D835Y | KIT | CSF1R (FMS) | PDGFR alpha | PDGFR beta | RET |
|---|---|---|---|---|---|---|---|---|
| 264 | | | | | | | | |
| 265 | | | | | | | | |
| 266 | | | | | | | | |
| 267 | | | | | | | | |
| 268 | | | | | | | | |
| 269 | | | | | | | | |
| 270 | | | | | | | | |
| 271 | | | | | | | | |
| 272 | | | | | | | | |
| 273 | | | | | | | | |
| 274 | | | | | | | | |
| 275 | | | | | | | | |
| 276 | | | | | | | | |
| 277 | | | | | | | | |
| 278 | | | | | | | | |

ADENINE DERIVATIVES AS PROTEIN KINASE INHIBITORS

FIELD OF THE INVENTION

The present invention is in the field of medicinal chemistry and pharmaceuticals.

BACKGROUND OF THE INVENTION

Cells process environmental signals via signalling and transcriptional networks, also known as signal transduction pathways, that culminate with appropriate regulation of output genes.

Protein kinases play a key role in almost all signal transduction pathways. The pivotal role of kinases is emphasized by the fact that the human genome encodes 518 protein kinases, representing one of the largest protein families. A kinase is a type of enzyme that transfers phosphate groups from high-energy donor molecules, such as adenosine triphosphate (ATP), to specific substrates, a process referred to as phosphorylation. The phosphorylation state of a substrate, whether it is a protein, lipid, or carbohydrate, can affect its activity, reactivity, and its ability to bind other molecules. Therefore, kinases are critical in metabolism, cell signalling, protein regulation, cellular transport, secretory processes, and many other cellular pathways.

It is becoming increasingly appreciated that dysregulation of signal transduction pathways involving protein kinases may be involved in the generation or progression of many diseases. Inhibiting kinases, and therefore phosphorylation, can treat these diseases. Thus, development of new classes of cell permeable ligands or protein kinase inhibitors that can modulate disease-relevant pathways is an important area for therapeutics.

During phosphorylation, the phosphate groups are usually added to the serine, threonine or tyrosine amino acid on the protein. Hence, protein kinase inhibitors can be subdivided or characterized by the amino acids whose phosphorylation is inhibited: most kinases act on both serine and threonine, the tyrosine kinases act on tyrosine, and some kinases act on all three amino acids. There are also protein kinases that phosphorylate other amino acids, such as histidine kinases.

Kinases have been implicated in diseases such as cancer, inflammatory disorders, cardiovascular diseases, viral induced diseases, circulatory diseases and fibro-proliferative diseases but kinases also play an important role in pain sensitization.

Inflammation is an evolutionarily conserved host reaction that is initiated in response to trauma, tissue damage and infection. It leads to changes in tissue homeostasis and blood flow, immune-cell activation and migration, and secretion of cytokines and mediators in a spatial-temporally coordinated manner. Progress in understanding of the mechanisms of the inflammatory response has identified various protein kinases that act as essential signalling components. Chronic inflammation is part of several disease states, such as rheumatoid arthritis, psoriasis, lupus erythematosus, inflammatory bowel disease and asthma. Increasing evidence suggests that neuro-inflammation is a contributor to pathology in various neurological disorders such as Alzheimer's disease (AD), amyotrophic lateral sclerosis, autoimmune disorders, prion diseases, stroke and traumatic brain injury.

Suppressing inflammatory responses by employing protein kinase inhibitors may be beneficial as a therapeutic approach to slowing progression of these inflammatory disorders (Matthias Gaestel et al., Nature Reviews Drug Discovery 8, 480-499; D. Martin Watterson et al., Journal of Molecular Neuroscience, 19, 1-2, pp 89-93).

Although protein kinases were not favoured as targets for analgesics, studies in the last decade have demonstrated important roles of these kinases in regulating neuronal plasticity and pain sensitization. Pathological pain or clinical pain refers to tissue injury-induced inflammatory pain and nerve injury-induced neuropathic pain and is often chronic. Pathological pain is an expression of neural plasticity that occurs both in the peripheral nervous system, termed peripheral sensitization, and in the central nervous system, termed central sensitization. Multiple protein kinases have been implicated in peripheral and central sensitization.

Inhibition of multiple protein kinases has been shown to attenuate inflammatory and neuropathic pain in different animal models (K. A Sluka, W. D Willis, Pain, Volume 71, Issue 2, June 1997, Pages 165-178).

Accordingly, there is still a great need to develop potent inhibitors of protein kinase that are useful in treating the various protein kinase-related conditions.

In the field of cancer, the first protein kinase inhibitors (e.g. Imatinib, Gefitinib) have already reached the market. In addition, a great number of protein kinase inhibitors are currently in various phases of clinical development.

WO 2004/022572 (Alchemia Pty Ltd) discloses classes of biologically active compounds interacting with kinases, and the preparation of these compounds.

EP 0269574 (Nippon Zoki Pharmaceutical Co. Ltd.) discloses adenosine compounds for use in the treatment of hypertension, cerebrovascular disease, cardiopathy or renal insufficiency.

WO 2003/104482 (Metabolic Engineering Laboratories Co., Ltd) discloses a composition for modulating cellular senescence and useful for the treatment of Alzheimer's disease or atherosclerosis, said composition comprising the inhibitor of protein kinase A such as adenosine 3'5'-cyclin phosphorothiolates.

WO 1996/040705 (Gensia Inc.) discloses adenosine kinase inhibitors compounds 149-175, 413-431, and 241-266, for use in the treatment of cardiovascular and cerebrovascular diseases, inflammation, arthritis, and cancer.

Palle et al. (Bioorganic & Medicinal Chemistry Letters 14 (2004) 535-539) discloses A1 adenosine partial or full agonists for use in the treatment of atrial fibrillation.

WO 2001/040245 (CV Therapeutics Inc.) discloses a method of cardioprotection by using adenosine A1 receptor partial or full agonists.

WO 2005/117882 (Incyte Corporation) discloses ligands of C5a receptor, for use in the treatment of diseases associated with metalloprotease activity such as arthritis, cancer, cardiovascular disorders, skin disorders, inflammation or allergic conditions.

Cottam et al. (Journal of Medicinal Chemistry, 1993, Vol. 36, No. 22) discloses adenosine kinase inhibitors with oral anti-inflammatory activity.

There is a need for protein kinase inhibitors which may overcome the disadvantages of current protein kinase therapy such as side effects, limited efficacy, the emerging of resistance, and compliance failures.

SUMMARY OF THE INVENTION

It is an objective of the present invention to provide protein kinase inhibitors, which can be used to treat a plurality of diseases.

It is an objective of the present invention to provide a collection of protein kinase inhibitors, in order to build up a chemical library for testing specific protein kinase inhibition, or for testing inhibition of specific combinations of protein kinases. Each chemical of the library has associated information stored in a database, with information such as the chemical structure, purity, quantity, physicochemical characteristics, and biological activities of each of the compounds.

It is an objective of the present invention to provide a chemical library of candidate compounds for testing specific protein kinase inhibition, useful for the pharmaceutical industry in its (pre-)clinical selection of drug candidates. It is an objective of the present invention to provide a method of inhibiting protein kinase activity, whether in vitro, in vivo, or in silico.

The present invention relates to inhibitors of protein kinase as well as to a method of inhibiting protein kinase activity, which exhibit at least one improved property in view of the compounds of the prior art. In particular, the inhibitors of the present invention are interesting in one or more of the following pharmacological related properties, i.e. potency profile, potency against specific kinases, decreased toxicity, decreased cytotoxicity, improved pharmacokinetics, acceptable dosage, processing ease, and the like.

The present invention relates to a compound suitable for use as a kinase inhibitor according to general formula (I) [compound (C), herein after], or the N-oxide, pharmaceutically acceptable salt, pharmaceutically acceptable solvate, or stereoisomer thereof,

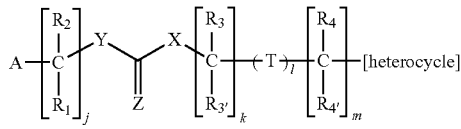

formula (I)

wherein:
each of A is independently selected from the group consisting of hydrogen, $C_{1-15}$ alkyl, $C_{2-15}$ alkenyl, $C_{2-15}$ alkynyl, cycloalkyl, heterocyclyl, aryl, heteroaryl, and aralkyl, wherein said alkyl, alkenyl, alkynyl, cycloalkyl, heterocyclyl, aryl, heteroaryl, and aralkyl, are optionally substituted with one or more substituents independently selected from the group consisting of halo, $NO_2$, alkyl, alkenyl, cycloalkyl, heterocyclyl, aryl, heteroaryl, $CF_3$, CN, $OR_{11}$, $SR_{11}$, $N(R_{11})_2$, $OC(R_{11})_2O$, $OC(R_{11})_2C(R_{11})_2O$, $S(O)R_{12}$, $SO_2R_{12}$, $SO_2N(R_{11})_2$, $S(O)_3R_{11}$, $P(O)(OR_{11})_2$, $SO_2NR_{11}COR_{12}$, $SO_2NR_{11}CO_2R_{12}$, $SO_2NR_{11}CON(R_{11})_2$, $NR_{11}COR_{12}$, $NR_{11}CO_2R_{12}$, $NR_{11}CON(R_{11})_2$, $NR_{11}C(NR_{11})NHR_{11}$, $COR_{11}$, $CON(R_{11})_2$, $CONR_{11}SO_2R_{12}$, $NR_{11}SO_2R_{12}$, $SO_2NR_{11}CO_2R_{12}$, $OCONR_{11}SO_2R_{12}$, $OC(O)R_{11}$, $C(O)OCH_2OC(O)R_{11}$, and $OCON(R_{11})_2$ and each optional alkyl, alkenyl, cycloalkyl, aryl, heterocyclyl, heteroaryl substituent is further optionally substituted with halo, $NO_2$, alkyl, cycloalkyl, aryl, $CF_3$, $N(R_{11})_2$, alkyl or aryl or heteroaryl amide, $NR_{11}COR_{12}$, $NR_{11}SO_2R_{12}$, $COR_{11}$, $CON(R_{11})_2$, $NR_{11}CON(Rn)_2$, $OC(O)R_{11}$, $OC(O)N(R_{11})_2$, $S(O)_3R_{11}$, $P(O)(OR_{11})_2$, $SR_{11}$, $S(O)R_{12}$, $SO_2R_{12}$, $SO_2N(R_{11})_2$, CN, or $OR_{11}$; and wherein each of $R_{11}$ and $R_{12}$, independently from each other and at each occurrence, are selected from the group consisting of hydrogen, $C_{1-15}$ alkyl, $C_{2-15}$ alkenyl, $C_{2-15}$ alkynyl, cycloalkyl, heterocyclyl, aryl, heteroaryl, aralkyl and $CF_3$, wherein said alkyl, alkenyl, alkynyl, cycloalkyl, heterocyclyl, aryl, heteroaryl, and aralkyl substituents are optionally substituted with halo, alkyl, cycloalkyl, heterocyclyl, mono- or dialkylamino, alkyl or aryl or heteroaryl amide, CN, $O—C_{1-6}$alkyl, $CF_3$, aryl, or heteroaryl;

each of X and Y, independently from each other and at each occurrence, are selected from O, C, S, $NR_7$; and wherein $R_7$ is selected from hydrogen, $C_{1-12}$ alkyl which is optionally substituted by a halogen atom, an aryl group or an aralkyl group;

each of Z is O, S, N—CN, N—$OR_8$; and wherein $R_8$ is selected from hydrogen, an $C_{1-12}$ alkyl which is optionally substituted by a halogen atom, an aryl group or an aralkyl group;

each of $R_1$ and $R_2$, independently from each other and at each occurrence, are selected from the group consisting of hydrogen; $C_{1-15}$ alkyl, $C_{2-15}$ alkenyl and $C_{2-15}$ alkynyl, wherein said $C_{1-15}$ alkyl, $C_{2-15}$ alkenyl, $C_{2-15}$ alkynyl are optionally substituted with a halogen atom, an aryl group or an aralkyl group; $OR_{13}$, $SR_{13}$ or $N(R_{13})_2$ wherein each of $R_{13}$, independent from each other, is selected from hydrogen or $C_{1-12}$ alkyl which is optionally substituted by a halogen atom, an aryl group or an aralkyl group, and j is an integer in the range from 0 to 7; with the proviso that when j=0 and Y=$NR_7$, then A and $R_7$ may form together a saturated or unsaturated cyclic moiety;

each of $R_3$, $R_3$', $R_4$ and $R_4$', independently from each other and at each occurrence, are selected from the group consisting of hydrogen, $C_{1-15}$ alkyl, $C_{2-15}$ alkenyl and $C_{2-15}$ alkynyl, wherein said $C_{1-15}$ alkyl, $C_{2-15}$ alkenyl, $C_{2-15}$ alkynyl are optionally substituted with a halogen atom, an aryl group or an aralkyl group;

each of T is selected from the group consisting of O, S, $NR_9$, or a divalent moiety of formula (T-a) to (T-e) wherein the second point of attachment can be at any carbon atom of the cyclic system, wherein the dash bond represents an optional double bond;

(T-a)

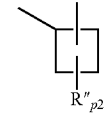
(T-b)

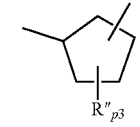
(T-c)

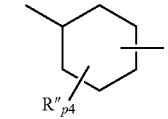
(T-d)

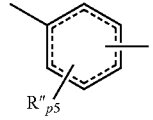
(T-e)

and wherein $R_9$ is selected from hydrogen or a $C_{1-12}$ alkyl which is optionally substituted by a halogen atom, an aryl group or an aralkyl group; and each of R" is selected independently and at each occurrence, from the group consisting of hydrogen, $C_{1-15}$ alkyl, $C_{2-15}$ alkenyl and $C_{2-15}$ alkynyl, wherein said $C_{1-15}$ alkyl, $C_{2-15}$ alkenyl, $C_{2-15}$ alkynyl are optionally substituted with a halogen atom, an aryl group or an aralkyl group; and each of p1 is an integer in the range from 0 to 4; each of p2 is an integer in the range from 0 to 6; each of p3 is an integer in the range from 0 to 8; each of p4 is an integer in the range from 0 to 10; each of p5 is an integer in the range from 0 to 8;

each of k is an integer in the range from 0 to 7; each of l is an integer in the range from 0 to 1; and each of m is an integer in the range from 0 to 7 and with the proviso that the sum of k and m is equal to or greater than 1, and with the proviso that when m is 0, l and k is 1, T is of formula T-a, each of R", $R_3$ and $R_3$. is hydrogen, A is $C_6H_5$, X and Z is O, Y is NH and the heterocycle is of following formula

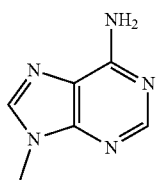

then j is an integer in the range from 1 to 7.

The present invention further relates to a pharmaceutical composition comprising a carrier, and as active ingredient an effective amount of a compound as defined in any one of the embodiments presented herein.

The present invention relates to a compound as defined in any one of the embodiments presented herein, for use as a medicament.

The present invention relates to a compound as defined in any one of the embodiments presented herein for use in the treatment of a disease selected from cancer, inflammatory disorders, cardiovascular diseases, viral induced diseases, circulatory diseases and fibro-proliferative diseases.

The present invention relates to a compound as defined in any one of the embodiments presented herein, for use in the treatment of pain sensitization.

The present invention further relates to a method of inhibiting protein kinase activity in a warm-blooded animal said method comprising the administration to an animal in need thereof, of a kinase-inhibitory effective amount of a compound according to any one of the embodiments presented herein.

The present invention further relates to a method of treating a disease selected from cancer, inflammatory disorders, cardiovascular diseases, viral induced diseases, circulatory diseases and fibro-proliferative diseases, in a warm-blooded animal said method comprising the administration to an animal in need thereof of an effective amount of a compound according to any one of the embodiments presented herein.

The present invention further relates to a method of treating pain sensitization, in a warm-blooded animal said method comprising the administration to an animal in need thereof of an effective amount of a compound according to any one of the embodiments presented herein.

DETAILED DESCRIPTION OF THE INVENTION

Figure 1A:
FIGS. 1A-1H describe tabulated data from biochemical assays used to measure protein kinase inhibition. The kinase binding assays were performed against different kinases using the SelectScreen Biochemical Kinase Profiling Service®. For all kinases, the Z'-Lyte® biochemical kinase assay technology was used except for FLT3-ITD where the LanthaScreen® kinase assay technology was used. Inhibitions were measured at 50 nM in duplicate for each compound and are reported in percentage. Shaded cells represent different levels of inhibition, with light grey representing less than 30% inhibition, middle-grey representing from 30% to 60% inhibition, and dark grey representing greater than 60% inhibition.

The present invention relates to a compound suitable for use as a kinase inhibitor according to general formula (I) [compound (C), herein after], or the N-oxide, pharmaceutically acceptable salt, pharmaceutically acceptable solvate, or stereoisomer thereof, formula (I)

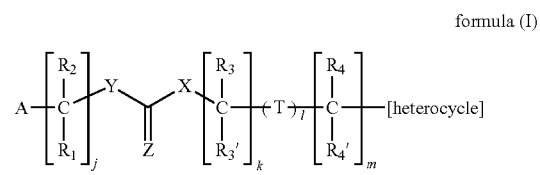

wherein:
each of A is independently selected from the group consisting of hydrogen, $C_{1-15}$ alkyl, $C_{2-15}$ alkenyl, $C_{2-15}$alkynyl, cycloalkyl, heterocyclyl, aryl, heteroaryl, and aralkyl, wherein said alkyl, alkenyl, alkynyl, cycloalkyl, heterocyclyl, aryl, heteroaryl, and aralkyl, are optionally substituted with one or more substituents independently selected from the group consisting of halo, $NO_2$, alkyl, alkenyl, cycloalkyl, heterocyclyl, aryl, heteroaryl, $CF_3$, CN, $OR_{11}$, $SR_{11}$, $N(R_{11})_2$, $OC(R_{11})_2O$, $OC(R_{11})_2C(R_{11})_2O$, $S(O)R_{12}$, $SO_2R_{12}$, $SO_2N(R_{11})_2$, $S(O)_3R_{11}$, $P(O)(OR_{11})_2$, $SO_2NR_{11}COR_2$, $SO_2NR_{11}CO_2R_{12}$, $SO_2NR_{11}CON(R_{11})_2$, $NR_{11}COR_{12}$, $NR_{11}CO_2R_{12}$, $NR_{11}CON(R_{11})_2$, $NR_{11}C(NR_{11})NHR_{11}$, $COR_{11}$, $CON(R_{11})_2$, $CONR_{11}SO_2R_{12}$, $NR_{11}SO_2R_{12}$, $SO_2NR_{11}CO_2R_{12}$, $OCONR_{11}SO_2R_{12}$, $OC(O)R_{11}$, $C(O)OCH_2OC(O)R_{11}$, and $OCON(R_{11})_2$ and each optional alkyl, alkenyl, cycloalkyl, aryl, heterocyclyl, heteroaryl substituent is further optionally substituted with halo, $NO_2$, alkyl, cycloalkyl, aryl, $CF_3$, $N(R_{11})_2$, alkyl or aryl or heteroaryl amide, $NR_{11}COR_{12}$, $NR_{11}SO_2R_{12}$, $COR_{11}$, $CON(R_{11})_2$, $NR_{11}CON(R_{11})_2$, $OC(O)R_{11}$, $OC(O)N(R_{11})_2$, $S(O)_3R_{11}$, $P(O)(OR_{11})_2$, $SR_{11}$, $S(O)R_{12}$, $SO_2R_{12}$, $SO_2N(R_{11})_2$, CN, or $OR_{11}$; and wherein each of $R_{11}$ and $R_{12}$, independently from each other and at each occurrence, are selected from the group consisting of hydrogen, $C_{1-15}$ alkyl, $C_{2-15}$ alkenyl, $C_{2-15}$ alkynyl, cycloalkyl, heterocyclyl, aryl, heteroaryl, aralkyl and $CF_3$, wherein said alkyl, alkenyl, alkynyl, cycloalkyl, heterocyclyl, aryl, heteroaryl, and aralkyl substituents are optionally substituted with halo, alkyl, cyclokalkyl, heterocyclyl, mono- or dialkylamino, alkyl or aryl or heteroaryl amide, CN, O—$C_{1-6}$alkyl, $CF_3$, aryl, or heteroaryl;

each of X and Y, independently from each other and at each occurrence, are selected from O, C, S, $NR_7$; and wherein $R_7$ is selected from hydrogen, $C_{12}$ alkyl which is optionally substituted by a halogen atom, an aryl group or an aralkyl group;

each of Z is O, S, N—CN, N—$OR_8$; and wherein $R_8$ is selected from hydrogen, an $C_{1-12}$ alkyl which is optionally substituted by a halogen atom, an aryl group or an aralkyl group;

each of $R_1$ and $R_2$, independently from each other and at each occurrence, are selected from the group consisting of hydrogen; $C_{1-15}$ alkyl, $C_{2-15}$ alkenyl and $C_{2-15}$ alkynyl, wherein said $C_{1-15}$ alkyl, $C_{2-15}$ alkenyl, $C_{2-15}$ alkynyl are optionally substituted with a halogen atom, an aryl group or an aralkyl group; $OR_{13}$, $SR_{13}$ or $N(R_{13})_2$ wherein each of $R_{13}$, independent from each other, is selected from hydrogen or $C_{1-12}$ alkyl which is optionally substituted by a halogen atom, an aryl group or an aralkyl group, and j is an integer in the range from 0 to 7; with the proviso that when j=0 and Y=$NR_7$, then A and $R_7$ may form together a saturated or unsaturated cyclic moiety;

each of $R_3$, $R_{3'}$, $R_4$ and $R_{4'}$, independently from each other and at each occurrence, are selected from the group consisting of hydrogen, $C_{1-15}$ alkyl, $C_{2-15}$ alkenyl and $C_{2-15}$ alkynyl, wherein said $C_{1-15}$ alkyl, $C_{2-15}$ alkenyl, $C_{2-15}$ alkynyl are optionally substituted with a halogen atom, an aryl group or an aralkyl group;

each of T is selected from the group consisting of O, S, $NR_9$, or a divalent moiety of formula (T-a) to (T-e) wherein the second point of attachment can be at any carbon atom of the cyclic system, wherein the dash bond represents an optional double bond;

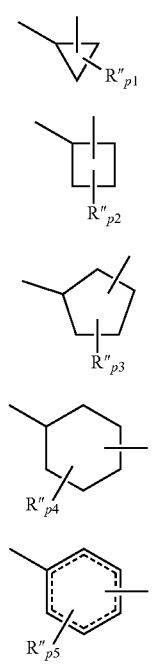

and wherein $R_9$ is selected from hydrogen or a $C_{1-12}$ alkyl which is optionally substituted by a halogen atom, an aryl group or an aralkyl group;

each of R" is selected independently and at each occurrence, from the group consisting of hydrogen, $C_{1-15}$alkyl, $C_{2-15}$ alkenyl and $C_{2-15}$ alkynyl, wherein said $C_{1-15}$ alkyl, $C_{2-15}$ alkenyl, $C_{2-15}$ alkynyl are optionally substituted with a halogen atom, an aryl group or an aralkyl group; and each of p1 is an integer in the range from 0 to 4; each of p2 is an integer in the range from 0 to 6; each of p3 is an integer in the range from 0 to 8; each of p4 is an integer in the range from 0 to 10; each of p5 is an integer in the range from 0 to 8;

each of k is an integer in the range from 0 to 7; each of l is an integer in the range from 0 to 1; and each of m is an integer in the range from 0 to 7 and with the proviso that the sum of k and m is equal to or greater than 1, and with the proviso that when m is 0, l and k is 1, T is of formula T-a, each of R", $R_3$, and $R_{3'}$ is hydrogen, A is $C_6H_5$, X and Z is O, Y is NH and the heterocycle is of following formula

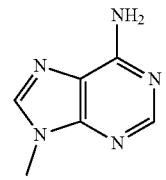

then j is an integer in the range from 1 to 7.

For the purpose of the present invention, the expression "[heterocycle]" refers to natural nucleobases and/or modified nucleobases.

For the purpose of the present invention, the expression "nucleobases" is intended to denote bases comprising purines and pyrimidines which include, for example the specific bases adenine, guanine, thymine, cytosine and uracil.

As such, modified nucleobases typically refers modified adenine, guanine, thymine, cytosine and/or uracil bases.

In one embodiment, the present invention provides modified nucleobases selected from the group consisting of (B-a) to (B-d):

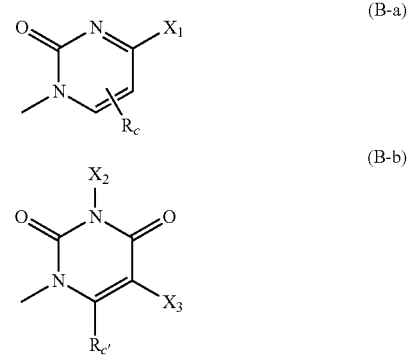

-continued

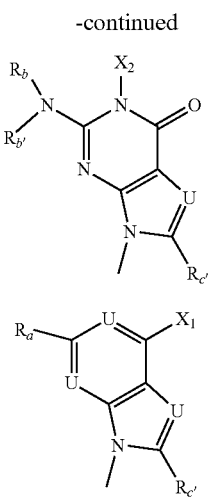

(B-c)

(B-d)

wherein:
each of $R_c$ and $R_{c'}$, independently and at each occurrence, are selected from the group consisting of hydrogen, halo, $C_{1-15}$ alkyl, $C_{2-15}$ alkenyl, $C_{2-15}$ alkynyl, heterocyclyl, aryl, and heteroaryl, wherein said alkyl, alkenyl, alkynyl, heterocyclyl, aryl, and heteroaryl are optionally substituted with one or more substituents selected from halo or an alkyl group; and each of c is an integer in the range from 0 to 2;

each of $R_a$ is independently selected from the group consisting of hydrogen, halo, $CF_3$, $N(R_{14})_2$, CN, $C_{1-15}$ alkyl, $C_{2-15}$ alkenyl, $C_{2-15}$ alkynyl, cycloalkyl, heterocyclyl, aryl, and heteroaryl, wherein said alkyl, cycloalkyl, heterocyclyl, aryl, and heteroaryl are optionally substituted with one or more substituents selected from halo, $C_{1-15}$ alkyl or $O-C_{1-6}$alkyl; and wherein each of $R_{14}$, independent from each other, is selected from hydrogen, $C_{1-15}$ alkyl, or cycloalkyl; preferably each of $R_a$ is independently selected from the group consisting of hydrogen, halo, $N(R_{14})_2$, heterocyclyl, and heteroaryl, wherein said heterocyclyl, and heteroaryl are optionally substituted with one or more substituents selected from halo or $C_{1-4}$ alkyl; preferably each of $R_{14}$, independent from each other, is selected from hydrogen, $C_{1-4}$ alkyl or cycloalkyl; or preferably each of $R_a$ is selected from $C_{1-15}$ alkyl, $C_{1-15}$ cycloalkyl, $C_{2-15}$ alkenyl, $C_{2-15}$ alkynyl, more preferably each of $R_a$ is $C_{1-10}$ alkyl, $C_{1-6}$ cycloalkyl, $C_{2-10}$ alkenyl, or $C_{2-10}$ alkynyl.

each of $X_1$ is independently selected from the group consisting of hydrogen, halo, and $N(R_b)_2$ wherein $R_b$ is hydrogen or a $C_{1-15}$ alkyl which is optionally substituted by a halogen atom, an aryl, a heterocylcyl or an aralkyl group, preferably $R_b$ is selected from hydrogen or a $C_{1-5}$ alkyl which is optionally substituted by an aryl, a heterocylcyl or an aralkyl group, most preferably $R_b$ is hydrogen;

each of $X_2$ is selected from hydrogen or $C_{1-15}$ alkyl which is optionally substituted with one or more substituents selected from halo, $C_{1-15}$ alkyl, or $O-C_{1-6}$alkyl; preferably $X_2$ is hydrogen or $C_{1-4}$ alkyl;

each of $X_3$ is selected from hydrogen, halo or $C_{1-15}$ alkyl which is optionally substituted with one or more substituents selected from halo, $C_{1-15}$ alkyl, or $O-C_{1-6}$alkyl; preferably $X_3$ is hydrogen, halo or $C_{1-4}$ alkyl;

each of U is independently selected from N or C—$R_d$ wherein $R_d$ is hydrogen, $C_{1-5}$ alkyl or halo; preferably U is N or C—$R_d$ wherein $R_d$ is hydrogen or halo; more preferably U is N;

In a preferred embodiment of the present invention, A is independently selected from the group consisting of hydrogen, $C_{1-10}$ alkyl, cycloalkyl, heterocyclyl, aryl, heteroaryl, and aralkyl, wherein said alkyl, cycloalkyl, heterocyclyl, aryl, heteroaryl, and aralkyl, are optionally substituted with one or more substituents independently selected from the group consisting of halo, alkyl, alkenyl, cycloalkyl, heterocyclyl, aryl, heteroaryl, $CF_3$, CN, $OR_{11}$, $N(R_{11})_2$, $OC(R_{11})_2O$, $OC(R_{11})_2C(R_{11})_2O$, $S(O)R_{12}$, $SO_2R_{12}$, $SO_2N(R_{11})_2$, $SO_2NR_{11}COR_{12}$, $NR_{11}COR_{12}$, $NR_{11}CON(R_{11})_2$, $COR_{11}$, $CON(R_{11})_2$, $OC(O)Rn$, $C(O)OCH_2OC(O)R_{11}$, and $OCON(R_{11})_2$ and each optional alkyl, alkenyl, cycloalkyl, aryl, heterocyclyl, heteroaryl substituent is further optionally substituted with halo, alkyl, cycloalkyl, aryl, $N(R_{11})_2$, $COR_{11}$, $CON(R_{11})_2$, $SR_1$, $SO_2R_{12}$, CN, or $OR_{11}$. More preferably A is independently selected from the group consisting of hydrogen, $C_{1-6}$ alkyl, cycloalkyl, heterocyclyl, aryl, and heteroaryl, wherein said alkyl, cycloalkyl, heterocyclyl, aryl, heteroaryl are optionally substituted with one or more substituents independently selected from the group consisting of halo, alkyl, alkenyl, cycloalkyl, heterocyclyl, aryl, heteroaryl, $CF_3$, CN, $OR_{11}$, $N(R_{11})_2$, $OC(R_{11})_2O$, $OC(R_{11})_2C(R_{11})_2O$, $SO_2R_{12}$, and $SO_2N(R_{11})_2$, and each optional alkyl, alkenyl, cycloalkyl, aryl, heterocyclyl, heteroaryl substituent is further optionally substituted with halo, alkyl, cycloalkyl, aryl, $N(R_{11})_2$, $CON(R_{11})_2$, $SO_2R_{12}$, or CN. Most preferably A is independently selected from the group consisting of hydrogen, aryl and heteroaryl, wherein said aryl, heteroaryl are optionally substituted with one or more substituents independently selected from the group consisting of halo, alkyl, $OR_{11}$, $OC(R_{11})_2O$, $OC(R_{11})_2C(R_{11})_2O$, $SO_2R_{12}$, and $SO_2N(R_{11})_2$ and in one embodiment of the present invention, each of $R_{11}$ and $R_{12}$, independently from each other and at each occurrence, are selected selected from the group consisting of hydrogen, $C_{1-5}$alkyl, heterocyclyl, aryl, aralkyl and $CF_3$, wherein said alkyl, heterocyclyl, aryl and aralkyl substituents are optionally substituted with halo or heterocyclyl.

In a preferred embodiment of compound (C) according to the present invention, X in compound (C) of general formula (I) is independently selected from O or $NR_7$ wherein $R_7$ is hydrogen or $C_{1-5}$ alkyl, preferably X in compound (C) of general formula (I) is O.

In a preferred embodiment of compound (C) according to the present invention, Y in compound (C) of general formula (I) is independently selected from O or NR, wherein $R_7$ is hydrogen or $C_{1-6}$ alkyl such as methyl, ethyl, propyl, isopropyl, butyl, tert-butyl, isobutyl, pentyl, hexyl and the like, preferably Y in compound (C) of general formula (I) is $NR_7$ wherein $R_7$ is hydrogen or methyl.

In a preferred embodiment of compound (C) according to the present invention, Z in compound (C) of general formula (I) is independently selected from O or S, preferably Z in compound (C) of general formula (I) is O.

In one embodiment of the present invention, each of $R_1$ and $R_2$, independently from each other and at each occurrence are selected from the group consisting of hydrogen; $C_{1-10}$ alkyl wherein said alkyl is optionally substituted with a halogen atom or an aryl group; $OR_{13}$ or $N(R_{13})_2$ wherein each of $R_{13}$, independent from each other, is selected from hydrogen or an $C_{1-10}$ alkyl which is optionally substituted by a halogen atom, an aryl group or an aralkyl group. Preferably each of $R_1$ and $R_2$, independently from each other and at each occurrence are selected from the group consisting of hydrogen; $C_{1-6}$ alkyl wherein said alkyl is optionally substituted with a halogen atom or an aryl group; $OR_{13}$ or $N(R_{13})_2$ wherein each of $R_{13}$, independent from each other, is selected from hydrogen or an $C_{1-10}$ alkyl which is optionally substituted by a halogen atom, an aryl group or an aralkyl group. More preferably each of $R_1$ and $R_2$, independently from each other and at each occurrence are selected from the group consisting of hydrogen and $C_{1-4}$ alkyl such as methyl, ethyl, propyl, isopropyl, butyl, tert-butyl, isobutyl, and the like.

In one embodiment of the present invention, each of $R_3$, $R_{3'}$, $R_4$ and $R_{4'}$, independently from each other and at each occurrence, are selected from the group consisting of hydrogen, $C_{1-10}$ alkyl and $C_{2-10}$ alkenyl wherein said alkyl and alkenyl, are optionally substituted with a halogen atom, an aryl group or an aralkyl group. Preferably each of $R_3$, $R_{3'}$, $R_4$ and $R_{4'}$, independently from each other and at each occurrence, are selected from the group consisting of hydrogen and $C_{1-5}$ alkyl wherein said alkyl is optionally substituted with a halogen atom. More preferably each of $R_3$, $R_{3'}$, $R_4$ and $R_{4'}$, independently from each other and at each occurrence, are selected from the group consisting of hydrogen and $C_{1-4}$ alkyl such as methyl, ethyl, propyl, isopropyl, butyl, tert-butyl, isobutyl and the like. Most preferably each of $R_3$, $R_{3'}$, $R_4$ and $R_{4'}$ are hydrogen.

In one embodiment of the present invention, each of R" is selected independently and at each occurrence, from the group consisting of hydrogen, $C_{1-10}$ alkyl and $C_{2-10}$ alkenyl wherein said alkyl and alkenyl, are optionally substituted with a halogen atom, an aryl group or an aralkyl group. Preferably each of R" is selected independently and at each occurrence, from the group consisting of hydrogen and $C_{1-5}$ alkyl wherein said alkyl is optionally substituted with a halogen atom. More preferably each of R" is selected independently and at each occurrence, from the group consisting of hydrogen and $C_{1-4}$ alkyl such as methyl, ethyl, propyl, isopropyl, butyl, tert-butyl, isobutyl and the like. Most preferably R" is hydrogen.

In one embodiment of the present invention, j is an integer in the range from 0 to 5, preferably j is an integer in the range from 0 to 3.

In one embodiment of the present invention, k is an integer in the range from 0 to 7, preferably k is an integer in the range from 2 to 5, more preferably k is 4 or 2.

In one embodiment of the present invention, m is an integer in the range from 0 to 7, preferably m is an integer in the range from 0 to 5, more preferably m is an integer in the range from 0 to 3, most preferably m is 0 or 1.

In one embodiment of the present invention, the compound (C) for use as a kinase inhibitor according to general formula (I), or the N-oxide, pharmaceutically acceptable salt, pharmaceutically acceptable solvate, or stereoisomer thereof, is used in the treatment of a disease mediated by a protein kinase, wherein the protein kinase is selected from the group consisting of ABL1, ACVR1B (ALK4), AKT1 (PKB alpha), AMPK A1/B1/G1, AURKA (Aurora A), BTK, CDK1/cyclin B, CHEK1 (CHK1), CSNK1G2 (CK1 gamma 2), CSNK2A1 (CK2 alpha 1), DYRK3, EGFR (ErbB1), EPHA2, ERBB2 (HER2), FGFR1, FLT3, FRAP1 (mTOR), GSK3B (GSK3 beta), IGF1R, IKBKB (IKK beta), INSR, IRAK4, JAK3, KDR (VEGFR2), KIT, LCK, MAP2K1 (MEK1), MAP4K4 (HGK), MAPK1 (ERK2), MAPK14 (p38 alpha), MAPK3 (ERK1), MAPK8 (JNK1), MARK2, MET (cMet), NEK1, PAK4, PDGFRB (PDGFR beta), PHKG2, PIM1, PLK1, PRKACA (PKA), PRKCB1 (PKC beta I), ROCK1, RPS6KA3 (RSK2), RPS6KB1 (p70S6K), SRC, SYK, and TEK (Tie2).

According to one embodiment of the present invention, the compound (C) for use as a kinase inhibitor, or the N-oxide, pharmaceutically acceptable salt, pharmaceutically acceptable solvate, or stereoisomer thereof, preferably is a compound chosen among those of formulae (II) to (V) [compounds (C) of class (I), herein after]:

formula (II)

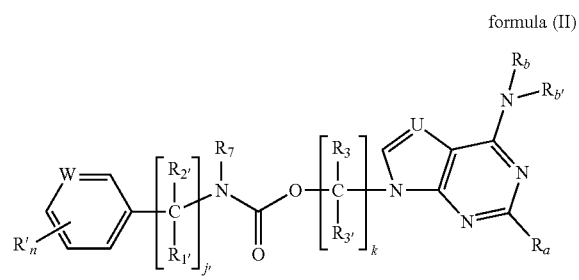

formula (III)

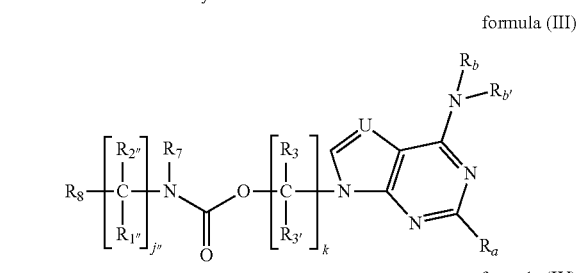

formula (IV)

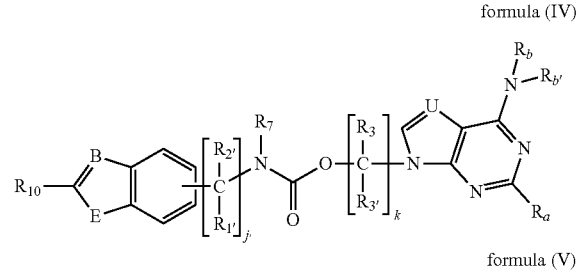

formula (V)

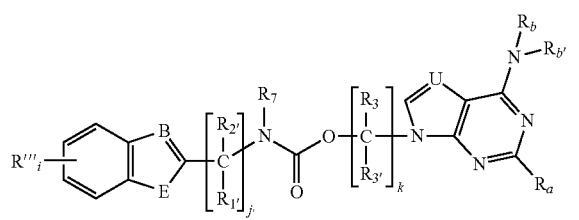

wherein $R_a$ and U have the same meaning as defined above and wherein:

each of R' and R''' independently from each other and at each occurrence, are selected from halo, $C_{1-6}$ alkyl, $C_{1-6}$ alkenyl, cycloalkyl, heterocyclyl, aryl, heteroaryl, $CF_3$, CN, $OR_{21}$, $N(R_{21})_2$, $OC(R_{21})_2O$, $OC(R_{21})_2C(R_{21})_2O$, $SO_2R_{22}$ or $SO_2N(R_{21})_2$, wherein said alkyl, alkenyl, cycloalkyl, aryl, heterocyclyl, heteroaryl group is further optionally substituted with one or more substituents selected from halo, alkyl, cycloalkyl, aryl, $N(R_{21})_2$, $CON(R_{21})_2$, $SO_2R_{22}$, or CN; wherein each of $R_{21}$ and $R_{22}$ are independently selected from the group consisting of hydrogen, $C_{1-5}$ alkyl, heterocyclyl, aryl, aralkyl and $CF_3$, wherein said alkyl, heterocyclyl, aryl and aralkyl substituents are optionally substituted with halo or heterocyclyl; and wherein R' may be attached to two carbon atoms of the aryl group thereby forming a bicyclic system; or alternatively when W is a nitrogen, R' may be attached to one carbon atom and the nitrogen atom of the aryl group thereby forming a bicyclic system and n is an integer in the range from 0 to 4, preferably n is an integer in the range from 0 to 3; and i is an integer in the range from 0 to 4, preferably i is 0 or 1;

each of $R_{1'}$, $R_{2'}$, $R_3$ and $R_{3'}$, independently from each other and at each occurrence, are selected from the group consisting of hydrogen, $C_{1-10}$ alkyl and $C_{2-10}$ alkenyl wherein said alkyl and alkenyl, are optionally substituted with a halogen atom, an aryl group or an aralkyl group; preferably each of $R_{1'}$, $R_{2'}$, $R_3$ and $R_{3'}$, independently from each other and at each occurrence, are selected from hydrogen or an $C_{1-4}$ alkyl;

each of $R_{1''}$ and $R_{2''}$, independently from each other and at each occurrence are selected from the group consisting of hydrogen; $C_{1-10}$ alkyl wherein said alkyl is optionally substituted with a halogen atom or an aryl group; $OR_{23}$ or $N(R_{23})_2$ wherein each of $R_{23}$, independent from each other, is selected from hydrogen or an $C_{1-10}$ alkyl which is optionally substituted by a halogen atom, an aryl group or an aralkyl group; preferably each of $R_{1''}$ and $R_{2''}$, independently from each other and at each occurrence are selected from the group consisting of hydrogen; $C_{1-5}$ alkyl; $OR_{23}$ wherein each of $R_{23}$, independent from each other, is selected from hydrogen or $C_{1-4}$ alkyl;

each of $R_b$ and $R_{b'}$, independent from each other and at each occurrence, are selected from hydrogen; an $C_{1-15}$ alkyl which is optionally substituted by a halogen atom, an aryl, a heterocylcyl or an aralkyl group; preferably each of $R_b$ and $R_{b'}$, independent from each other and at each occurrence, are each selected from hydrogen; a $C_{1-5}$ alkyl which is optionally substituted by an aryl, a heterocylcyl or an aralkyl group, most preferably $R_b$ is hydrogen;

each of $R_7$ is independently selected from hydrogen or $C_{1-6}$ alkyl such as, for example, methyl, ethyl, propyl, isopropyl, butyl, tert-butyl, isobutyl, pentyl, hexyl and the like; preferably $R_7$ is hydrogen;

each of k is an integer in the range from 2 to 5;

each of W is selected, independently and at each occurrence, from C-halo, C—$R_{24}$, O or N; and wherein $R_{24}$ is selected from hydrogen or an $C_{1-10}$ alkyl which is optionally substituted by a halogen atom, an aryl group or an aralkyl group, preferably W is selected, independently and at each occurrence, from C-halo, C—$R_{24}$ or N; and preferably $R_{24}$ is hydrogen or $C_{1-5}$ alkyl;

each of E is independently selected from $CH_2$, O, CH-halo or $NR_{25}$; and wherein $R_{25}$ is selected from hydrogen or an $C_{1-10}$ alkyl which is optionally substituted by a halogen atom, an aryl group or an aralkyl group; preferably each of E is independently selected from $CH_2$, O, or $NR_{25}$; and preferably $R_{25}$ is selected from hydrogen or $C_{1-5}$ alkyl;

each of B is selected, independently and at each occurrence, from C-halo, C—$R_{26}$, O, or N; and wherein $R_{26}$ is selected from hydrogen or an $C_{1-10}$ alkyl which is optionally substituted by a halogen atom, an aryl group or an aralkyl group; preferably each of B is selected, independently and at each occurrence, from C—$R_{26}$, O, N; and preferably $R_{26}$ is selected from hydrogen; $C_{1-5}$ alkyl;

each of j' is an integer in the range from 0 to 5, preferably j' is an integer in the range from 1 to 3;

each of j" is an integer in the range from 0 to 15, preferably j" is an integer in the range from 0 to 8, more preferably j" is an integer in the range from 0 to 4;

each of $R_8$ is independently selected from the group consisting of hydrogen, or the moiety of formula (R8-a) wherein G is N or C; wherein R* is selected from $C_{1-6}$ alkyl, OH, O—$C_{1-6}$alkyl, an aryl or aralkyl group and R* may be attached to one atom, including G, or two atoms of the cyclic group thereby forming a bicyclic system; wherein h is an integer in the range between 0 to 4; and wherein o is an integer in the range between 0 to 1; preferably each of $R_8$ is independently selected from the group consisting of hydrogen, or the moiety of formula (R8-a) wherein G is N or C; preferably R* is selected from OH, an aryl or aralkyl group and R* may be attached to one atom, including G, or two atoms of the cyclic group thereby forming a bicyclic system; preferably h is an integer in the range between 1 to 3; preferably o is 0;

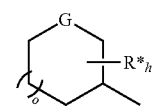

(R8-a)

each of $R_{10}$ is independently selected from hydrogen, halo, $C_{1-6}$ alkyl, $C_{1-6}$ alkenyl, cycloalkyl or $N(R_{27})_2$; and wherein $R_{27}$ is independently selected from hydrogen or an $C_{1-10}$ alkyl which is optionally substituted by a halogen atom, an aryl group or an aralkyl group, preferably each of $R_{10}$ is independently selected from hydrogen, $C_{1-4}$ alkyl, cycloalkyl, or $N(R_{27})_2$; and preferably $R_{27}$ is independently selected from hydrogen or an $C_{1-5}$ alkyl;

In compounds (C) according to the present invention, preferably $R_{1''}$, $R_{2'}$, $R_{2''}$, $R_3$, $R_4$, $R_{3'}$, $R_{4'}$, $R_7$, $R_b$ and $R_{b'}$ are hydrogen and U is N. Preferred compounds (C) of class (I) are thus selected from those of formula (II-a) to (IV-a) herein below:

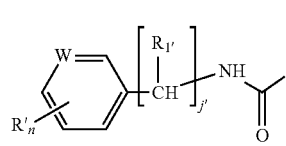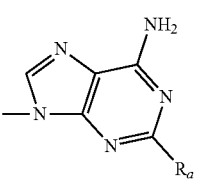

formula (II-a)

-continued

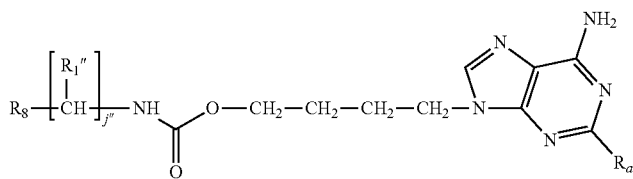

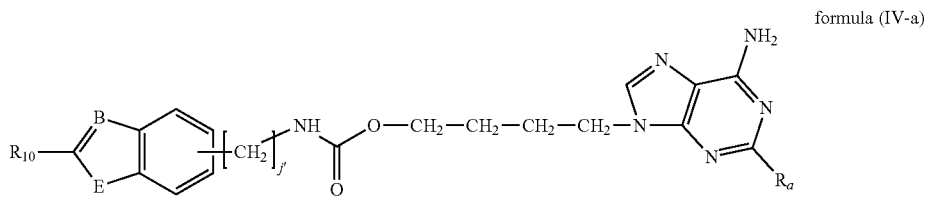

formula (III-a)

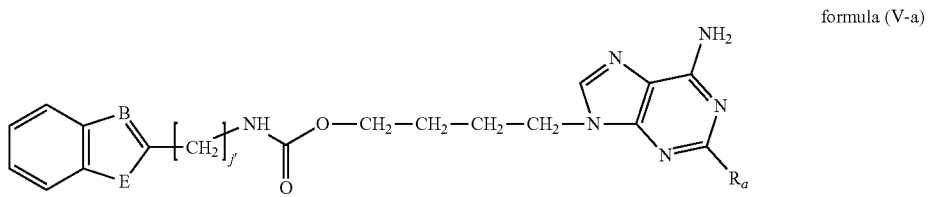

formula (IV-a)

formula (V-a)

wherein R' has the same meaning as defined above for formula (II) to (V) and wherein:
- each of $R_a$ is independently selected from the group consisting of hydrogen, halo, $N(R_{14})_2$, heterocyclyl, and heteroaryl, wherein said heterocyclyl, and heteroaryl are optionally substituted with one or more substituents selected from halo or $C_{1-4}$ alkyl; preferably each of $R_{14}$, independent from each other, is selected from hydrogen, $C_{1-4}$ alkyl, or cycloalkyl; or preferably each of $R_a$ is selected from $C_{1-15}$ alkyl, $C_{1-15}$ cycloalkyl, $C_{2-15}$ alkenyl, or $C_{2-15}$ alkynyl, more preferably each of $R_a$ is selected from $C_{1-10}$ alkyl, $C_{1-6}$ cycloalkyl, $C_{2-10}$ alkenyl, $C_{2-10}$ alkynyl;
- each of $R_{1'}$ is independently selected from hydrogen or $C_{1-4}$ alkyl;
- each of $R_{1''}$ is independently selected from hydrogen, $C_{1-5}$ alkyl, or $OR_{23}$ wherein each of $R_{23}$, independent from each other, is selected from hydrogen or $C_{1-4}$ alkyl;
- each of W is selected, independently and at each occurrence, from C-halo, C—$R_{24}$ or N; and wherein $R_{24}$ is hydrogen or $C_{1-5}$ alkyl;
- each of $R_6$ is independently selected from the group consisting of hydrogen, or the moiety of formula (R8-a) wherein G is N or C; and wherein R* is selected from OH, an aryl or aralkyl group and each R* may be attached to one atom, including G, or two atoms of the cyclic group thereby forming a bicyclic system; and h is an integer in the range between 1 to 3;

(R8-b)

- each of E is independently selected from $CH_2$, O or $NR_{25}$; and $R_{25}$ is selected from hydrogen or $C_{1-5}$ alkyl;
- each of B is selected, independently and at each occurrence, from C—$R_{26}$, O or N; and preferably $R_{26}$ is selected from hydrogen or $C_{1-5}$ alkyl;
- each of $R_{10}$ is independently selected from hydrogen, $C_{1-4}$ alkyl, cycloalkyl or $N(R_{27})_2$; and $R_{27}$ is selected from hydrogen or $C_{1-5}$ alkyl;
- each of j' is an integer in the range from 1 to 3;
- each of j'' is an integer in the range from 0 to 4.

In one embodiment of the present invention, the compounds (C) of class (I) are selected from those of formula (II-a) and (IV-a).

In a preferred embodiment of the present invention, the compound (C), according to the present invention, for use as a kinase inhibitor according to general formula (II-a) is a compound chosen among those of formulae (II-a-1) to (II-a-7) to herein below:

formula (II-a-1)

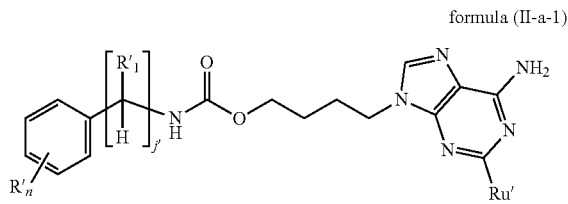

wherein Ru' is hydrogen; $C_6H_5$; heteroaryl selected from the group consisting of furanyl, pyrrolyl, isoxazolyl, pyrazolyl, and pyridinyl, wherein said heteroaryl is optionally further substituted with methyl; aryl and wherein said aryl is optionally further substituted with —CN, —$CH_3$, F, or —$OCH_3$; and each of R' is selected from the group consisting of $CF_3$; hydrogen; halo; heterocyclyl; $C_6H_5$; $OCH_3$; $CH_3$; heteroaryl selected from the group consisting of furanyl, pyrrolyl, isoxazolyl, pyrazolyl, and pyridinyl and wherein said heteroaryl is optionally further substituted with methyl; and aryl wherein said aryl is optionally substituted with CN or $CONH_2$; and n is an integer in the range from 0 to 3; and each of $R_1'$ is an hydrogen or a linear or branched $C_zH_{2z+1}$ wherein z is an integer from 1 to 5 and j' is an integer in the range from 1 to 3.

formula (II-a-2)

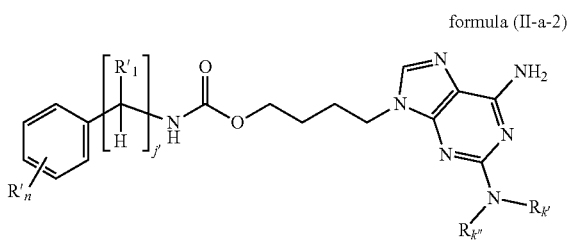

wherein each of R' is selected from the group consisting of hydrogen, halo, $CF_3$, heterocyclyl, aryl, and a linear or branched $C_wH_{2w+1}$ wherein w is an integer from 1 to 5, and n is an integer in the range from 0 to 3 and each of R1' is an hydrogen or a linear or branched $C_zH_{2z+1}$ wherein z is an integer from 1 to 5 and j' is an integer in the range from 1 to 3 and $R_{k'}$ and $R_{k''}$ are independently from each other and at each occurrence selected from H, $C_{1-4}$ alkyl and $C_{1-4}$ cycloalkyl, $R_{k'}$ and $R_{k''}$ may also form together with the nitrogen N a heterocyclyl such as azetidine or pyrrolidine, preferably $R_{k'}$ and $R_{k''}$ are hydrogen, methyl, isobutyl and cyclopropyl.

formula (II-a-3)

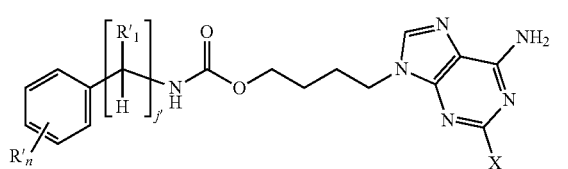

wherein each of R' is selected from the group consisting of hydrogen; halo; heterocyclyl; $C_{1-5}$ cycloalkyl; $C_{1-3}$ alkenyl; $C_{1-3}$ alkynyl; $C_6H_5$; $CF_3$; $CH_3$; CN; heteroaryl selected from the group consisting of furanyl, pyrrolyl, isoxazolyl, pyrazolyl, and pyridinyl and wherein said heteroaryl is optionally further substituted with methyl; aryl wherein said aryl is optionally substituted with CN or $CONH_2$; $OR_{21}$; $N(R_{21})_2$ wherein each of $R_{21}$ is independently selected from the group consisting of hydrogen, $C_{1-5}$ alkyl, heterocyclyl, aryl, aralkyl, and $CF_3$; and a linear or branched $C_wH_{2w+1}$ wherein w is an integer from 1 to 5, and n is an integer in the range from 0 to 3, and $R_1'$ is an hydrogen or a linear or branched $C_zH_{2z+1}$ wherein z is an integer from 1 to 5 and j' is an integer in the range from 1 to 3 and X is Cl or F.

formula (II-a-4)

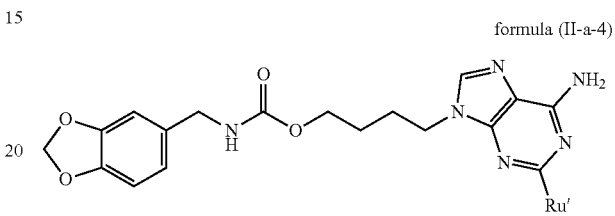

wherein Ru' is hydrogen; halo; cyclopropyl; heteroaryl selected from the group consisting of furanyl, pyrrolyl, isoxazolyl, pyrazolyl, and pyridinyl; $C_6H_5$ and wherein said heteroaryl is optionally further substituted with methyl; $N(R_{21})_2$, and wherein each of $R_{21}$ is independently selected from the group consisting of hydrogen, methyl, cyclopropyl, and isobutyl.

formula (II-a-5)

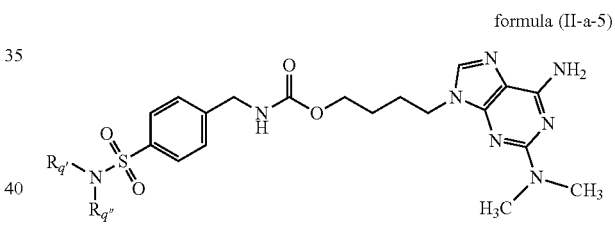

wherein each of $R_{q'}$ and $R_{q''}$ are independently from each other and at each occurrence selected from H, $C_{1-5}$ alkyl, heterocyclyl, aryl, and aralkyl, wherein said aryl is optionally further substituted with a $C_{1-5}$ alkyl, halo or $CF_3$.

formula (II-a-6)

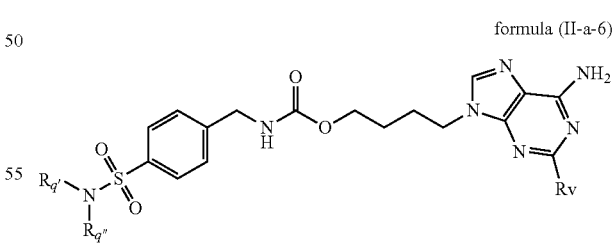

wherein each of $R_q'$ and $R_q''$ are independently from each other and at each occurrence selected from H, $C_{1-5}$ alkyl, cycloalkyl, heterocyclyl, aryl, aralkyl and heteroaralkyl wherein said aryl is optionally further substituted with a $C_{1-5}$ alkyl, halo, OMe, CN, or $CF_3$ and Rv is selected from halo or $OR_{k''}$ wherein $R_{k''}$ is selected from $C_{1-5}$ alkyl or $C_{1-5}$ cycloalkyl, preferably $R_k$ is methyl, ethyl, propyl, isopropyl, isobutyl, methylcyclopentyl.

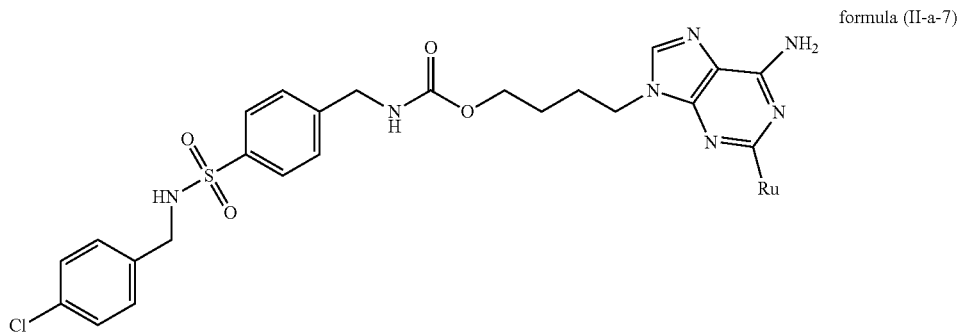

formula (II-a-7)

wherein $R_u$ is selected from the group consisting of —$SR_m$, $C_{1-5}$ alkyl, $C_{1-3}$ alkenyl or $C_{1-3}$ alkynyl wherein $R_m$ is a linear or branched $C_zH_{2z+1}$ wherein z is an integer from 1 to 5.

In a preferred embodiment of the present invention, the compound (C), according to the present invention, for use as a kinase inhibitor according to general formula (IV-a) is a compound of formula (IV-a-1) or formula (IV-a-2), herein below:

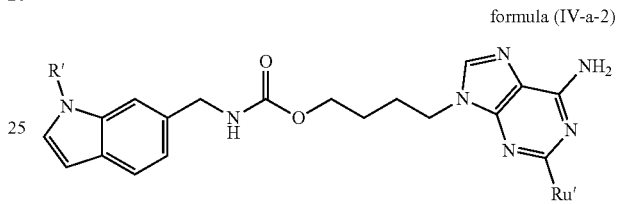

formula (IV-a-1)

wherein Ru''' is selected from the group consisting of halo, azetidine, aryl, heteroaryl selected from the group consisting of furanyl, pyrrolyl, isoxazolyl, pyrazolyl and pyridinyl and wherein said aryl is optionally further substituted with —CN, —$CH_3$, F, or —$OCH_3$.

formula (IV-a-2)

wherein Ru' is selected from the group consisting of halo; heteroaryl selected from the group consisting of furanyl, pyrrolyl, isoxazolyl, pyrazolyl, and pyridinyl; aryl and wherein said aryl is optionally further substituted with —CN, —$CH_3$, F, or —$OCH_3$; R' is hydrogen or $C_{1-5}$ alkyl.

According to one embodiment of the present invention, the compound (C) for use as a kinase inhibitor, or the N-oxide, pharmaceutically acceptable salt, pharmaceutically acceptable solvate, or stereoisomer thereof, preferably is a compound chosen among those of formulae (VI) to (IX) [compounds (C) of class (II), herein after]:

formula (VI)

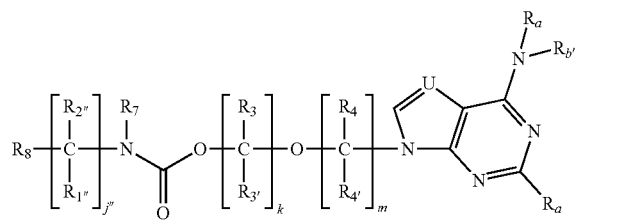

formula (VII)

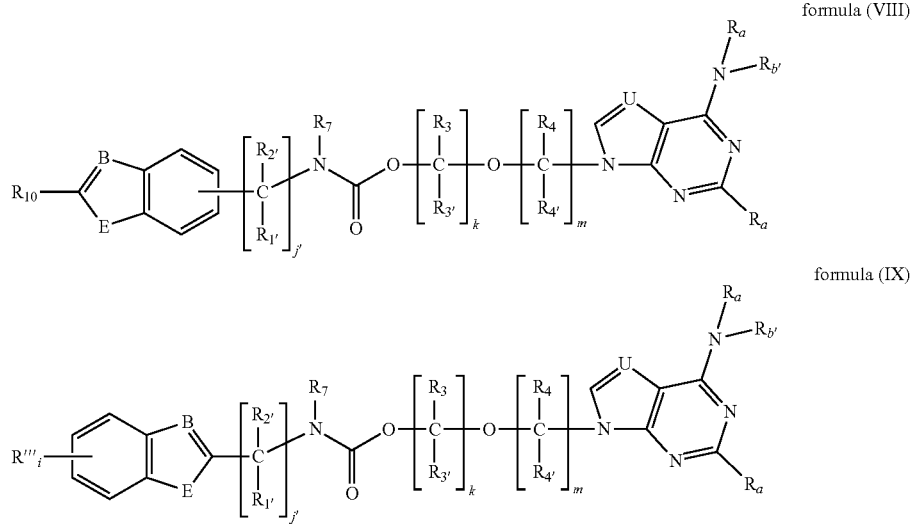

formula (VIII)

formula (IX)

wherein R', R''', $R_1$', $R_2$', $R_1$'', $R_2$'', $R_3$, $R_4$, $R_3$', $R_4$', $R_8$, $R_{10}$, $R_a$, $R_b$, $R_b'$, U, W, B, E, j', j'', i and n have the same meaning as defined above for formula (II) to (V); and wherein k and m are each independently and at each occurrence selected from an integer in the range from 1 to 4, preferably k is 2 and m is 1.

In compounds (C) according to the present invention, preferably, $R_1$''', $R_2$', $R_2$''', $R_3$, $R_4$, $R_3$', $R_4$', $R_7$, $R_b$ and $R_b'$ are hydrogen and U is N. Preferred compounds (C) of class (II) are thus selected from those of formula (VI-a) to (IX-a) herein below:

wherein W, B, E, R', $R_1$', $R_1$'', $R_8$, $R_{10}$, $R_a$, j', j'' and n have the same meaning as defined above for formula (II-a) to (V-a).

In one embodiment of the present invention, the compounds (C) of class (II) are selected from those of formula (VI-a) and (VIII-a).

According to one embodiment of the present invention, the compound (C) for use as a kinase inhibitor, or the N-oxide, pharmaceutically acceptable salt, pharmaceutically acceptable solvate, or stereoisomer thereof, preferably is a compound chosen among those of formulae (IX') to (XII) [compounds (C) of class (III), herein after]:

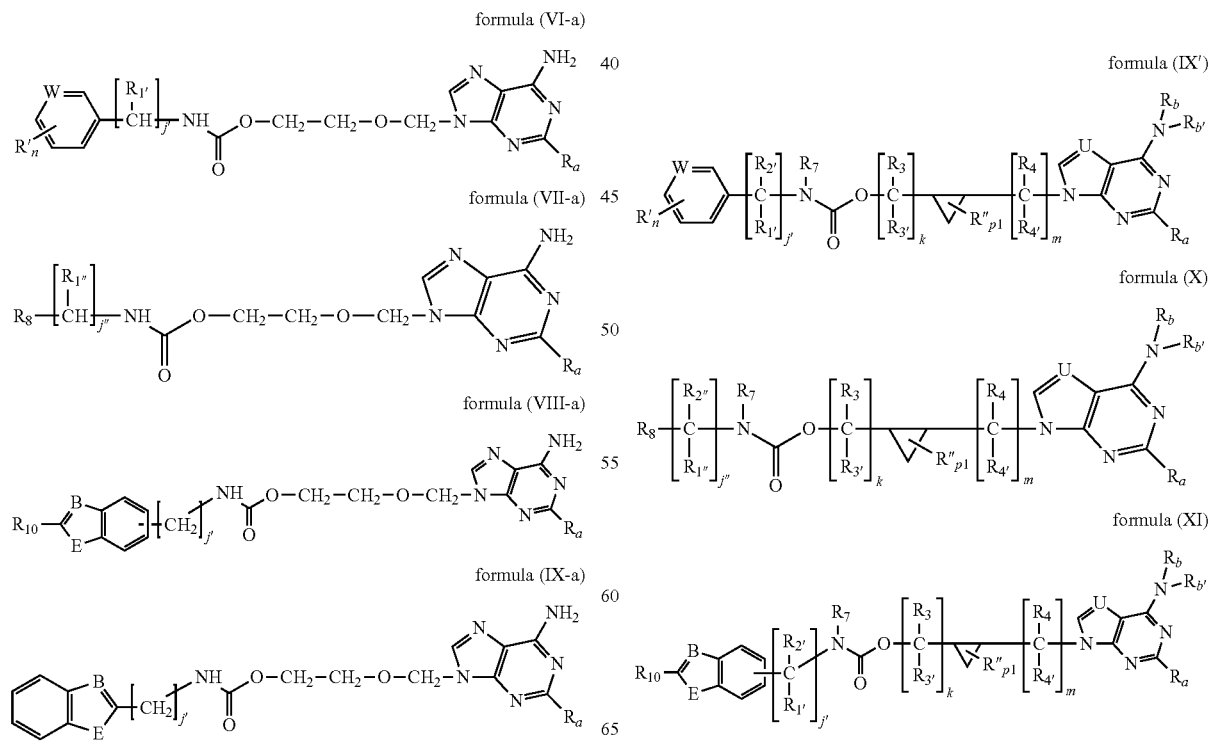

-continued formula (XII)

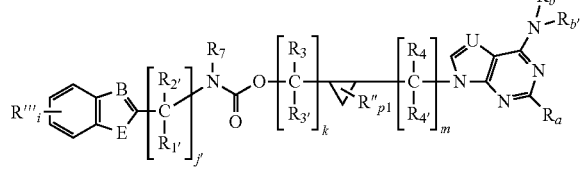

wherein R', R''', $R_{1'}$, $R_{2'}$, $R_{1''}$, $R_{2''}$, $R_3$, $R_4$, $R_{3'}$, $R_{4'}$, $R_8$, $R_{10}$, $R_a$, $R_b$, $R_{b'}$, U, W, B, E, j', j'', i and n have the same meaning as defined above for formula (II) to (V); and wherein k and m are each independently and at each occurrence selected from an integer in the range from 0 to 4, preferably k and m are 1; wherein p1 is an integer in the range from 0 to 2, preferably p1 is 0; and wherein R'' is independently selected from hydrogen, $C_{1-15}$ alkyl, $C_{2-15}$ alkenyl, $C_{2-15}$ alkynyl, wherein said $C_{1-15}$ alkyl, $C_{2-15}$ alkenyl or $C_{2-15}$ alkynyl are optionally substituted with a halogen atom, an aryl group or an aralkyl group, preferably R'' is independently selected from hydrogen or $C_{1-4}$ alkyl such as methyl, ethyl, propyl, isopropyl, butyl, tert-butyl, isobutyl and the like, and with the proviso when in formula (IX'), W is C—H, R' and R'' is hydrogen, m is 0, k is 1, $R_3$, $R_3'$ and $R_7$ is hydrogen then j' is an integer in the range from 1 to 3.

In compounds (C) according to the present invention, preferably, $R_{1'''}$, $R_{2'}$, $R_{2''}$, $R_3$, $R_4$, $R_{3'}$, $R_{4'}$, $R_7$, $R_b$ and $R_{b'}$ are hydrogen and U is N. Preferred compounds (C) of class (III) are thus selected from those of formula (IX-a) to (XII-a) herein below:

formula (IX-a)

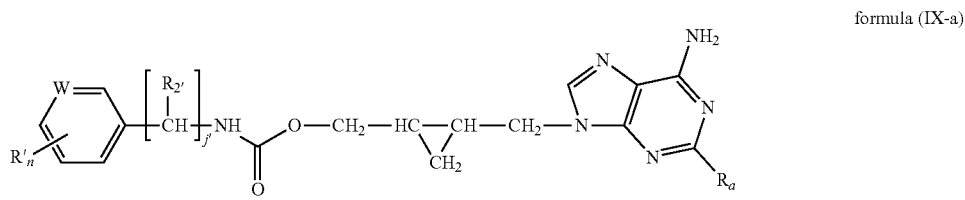

formula (X-a)

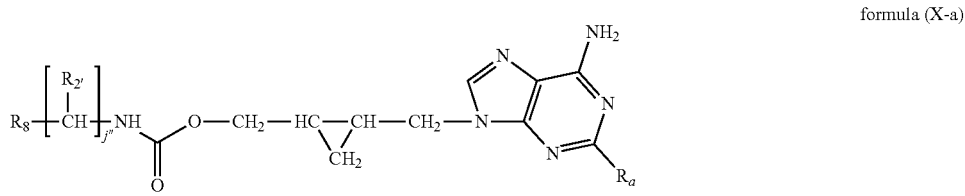

formula (XI-a)

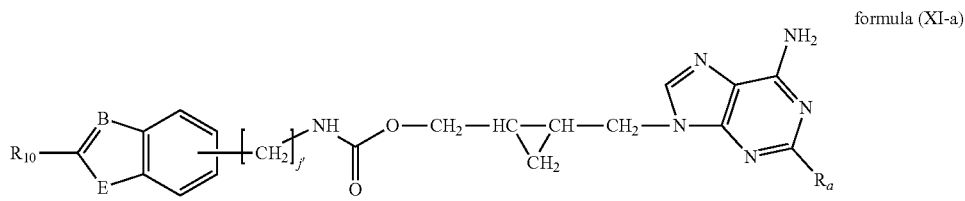

formula (XII-a)

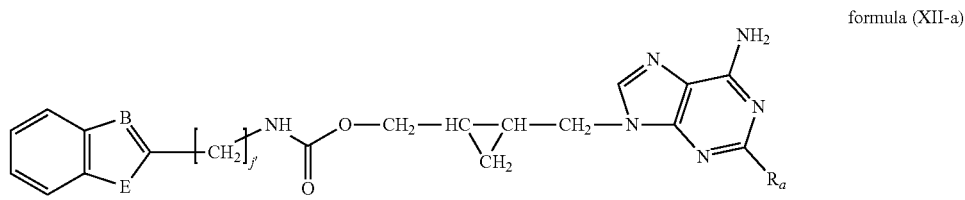

wherein W, B, E, R', $R_{1'}$, $R_{1''}$ $R_8$, $R_{10}$, $R_a$, j', j'' and n have the same meaning as defined above for formula (II-a) to (V-a).

acceptable solvate, or stereoisomer thereof, preferably is a compound chosen among those of formulae (XIII) to (XVI) [compounds (C) of class (IV), herein after]:

formula (XIII)

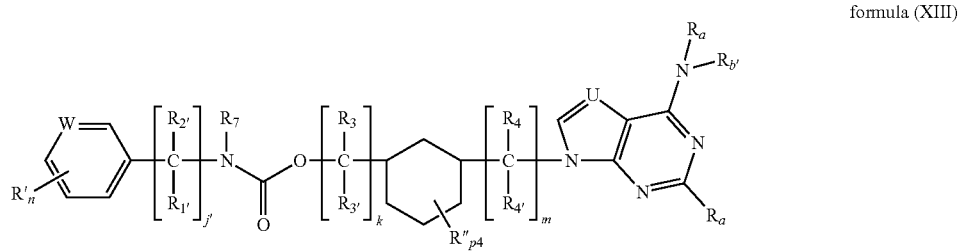

formula (XIV)

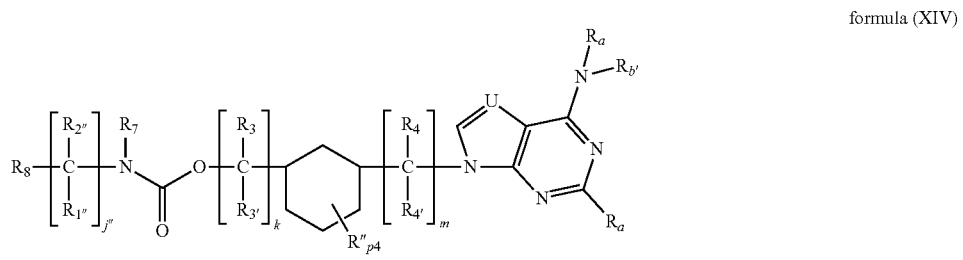

formula (XV)

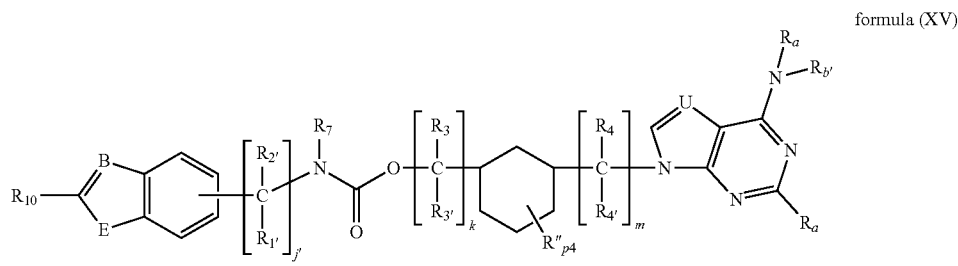

formula (XVI)

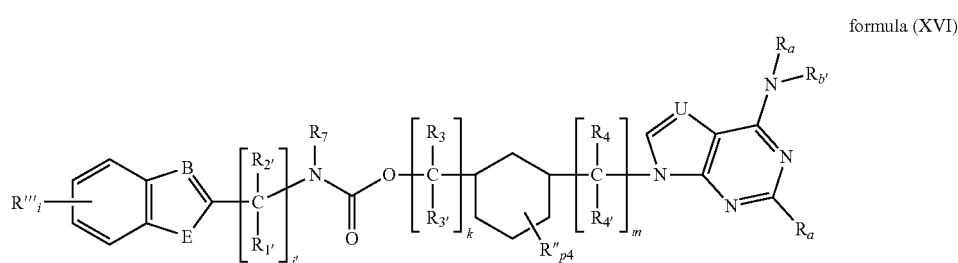

In one embodiment of the present invention, the compounds (C) of class (III) are selected from those of formula (IX-a) and (XI-a).

According to one embodiment of the present invention, the compound (C) for use as a kinase inhibitor, or the N-oxide, pharmaceutically acceptable salt, pharmaceutically wherein R', R''', $R_{1'}$, $R_{2'}$, $R_{1'''}$, $R_{2''}$, $R_3$, $R_4$, $R_{3'}$, $R_{4'}$, $R_8$, $R_{10}$, $R_a$, $R_b$, $R_{b'}$, U, W, B, E, j', j'', i and n have the same meaning as defined above for formula (II) to (V); wherein R'' has the same meaning as defined above for formula (IX) to (XII); wherein k and m are each independently and at each occurrence selected from an integer in the range from 0 to 4, preferably k is 0 and m is 0; wherein p4 is an integer in the range from 0 to 6, preferably p4 is an integer in the range from 0 to 3, more preferably p4 is 0.

In compounds (C) according to the present invention, preferably, $R_{1'''}$, $R_{2'}$, $R_{2'''}$, $R_3$, $R_4$, $R_{3'}$, $R_{4'}$, $R_7$, $R_b$ and $R_{b'}$ are hydrogen and U is N. Preferred compounds (C) of class (IV) are thus selected from those of formula (XIII-a) to (XVI-a) herein below:

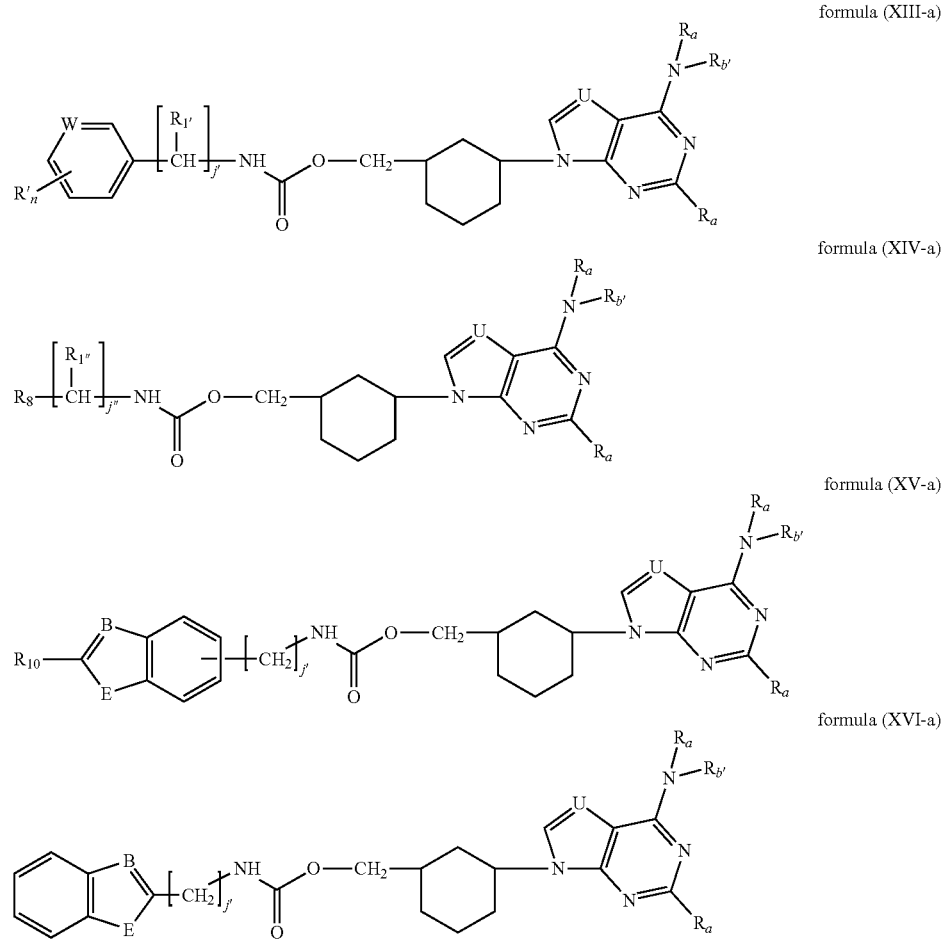

formula (XIII-a)

formula (XIV-a)

formula (XV-a)

formula (XVI-a)

wherein W, B, E, R', $R_{1'}$, $R_{1''}$, $R_8$, $R_{10}$, $R_a$, j', j'' and n have the same meaning as defined above for formula (III-a) to (V-a).

In one embodiment of the present invention, the compounds (C) of class (IV) are selected from those of formula (XIII-a) and (XV-a).

According to one embodiment of the present invention, the compound (C) for use as a kinase inhibitor, or the N-oxide, pharmaceutically acceptable salt, pharmaceutically acceptable solvate, or stereoisomer thereof, preferably is a compound chosen among those of formulae (XVII) to (XX) [compounds (C) of class (V), herein after]:

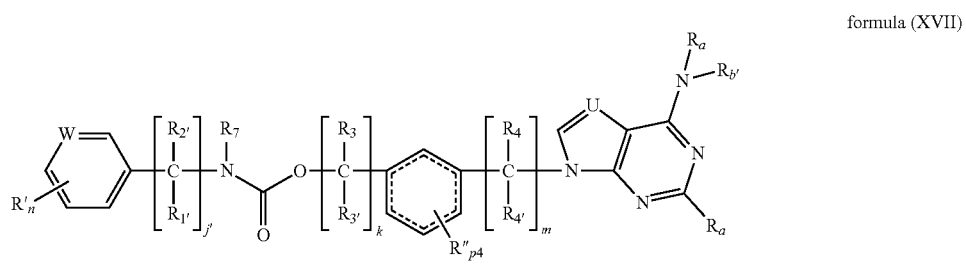

formula (XVII)

-continued formula (XVIII)
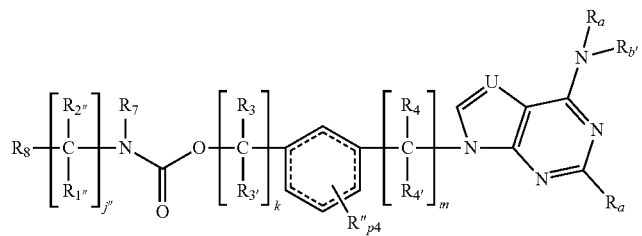

formula (XIX)
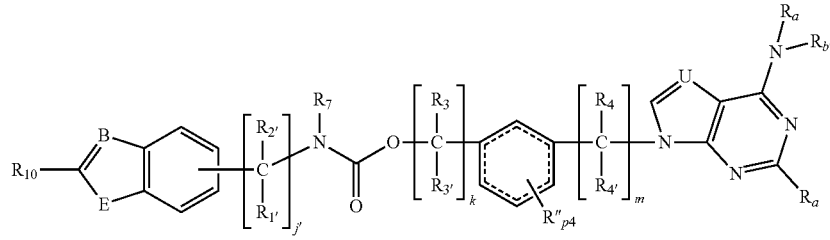

formula (XX)
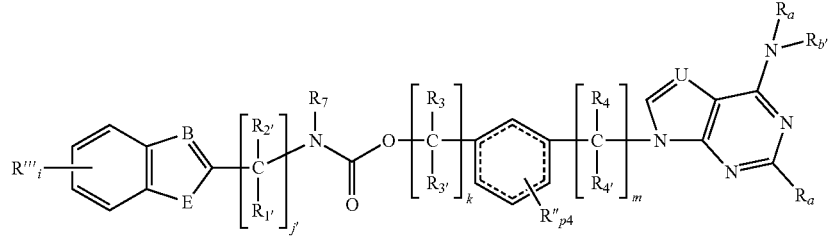

wherein R', R''', $R_1$', $R_2$', $R_1$''', $R_2$'', $R_3$, $R_4$, $R_3$', $R_4$', $R_8$, $R_{10}$, $R_a$, $R_b$, $R_{b'}$, U, W, B, E, j', j'', i and n have the same meaning as defined above for formula (II) to (V); wherein R'' has the same meaning as defined above for formula (IX) to (XII); wherein the dash bond represents at least one double bond; wherein k and m are each independently and at each occurrence selected from an integer in the range from 0 to 4, preferably k is 1 and m is 0; wherein p5 is an integer in the range from 0 to 4; preferably p5 is an integer in the range from 0 to 2, more preferably p5 is 0.

In compounds (C) according to the present invention, preferably, $R_1$''', $R_2$', $R_2$'', $R_3$, $R_4$, $R_3$', $R_4$', $R_7$, $R_b$ and $R_{b'}$ are hydrogen and U is N. Preferred compounds (C) of class (V) are thus selected from those of formula (XVII-a) to (XX-a) herein below:

formula (XVII-a)
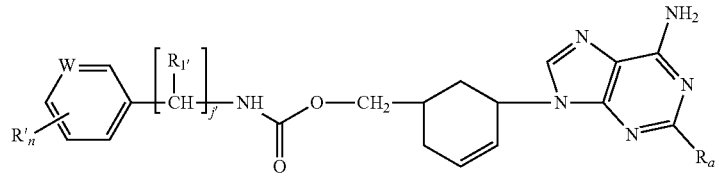

formula (XVIII-a)

formula (XIX-a)
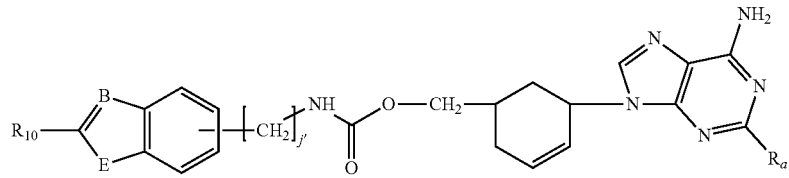

formula (XX-a)

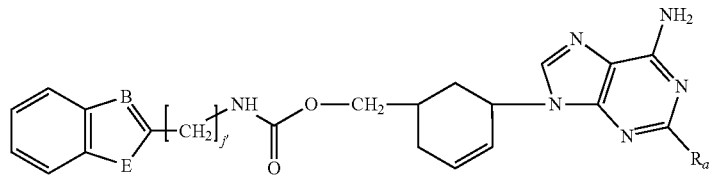

wherein W, B, E, R', $R_{1'}$, $R_{1''}$, $R_8$, $R_{10}$, $R_a$, j', j'' and n have the same meaning as defined above for formula (II-a) to (V-a).

In one embodiment of the present invention, the compounds (C) of class (V) are selected from those of formula (XVII-a) and (XIX-a).

According to one embodiment of the present invention, the compound (C) for use as a kinase inhibitor, or the N-oxide, pharmaceutically acceptable salt, pharmaceutically acceptable solvate, or stereoisomer thereof, preferably is a compound chosen among those of formulae (XXI) to (XXIV) [compounds (C) of class (VI), herein after]:

wherein R', R''', $R_{1'}$, $R_{2'}$, $R_{1'''}$, $R_{2'''}$, $R_3$, $R_4$, $R_{3'}$, $R_{4'}$, $R_8$, $R_{10}$, $R_a$, $R_b$, $R_{b'}$, U, W, B, E, j', j'', i and n have the same meaning as defined above for formula (I) to (V); wherein R'' has the same meaning as defined above for formula (IX) to (XII); wherein k and m are each independently and at each occurrence selected from an integer in the range from 0 to 4, preferably k is 1 and m is 0; wherein p4 is an integer in the range from 0 to 6; preferably p4 is an integer in the range from 0 to 3, more preferably p4 is 0.

In compounds (C) according to the present invention, preferably, $R_{1'''}$, $R_{2'}$, $R_{2'''}$, $R_3$, $R_4$, $R_{3'}$, $R_{4'}$, $R_7$, $R_b$ and $R_{b'}$ are formula (XXI)

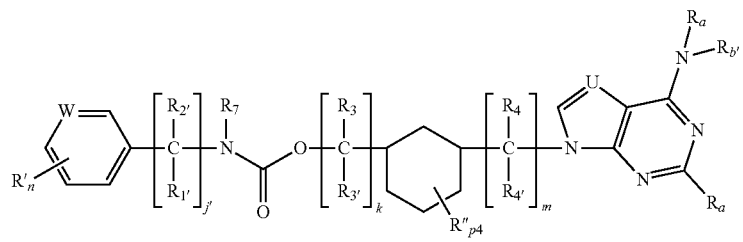

formula (XXII)

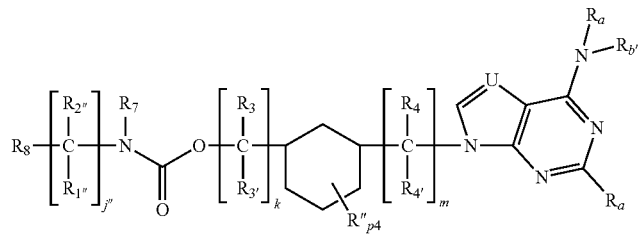

formula (XXIII)

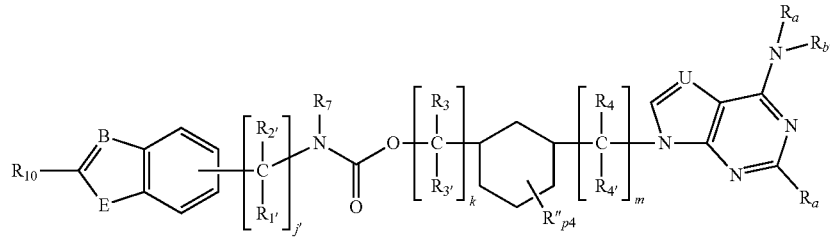

formula (XIV)

hydrogen and U is N. Preferred compounds (C) of class (VI) are thus selected from those of formula (XI-a) to (XIII-a) herein below:

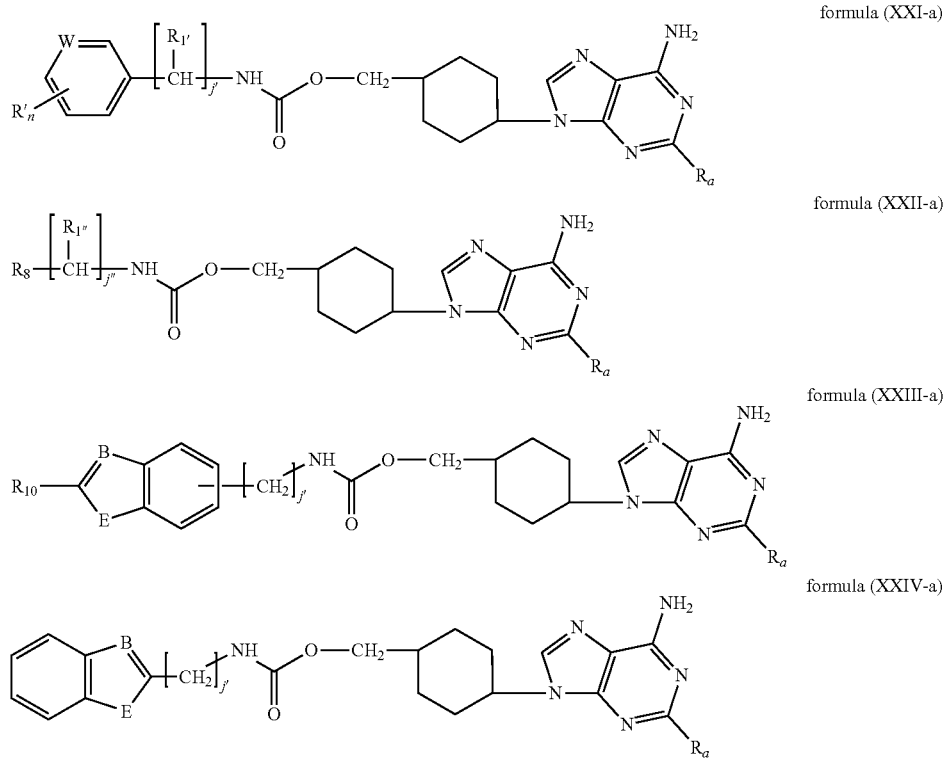

formula (XXI-a)

formula (XXII-a)

formula (XXIII-a)

formula (XXIV-a)

wherein W, B, E, R', $R_{1'}$, $R_{1''}$ $R_8$, $R_{10}$, $R_a$, j', j" and n have the same meaning as defined above for formula (II-a) to (V-a).

In one embodiment of the present invention, the compounds (C) of class (VI) are selected from those of formula (XXI-a) and (XXIII-a).

In a preferred embodiment of the compound (C) according to the present invention, A in compound (C) of general formula (I) is independently selected from the following moieties:

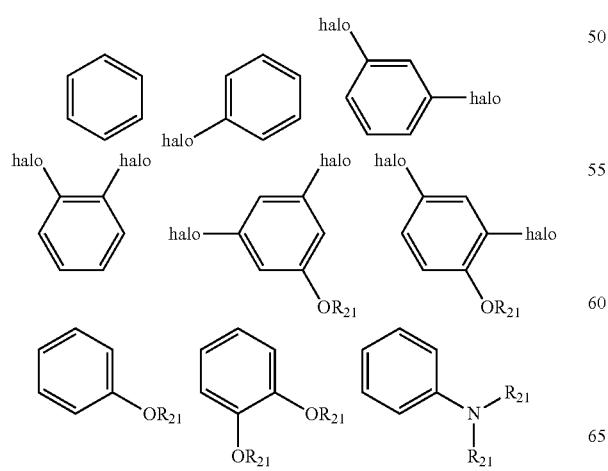

-continued

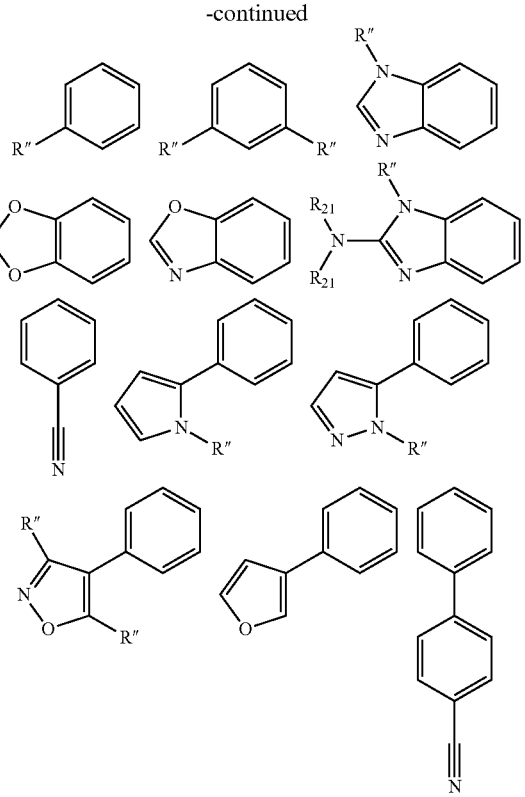

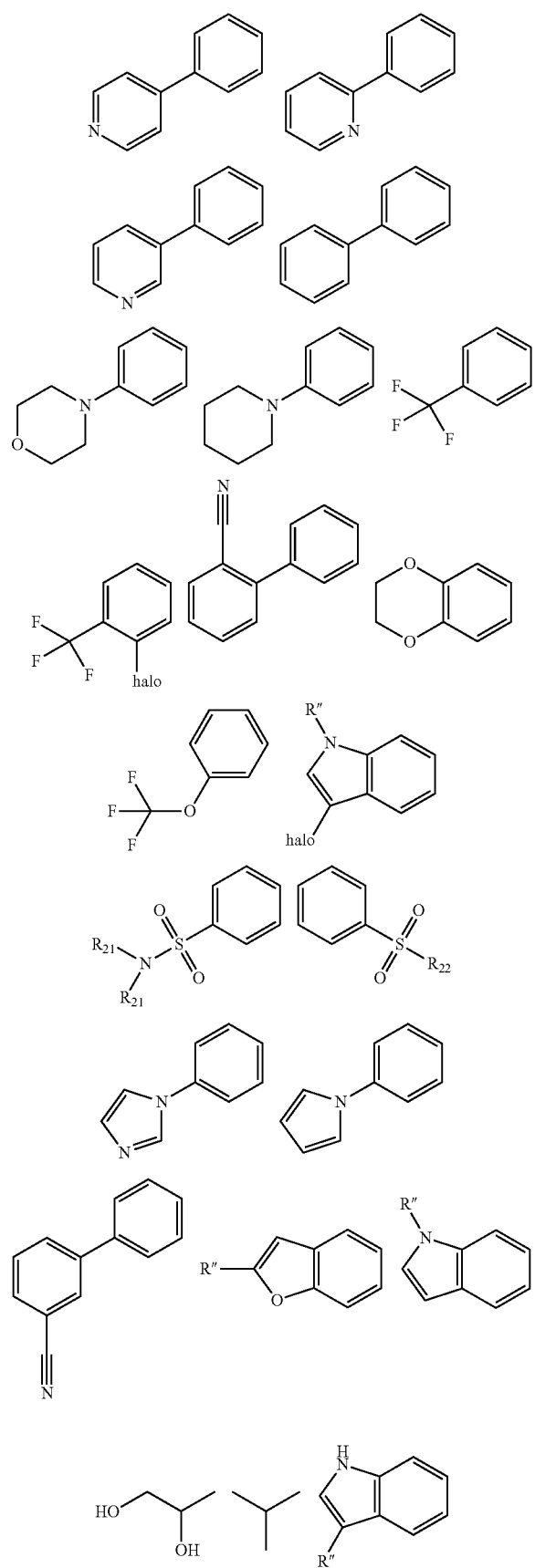
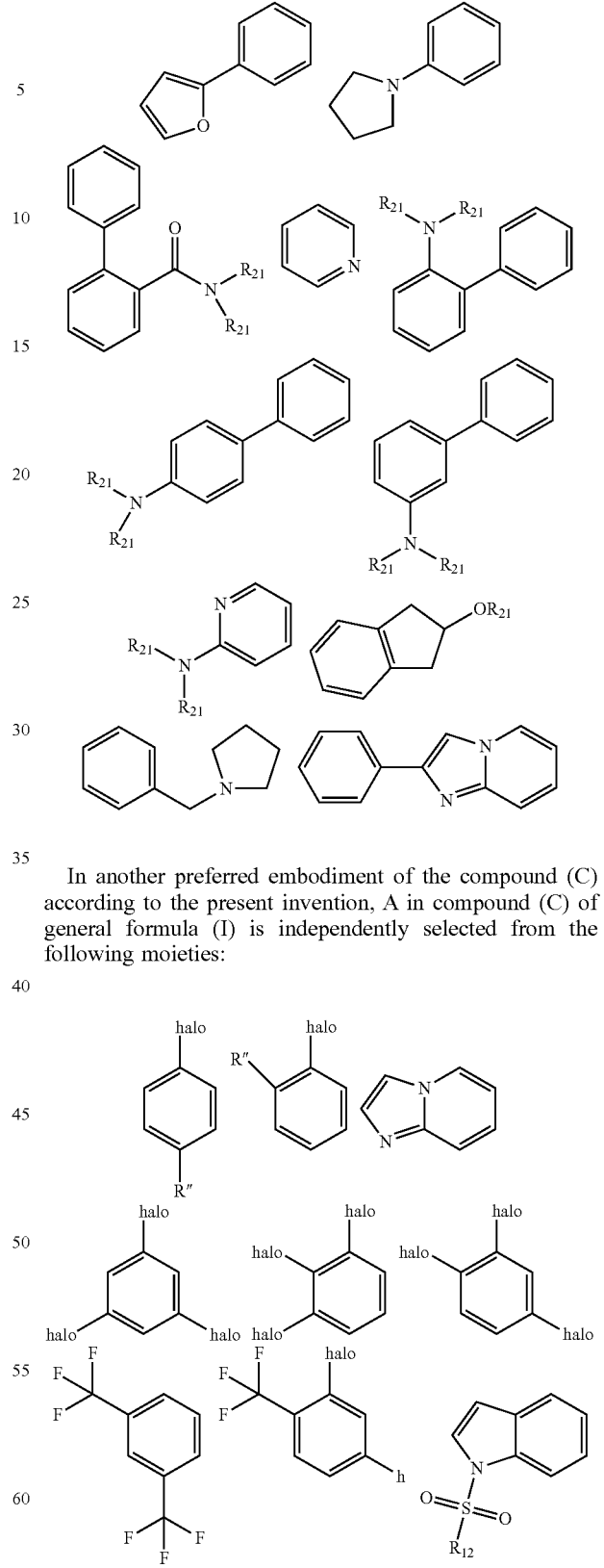
In another preferred embodiment of the compound (C) according to the present invention, A in compound (C) of general formula (I) is independently selected from the following moieties:
In a preferred embodiment of the present invention, the compound (C), according to the present invention, for use as a kinase inhibitor according to general formula (II) is a compound chosen among those of formulae (XXVI) to (LIX); (LXIV) to (CXIII) or (CLVIII) to herein below:
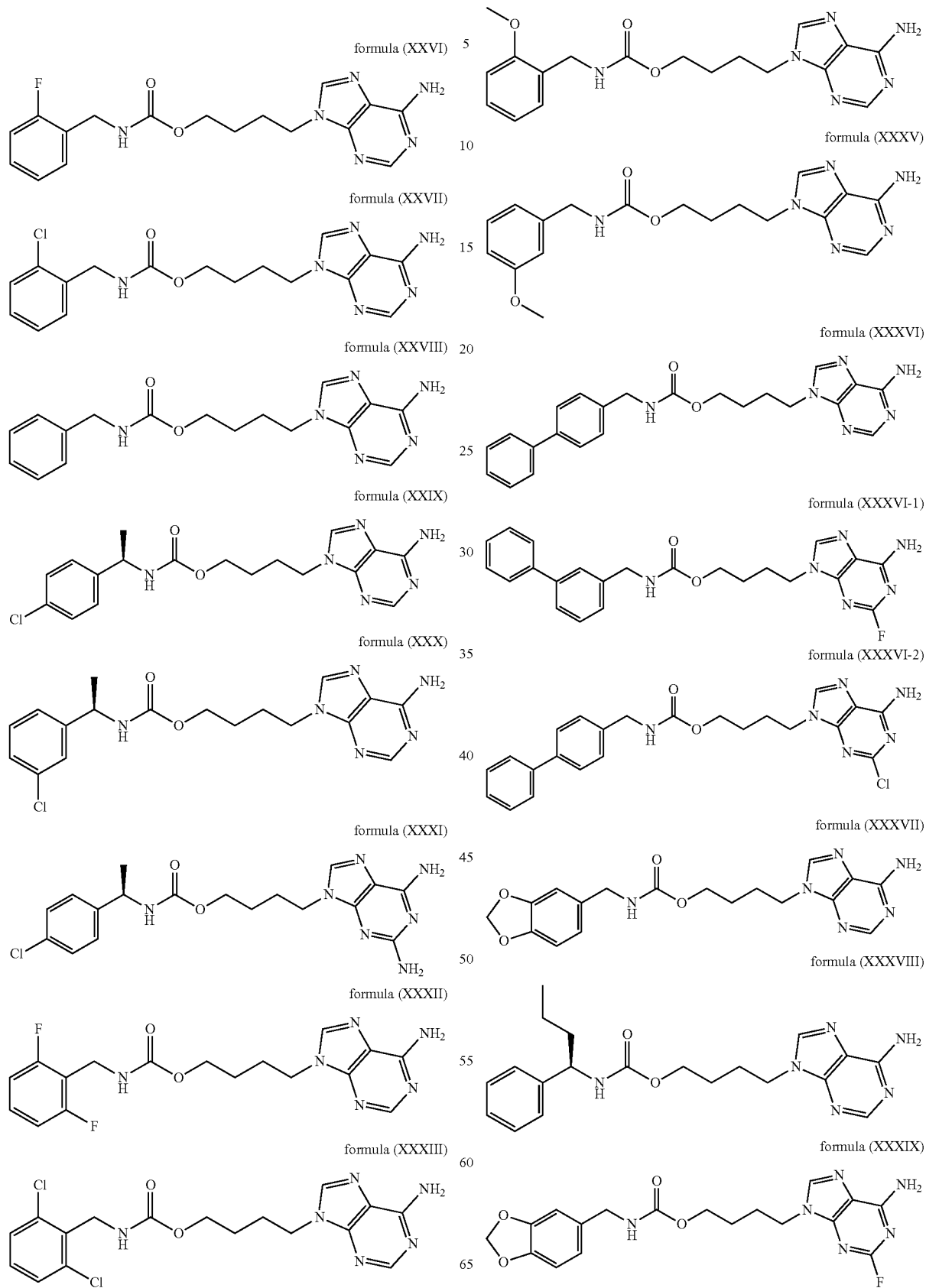

formula (XL)
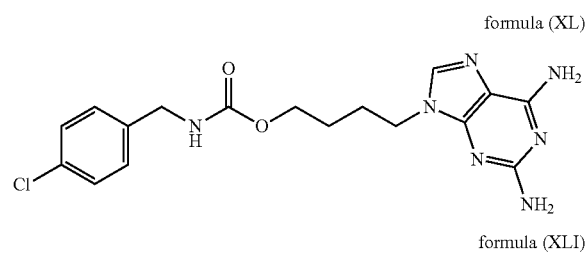
formula (XLI)
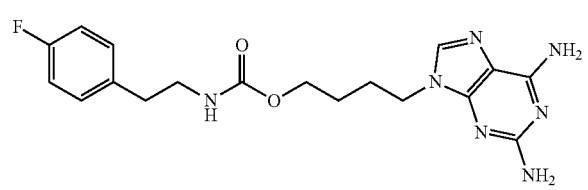
formula (XLII)
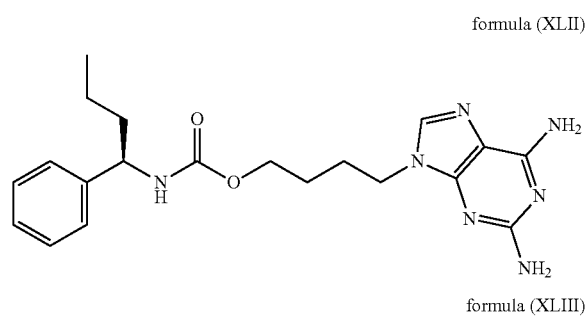
formula (XLIII)
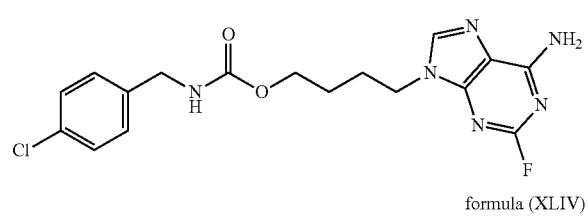
formula (XLIV)
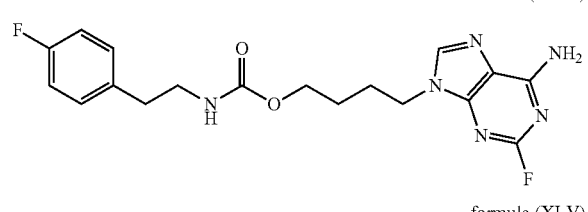
formula (XLV)
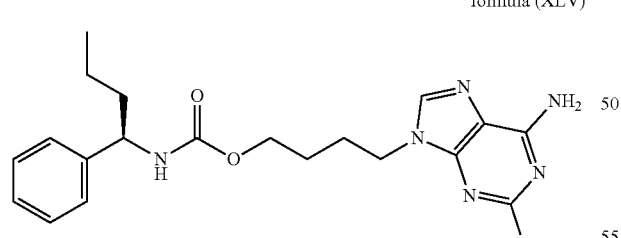
formula (XLVI)
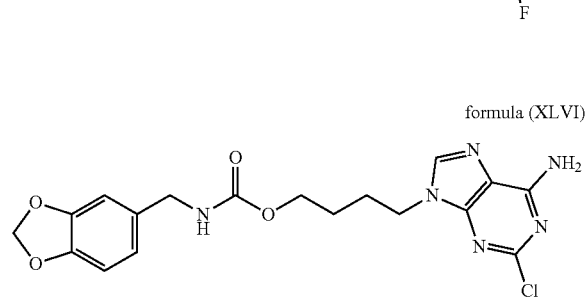
formula (XLVI-1)
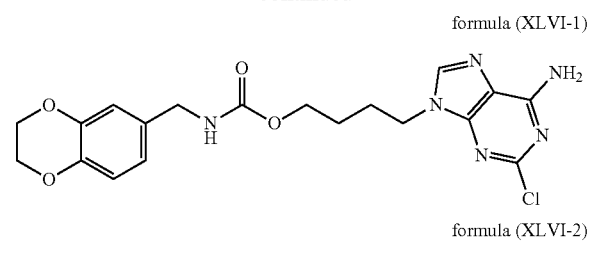
formula (XLVI-2)
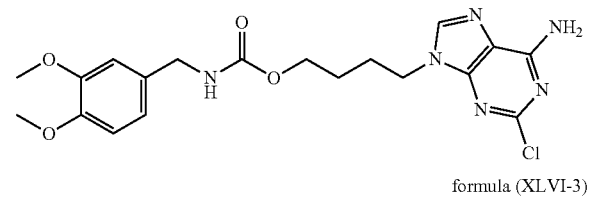
formula (XLVI-3)
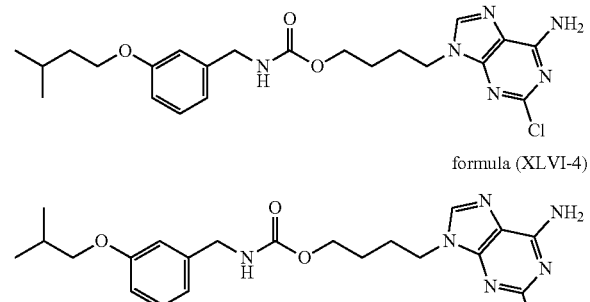
formula (XLVI-4)
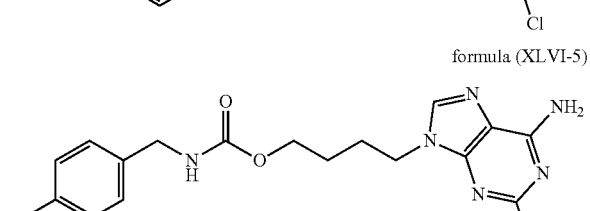
formula (XLVI-5)
formula (XLVI-6)
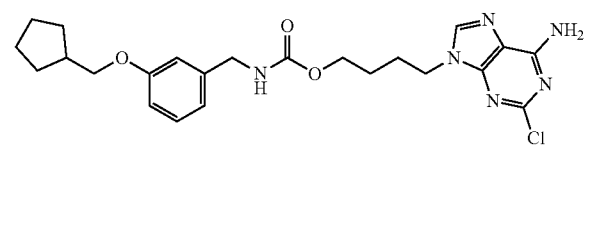
formula (XLVI-7)
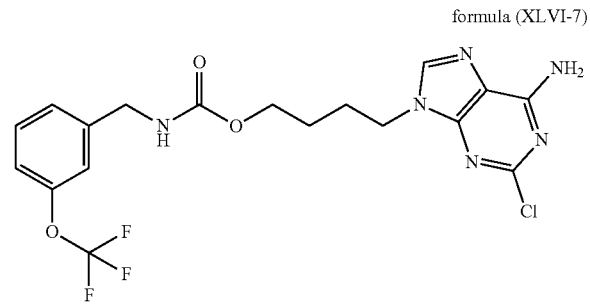

formula (XLVI-8)
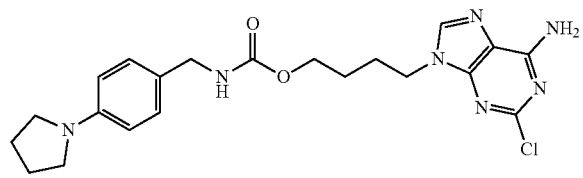
formula (XLVI-9)
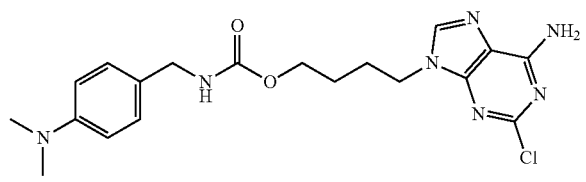
formula (XLVII)
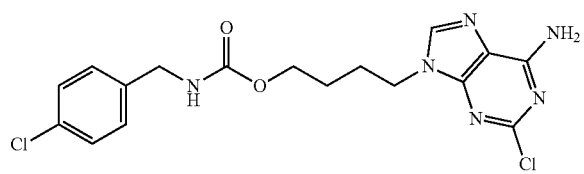
formula (XLVII-1)
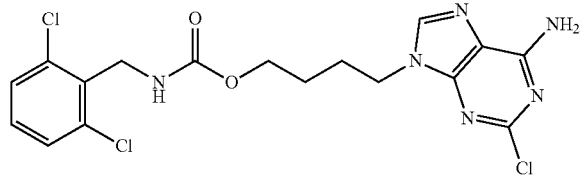
formula (XLVIII)
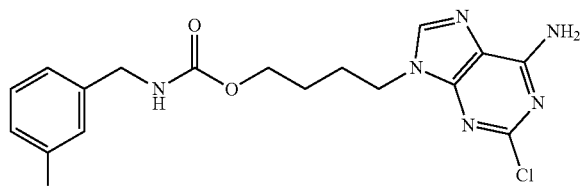
formula (XLIX)
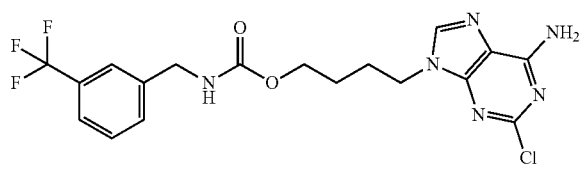
formula (XLIX-1)
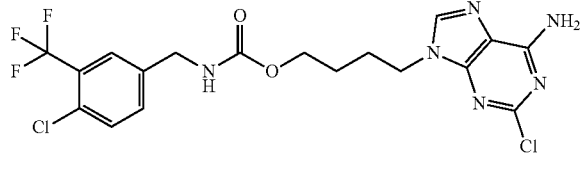
formula (L)
formula (LI)
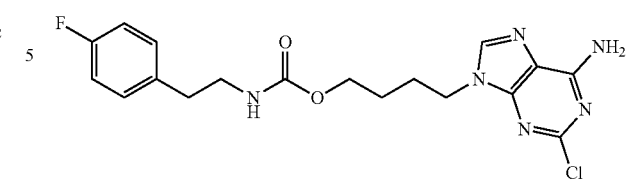
formula (LI-1)
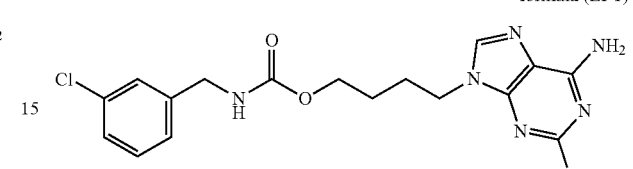
formula (LI-2)
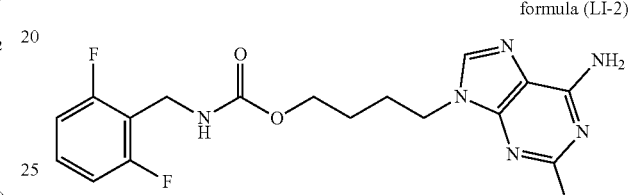
formula (LI-3)
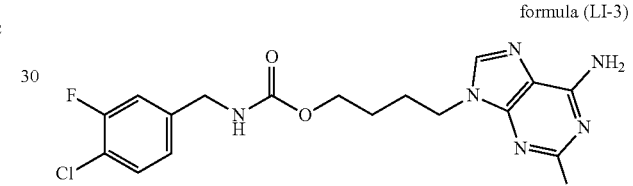
formula (LI-4)
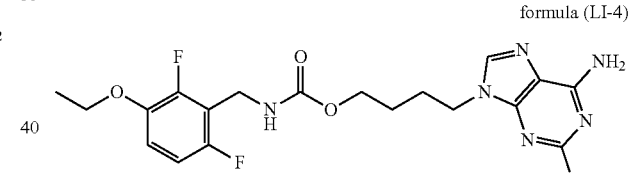
formula (LI-5)
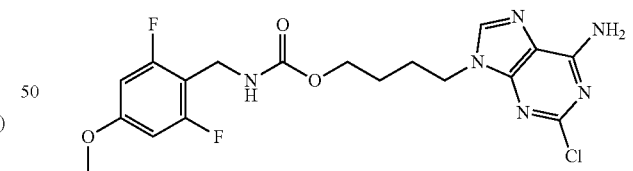
formula (LI-6)
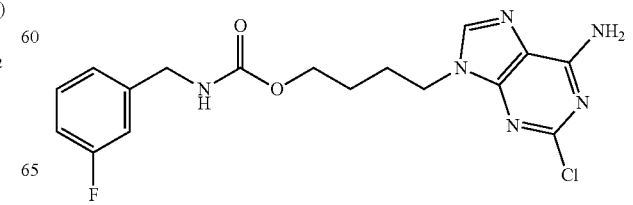

-continued formula (LI-7)

formula (LII)

formula (LIII)

formula (LIII-1)

formula (LIII-2)

formula (LIII-3)

formula (LIII-4)

formula (LIII-5)

formula (LIII-6)

formula (LIII-7)

formula (LIII-8)

formula (LIII-9)

-continued
formula (LIV)
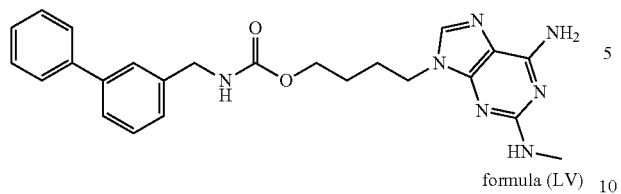
formula (LV)
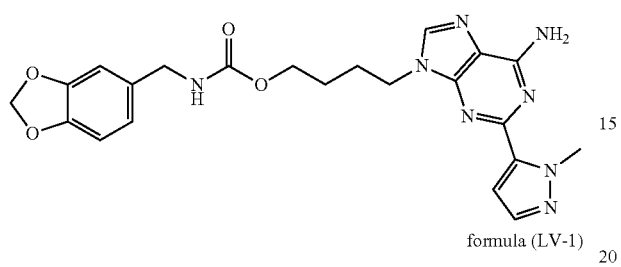
formula (LV-1)
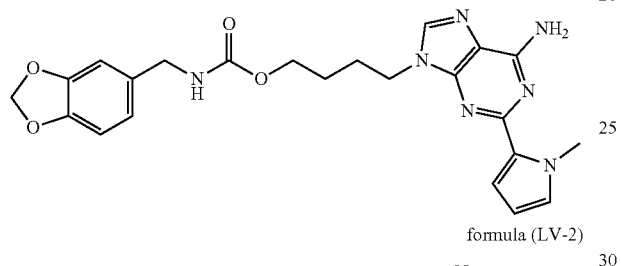
formula (LV-2)

formula (LVI)
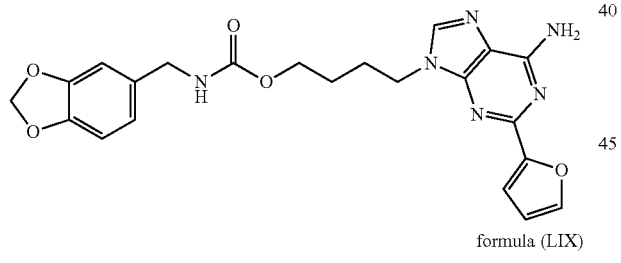
formula (LVII)
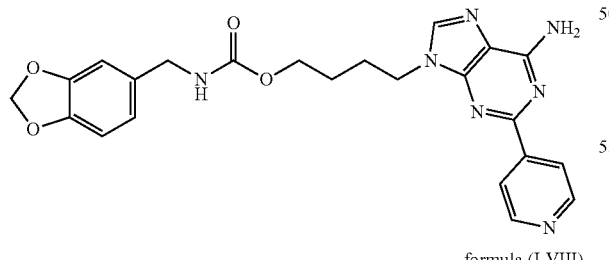
formula (LVIII)
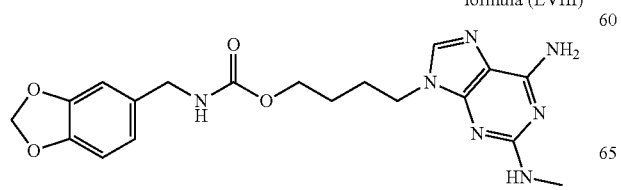
-continued
formula (LVIII-1)
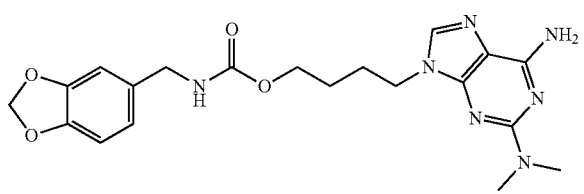
formula (CLVIII)
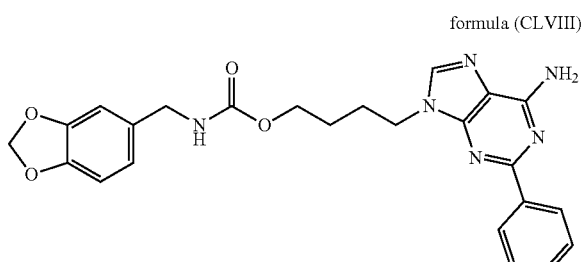
formula (LXIV)
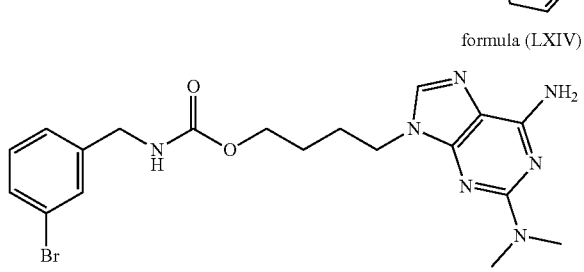
formula (LXV)
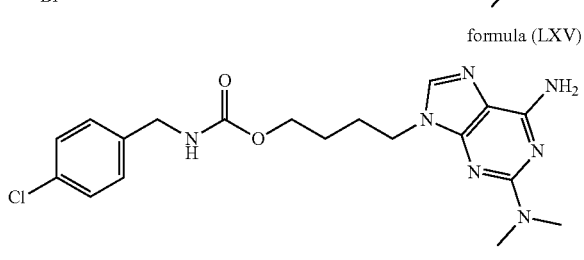
formula (LXVI)
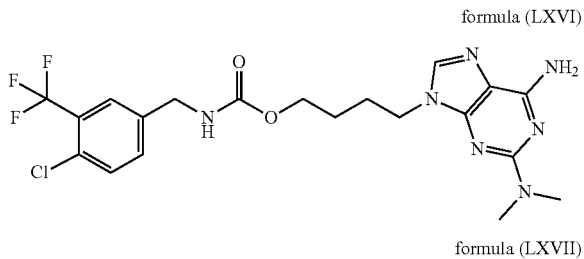
formula (LXVII)
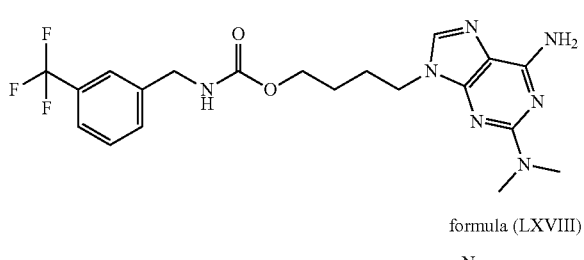
formula (LXVIII)
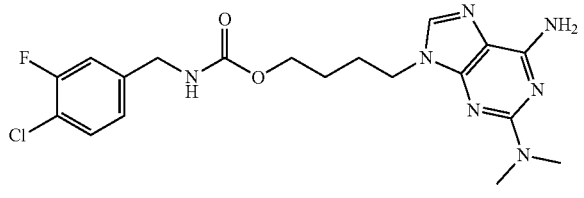

formula (LXIX)
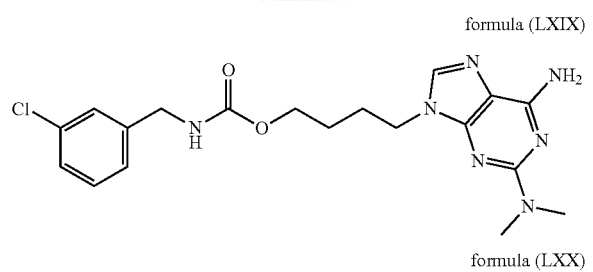
formula (LXX)
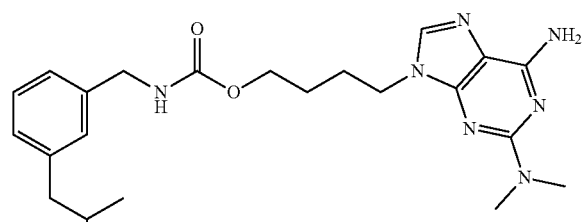
formula (LXXI)
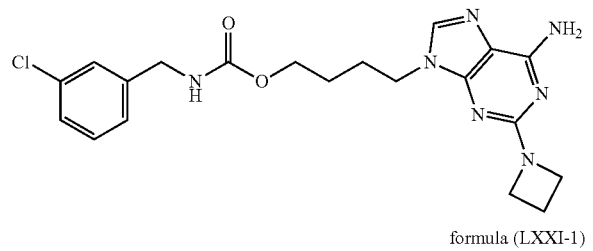
formula (LXXI-1)
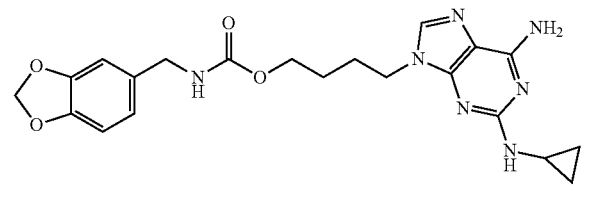
formula (LXXI-2)
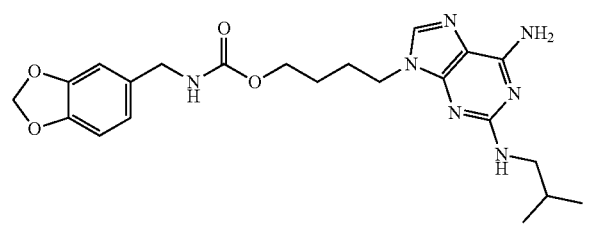
formula (LXXII)
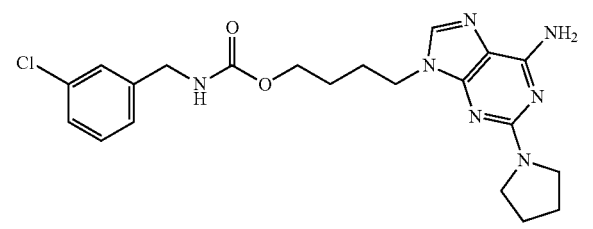
formula (LXXIII)
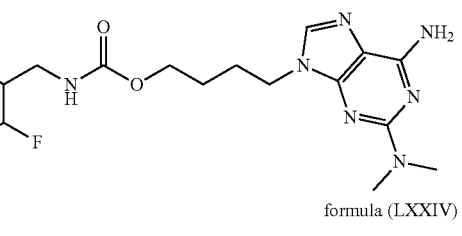
formula (LXXIV)

formula (LXXV)
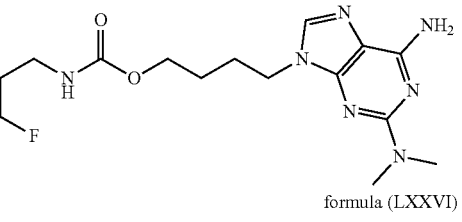
formula (LXXVI)
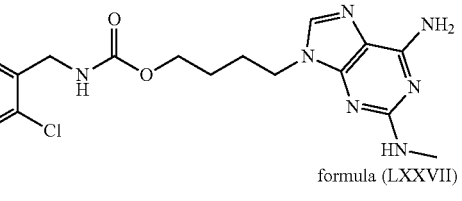
formula (LXXVII)
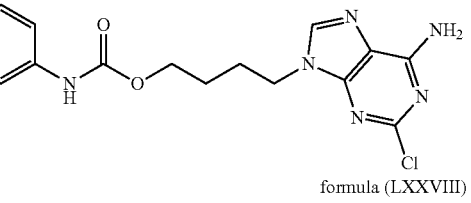
formula (LXXVIII)
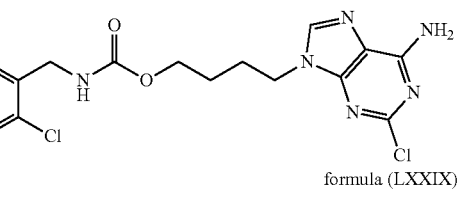
formula (LXXIX)
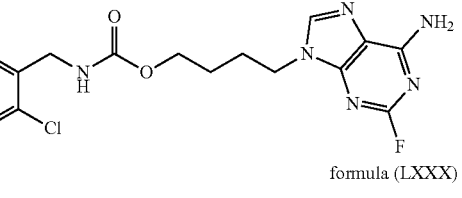
formula (LXXX)
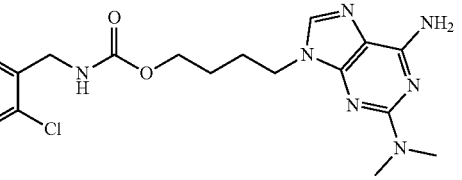

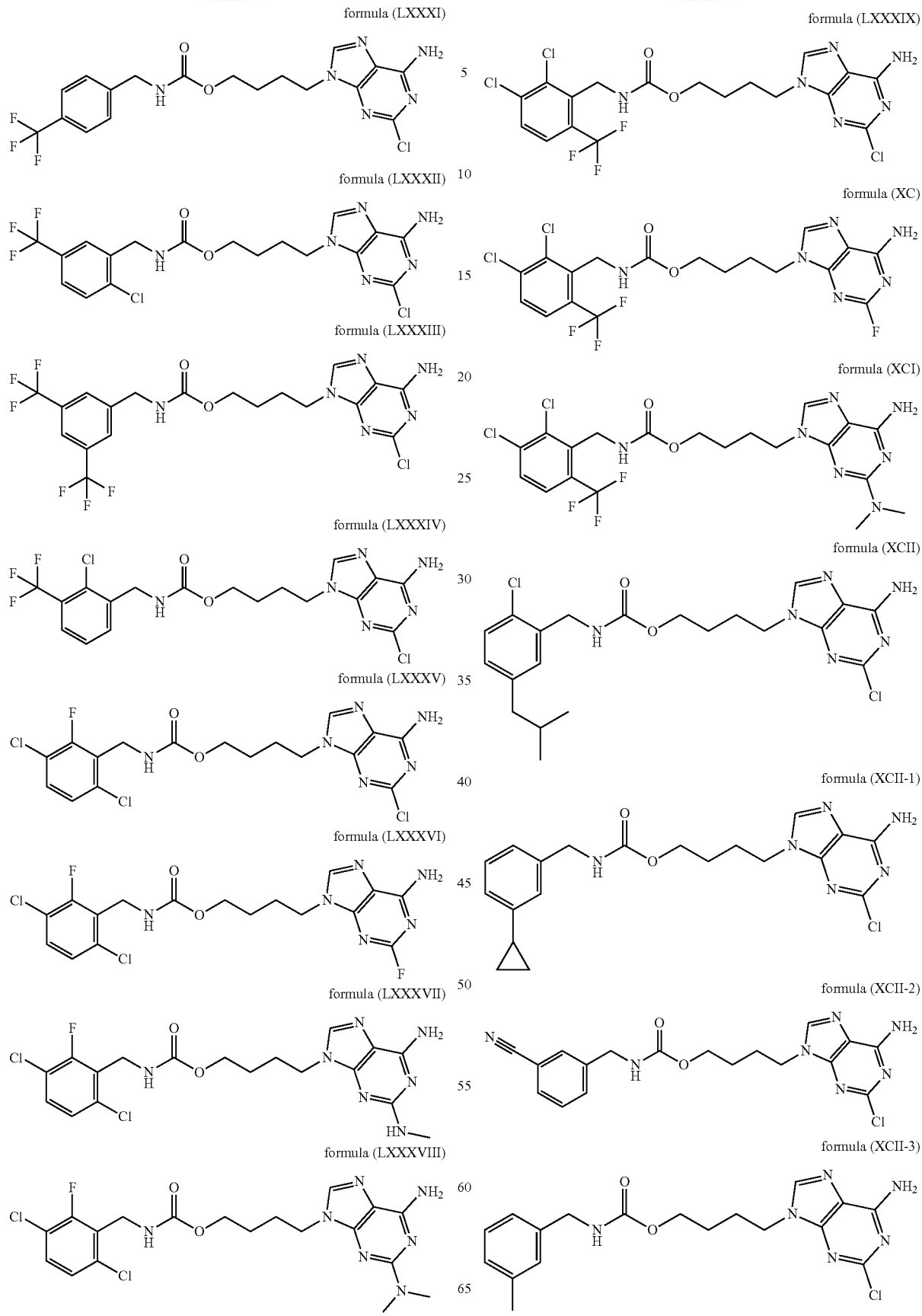

formula (XCII-4)
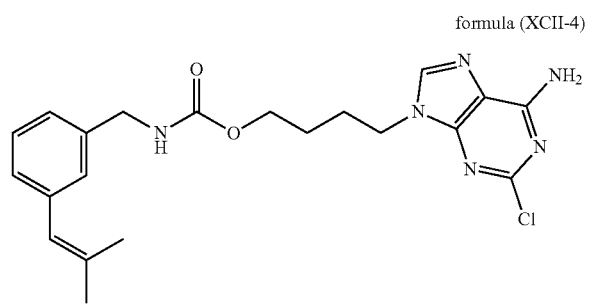
formula (XCII-5)
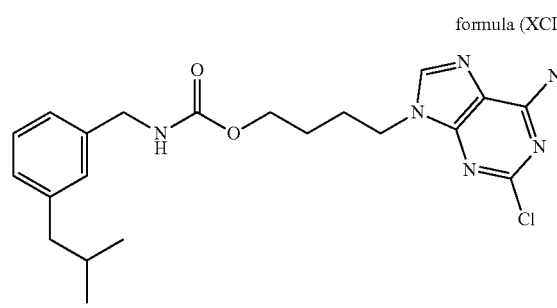
formula (XCII-6)
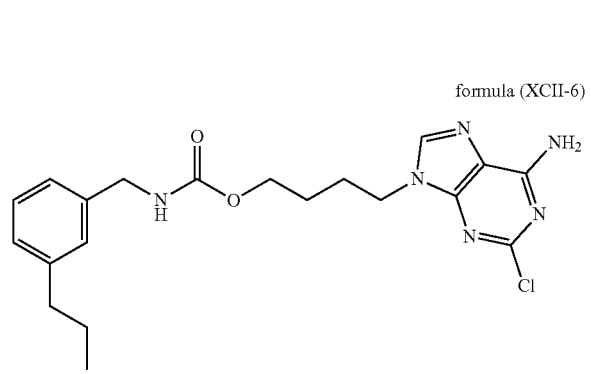
formula (XCII-7)
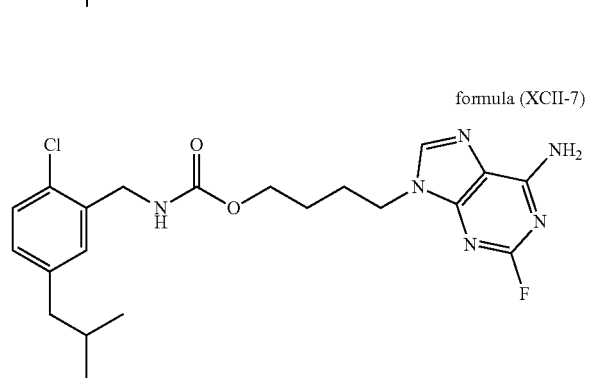
formula (XCIV)
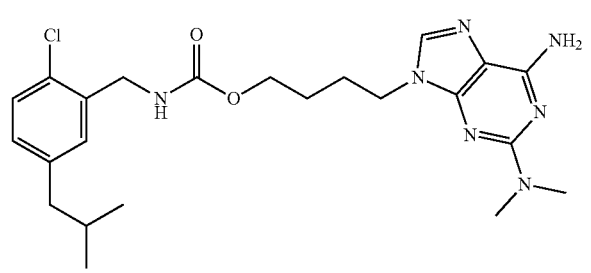
formula (XCV)
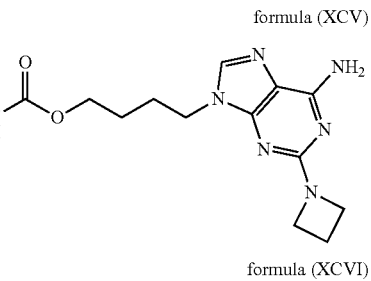
formula (XCVI)
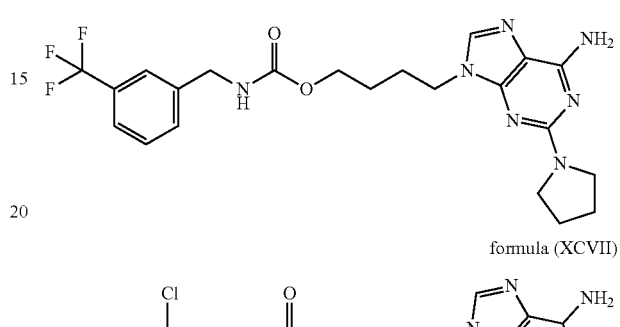
formula (XCVII)
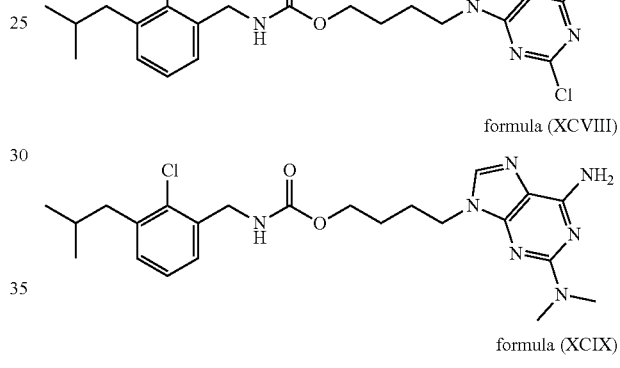
formula (XCVIII)
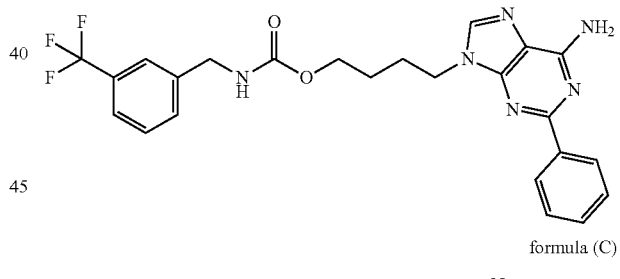
formula (XCIX)
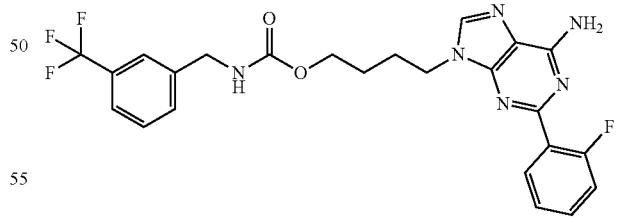
formula (C)
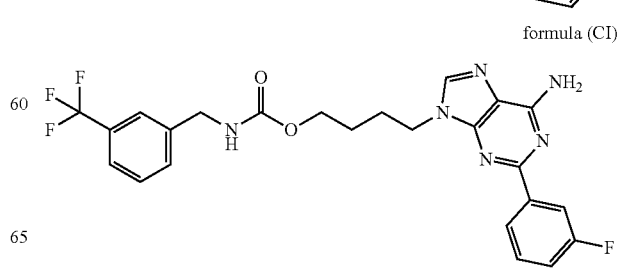
formula (CI)

formula (CII)
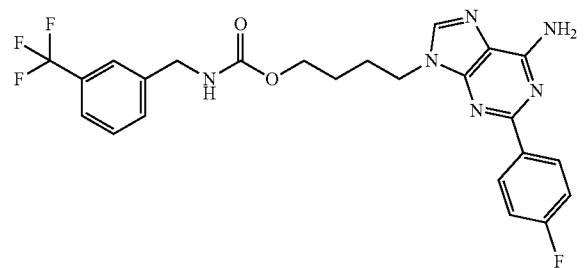
formula (CVIII)
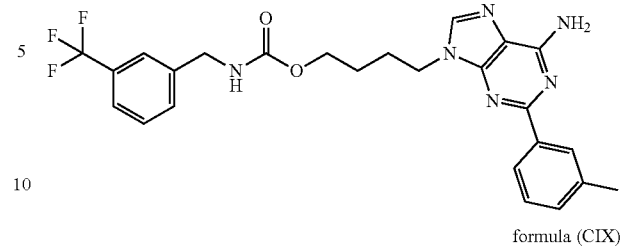
formula (CIII)
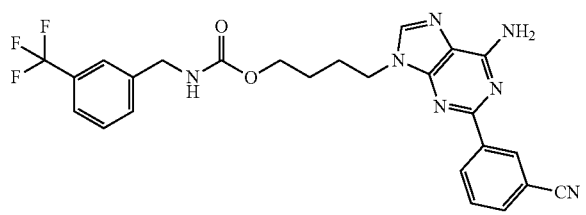
formula (CIX)
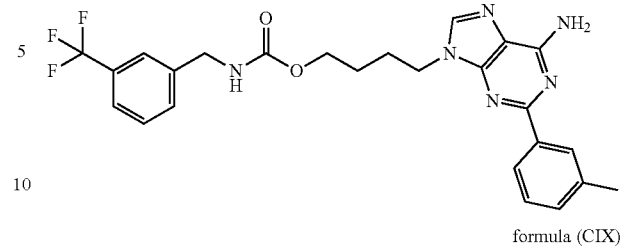
formula (CIV)
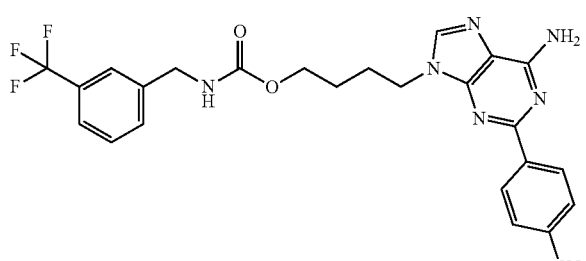
formula (CX)
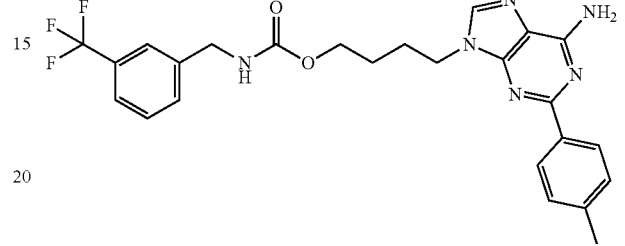
formula (CV)
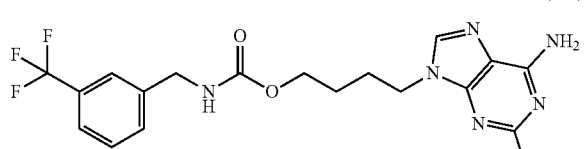
formula (CXI)
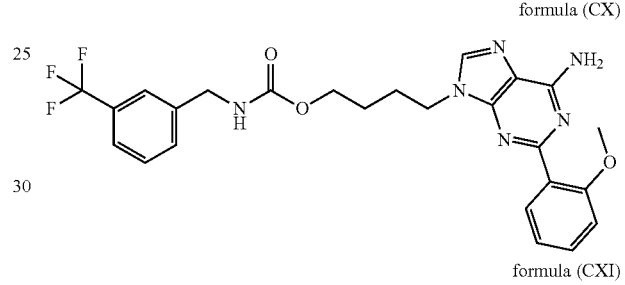
formula (CVI)
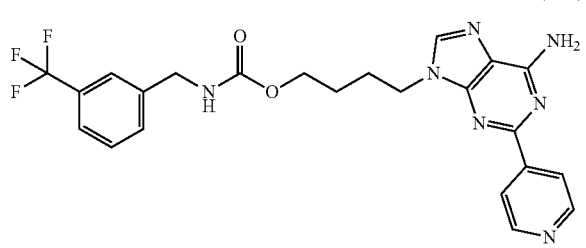
formula (CXII)
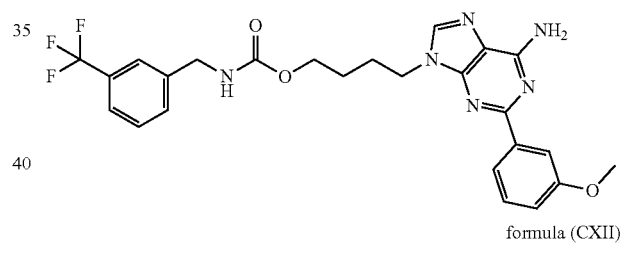
formula (CVII)
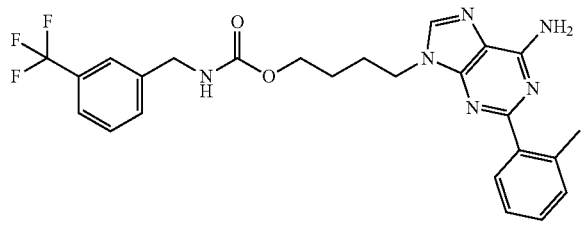
formula (CXIII)
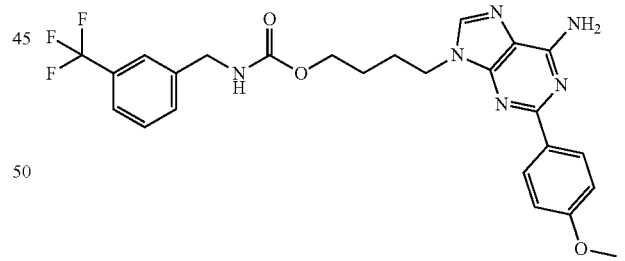
In a preferred embodiment of the present invention, the compound (C), according to the present invention, for use as a kinase inhibitor according to general formula (II) is a compound chosen among those of formulae (CXIV) to (CXLVII) herein below
formula (CXIV)
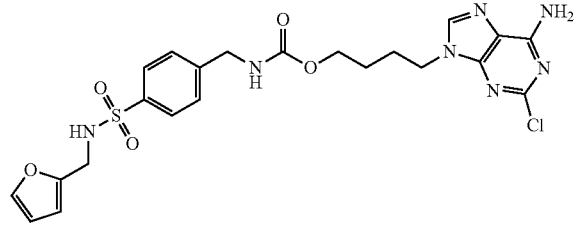
formula (CXV)
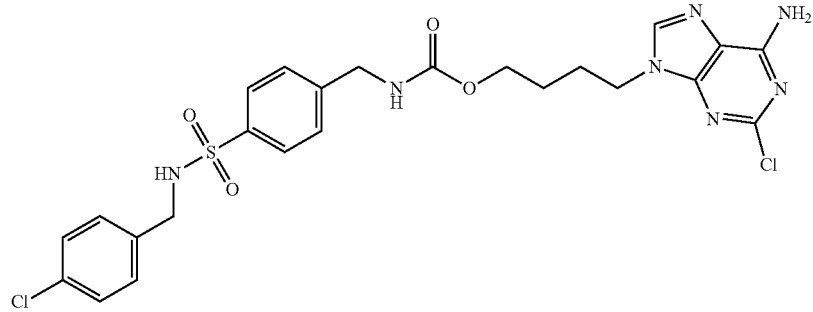
formula (CXVI)
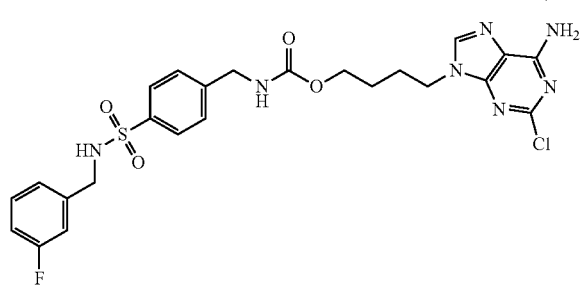
formula (CXVII)
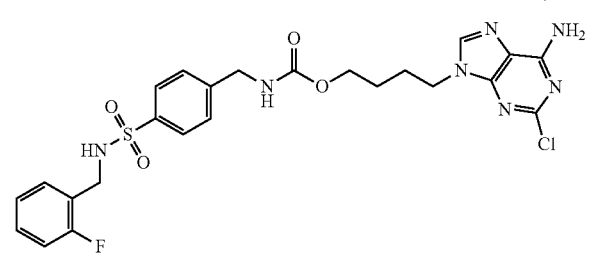
formula (CXVIII)
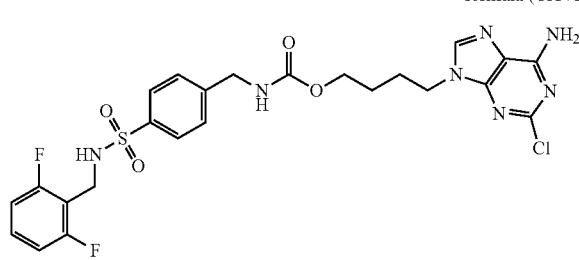
formula (CXIX)
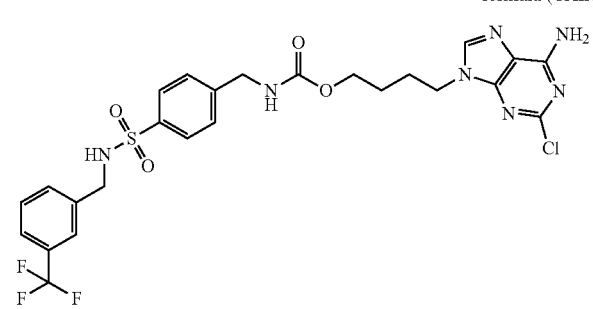
formula (CXX)
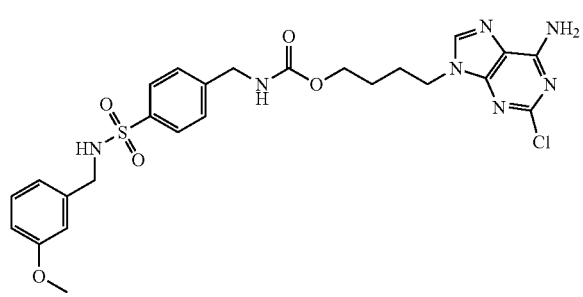
formula (CXXI)
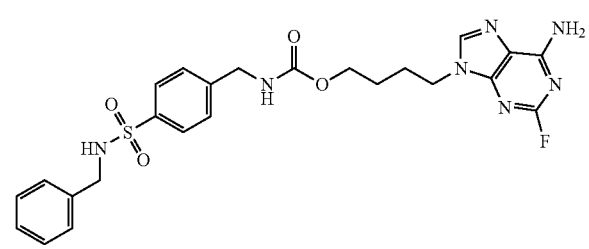

formula (CXXI-1)
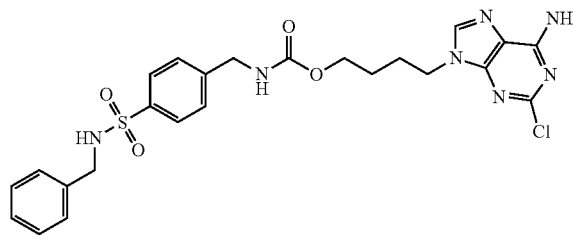
formula (CXXI-2)
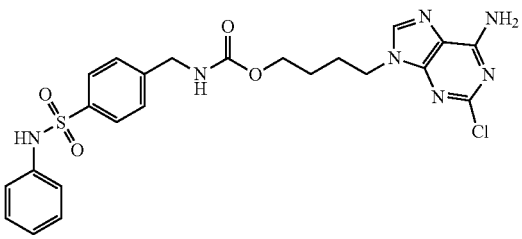
formula (CXXI-3)
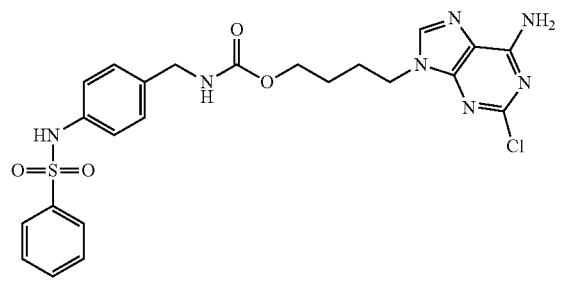
formula (CXXI-4)
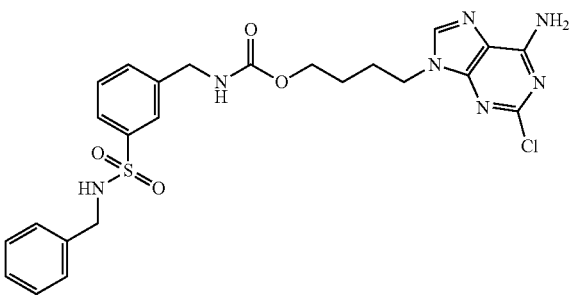
formula (CXXII)
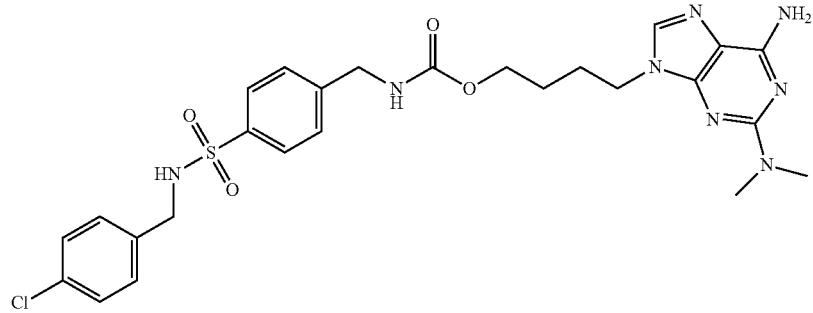
formula (CXXIII)
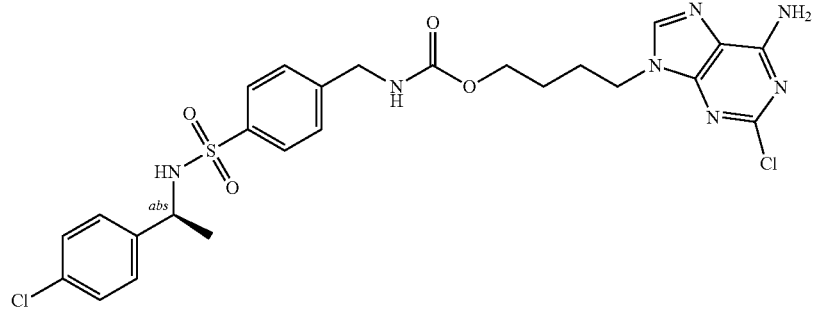
formula (CXXIV)
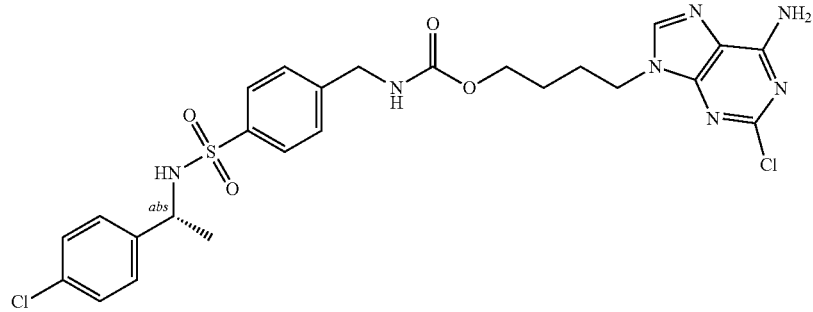

-continued
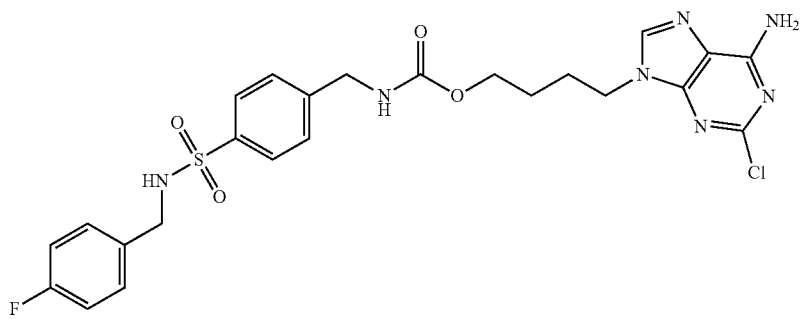
formula (CXXV)
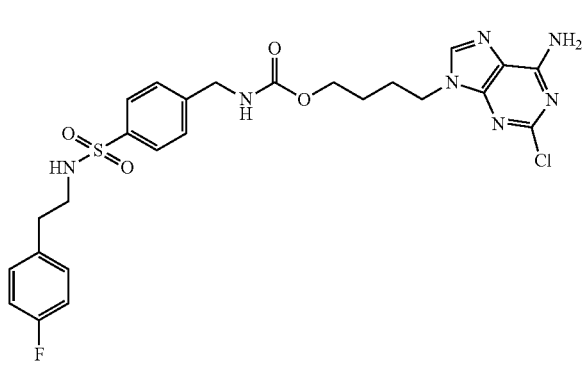
formula (CXXV-1)
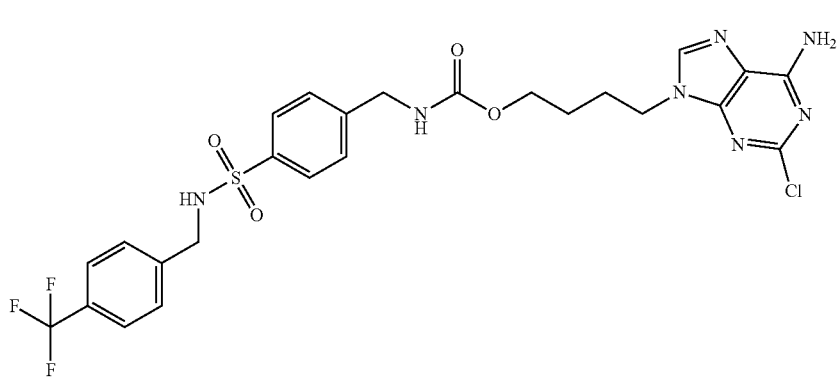
formula (CXXVI)
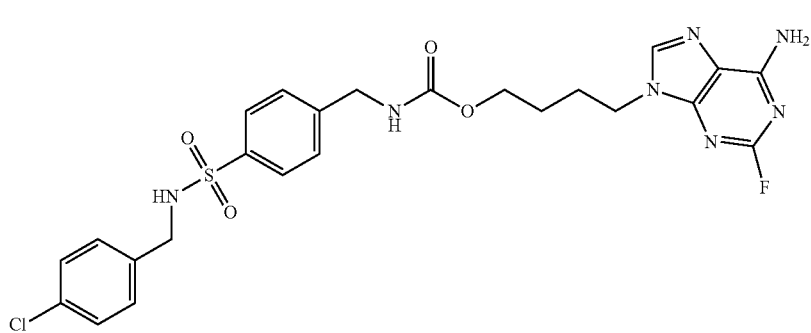
formula (CXXVII)

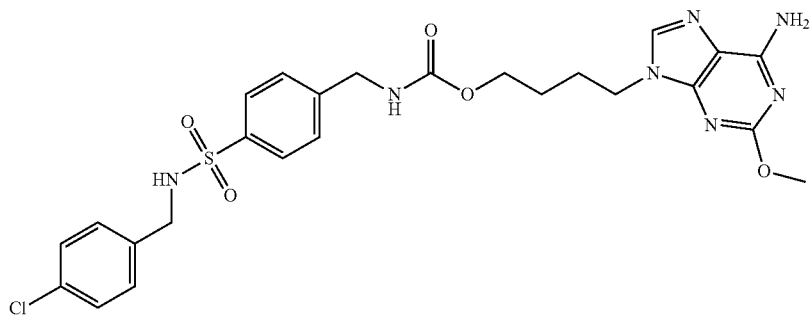
formula (CXXVIII)
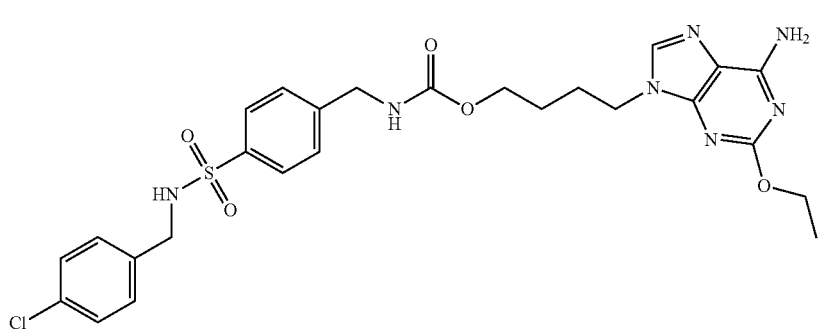
formula (CXXIX)
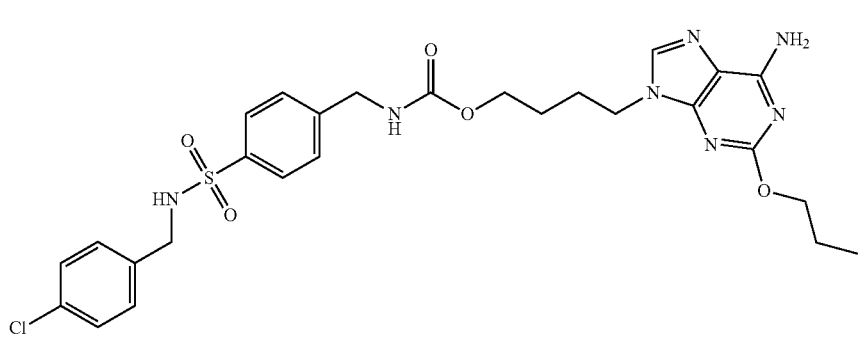
formula (CXXX)
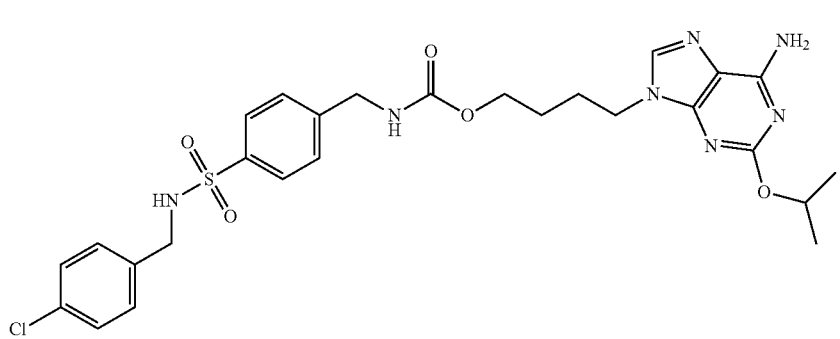
formula (CXXXI)
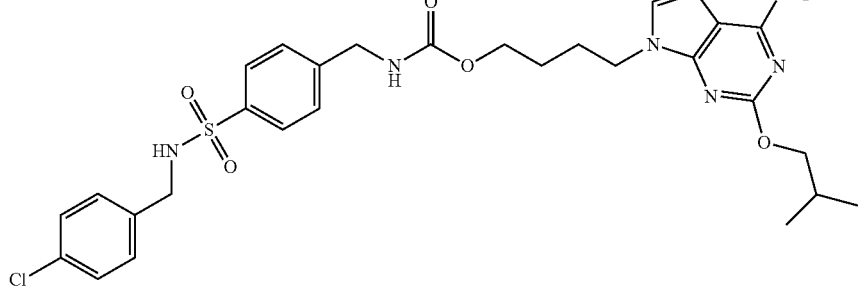
formula (CXXXII)

-continued
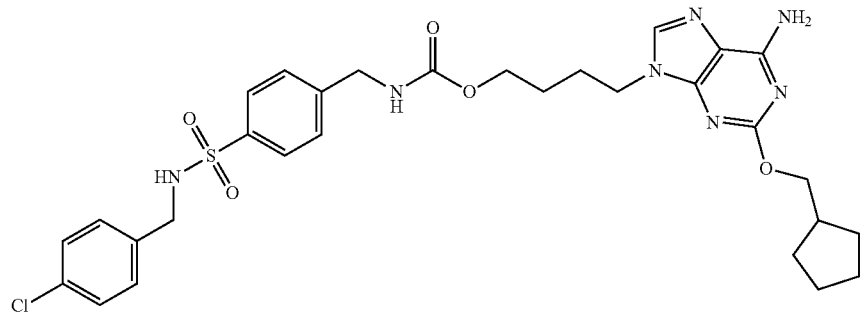
formula (CXXXIII)
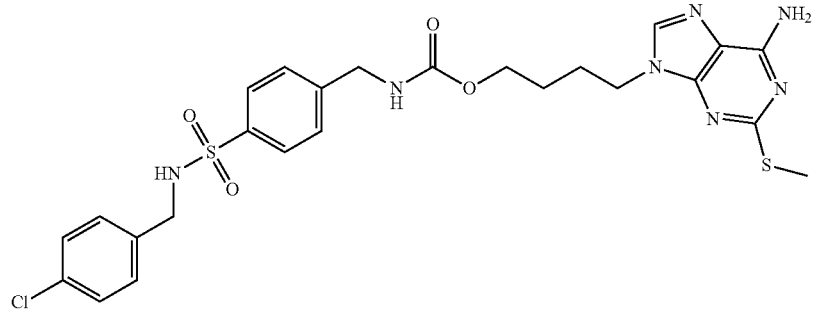
formula (CXXXIV)
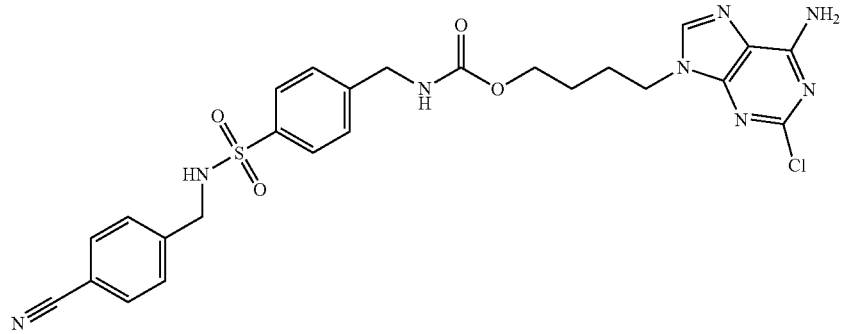
formula (CXXXV)
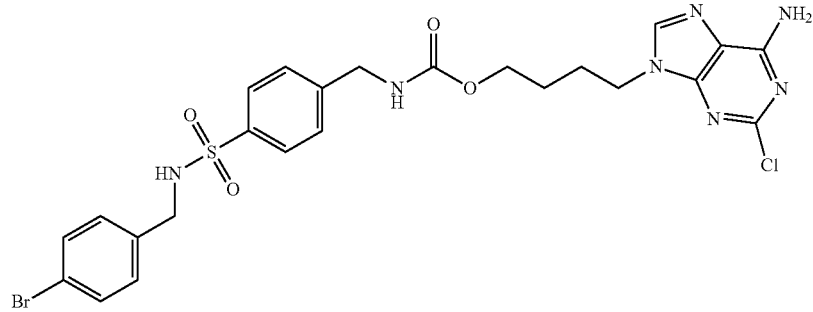
formula (CXXXVI)
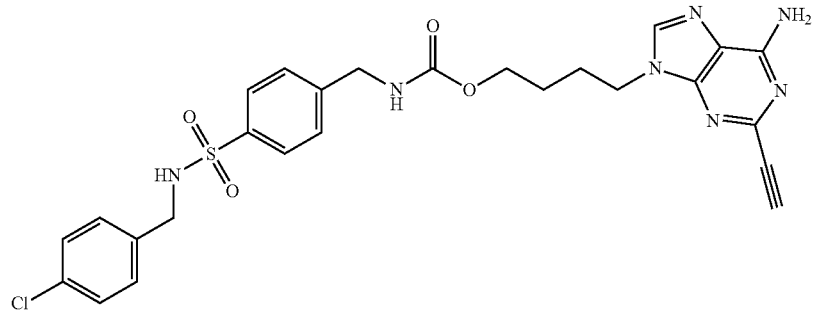
formula (CXXXVII)

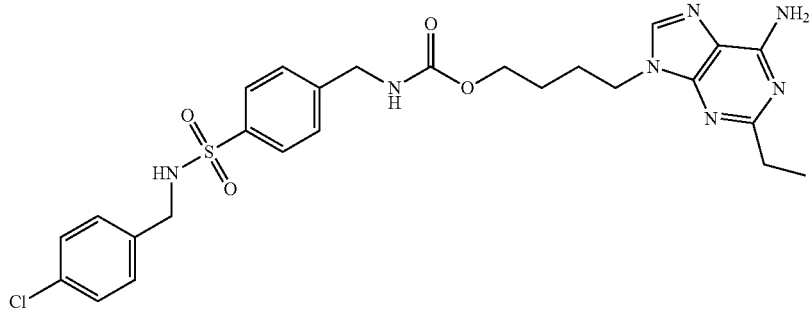
formula (CXXXVIII)
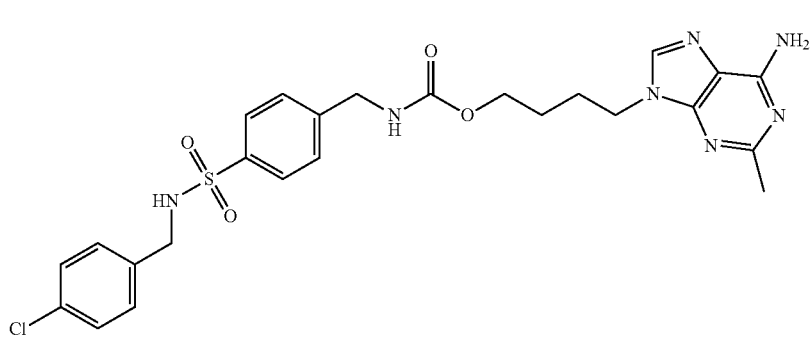
formula (CXXXIX)
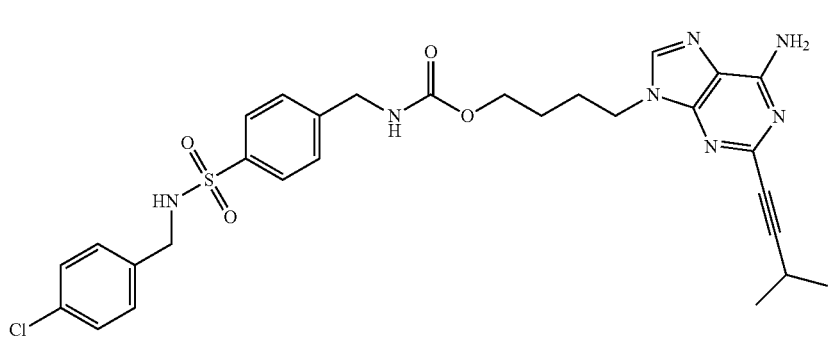
formula (CXL)
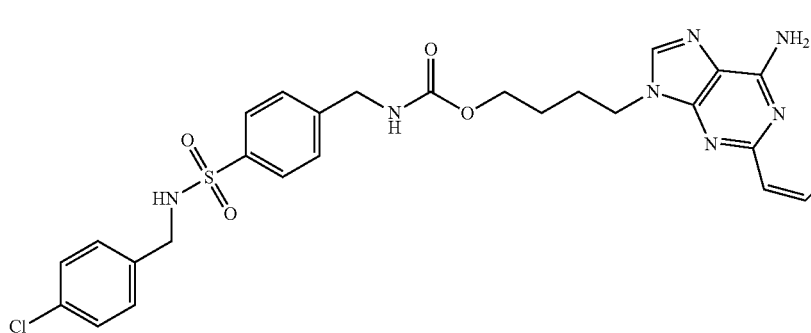
formula (CXLI)
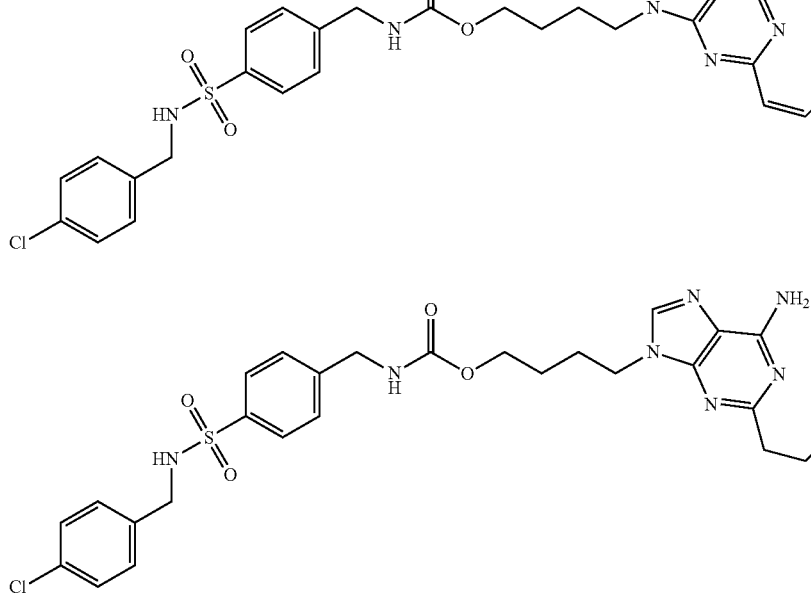
formula (CXLII)

formula (CXLIII)
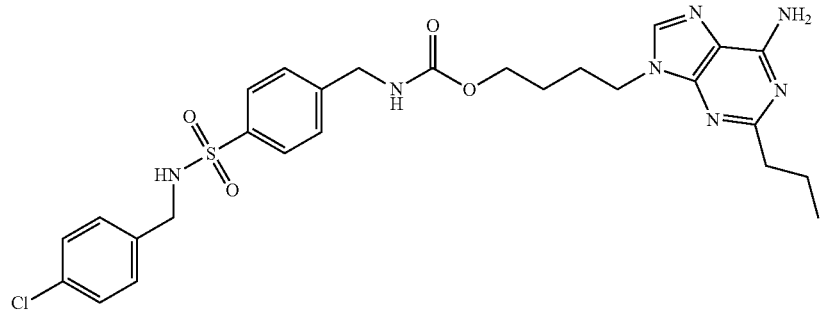
formula (CXLIV)
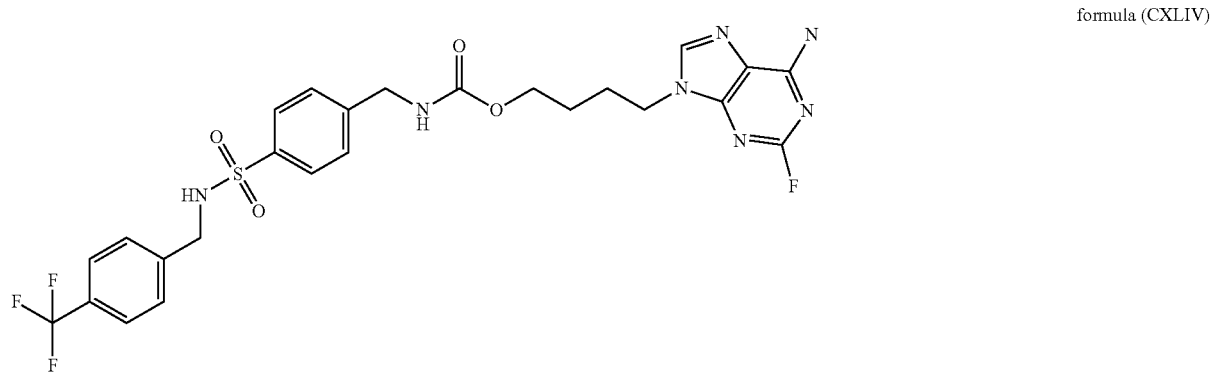
formula (CXLV) formula (CXLVI)
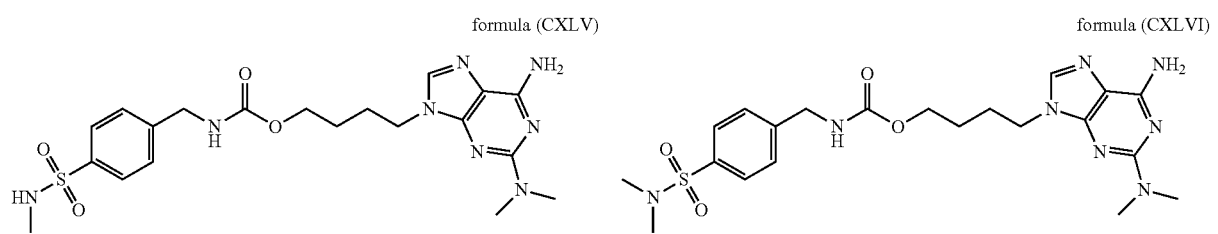
formula (CXLVI-1) formula (CXLVI-2)
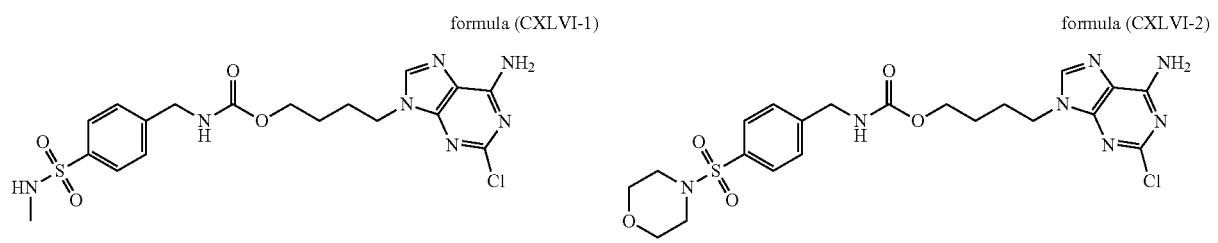
formula (CXLVI-3) formula (CXLVII)
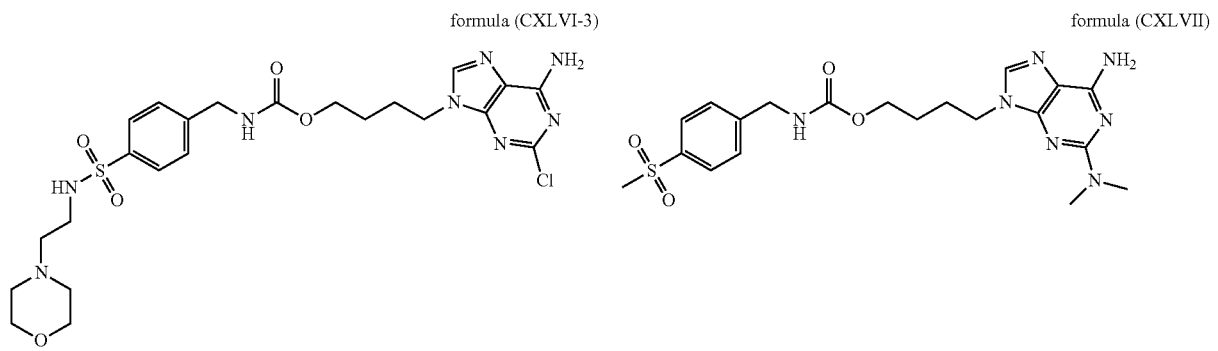

In a preferred embodiment of the present invention, the compound (C), according to the present invention, for use as a kinase inhibitor according to general formula (IV) is a compound chosen among those of formulae (CXLVIII) to (CLVII), (CLIX) to (CLXX) or (XXV) to (XXV-13) herein below:
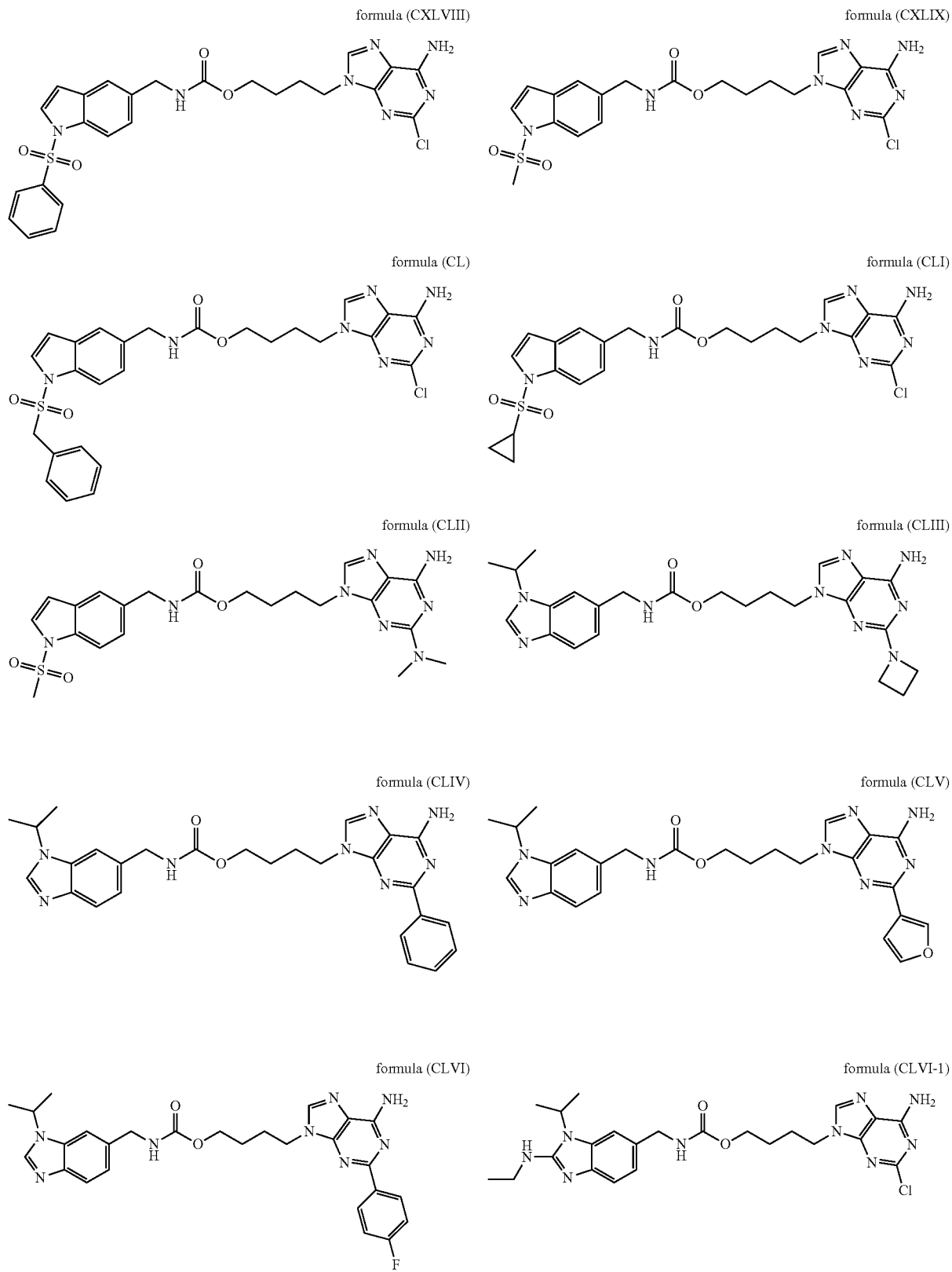

formula (CLVII)
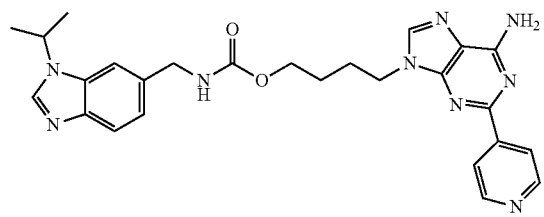
formula (CLIX)
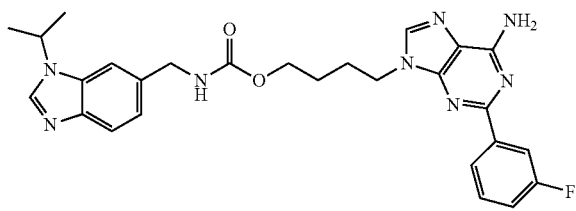
formula (CLX)
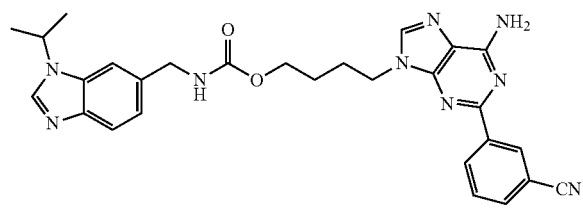
formula (CLXII)
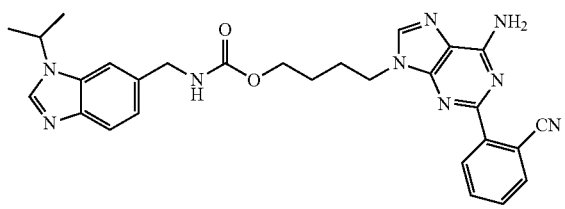
formula (CLXIII)
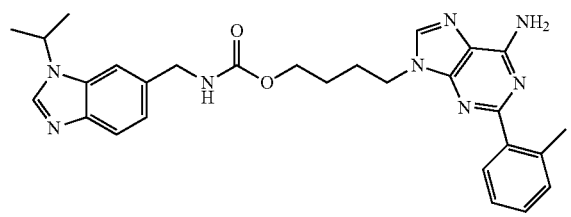
formula (CLXIV)
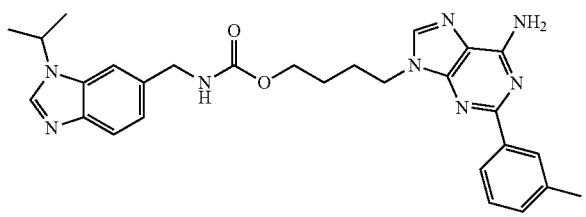
formula (CLXV)
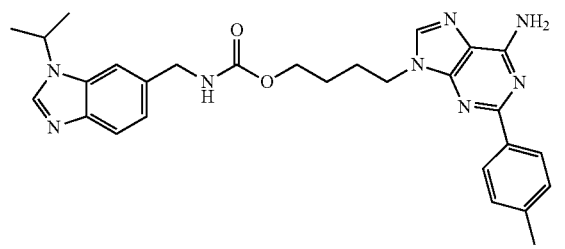
formula (CLXVI)
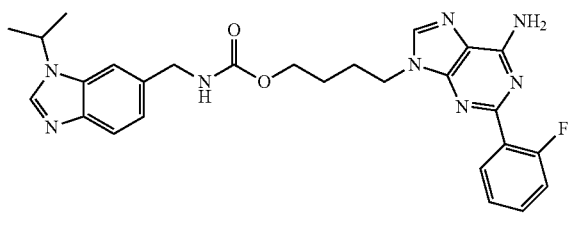
formula (CLXVII)
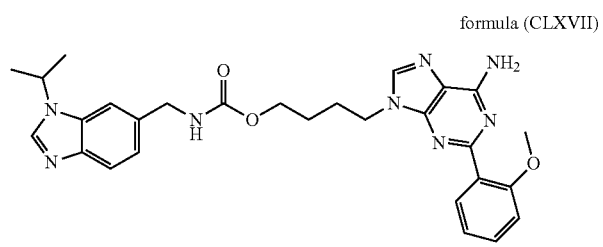
formula (CLXVIII)
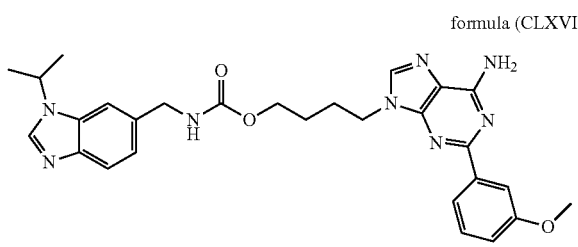
formula (CLXIX)
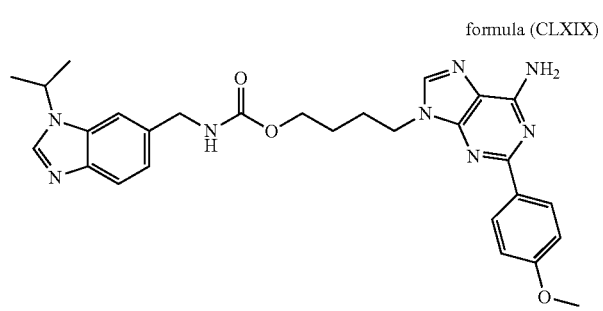
formula (CLXX)
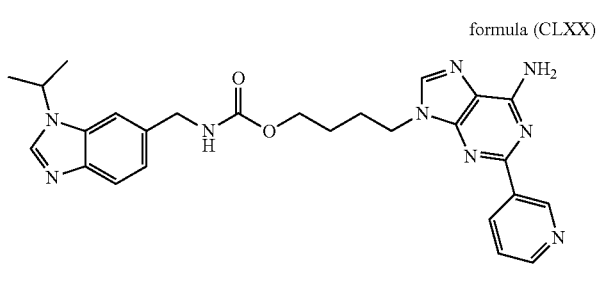

formula (XXV)
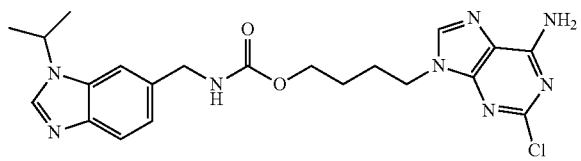
formula (XXV-1)
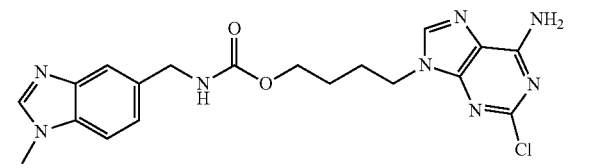
formula (XXV-2)
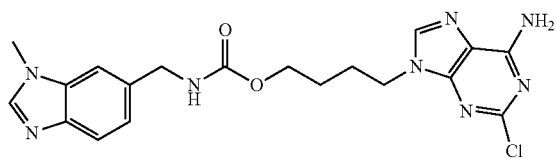
formula (XXV-3)
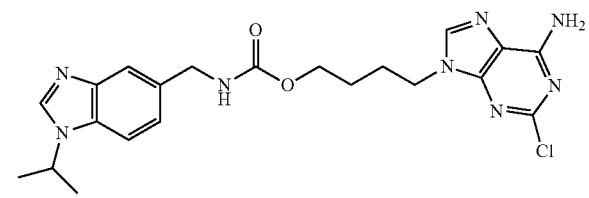
formula (XXV-4)
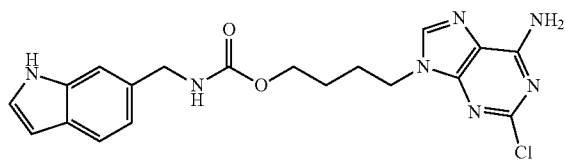
formula (XXV-5)
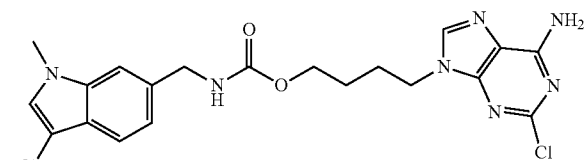
formula (XXV-6)
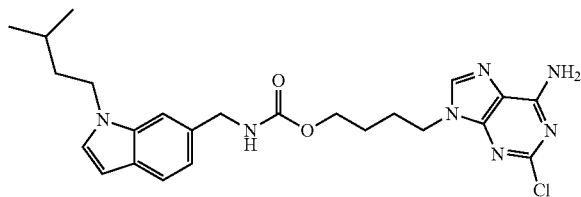
formula (XXV-7)
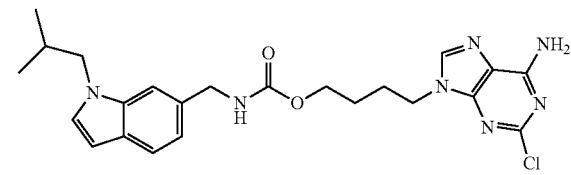
formula (XXV-8)
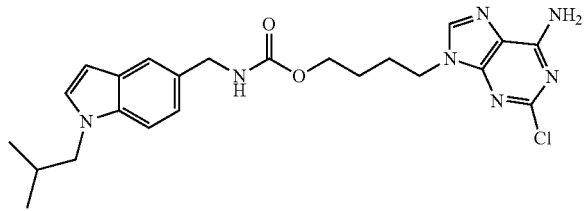
formula (XXV-9)
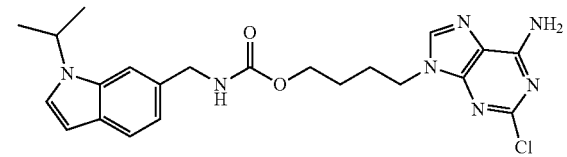
formula (XXV-10)
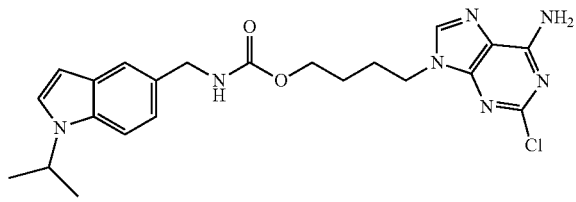
formula (XXV-11)
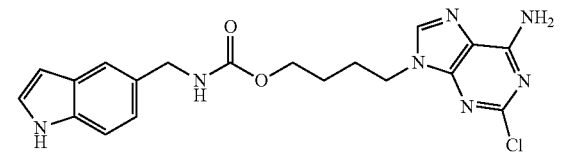
formula (XXV-12)
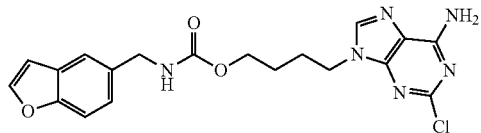
formula (XXV-13)
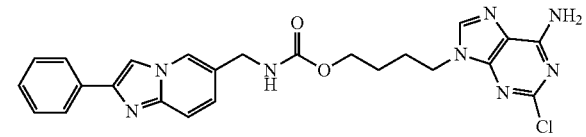

In a preferred embodiment of the present invention, the compound (C), according to the present invention, for use as a kinase inhibitor according to general formula (XVII) is a compound of formula (LX)

formula (LX)

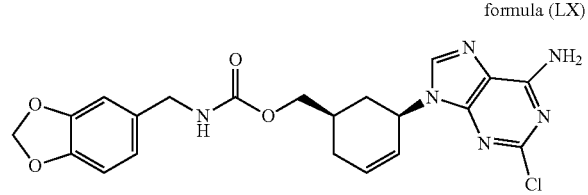 [SMILES: Nc1nc(Cl)nc2c1ncn2[C@H]1C=CC[C@@H](COC(=O)NCc2ccc3c(c2)OCO3)C1]

In a preferred embodiment of the present invention, the compound (C), according to the present invention, for use as a kinase inhibitor according to general formula (XIII) is chosen among those of formula (LXI) or (LXII) herein below:

formula (LXI)

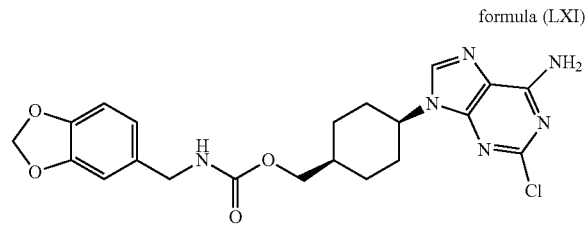

formula (LXII)

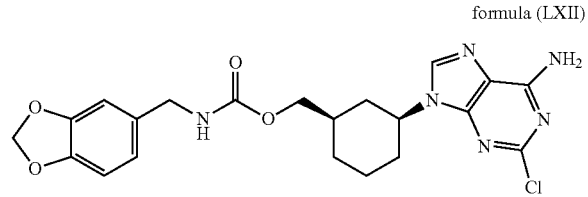

In a preferred embodiment of the present invention, the compound (C), according to the present invention, for use as a kinase inhibitor according to general formula (IX') is a compound according to formula (LXIII) herein below formula (LXIII)

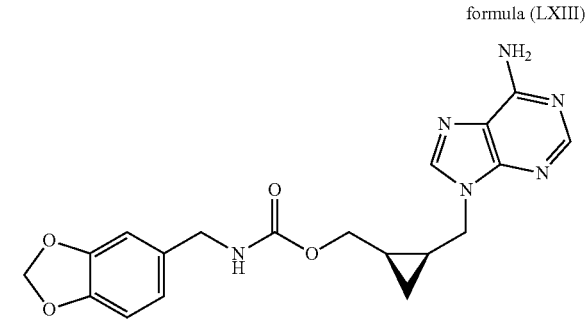

In a more preferred embodiment of the present invention, the compound (C), according to the present invention, for use as a kinase inhibitor according to general formula (I), or the N-oxide, pharmaceutically acceptable salt, pharmaceutically acceptable solvate, or stereoisomer thereof, is a compound of formula (XXV), as defined above.

The present invention further relates to an in vitro method of inhibiting protein kinase activity which comprises contacting a protein kinase with a compound of formula (I) [compound (C), herein after], as defined above, or the N-oxide, pharmaceutically acceptable salt, pharmaceutically acceptable solvate, or stereoisomer thereof, formula (I)

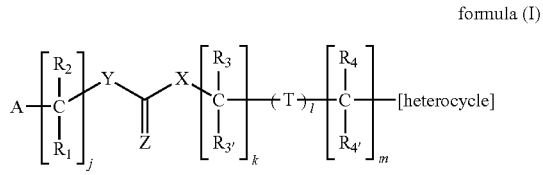

wherein:

each of A is independently selected from the group consisting of hydrogen, $C_{1-15}$ alkyl, $C_{2-15}$ alkenyl, $C_{2-15}$alkynyl, cycloalkyl, heterocyclyl, aryl, heteroaryl, and aralkyl, wherein said alkyl, alkenyl, alkynyl, cycloalkyl, heterocyclyl, aryl, heteroaryl, and aralkyl, are optionally substituted with one or more substituents independently selected from the group consisting of halo, $NO_2$, alkyl, alkenyl, cycloalkyl, heterocyclyl, aryl, heteroaryl, $CF_3$, CN, $OR_{11}$, $SR_{11}$, $N(R_{11})_2$, $OC(R_{11})_2O$, $OC(R_{11})_2C(R_{11})_2O$, $S(O)R_{12}$, $SO_2R_{12}$, $SO_2N(R_{11})_2$, $S(O)_3R_{11}$, $P(O)(OR_{11})_2$, $SO_2NR_{11}COR_2$, $SO_2NR_{11}CO_2R_{12}$, $SO_2NR_{11}CON(R_{11})_2$, $NR_{11}COR_{12}$, $NR_{11}CO_2R_{12}$, $NR_{11}CON(R_{11})_2$, $NR_{11}C(NR_{11})NHR_{11}$, $COR_{11}$, $CON(R_{11})_2$, $CONR_{11}SO_2R_{12}$, $NR_{11}SO_2R_{12}$, $SO_2NR_{11}CO_2R_{12}$, $OCONR_{11}SO_2R_{12}$, $OC(O)R_{11}$, $C(O)OCH_2OC(O)R_{11}$, and $OCON(R_{11})_2$ and each optional alkyl, alkenyl, cycloalkyl, aryl, heterocyclyl, heteroaryl substituent is further optionally substituted with halo, $NO_2$, alkyl, cycloalkyl, aryl, $CF_3$, $N(R_{11})_2$, alkyl or aryl or heteroaryl amide, $NR_{11}COR_{12}$, $NR_{11}SO_2R_{12}$, $COR_{11}$, $CON(R_{11})_2$, $NR_{11}CON(R_{11})_2$, $OC(O)R_{11}$, $OC(O)N(R_{11})_2$, $S(O)_3R_{11}$, $P(O)(OR_{11})_2$, $SR_{11}$, $S(O)R_{12}$, $SO_2R_{12}$, $SO_2N(R_{11})_2$, CN, or $OR_{11}$; and wherein each of $R_{11}$ and $R_{12}$, independently from each other and at each occurrence, are selected from the group consisting of hydrogen, $C_{1-15}$ alkyl, $C_{2-15}$ alkenyl, $C_{2-15}$alkynyl, cycloalkyl, heterocyclyl, aryl, heteroaryl, aralkyl and $CF_3$, wherein said alkyl, alkenyl, alkynyl, cycloalkyl, heterocyclyl, aryl, heteroaryl, and aralkyl substituents are optionally substituted with halo, alkyl, cyclokalkyl, heterocyclyl, mono- or dialkylamino, alkyl or aryl or heteroaryl amide, CN, O—$C_{1-6}$alkyl, $CF_3$, aryl, or heteroaryl;

each of X and Y, independently from each other and at each occurrence, are selected from O, C, S, $NR_7$; and wherein $R_7$ is selected from hydrogen, $C_{1-12}$ alkyl which is optionally substituted by a halogen atom, an aryl group or an aralkyl group;

each of Z is O, S, N—CN, N—$OR_8$; and wherein $R_8$ is selected from hydrogen, an $C_{1-12}$ alkyl which is optionally substituted by a halogen atom, an aryl group or an aralkyl group;

each of $R_1$ and $R_2$, independently from each other and at each occurrence, are selected from the group consisting of hydrogen; $C_{1-15}$ alkyl, $C_{2-15}$ alkenyl and $C_{2-15}$ alkynyl, wherein said $C_{1-15}$ alkyl, $C_{2-15}$ alkenyl, $C_{2-15}$ alkynyl are optionally substituted with a halogen atom, an aryl group or an aralkyl group; $OR_{13}$, $SR_{13}$ or $N(R_{13})_2$ wherein each of $R_{13}$, independent from each other, is selected from hydrogen or $C_{1-12}$ alkyl which is optionally substituted by a halogen atom, an aryl group or an aralkyl group, and j is an integer in the range from 0 to 7; with the proviso that when j=0 and Y=NR$_7$, then A and R$_7$ may form together a saturated or unsaturated cyclic moiety;

each of R$_3$, R$_{3'}$, R$_4$ and R$_{4'}$, independently from each other and at each occurrence, are selected from the group consisting of hydrogen, C$_{1-15}$ alkyl, C$_{2-15}$ alkenyl and C$_{2-15}$ alkynyl, wherein said C$_{1-15}$ alkyl, C$_{2-15}$ alkenyl, C$_{2-15}$ alkynyl are optionally substituted with a halogen atom, an aryl group or an aralkyl group;

each of T is selected from the group consisting of O, S, NR$_9$, or a divalent moiety of formula (T-a) to (T-e) wherein the second point of attachment can be at any carbon atom of the cyclic system, wherein the dash bond represents an optional double bond;

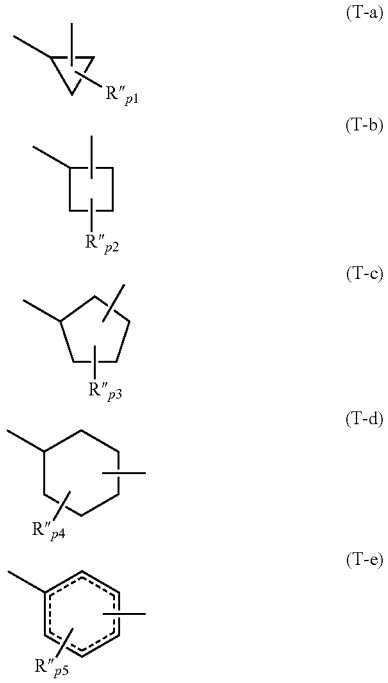

and wherein R$_9$ is selected from hydrogen or a C$_{1-12}$ alkyl which is optionally substituted by a halogen atom, an aryl group or an aralkyl group;

each of R" is selected independently and at each occurrence, from the group consisting of hydrogen, C$_{1-15}$ alkyl, C$_{2-15}$ alkenyl and C$_{2-15}$ alkynyl, wherein said C$_{1-15}$alkyl, C$_{2-15}$ alkenyl, C$_{2-15}$ alkynyl are optionally substituted with a halogen atom, an aryl group or an aralkyl group; and each of p1 is an integer in the range from 0 to 4; each of p2 is an integer in the range from 0 to 6; each of p3 is an integer in the range from 0 to 8; each of p4 is an integer in the range from 0 to 10; each of p5 is an integer in the range from 0 to 8;

each of k is an integer in the range from 0 to 7; each of l is an integer in the range from 0 to 1; and each of m is an integer in the range from 0 to 7 and with the proviso that the sum of k and m is equal to or greater than 1.

It is further understood that all definitions and preferences as described for compound (C) above equally apply for this embodiment and all further embodiments, as described below.

As used in the foregoing and hereinafter, the following definitions apply unless otherwise noted.

The term halo—alone or in combination means all halogens, that is, chloro (Cl), bromo (Br), fluoro (F), iodo (I).

The term alkyl—alone or in combination means an alkane-derived radical containing from 1 to 20, preferably 1 to 15 carbon atoms, unless otherwise specified, for example CF-G alkyl defines a straight or branched alkyl radical having from F to G carbon atoms, e.g. C$_{1-4}$ alkyl defines a straight or branched alkyl radical having from 1 to 4 carbon atoms such as for example methyl, ethyl, 1-propyl, 2-propyl, I-butyl, 2-butyl, 2-methyl-1-propyl. An alkyl group may be a straight chain alkyl or branched alkyl. Preferably, straight or branched alkyl groups containing from 1-15, more preferably 1 to 8, even more preferably 1-6 and most preferably 1-4, carbon atoms, such as methyl, ethyl, propyl, isopropyl, butyl, t-butyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl.

The term alkenyl—alone or in combination means a straight or branched hydrocarbon containing 2-20, preferably 2-17, more preferably 2-10, even more preferably 2-8, most preferably 2-4, carbon atoms, unless otherwise specified and at least one, preferably 1-3, more preferably 1-2, most preferably one, carbon to carbon double bond. Examples of alkenyl groups include ethenyl, propenyl, isopropenyl, butenyl, cyclohexenyl, cyclohexenylalkyl and the like. Alkenyl also includes a straight chain or branched alkenyl group that contains or is interrupted by a cycloalkyl portion. Carbon to carbon double bonds may be either contained within a cycloalkyl portion, with the exception of cyclopropyl, or within a straight chain or branched portion.

The term alkynyl—alone or in combination means a straight or branched hydrocarbon containing 2-20, preferably 2-17, more preferably 2-10, even more preferably 2-8, most preferably 2-4, carbon atoms containing at least one, preferably one, carbon to carbon triple bond. Examples of alkynyl groups include ethynyl, propynyl, butynyl and the like.

The term aryl—alone or in combination means phenyl, naphthyl or anthracenyl optionally carbocyclic fused with a cycloalkyl or heterocyclyl of preferably 5-7, more preferably 5-6, ring members and/or optionally substituted with 1 to 5 groups or substituent, An aryl may be optionally substituted whereby the substituent is attached at one point to the aryl or whereby the substituent is attached at two points to the aryl to form a bicyclic system e.g. benzodioxole, benzodioxan, benzimidazole.

The term heteroaryl—alone or in combination means a monocyclic aromatic ring structure containing 5 or 6 ring atoms, or a bicyclic aromatic group having 8 to 10 atoms, containing one or more, preferably 1-4, more preferably 1-3, heteroatoms independently selected from the group O, S, and N, and optionally substituted with 1 to 5 groups or substituents. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzo-triazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

The term heterocyclyl—alone or in combination is intended to denote a saturated, partially unsaturated or completely unsaturated monocycle, bicycle, or tricycle having 3 to 12 carbon atoms and containing 1, 2, 3, or 4 heteroatoms each independently selected from O, S, P or N, and are optionally benzo fused or fused heteroaryl of 5-6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. In each case the heterocyclyl may be condensed with an aryl to form a bicyclic ring system.

The term cycloalkyl refers to a cyclic or polycyclic alkyl group containing 3 to 15 carbon atoms. Preferably, cycloalkyl groups are monocyclic, bicyclic or tricyclic ring systems of 3-8, more preferably 3-6, ring members per ring, such as cyclopropyl, cyclopentyl, cyclohexyl, adamantyl and the like.

The term aralkyl refers to organic compounds containing an aromatic nucleus to which an alkyl radical is bonded. These alkyl radicals include methyl, ethyl, propyl, butyl, octyl, etc. radicals. The term aralkyl is thus seen to include aralkyl hydrocarbons such as the alkyl benzenes, and the various alkyl naphthalenes. From this definition of the term aralkyl compound it is seen that the term includes compounds such as benzyl, the three isomeric xylyls, the two isomeric trimethyl benzenes, ethyl benzene, p-methyl biphenyl, a-methyl naphthalene, etc.

The present invention further relates to a pharmaceutical composition comprising a carrier, and as active ingredient an effective amount of a compound (C) of formula (I) as specified herein, or a compound of any of the subgroups of compounds of formula (II)-(LXIII) and (I-a)-(XXIV-a) as specified herein, and as defined in any one of the embodiments presented herein.

The present invention relates to a compound (C) of formula (I) as specified herein, or a compound of any of the subgroups of compounds of formula (II)-(LXIII) and (I-a)-(XXIV-a) as specified herein, and as defined in any one of the embodiments presented herein, for use as a medicament.

The present invention relates to a compound (C) of formula (I) as specified herein, or a compound of any of the subgroups of compounds of formula (II)-(LXIII) and (I-a)-(XXIV-a) as specified herein, and as defined in any one of the embodiments presented herein, for use in the treatment of a disease selected from cancer, inflammatory disorders, cardiovascular diseases, viral induced diseases, circulatory diseases, fibro-proliferative diseases and pain sensitization disorders.

The present invention further relates to a method of inhibiting protein kinase activity in a warm-blooded animal said method comprising the administration to an animal in need thereof, of a kinase-inhibitory effective amount of a compound (C) of formula (I) as specified herein, or a compound of any of the subgroups of compounds of formula (II)-(LXIII) and (I-a)-(XXIV-a) as specified herein, and according to any one of the embodiments presented herein.

The present invention further relates to a method of inhibiting protein kinase activity in a warm-blooded animal said method comprising the administration to an animal in need thereof, of a kinase-inhibitory effective amount of a compound (C) of formula (I) as specified herein, or a compound of any of the subgroups of compounds of formula (II)-(LXIII) and (I-a)-(XXIV-a) as specified herein, and according to any one of the embodiments presented herein, wherein the protein kinase is selected from the group consisting of ABL1, ACVR1B (ALK4), AKT1 (PKB alpha), AMPK A1/B1/G1, AURKA (Aurora A), BTK, CDK1/cyclin B, CHEK1 (CHK1), CSNK1G2 (CK1 gamma 2), CSNK2A1 (CK2 alpha 1), DYRK3, EGFR (ErbB1), EPHA2, ERBB2 (HER2), FGFR1, FLT3, FRAP1 (mTOR), GSK3B (GSK3 beta), IGF1R, IKBKB (IKK beta), INSR, IRAK4, JAK3, KDR (VEGFR2), KIT, LCK, MAP2K1 (MEK1), MAP4K4 (HGK), MAPK1 (ERK2), MAPK14 (p38 alpha), MAPK3 (ERK1), MAPK8 (JNK1), MARK2, MET (cMet), NEK1, PAK4, PDGFRB (PDGFR beta), PHKG2, PIM1, PLK1, PRKACA (PKA), PRKCB1 (PKC beta I), ROCK1, RPS6KA3 (RSK2), RPS6KB1 (p70S6K), SRC, SYK, and TEK (Tie2).

The present invention further relates to a method of treating a disease selected from cancer, inflammatory disorders, cardiovascular diseases, viral induced diseases, circulatory diseases, fibro-proliferative diseases and the treatment of pain sensitization, in a warm-blooded animal said method comprising the administration to an animal in need thereof of an effective amount of a compound (C) of formula (I) as specified herein, or a compound of any of the subgroups of compounds of formula (II)-(LXIII) and (I-a)-(XXIV-a) as specified herein, and according to any one of the embodiments presented herein.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent. Whenever used hereinafter, the term "compounds (C) of formula (I)", or "the present compounds" or similar terms, it is meant to include all the compounds (C) of formula (I), N-oxides, addition salts, and stereochemically isomeric forms. One embodiment comprises the compounds (C) of formula (I) or any subgroup of compounds of formula (II)-(LXIII) and (I-a)-(XXIV-a) specified herein, as well as the N-oxides, salts, as the possible stereoisomeric forms thereof. Another embodiment comprises the compounds (C) of formula (I) or any subgroup of compounds of formula (II)-(LXIII) and (I-a)-(XXIV-a) specified herein, as well as the salts as the possible stereoisomeric forms thereof.

The compound (C) of formula (I) as specified herein, or a compound of any of the subgroups of compounds of formula (II)-(LXIII) and (I-a)-(XXIV-a) as specified herein, have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compound (C) of formula (I) as specified herein, or a compound of any of the subgroups of compounds of formula (II)-(LXIII) and (I-a)-(XXIV-a) as specified herein, may possess.

Unless otherwise mentioned or indicated, the chemical designation of a compound (C) of formula (I) as specified herein, or a compound of any of the subgroups of compounds of formula (II)-(LXIII) and (I-a)-(XXIV-a) as specified herein, encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compound (C) of formula (I) as specified herein, or a compound of any of the subgroups of compounds of formula (II)-(LXIII) and (I-a)-(XXIV-a) as specified herein, and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application procedures known in the art. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds (C) of formula (I) as specified herein, or a compound of any of the subgroups of compounds of formula (II)-(LXIII) and (I-a)-(XXIV-a) as specified herein, can be obtained separately by conventional methods. Appropriate physical separation methods that may advantageously be employed are, for example, selective crystallization and chromatography, e.g. column chromatography.

For some of the compound (C) of formula (I) as specified herein, or a compound of any of the subgroups of compounds of formula (II)-(LXIII) and (I-a)-(XXIV-a) as specified herein, N-oxides, salts, solvates, and the intermediates used in the preparation thereof, the absolute stereochemical configuration was not experimentally determined.

A person skilled in the art is able to determine the absolute configuration of such compounds using art-known methods such as, for example, X-ray diffraction.

The present invention is also intended to include all isotopes of atoms occurring on the present compound (C) of formula (I) as specified herein, or a compound of any of the subgroups of compounds of formula (II)-(LXIII) and (I-a)-(XXIV-a) as specified herein. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compound (C) of formula (I) as specified herein, or a compound of any of the subgroups of compounds of formula (II)-(LXIII) and (I-a)-(XXIV-a) as specified herein, are those wherein the counterion is pharmaceutically acceptable, which salts can be referred to as pharmaceutically acceptable acid and base addition salts. However, salts of acids and bases that are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove are meant to comprise the therapeutically active non-toxic acid and base addition salt forms that the compounds (C) of formula (I) as specified herein, or a compound of any of the subgroups of compounds of formula (II)-(LXIII) and (I-a)-(XXIV-a) as specified herein, are able to form. The pharmaceutically acceptable acid addition salts can conveniently be obtained by treating the base form with such appropriate acid in an anion form. Appropriate anions comprise, for example, trifluoroacetate, acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and the like. The counterion of choice can be introduced using ion exchange resins. Conversely said salt forms can be converted by treatment with an appropriate base into the free base form.

The compounds (C) of formula (I) as specified herein, or a compound of any of the subgroups of compounds of formula (II)-(LXIII) and (I-a)-(XXIV-a) as specified herein, containing an acidic proton may also be converted into their nontoxic metal or amine addition salt forms by treatment with appropriate organic and inorganic bases in a cation form. Appropriate basic salts comprise those formed with organic cations such as benzathine, chloroprocaine, choline, diethanolamine, ethylenediamine, meglumine, procaine, and the like; and those formed with metallic cations such as aluminum, calcium, lithium, magnesium, potassium, sodium, zinc, and the like. Conversely said salt forms can be converted by treatment with an appropriate acid into the free form.

The term addition salt as used hereinabove also comprises the solvates which the compound (C) of formula (I) as specified herein, or a compound of any of the subgroups of compounds of formula (II)-(LXIII) and (I-a)-(XXIV-a) as specified herein, as well as the salts thereof, are able to form. Such solvates are for example hydrates, alcoholates and the like.

The N-oxide forms of the present compound (C) of formula (I) as specified herein, or a compound of any of the subgroups of compounds of formula (II)-(LXIII) and (I-a)-(XXIV-a) as specified herein, are meant to comprise the compounds of formula (I) wherein one or several nitrogen atoms are oxidized to the so-called N-oxide.

It will be appreciated that the compound (C) of formula (I) as specified herein, or a compound of any of the subgroups of compounds of formula (II)-(LXIII) and (I-a)-(XXIV-a) as specified herein, may have metal binding, chelating, complex forming properties and therefore may exist as metal complexes or metal chelates. Such metalated derivatives of the compound (C) of formula (I) as specified herein, or a compound of any of the subgroups of compounds of formula (II)-(LXIII) and (I-a)-(XXIV-a) as specified herein, are intended to be included within the scope of the present invention.

Some of the compound (C) of formula (I) as specified herein, or a compound of any of the subgroups of compounds of formula (II)-(LXIII) and (I-a)-(XXIV-a) as specified herein, may also exist in their tautomeric form. Such forms although not explicitly indicated in the above formula are intended to be included within the scope of the present invention.

In a further aspect, the present invention concerns a pharmaceutical composition comprising a therapeutically effective amount of a compound (C) of formula (I) as specified herein, or a compound of any of the subgroups of compounds of formula (II)-(LXIII) and (I-a)-(XXIV-a) as specified herein, and a pharmaceutically acceptable carrier. A therapeutically effective amount in this context is an amount sufficient to prophylactically act against, to stabilize or reduce illnesses mediated by protein kinases in ill subjects or subjects being at risk of being ill, in particular a protein kinase selected from the group consisting of ABL1, ACVR1B (ALK4), AKT1 (PKB alpha), AMPK A1/B1/G1, AURKA (Aurora A), BTK, CDK1/cyclin B, CHEK1 (CHK1), CSNK1G2 (CK1 gamma 2), CSNK2A1 (CK2 alpha 1), DYRK3, EGFR (ErbB1), EPHA2, ERBB2 (HER2), FGFR1, FLT3, FRAP1 (mTOR), GSK3B (GSK3 beta), IGF1R, IKBKB (IKK beta), INSR, IRAK4, JAK3, KDR (VEGFR2), KIT, LCK, MAP2K1 (MEK1), MAP4K4 (HGK), MAPK1 (ERK2), MAPK14 (p38 alpha), MAPK3 (ERK1), MAPK8 (JNK1), MARK2, MET (cMet), NEK1, PAK4, PDGFRB (PDGFR beta), PHKG2, PIM1, PLK1, PRKACA (PKA), PRKCB1 (PKC beta I), ROCK1, RPS6KA3 (RSK2), RPS6KB1 (p70S6K), SRC, SYK, and TEK (Tie2). Examples of illnesses mediated by protein kinases include in particular cancer, inflammatory disorders, cardiovascular diseases, viral induced diseases, circulatory diseases, fibro-proliferative diseases and pain sensitization disorders.

In still a further aspect, this invention relates to a process of preparing a pharmaceutical composition as specified herein, which comprises intimately mixing a pharmaceutically acceptable carrier with a therapeutically effective amount of a compound (C) of formula (I), as specified herein, or of a compound of any of the subgroups of compounds of formula (II)-(LXIII) and (I-a)-(XXIV-a) as specified herein.

Therefore, the compounds (C) of formula (I) as specified herein, or a compound of any of the subgroups of compounds of formula (II)-(LXIII) and (I-a)-(XXIV-a) as specified herein, may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets.

Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds (C) of formula (I) as specified herein, or a compound of any of the subgroups of compounds of formula (II)-(LXIII) and (I-a)-(XXIV-a) as specified herein, of the present invention may also be administered via oral inhalation or insufflation by means of methods and formulations employed in the art for administration via this way. Thus, in general the compound (C) of formula (I) as specified herein, or a compound of any of the subgroups of compounds of formula (II)-(LXIII) and (I-a)-(XXIV-a) as specified herein, may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound (C) of formula (I) as specified herein, or a compound of any of the subgroups of compounds of formula (II)-(LXIII) and (I-a)-(XXIV-a) as specified herein, and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compound (C) of formula (I) as specified herein, or a compound of any of the subgroups of compounds of formula (II)-(LXIII) and (I-a)-(XXIV-a) as specified herein, show kinase inhibition properties. Illnesses and diseases treatable using the compounds and methods of the present invention include protein kinase mediated diseases like cancer, inflammatory disorders, cardiovascular diseases, viral induced diseases, circulatory diseases, fibro-proliferative diseases and pain sensitization disorders. Many of the compounds of this invention may show a favourable pharmacokinetic profile and have attractive properties in terms of bioavailability, including an acceptable half-life, AUC (area under the curve) and peak values and lacking unfavourable phenomena such as insufficient quick onset and tissue retention.

The combinations of the present invention may be used as medicaments. Said use as a medicine or method of treatment comprises the systemic administration to ill subjects of an amount effective to combat the conditions associated with the illnesses. Consequently, the combinations of the present invention can be used in the manufacture of a medicament useful for treating, preventing or combating illness or disease associated with protein kinases including cancer, inflammatory disorders, cardiovascular diseases, viral induced diseases, circulatory diseases, fibro-proliferative diseases and pain sensitization disorders.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated.

In general it is contemplated that an antiviral effective daily amount would be from 0.01 mg to 1500 mg daily, more preferably from 0.1 mg to 50 mg daily. It may be appropriate to administer the required dose as one, two, three, four or more (sub-)doses at appropriate intervals throughout the day. Said (sub-)doses may be formulated as unit dosage forms, for example, containing 1 to 1000 mg, and in particular 5 to 200 mg of active ingredient per unit dosage form.

The exact dosage and frequency of administration depends on the particular compound (C) of formula (I), or the particular compound of any of the subgroups of compounds of formula (II)-(LXIII) and (I-a)-(XXIV-a) as specified herein, used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

EXAMPLES

Example 1: General Procedure for the Synthesis of Carbamate Acyclic Purine Nucleoside Analogues The following procedure illustrates the preparation of several carbamate acyclic purine nucleoside analogues, the synthetic scheme is outlined below. The synthesis starts with alkylation of the purine with an appropriate haloalkylacetate on the $N^9$ position of the adenine ring in step (1), in step (2) the acetate group is removed. In step (3), the final step, the preparation of the carbamate acyclic nucleoside from the corresponding alcohol via activation by carbonyldiimidazole (CDI) followed by reaction with the appropriate amine (3). The synthesis of various amine intermediates, as used in step (3), is illustrated in example 6 below. Examples of the structures of the final compounds can be found in Table 1 below.

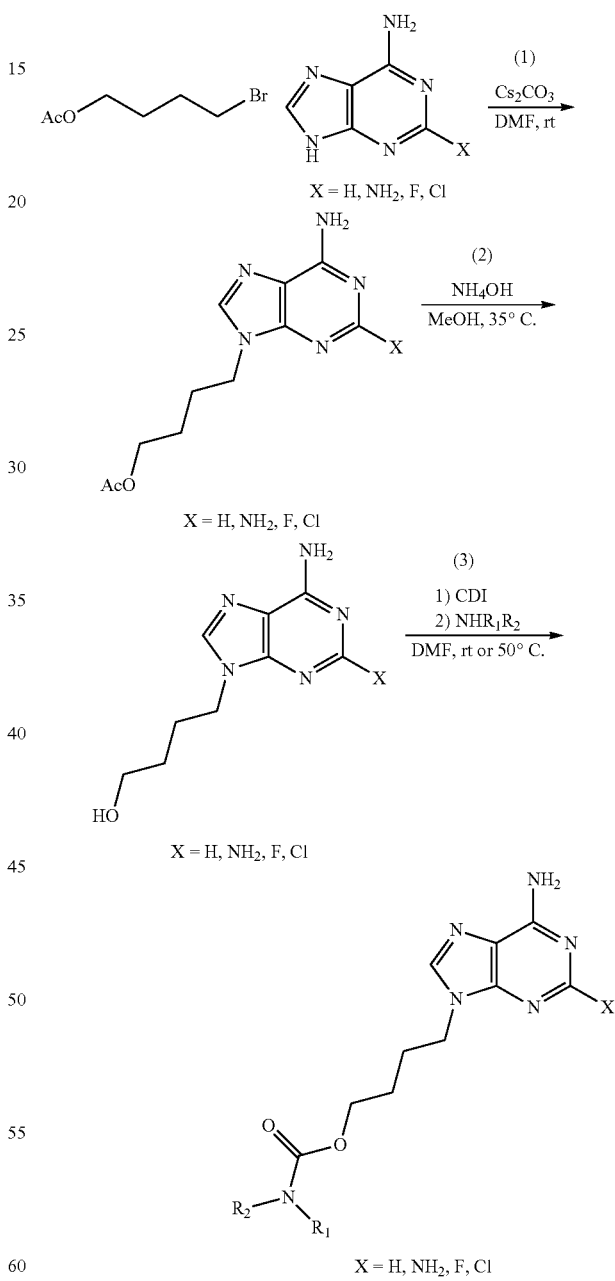

Step (1):

To a stirred mixture of a suitable purine (1 equiv.) and cesium carbonate (1.2 equiv.) in dry DMF (1.5 mL/mmol), 4-bromobutylacetate (1.2 equiv.) was added dropwise under azote atmosphere. The reaction mixture was left at room temperature overnight. The solvent was then evaporated under reduced pressure and the residue was partitioned between DCM and water. The organic layer was extracted twice with DCM. The combined organic layers were dried over $Na_2SO_4$, filtered and concentrated under vacuum. The crude was then purified by flash column chromatography (0-10% MeOH in DCM) to afford the expected compound.

The following compounds are examples illustrating step (1):

4-(6-aminopurin-9-yl)butyl acetate was prepared from adenine (1.35 g, 10 mmol). Yield: 2.12 g (85%) of the title compound as a white powder. $^1$H NMR (300 MHz, $CDCl_3$) δ 8.36 (s, 1H), 7.80 (s, 1H), 5.71 (bs, 2H), 4.24 (t, J=7.2 Hz, 2H), 4.10 (t, J=6.4 Hz, 2H), 2.04 (s, 3H), 2.00-1.94 (m, 2H), 1.72-1.65 (m, 2H), 4-(6-amino-2-chloro-purin-9-yl)butyl acetate was prepared from 2-chloroadenine (2.5 g, 15 mmol). Yield: 3.55 g (83%) of the title compound as a white powder. $^1$H NMR (300 MHz, $CDCl_3$) δ 7.77 (s, 1H), 6.15 (bs, 2H), 4.21 (t, J=7.2 Hz, 2H), 4.11 (t, J=6.4 Hz, 2H), 2.05 (s, 3H), 2.02-1.93 (m, 2H), 1.73-1.63 (m, 2H).

4-(6-amino-2-fluoro-purin-9-yl)butyl acetate was prepared from 2-fluoroadenine (530 mg, 1.98 mmol) following the general procedure except that no extraction was performed. Yield: 384 mg (86%) of the title compound as a white powder. $^1$H NMR (300 MHz, $CDCl_3$) δ 7.75 (s, 1H), 5.72 (bs, 2H), 4.18 (t, J=7.1 Hz, 2H), 4.11 (t, J=6.4 Hz, 2H), 2.05 (s, 3H), 1.99-1.91 (m, 2H), 1.72-1.65 (m, 2H).

4-(6-amino-2-amino-purin-9-yl)butyl acetate was prepared from 2-aminoadenine (300 mg, 2.00 mmol) following the general procedure except that no extraction was performed. Yield: 345 mg (65%) of the title compound as a white powder. $^1$H NMR (300 MHz, DMSO-$d_6$) δ 7.70 (s, 1H), 6.62 (bs, 2H), 5.76 (bs, 2H), 4.02-3.94 (m, 4H), 1.99 (s, 3H), 1.83-1.73 (m, 2H), 1.57-1.48 (m, 2H).

Step (2):

An aqueous ammonia solution (28%, 2.5 mL/mmol) was added to a stirred suspension of the protected compound in MeOH (2.5 mL/mmol). The reaction mixture was heated to 35° C. and stirred overnight. Concentration of the reaction mixture under vacuum followed by a purification by flash column chromatography (0-20% MeOH in DCM) provided the deprotected compound. The following compounds are examples illustrating step (2):

4-(6-aminopurin-9-yl)butan-1-ol was prepared from 4-(6-aminopurin-9-yl)butyl acetate (2.07 g, 8.3 mmol). Yield: 1.51 g (87%) of the title compound as a white powder. $^1$H NMR (300 MHz, DMSO-$d_6$) δ 8.14 (s, 1H), 8.13 (s, 1H), 7.17 (bs, 2H), 4.44 (t, J=4.7 Hz, 1H), 4.15 (t, J=7.1 Hz, 2H), 3.43-3.37 (m, 2H), 1.88-1.78 (m, 2H), 1.42-1.33 (m, 2H).

4-(6-amino-2-chloro-purin-9-yl)butan-1-ol was prepared from 4-(6-amino-2-chloro-purin-9-yl)butyl acetate (2.32 g, 8.18 mmol). Yield: 1.92 g (97%) of the title compound as a white powder. $^1$H NMR (300 MHz, DMSO-$d_6$) δ 8.16 (s, 1H), 7.73 (bs, 2H), 4.44 (t, J=5.2 Hz, 1H), 4.10 (t, J=7.1 Hz, 2H), 3.42-3.37 (m, 2H), 1.85-1.78 (m, 2H), 1.42-1.32 (m, 2H).

4-(6-amino-2-fluoro-purin-9-yl)butan-1-ol was prepared from 4-(6-amino-2-fluoro-purin-9-yl)butyl acetate (530 mg, 1.98 mmol). Yield: 384 mg (86%) of the title compound as a white powder. $^1$H NMR (300 MHz, DMSO-$d_6$) δ 8.12 (s, 1H), 7.75 (bs, 2H), 4.44 (t, J=5.2 Hz, 1H), 4.08 (t, J=7.1 Hz, 2H), 3.43-3.37 (m, 2H), 1.85-1.76 (m, 2H), 1.42-1.32 (m, 2H).

4-(6-amino-2-amino-purin-9-yl)butan-1-ol was prepared from 4-(6-amino-2-amino-purin-9-yl)butyl acetate (339 mg, 1.28 mmol). Yield: 274 mg (96%) of the title compound as a white powder. $^1$H NMR (300 MHz, DMSO-$d_6$) δ 7.69 (s, 1H), 6.60 (bs, 2H), 5.75 (bs, 2H), 4.44 (t, J=5.2 Hz, 1H), 3.95 (t, J=7.1 Hz, 2H), 3.43-3.36 (m, 2H), 1.80-1.71 (m, 2H), 1.42-1.33 (m, 2H).

Step (3):

To a stirred solution of the compound (1 equiv.) in DMF (2 mL), carbonyldiimidazole (1.5 equiv.) was added under azote atmosphere. After 2 hours of stirring at room temperature, the appropriate amine (3 equiv.) was added and the reaction mixture was stirred at room temperature or 50° C. until completion. The solvent was then removed under reduced pressure and the residue purified by flash column chromatography (0-10% MeOH in DCM) and by reverse-phase chromatography (0-100% MeOH in water) to give the carbamate derivative. In some cases, an additional trituration with $Et_2O$ was necessary to remove residual free amine.

The following compounds are examples illustrating step (3):

4-(6-aminopurin-9-yl)butyl N-(1,3-benzodioxol-5-ylmethyl)carbamate was prepared from 4-(6-aminopurin-9-yl)butan-1-ol (62 mg, 0.3 mmol). Yield: 75 mg (60%) of the title compounds as a white powder. $^1$H NMR (300 MHz, DMSO-$d_6$) δ 8.12 (s, 1H), 7.60 (t, J=5.9 Hz, 1H), 7.18 (bs, 2H), 6.83-6.78 (m, 2H), 6.67-6.70 (m, 2H), 5.97 (s, 2H), 4.16 (t, J=6.9 Hz, 2H), 4.05 (d, J=6.1 Hz, 2H), 3.97 (t, J=6.5 Hz, 2H), 1.89-1.79 (m, 2H), 1.56-1.46 (m, 2H).

4-(6-amino-2-chloro-purin-9-yl)butyl-N-[[(3-(trifluoromethyl)phenyl]methyl] carbamate was prepared from 4-(6-amino-2-chloro-purin-9-yl)butan-1-ol (48 mg, 0.2 mmol). Yield: 54 mg (61%) of the title compounds as a white powder. $^1$H NMR (300 MHz, DMSO-$d_6$) δ 8.15 (s, 1H), 7.79-7.74 (m, 3H), 7-58.7.54 (m, 4H), 4.26 (d, J=6.1 Hz, 2H), 4.12 (t, J=6.9 Hz, 2H), 3.99 (t, J=6.4 Hz, 2H), 1.87-1.78 (m, 2H), 1.58-1.48 (m, 2H).

4-(6-amino-2-chloro-purin-9-yl)butyl-N-[(3-isopropyl-benzimidazol-5-yl)methyl] carbamate was prepared from 4-(6-amino-2-chloro-purin-9-yl)butan-1-ol (60 mg, 0.25 mmol). Yield: 98 mg (87%) of the title compounds as a white powder. $^1$H NMR (300 MHz, DMSO-$d_6$) δ 8.27 (s, 1H), 8.15 (s, 1H), 7.73 (bs, 2H), 7.68 (t, J=5.9 Hz, 1H), 7.56 (d, J=8.1 Hz, 1H), 7.46 (s, 1H), 7.09 (dd, J=7.1, 1.2 Hz, 1H), 4.68 (sept, J=6.6 Hz, 1H), 4.29 (d, J=6.0 Hz, 2H), 4.12 (t, J=7.2 Hz, 2H), 3.99 (t, J=6.6 Hz, 2H), 1.87-1.78 (m, 2H), 1.58-1.50 (m, 8H). ESI-MS: 457.0 (M+H)$^+$.

4-(6-amino-2-chloro-purin-9-yl)butyl-N-[[4-[2-(4-fluoro-phenyl)ethylsulfamoyl] phenyl]methyl]carbamate was prepared from 4-(6-amino-2-chloro-purin-9-yl)butan-1-ol (48 mg, 0.2 mmol). Yield: 80 mg (70%) of the title compounds as a white powder. $^1$H NMR (300 MHz, DMSO-$d_6$) δ 8.16 (s, 1H), 7.76-7.71 (m, 5H), 7-43.7.41 (m, 2H), 7.19-7.16 (m, 2H), 7.09-7.05 (m, 2H), 4.24 (d, J=6.3 Hz, 2H), 4.13 (t, J=6.8 Hz, 2H), 3.99 (t, J=6.4 Hz, 2H), 2.93 (t, J=7.4 Hz, 2H), 2.67 (t, J=7.0 Hz, 2H), 1.87-1.80 (m, 2H), 1.57-1.50 (m, 2H).

Example 2A: General Procedure for the Preparation of 2-Substituted Alkyl or Aryl Purine Acyclic Nucleoside Analogues

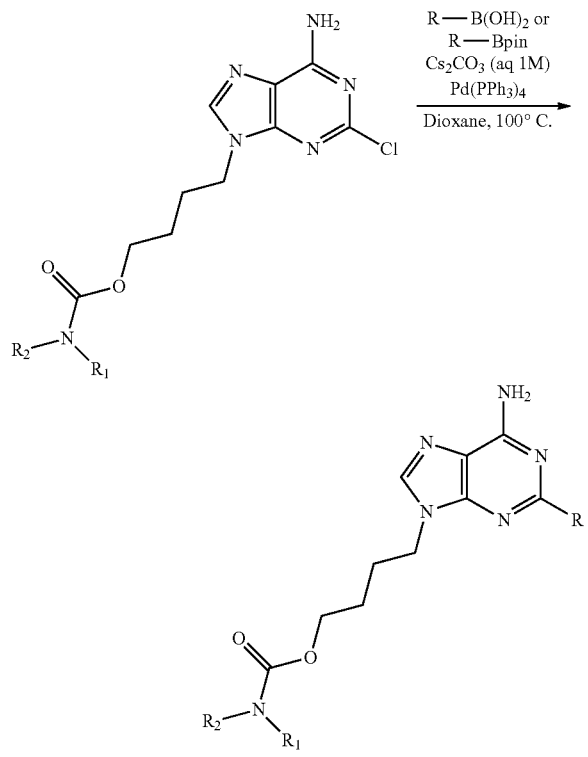

A (Hetero)aryl- or alkyl-boronic acid (R—B(OH)$_2$)) or pinacol ester (R—Bpin) (0.3 mmol, 1.5 equiv.) and aqueous cesium carbonate (1M, 0.6 mmol, 3 equiv.) were added to a stirred solution of the 4-(6-amino-2-chloro-purin-9-yl)butyl-carbamate derivative (0.2 mmol, 1 equiv.) in dioxane (2 mL). The reaction mixture was purged three times with azote, then Pd(PPh$_3$)$_4$ (23 mg, 0.02 mmol, 0.1 equiv.) was introduced. The reaction mixture was warmed to 100° C. overnight. Evaporation of the solvent under reduced pressure and purification of the crude mixture by flash column chromatography (0-10% MeOH in DCM) yielded the expected compound.

The following compounds are examples illustrating this procedure:

4-[6-amino-2-(3-furyl)purin-9-yl]butyl N-(1,3-benzodioxol-5-ylmethyl)carbamate was prepared from 4-(6-amino-2-chloro-purin-9-yl)butyl N-(1,3-benzodioxol-5-ylmethyl) carbamate. Yield: 84 mg (93%) of the title compound as a white powder. $^1$H NMR (300 MHz, DMSO-d$_6$) δ 8.16-8.14 (m, 1H), 8.11 (s, 1H), 7.71 (t, J=1.7 Hz, 1H), 7.58 (t, J=5.8 Hz, 1H), 7.16 (bs, 2H), 6.96 (dd, J=1.8, 0.7 Hz, 1H), 6.83-6.78 (m, 2H), 6.71-6.68 (m, 1H), 5.97 (s, 2H), 4.21 (t, J=6.8 Hz, 2H), 4.06-4.00 (m, 4H), 1.91-1.84 (m, 2H), 1.58-1.51 (m, 2H).

4-[6-amino-2-(2-furyl)purin-9-yl]butyl N-(1,3-benzodioxol-5-ylmethyl)carbamate was prepared from 4-(6-amino-2-chloro-purin-9-yl)butyl N-(1,3-benzodioxol-5-ylmethyl) carbamate. Yield: 64 mg (71%) of the title compound as a white powder. $^1$H NMR (300 MHz, DMSO-d$_6$) δ 8.14 (s, 1H), 7.79-7.78 (m, 1H), 7.58 (t, J=5.8 Hz, 1H), 7.27 (bs, 2H), 7.06 (dd, J=3.3, 0.8 Hz, 1H), 6.83-6.78 (m, 2H), 6.70-6.68 (m, 1H), 6.60 (dd, J=1.8, 3.3 Hz, 1H), 5.97 (s, 2H), 4.19 (t, J=6.7 Hz, 2H), 4.06-3.98 (m, 4H), 1.90-1.83 (m, 2H), 1.59-1.52 (m, 2H).

4-[6-amino-2-(2-methylpyrazol-3-yl)purin-9-yl]butyl-N-(1,3-benzodioxol-5-ylmethyl)carbamate was prepared from 4-(6-amino-2-chloro-purin-9-yl)butyl N-(1,3-benzodioxol-5-ylmethyl)carbamate. Yield: 49 mg (53%) of the title compound as a white powder. $^1$H NMR (300 MHz, DMSO-d$_6$) δ 8.18 (s, 1H), 7.57 (t, J=5.8 Hz, 1H), 7.42 (d, J=1.9 Hz, 1H), 7.34 (bs, 2H), 6.82-6.78 (m, 3H), 6.70-6.67 (m, 1H), 5.97 (s, 2H), 4.26 (s, 3H), 4.22 (t, J=6.9 Hz, 2H), 4.05 (d, J=6.1 Hz, 2H), 3.99 (t, J=6.6 Hz, 2H), 1.92-1.85 (m, 2H), 1.58-1.49 (m, 2H).

4-[6-amino-2-(4-pyridyl)purin-9-yl]butyl-N-(1,3-benzodioxol-5-ylmethyl) carbamate was prepared from 4-(6-amino-2-chloro-purin-9-yl)butyl N-(1,3-benzodioxol-5-ylmethyl)carbamate. Yield: 65 mg (71%) of the title compound as a yellow powder. $^1$H NMR (300 MHz, DMSO-d$_6$) δ 8.69-8.67 (m, 2H), 8.23-8.21 (m, 3H), 7.59 (t, J=6.0 Hz, 1H), 7.42 (bs, 2H), 6.82-6.69 (m, 3H), 5.96 (s, 2H), 4.27 (t, J=6.8 Hz, 2H), 4.06-4.00 (m, 4H), 1.95-1.90 (m, 2H), 1.59-1.52 (m, 2H).

4-(6-amino-2-cyclopropyl-purin-9-yl)butyl-N-(1,3-benzodioxol-5-ylmethyl) carbamate was prepared from 4-(6-amino-2-chloro-purin-9-yl)butyl N-(1,3-benzodioxol-5-ylmethyl)carbamate. Yield: 25 mg (29%) of the title compound as a white powder. $^1$H NMR (300 MHz, CDCl$_3$) δ 7.72 (s, 1H), 7.01 (bs, 1H), 6.70-6.67 (m, 3H), 5.87 (s, 2H), 4.19-4.04 (m, 6H), 2.22-2.13 (m, 1H), 1.90-1.82 (m, 2H), 1.59-1.52 (m, 2H), 1.19-1.02 (m, 4H).

When R is a methyl group, the general procedure is described in example 5, see below.

Example 2B: General Procedure for the Preparation of 2-Alkoxide Purine Acyclic Nucleoside Analogues -continued

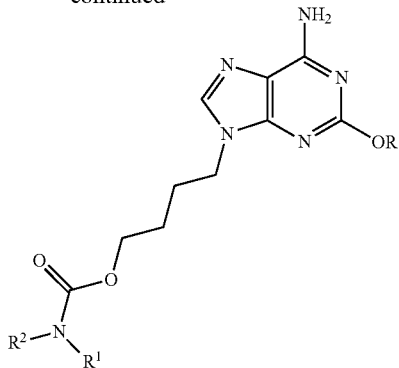

Step 1:

To 4-(6-amino-2-chloro-purin-9-yl)butan-1-ol (1 equiv.), prepared in example 1-step 2, the appropriate alcohol (30 equiv.) and sodium tert-butoxide (3 equiv.) were added. NB: In the case of the methoxy group, sodium methoxide (7.5 equiv.) was used. The reaction mixture was heated to 100-150° C. in the microwave until completion (10-90 min). The solvent was then evaporated under reduced pressure and the residue purified by flash column chromatography (0-10% MeOH in DCM) to afford the expected compound.

The following compounds are examples illustrating step 1:

4-(6-amino-2-methoxy-purin-9-yl)butan-1-ol was prepared from 4-(6-amino-2-chloro-purin-9-yl)butan-1-ol (241 mg, 1.0 mmol) after 10 min of microwave irradiation at 100° C. Yield: 172 mg (73%) of the title compound as a white powder. ESI-MS: 238.3 (M+H)$^+$. 4-(6-amino-2-ethoxy-purin-9-yl)butan-1-ol was prepared from 4-(6-amino-2-chloro-purin-9-yl)butan-1-ol (84 mg, 0.35 mmol) after 15 min of microwave irradiation at 100° C. Yield: 45 mg (51%) of the title compound as a white powder. ESI-MS: 252.4 (M+H)$^+$. 4-(6-amino-2-propoxy-purin-9-yl)butan-1-ol was prepared from 4-(6-amino-2-chloro-purin-9-yl)butan-1-ol (84 mg, 0.35 mmol) after 1h of microwave irradiation at 100° C. Yield: 52 mg (56%) of the title compound as a white powder. ESI-MS: 266.4 (M+H)$^+$.

4-(6-amino-2-isopropoxy-purin-9-yl)butan-1-ol was prepared from 4-(6-amino-2-chloro-purin-9-yl)butan-1-ol (84 mg, 0.35 mmol) after 1 h30 of microwave irradiation at 100° C. and 30 min at 150° C. Yield: 26 mg (28%) of the title compound as a white powder. ESI-MS: 266.4 (M+H)$^+$.

4-(6-amino-2-isobutoxy-purin-9-yl)butan-1-ol was prepared from 4-(6-amino-2-chloro-purin-9-yl)butan-1-ol (84 mg, 0.35 mmol) after 30 min of microwave irradiation at 100° C. and 30 min at 150° C. Yield: 46 mg (47%) of the title compound as a white powder. 4-[6-amino-2-(cyclopentylmethoxy)purin-9-yl]butan-1-ol was prepared from 4-(6-amino-2-chloro-purin-9-yl)butan-1-ol (84 mg, 0.35 mmol) after 30 min of microwave irradiation at 150° C. Yield: 40 mg (37%) of the title compound as a white powder. ESI-MS: 266.4 (M+H)$^+$.

Step 2:

To a stirred solution of 2-alkoxy derivative (1 equiv.) in DMF (10 mL), was added carbonydiimidazole (1.5 equiv.) under azote atmosphere. After 2 hours of stirring at room temperature, the appropriate amine (1.5 equiv.) was added and the reaction mixture was stirred at 50° C. over weekend. The solvent was then removed under reduced pressure and the residue purified by flash column chromatography (0-10% MeOH in DCM) and by reverse-phase chromatography (0-100% MeOH in water) to give the carbamate derivative.

The following compounds are examples illustrating step 2:

4-(6-amino-2-methoxy-purin-9-yl)butyl N-[[4-[(4-chlorophenyl)methylsulfamoyl]-phenyl]methyl] carbamate was prepared from 4-(6-amino-2-methoxy-purin-9-yl)butan-1-ol (47 mg, 0.2 mmol). Yield: 49 mg (43%) as a white powder, ESI-MS: 574.6 (M+H)$^+$.

4-(6-amino-2-ethoxy-purin-9-yl)butyl N-[[4-[(4-chlorophenyl)methylsulfamoyl]-phenyl]methyl] carbamate was prepared from 4-(6-amino-2-ethoxy-purin-9-yl)butan-1-ol (45 mg, 0.18 mmol). Yield: 79 mg (75%) as a white powder. ESI-MS: 589.4 (M+H)$^+$.

4-(6-amino-2-propoxy-purin-9-yl)butyl N-[[4-[(4-chlorophenyl)methylsulfamoyl]-phenyl]methyl] carbamate was prepared from 4-(6-amino-2-propoxy-purin-9-yl)butan-1-ol (45 mg, 0.18 mmol). Yield: 73 mg (65%) as a white powder. $^1$H NMR (300 MHz, DMSO-d$_6$) δ 8.16 (s, 1H), 7.93 (s, 1H), 7.78-7.73 (m, 3H), 7.43-7.41 (m, 2H), 7.35-7.32 (m, 2H), 7.26-7.23 (m, 2H), 7.15 (bs, 2H), 4.24 (d, J=5.9 Hz, 2H), 4.15 (t, J=6.6 Hz, 2H), 4.08 (t, J=6.7 Hz, 2H), 4.00 (t, J=6.5 Hz, 2H), 3.95 (bs, 2H), 1.88-1.81 (m, 2H), 1.69 (quint., J=7.1 Hz, 2H), 1.57-1.47 (m, 2H), 0.95 (t, J=7.3 Hz, 2H).

4-(6-amino-2-isopropoxy-purin-9-yl)butyl N-[[4[(4chlorophenyl) methylsulfamoyl]-phenyl]methyl] carbamate was prepared from 4-(6-amino-2-isopropoxy-purin-9-yl)butan-1-ol (26 mg, 0.10 mmol). Yield: 36 mg (60%) as a white powder. $^1$H NMR (300 MHz, DMSO-d$_6$) d 8.15 (s, 1H), 7.92 (s, 1H), 7.79-7.70 (m, 3H), 7.43-7.41 (m, 2H), 7.35-7.33 (m, 2H), 7.26-7.23 (m, 2H), 7.11 (bs, 2H), 5.20-5.09 (m, 1H), 4.24 (d, J=6.0 Hz, 2H), 4.07 (t, J=6.7 Hz, 2H), 4.00 (t, J=6.6 Hz, 2H), 3.95 (bs, 2H), 1.88-1.77 (m, 2H), 1.57-1.48 (m, 2H), 1.26 (d, J=6.2 Hz, 6H).

4-(6-amino-2-isobutoxy-purin-9-yl)butyl N-[[4-[(4-chlorophenyl) methylsulfamoyl]-phenyl]methyl] carbamate was prepared from 4-(6-amino-2-isobutoxy-purin-9-yl)butan-1-ol (46 mg, 0.16 mmol). Yield: 60 mg (61%) as a white powder. $^1$H NMR (300 MHz, DMSO-d$_6$) d 8.16 (s, 1H), 7.94 (s. 1H), 7.80-7.70 (m, 3H), 7.43-7.41 (m, 2H), 7.35-7.33 (m, 2H), 7.26-7.23 (m, 2H), 7.16 (bs, 2H), 4.24 (d, J=6.0 Hz, 2H), 4.08 (t, J=6.6 Hz, 2H), 4.09-3.95 (m, 6H), 2.05-1.91 (m, 1H), 1.88-1.79 (m, 2H), 1.57-1.48 (m, 2H), 0.95 (d, J=6.7 Hz, 6H).

4-(6-amino-2-cyclopentylmethoxy-purin-9-yl)butyl N [[4 [(4chlorophenyl) methylsulfamoyl]phenyl]methyl] carbamate was prepared from 4-(6-amino-2-cyclopentylmethoxy-purin-9-yl)butan-1-ol (40 mg, 0.13 mmol). Yield: 52 mg (63%) as a white powder. $^1$H NMR (300 MHz, DMSO-d$_6$) d 8.16 (s, 1H), 7.93 (s, 1H), 7.80-7.70 (m, 3H), 7.43-7.41 (m, 2H), 7.35-7.32 (m, 2H), 7.26-7.23 (m, 2H), 7.15 (bs, 2H), 4.25 (d, J=5.9 Hz, 2H), 4.10-3.99 (m, 6H), 3.95 (bs, 2H), 2.31-2.21 (m, 1H), 1.88-1.67 (m, 4H), 1.62-1.48 (m, 6H), 1.35-1.24 (m, 2H).

Example 2C: Preparation of 2-Methylsulfanyl Purine Acyclic Nucleoside Analogues

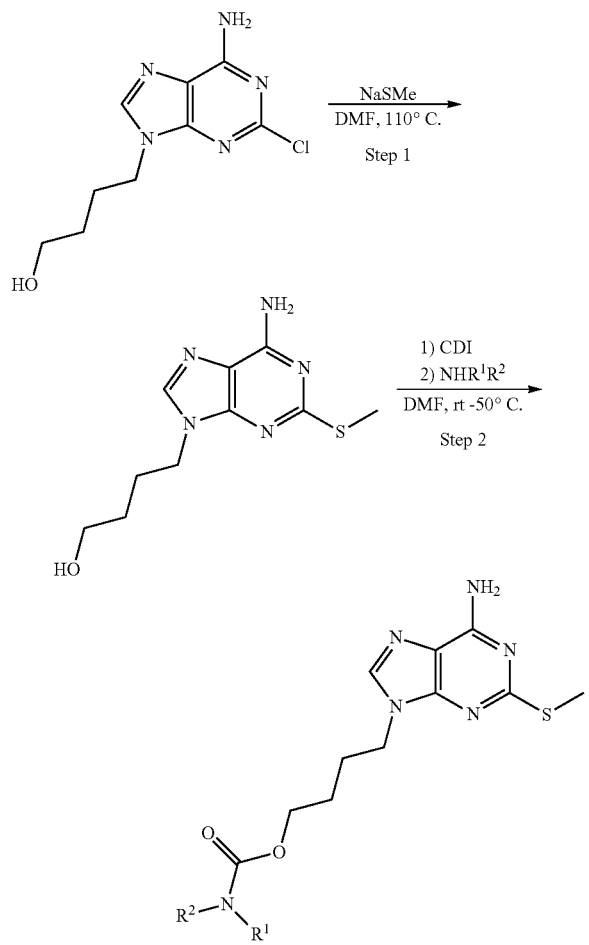

Step 1:

To a stirred solution of 4-(6-amino-2-chloro-purin-9-yl)butan-1-ol (84 mg, 0.35 mmol, 1 equiv.), prepared in example 1-step 2, in DMF (3.5 mL), sodium thiomethoxide (245 mg, 3.5 mmol, 10 equiv.) was added. The reaction mixture was warmed to 110° C. for 6 hours. Then, water was added and the mixture was extracted with ethyl acetate. The aqueous layer was then extracted twice. The combined organic layers were washed with brine, dried over $Na_2SO_4$ and concentrated to provide 4-(6-amino-2-methylsulfanyl-purin-9-yl)butan-1-ol (65 mg, 74%) as a white powder, which was used in the next step without further purification. ESI-MS: 254.3 $(M+H)^+$.

Step 2:

To a stirred solution of 2-methylsulfanyl derivative (1 equiv.) in DMF (10 mL), was added carbonydiimidazole (1.5 equiv.) under azote atmosphere. After 2 hours of stirring at room temperature, the appropriate amine (1.5 equiv.) was added and the reaction mixture was stirred at 50° C. over weekend. The solvent was then removed under reduced pressure and the residue purified by flash column chromatography (0-10% MeOH in DCM) and by reverse-phase chromatography (0-100% MeOH in water) to give the carbamate derivative.

The following compounds are examples illustrating step 2:

4-(6-amino-2-methylsulfanyl-purin-9-yl)butyl-N-[[4-[(4 chlorophenyl) methylsulfamoyl]phenyl]methyl] carbamate was prepared from 4-(6-amino-2-methylsulfanyl-purin-9-yl) butan-1-ol (65 mg, 0.26 mmol). Yield: 73 mg (48%) as a white powder. $^1$H NMR (300 MHz, DMSO-$d_6$) d 8.15 (s, 1H), 8.02 (s, 1H), 7.79-7.73 (m, 3H), 7.44-7.41 (m, 2H), 7.35-7.32 (m, 2H), 7.26-7.23 (m, 4H), 4.25 (d, J=5.9 Hz, 2H), 4.13 (t, J=6.6 Hz, 2H), 4.01 (t, J=6.6 Hz, 2H), 3.95 (bs, 2H), 2.46 (s, 3H), 1.90-1.81 (m, 2H), 1.57-1.48 (m, 2H).

Example 3: Preparation of 2-Iodo-2-Chloro Purine Acyclic Nucleoside Analogue

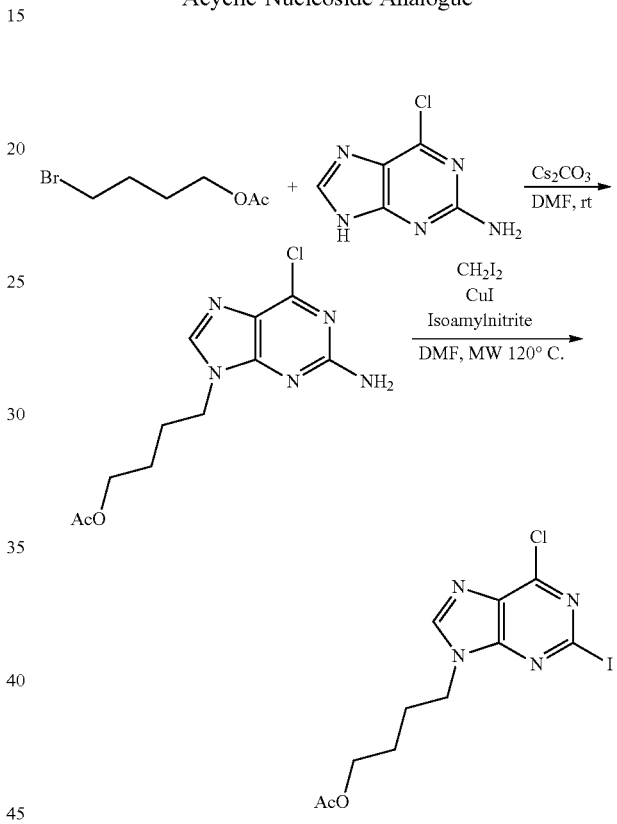

To a stirred suspension 2-amino-6-chloropurine (1.70 g, 10 mmol, 1 equiv.) in DMF (25 mL), were added cesium carbonate (3.90 g, 12 mmol, 1.2 equiv.) and 4-bromobutyl acetate (1.74 mL, 12 mmol, 1.2 equiv.) dropwise. The reaction mixture was stirred at room temperature overnight under azote atmosphere. The solvent was then removed under reduced pressure and the residue purified by flash column chromatography (0-10% MeOH in DCM) to provide 4-(2-amino-6-chloro-purin-9-yl)butyl acetate (2.15 g, 76%) as a white powder.

To a stirred suspension of 4-(2-amino-6-chloro-purin-9-yl)butyl acetate (284 mg, 1.0 mmol, 1 equiv.), obtained from the previous step, in DMF (5 mL), were added copper(I) iodide (19 mg, 0.1 mmol, 0.1 equiv.), diiodomethane (1.20 mL, 15 mmol, 15 equiv.) and isoamyl nitrite (0.67 mL, 5 mmol, 5 equiv.). The reaction mixture was heated to 120° C. for 2h in the microwave. The solvents were evaporated under reduced pressure. The resultant oil was then purified by flash column chromatography (0-50% EtOAc in cyclohexane) to give 4-(6-chloro-2-iodo-purin-9-yl)butyl acetate (281 mg, 71%) as a brown powder. ESI-MS: 395.4 $(M+H)^+$.

Example 4: General Procedure for the Preparation of 2-Alkynyl Purine Acyclic Nucleoside Analogues

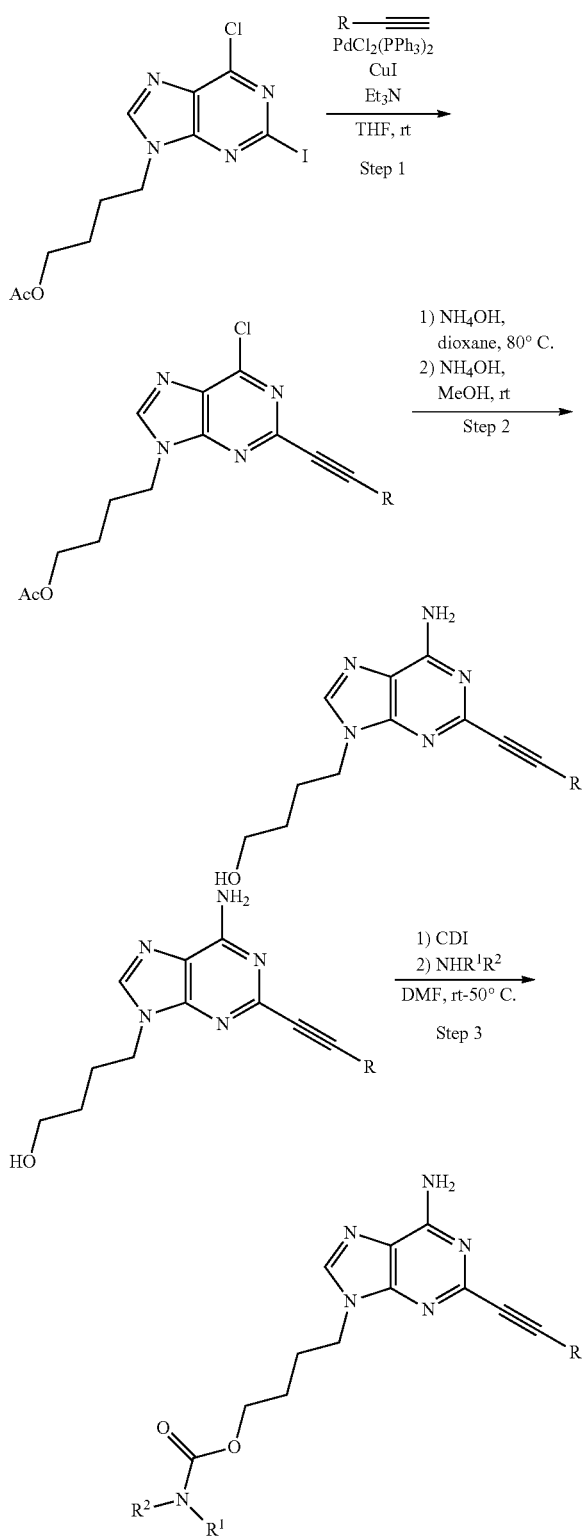

Step 1:

To a stirred solution of 4-(6-chloro-2-iodo-purin-9-yl) butyl acetate (118 mg, 0.30 mmol, 1 equiv.) in THF (3 mL) under azote atmosphere, were added triethylamine (100 µL, 0.72 mmol, 2.4 equiv.), bis(triphenylphosphine)palladium (II) chloride (11 mg, 0.015 mmol, 0.05 equiv.) and copper (1) iodide (6 mg, 0.03 mmol, 0.1 equiv.). Then, the appropriate alkyne (0.36 mmol, 1.2 equiv) was added dropwise and the reaction mixture was stirred at room temperature until completion (1-22h). The solvent was then evaporated under reduced pressure and the crude purified by flash column chromatography (0-50% EtOAc in cyclohexane) to yield the expected compound.

The following compounds are examples illustrating step 1:

4-[6-chloro-2-(2-trimethylsilylethynyl)purin-9-yl]butyl acetate was prepared from 4-(6-chloro-2-iodo-purin-9-yl) butyl acetate. Yield: 101 mg (92%) of the title compound as a pale yellow oil. ESI-MS: 365.6 (M+H)$^+$.

4-[6-chloro-2-(3-methylbut-1-ynyl)purin-9-yl]butyl acetate was prepared from 4-(6-chloro-2-iodo-purin-9-yl) butyl acetate. Yield: 86 mg (86%) of the title compound as a yellow oil. ESI-MS: 335.4 (M+H)$^+$.

Step 2:

A solution of 2-alkynyl derivative (1 equiv.) in dioxane (10 mL/mmol) was placed in an autoclave. Aqueous ammonia solution (28%, 10 mL/mmol) was added and the reaction mixture was heated to 80° C. overnight. The solvents were then removed under reduced pressure. The residue was dissolved in methanol (5 mL/mmol) and aqueous ammonia solution (28%, 5 mL/mmol) was added. The resulting solution was stirred at room temperature until complete removal of the acetate group (3-6h). The solvents were evaporated under reduced pressure and the crude purified by flash column chromatography (0-20% MeOH in DCM) to give the expected compound.

The following compounds are examples illustrating step 2:

4-(6-amino-2-ethynyl-purin-9-yl)butan-1-ol was prepared from 4-[6-chloro-2-(2-trimethylsilylethynyl)purin-9-yl] butyl acetate (101 mg, 0.28 mmol). Yield: 43 mg (67%) of the title compound as a yellow powder. ESI-MS: 232.3 (M+H)$^+$.

4-[6-amino-2-(3-methylbut-1-ynyl)purin-9-yl]butan-1-ol was prepared from 4-[6-chloro-2-(3-methylbut-1-ynyl)purin-9-yl]butyl acetate (86 mg, 0.26 mmol). Yield: 52 mg (73%) of the title compound as a beige powder.

Step 3:

To a stirred solution of alkynyl derivative (1 equiv.) in DMF (10 mL), was added carbonydiimidazole (1.5 equiv.) under azote atmosphere. After 2 hours of stirring at room temperature, the appropriate amine (1.5 equiv.) was added and the reaction mixture was stirred at 50° C. over weekend. The solvent was then removed under reduced pressure and the residue purified by flash column chromatography (0-10% MeOH in DCM) and by reverse-phase chromatography (0-100% MeOH in water) to give the carbamate derivative.

The following compounds are examples illustrating step 3:

4-(6-amino-2-ethynyl-purin-9-yl)butyl N-[[4-[(4chlorophenyl)methylsulfamoyl]-phenyl]methyl]carbamate was prepared from 4-(6-amino-2-ethynyl-purin-9-yl)butan-1-ol (41 mg, 0.18 mmol). Yield: 72 mg (71%) of the title compound as a white powder. ESI-MS: 568.5 (M+H)$^+$.

4-[6-amino-2-(3-methylbut-1-ynyl)purin-9-yl]butyl N-[[4-[(4 chlorophenyl)methylsulfamoyl]phenyl]methyl] carbamate was prepared from 4-[6-amino-2-(3-methylbut- 1-ynyl)purin-9-yl]butan-1-ol (49 mg, 0.18 mmol). Yield: 75 mg (69%) of the title compound as a white powder. ESI-MS: 610.6 (M+H)$^+$.

Example 5: General Procedure for the Preparation of 2-Alkenyl and 2-Methyl Purine Acyclic Nucleoside Analogues

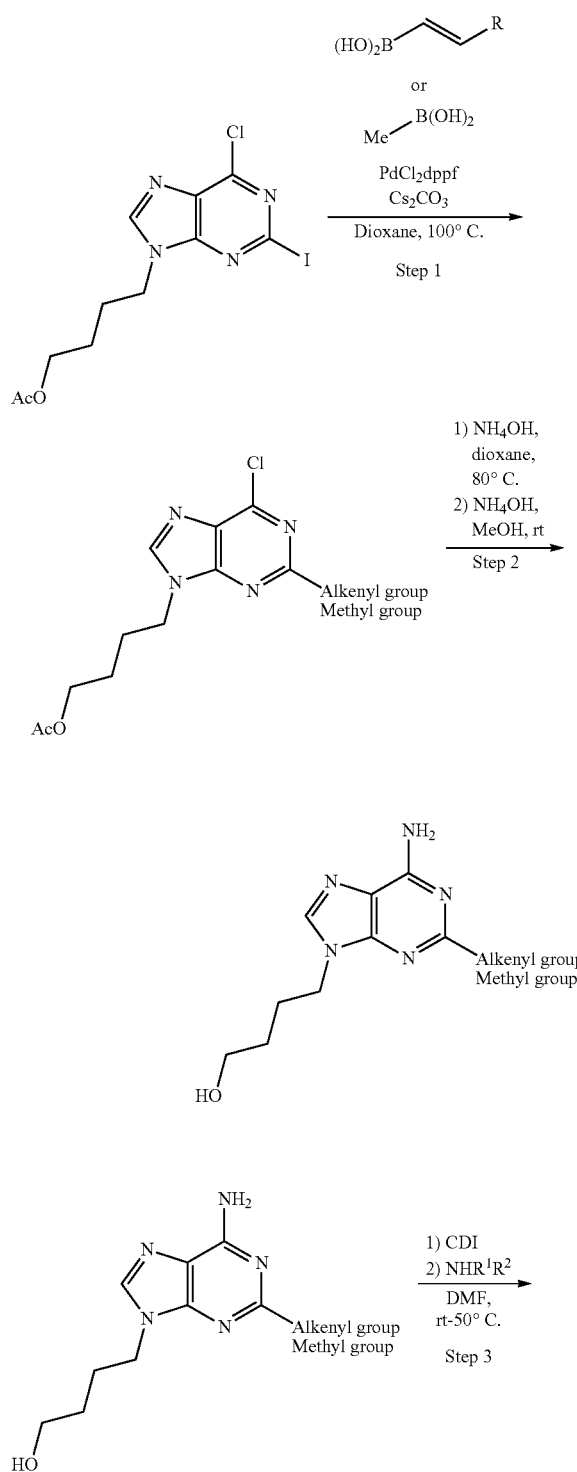

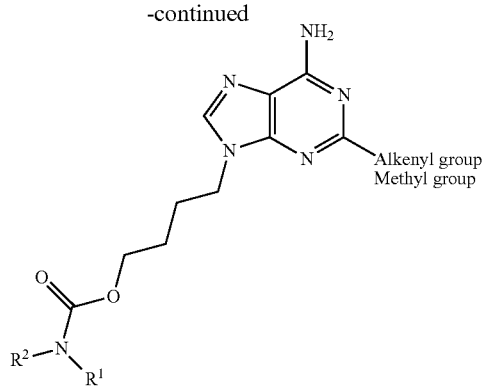

Step 1:

To a stirred solution of 4-(6-chloro-2-iodo-purin-9-yl) butyl acetate (118 mg, 0.30 mmol, 1 equiv.) in dioxane (3 mL) under azote atmosphere, were added cesium carbonate (234 mg, 0.72 mmol, 2.4 equiv.), alkenylboronic acid or methylboronic acid (1.2 equiv.) and 1,1'-bis(diphenylphosphino)ferrocene-palladium(II)dichloride dichloromethane complex (24 mg, 0.03 mmol, 0.1 equiv.). The reaction mixture was warmed to 100° C. until completion (4-5h). The solvent was then evaporated under reduced pressure and the crude residue purified by flash column chromatography (0-50% EtOAc in cyclohexane) to yield the expected compound.

The following compounds are examples illustrating step 1:

4-[6-chloro-2-[(Z)-prop-1-enyl]purin-9-yl]butyl acetate was prepared from 4-(6-chloro-2-iodo-purin-9-yl)butyl acetate. Yield: 61 mg (62%) of the title compound as a brown oil. ESI-MS: 309.4 (M+H)$^+$.

4-(6-chloro-2-methyl-purin-9-yl)butyl acetate was prepared from 4-(6-chloro-2-iodo-purin-9-yl)butyl acetate, Yield: 42 mg (49%) of the title compound as a yellow oil. ESI-MS: 283.5 (M+H)$^+$.

Step 2:

A solution of 2-alkenyl or 2-methyl derivative (1 equiv.) in dioxane (10 mL/mmol) was placed in an autoclave. Aqueous ammonia solution (28%, 10 mL/mmol) was added and the reaction mixture was heated to 80° C. overnight. The solvents were then removed under reduced pressure. The residue was dissolved in methanol (5 mL/mmol) and aqueous ammonia solution (28%, 5 mL/mmol) was added. The resulting solution was stirred at room temperature until complete removal of the acetate group (3-6h). The solvents were evaporated under reduced pressure and the crude purified by flash column chromatography (0-20% MeOH in DCM) to give the expected compound.

The following compounds are examples illustrating step 2:

4-[6-amino-2-[(Z)-prop-1-enyl]purin-9-yl]butan-1-ol was prepared from 4-[6-chloro-2-[(Z)-prop-1-enyl]purin-9-yl] butyl acetate (61 mg, 0.20 mmol). Yield: 45 mg (92%) of the title compound as a white powder.

4-(6-amino-2-methyl-purin-9-yl)butan-1-ol was prepared from 4-(6-chloro-2-methyl-purin-9-yl)butyl acetate (86 mg, 0.26 mmol). Yield: 40 mg (83%) of the title compound as a white powder. ESI-MS: 222.3 (M+H)$^+$.

Step 3:

To a stirred solution of 2-alkenyl or 2-methyl derivative (1 equiv.) in DMF (10 mL), was added carbonydiimidazole (1.5 equiv.) under azote atmosphere. After 2 hours of stirring at room temperature, the appropriate amine (1.5 equiv.) was added and the reaction mixture was stirred at 50° C. over weekend. The solvent was then removed under reduced pressure and the residue purified by flash column chromatography (0-10% MeOH in DCM) and by reverse-phase chromatography (0-100% MeOH in water) to give the carbamate derivative.

The following compounds are examples illustrating step 3:

4-[6-amino-2-[(Z)-prop-1-enyl]purin-9-yl]butyl N-[[4-[(4 chlorophenyl)methylsulfamoyl]phenyl]methyl]carbamate was prepared from 4-[6-amino-2-[(Z)-prop-1-enyl]purin-9-yl]butan-1-ol (45 mg, 0.18 mmol). Yield: 48 mg (46%) of the title compound as a white powder. ESI-MS: 584.6 $(M+H)^+$.

4-(6-amino-2-methyl-purin-9-yl)butyl N-[[4-[(4-chlorophenyl)methylsulfamoyl]phenyl]methyl]carbamate was prepared from 4-(6-amino-2-methyl-purin-9-yl)butan-1-ol (40 mg, 0.18 mmol). Yield: 64 mg (64%) of the title compound as a white powder. $^1$H NMR (300 MHz, DMSO-$d_6$) d 8.16 (s, 1H), 8.05 (s, 1H), 7.81-7.72 (m, 3H), 7.44-7.41 (m, 2H), 7.35-7.33 (m, 2H), 7.26-7.23 (m, 2H), 7.06 (bs, 2H), 4.24 (d, J=6.2 Hz, 2H), 4.13 (t, J=6.9 Hz, 2H), 4.00 (t, J=6.4 Hz, 2H), 3.94 (s, 2H), 2.39 (s, 3H), 1.89-1.79 (m, 2H), 1.57-1.47 (m, 2H).

Example 6: General Procedure for the Preparation of 2-Alkyl Purine Acyclic Nucleoside Analogues

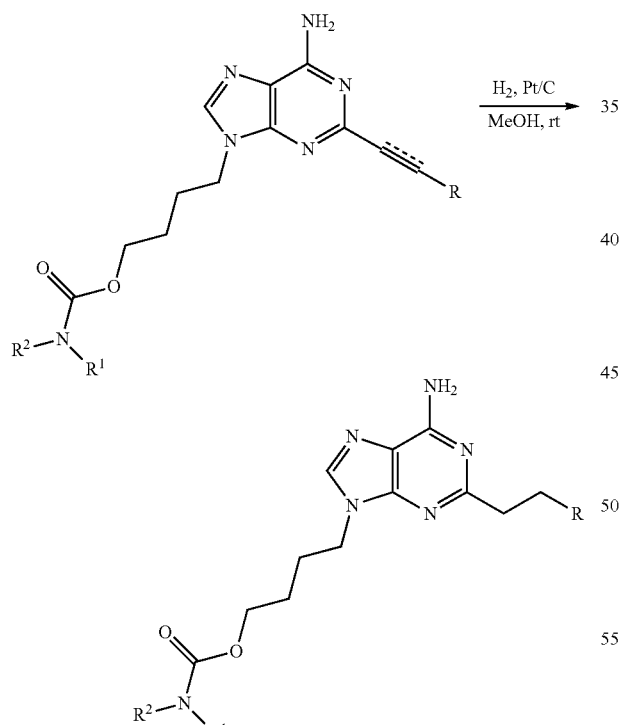

To a stirred solution of 2-alkenyl or alkynyl derivative (1 equiv.) in MeOH (10 mL/mmol), was added 10% platinum on carbon (~20 wt %) under azote atmosphere. Hydrogen gas was bubbled through the reaction mixture for 10 min and the mixture was stirred under hydrogen atmosphere until completion (18-72h). The mixture was passed through a plug of celite and the solvent was removed under reduced pressure. Purification by flash column chromatography (0-10% MeOH in DCM) yielded the expected derivative.

The following compounds are examples illustrating this procedure:

4-(6-amino-2-propyl-purin-9-yl)butyl N-[[4-[(4-chlorophenyl)methylsulfamoyl]-phenyl]methyl] carbamate was prepared from 4-[6-amino-2-[(Z)-prop-1-enyl]purin-9-yl]butyl N-[[4-[(4-chlorophenyl)methylsulfamoyl]phenyl]methyl]carbamate (36 mg, 0.06 mmol). Yield: 22 mg (63%) of the title compound as a white powder. ESI-MS: 586.6 $(M+H)^-$. 4-(6-amino-2-ethyl-purin-9-yl)butyl N-[[4[(4chlorophenyl)methylsulfamoyl]phenyl]methyl] carbamate was prepared from 4-(6-amino-2-ethynyl-purin-9-yl)butyl N-[[4-[(4-chlorophenyl)methylsulfamoyl]phenyl]methyl] carbamate (57 mg, 0.10 mmol). Yield: 44 mg (77%) of the title compound as a white powder. $^1$H NMR (300 MHz, DMSO-$d_6$) d 8.16 (s, 1H), 8.05 (s, 1H), 7.80-7.73 (m, 3H), 7.43-7.41 (m, 2H), 7.35-7.33 (m, 2H), 7.26-7.23 (m, 2H), 7.04 (bs, 2H), 4.24 (d, J=6.0 Hz, 2H), 4.14 (t, J=6.6 Hz, 2H), 4.00 (t, J=6.4 Hz, 2H), 3.95 (s, 2H), 2.66 (q, J=7.4 Hz, 2H), 1.89-1.80 (m, 2H), 1.57-1.49 (m, 2H), 1.22 (t, J=7.4 Hz, 3H). ESI-MS: 572.5 $(M+H)^+$.

4-(6-amino-2-isopentyl-purin-9-yl)butyl N-[[4-[(4-chlorophenyl)methylsulfamoyl]-phenyl]methyl]carbamate was prepared from 4-[6-amino-2-(3-methylbut-1-ynyl)purin-9-yl]buty N-[[4-[(4chlorophenyl)methylsulfamoyl]-phenyl]methyl]carbamate (57 mg, 0.09 mmol). Yield: 28 mg (51%) of the title compound as a white powder. ESI-MS: 614.6 $(M+H)^+$.

Example 7: General Procedure for the Preparation of 2-Substituted Amino Acyclic Purine Nucleoside Analogues

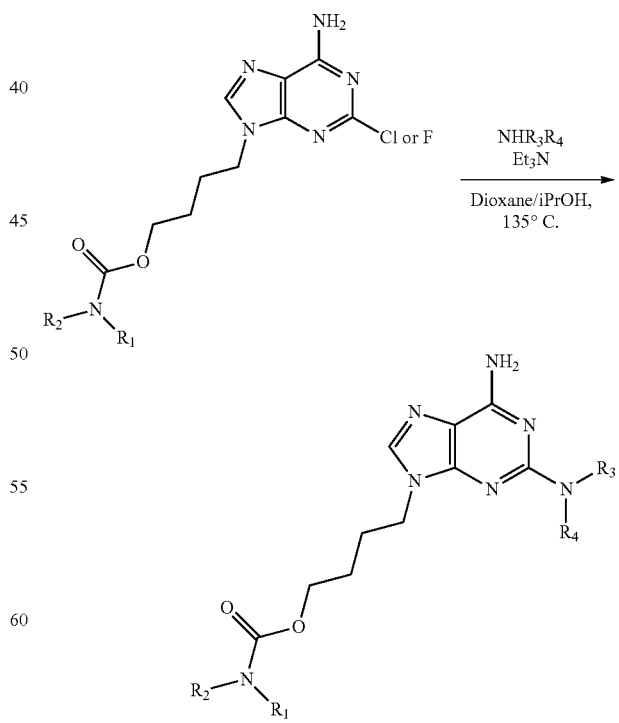

To a stirred suspension of a 4-(6-amino-2-chloro-purin-9-yl)butyl-carbamate or a 4-(6-amino-2-fluoro-purin-9-yl)

butyl-carbamate derivative (0.2 mmol, 1 equiv.) in 2-propanol/dioxane (2/1 mL), triethylamine (0.6 mmol, 3 equiv.) and the appropriate amine (2 mmol, 10 equiv.) was added under azote atmosphere. The reaction mixture was warmed to 1350° C. in a sealed flask until completion. The solvent was removed under reduced pressure and the residue was purified by flash column chromatography (0-10% MeOH in DCM) and/or reverse-phase chromatography (0-100% MeOH in water) to give the expected compound.

The following compounds are examples illustrating this procedure: 4-[6-amino-2-(methylamino)purin-9-yl]butyl-N-(1,3-benzodioxol-5-ylmethyl) carbamate was prepared from 4-(6-amino-2-chloro-purin-9-yl)butyl N-(1,3-benzodioxol-5-ylmethyl)carbamate. Yield: 58 mg (70%) of the title compound as a beige powder. $^1$H NMR (300 MHz, DMSO-$d_6$) δ 7.68 (s, 1H), 7.58 (t, J=6.3 Hz, 1H), 6.83-6.79 (m, 2H), 6.70-6.68 (m, 1H), 6.62 (bs, 2H), 6.15 (q, J=6.2 Hz, 1H), 5.97 (s, 2H), 4.07 (d, J=6.1 Hz, 2H), 3.99 (t, J=6.5 Hz, 4H), 2.75 (d, J=4.7 Hz, 3H), 1.84-1.75 (m, 2H), 1.55-1.48 (m, 2H).

4-[6-amino-2-(dimethylamino)purin-9-yl]butyl-N-(1,3-benzodioxol-5-ylmethyl) carbamate was prepared from 4-(6-amino-2-chloro-purin-9-yl)butyl N-(1,3-benzodioxol-5-ylmethyl)carbamate. Yield: 50 mg (59%) of the title compound as a white powder. $^1$H NMR (300 MHz, DMSO-$d_6$) δ 7.52 (s, 1H), 7.39 (t, J=6.3 Hz, 1H), 6.61-6.58 (m, 2H), 6.52-6.47 (m, 1H), 5.75 (s, 2H), 3.85-3.75 (m, 6H), 3.99 (t, J=6.5 Hz, 4H), 2.83 (s, 6H), 1.62-1.56 (m, 2H), 1.30-1.25 (m, 2H).

4-[6-amino-2-(methylamino)purin-9-yl]butyl-N-[[3-(trifluoromethyl)phenyl]methyl] was prepared from 4-(6-amino-2-chloro-purin-9-yl)butyl N-[[3-(trifluoromethyl)phenyl]methyl]carbamate. Yield: 65 mg (75%) of the title compound as a white powder. $^1$H NMR (300 MHz, DMSO-$d_6$) δ 7.77 (t, J=6.3 Hz, 1H), 7.69 (s, 1H), 6.60-6.55 (m, 4H), 6.62 (bs, 2H), 6.16-6.13 (m, 1H), 4.26 (d, J=6.2 Hz, 2H), 4.02-3.98 (m, 4H), 2.75 (d, J=4.7 Hz, 3H), 1.84-1.77 (m, 2H), 1.55-1.45 (m, 2H).

Example 8: General Procedure for the Preparation of 3-(Hetero)Aryl, or Alkylenyl Benzylcarbamate Acyclic Purine Nucleoside Analogues

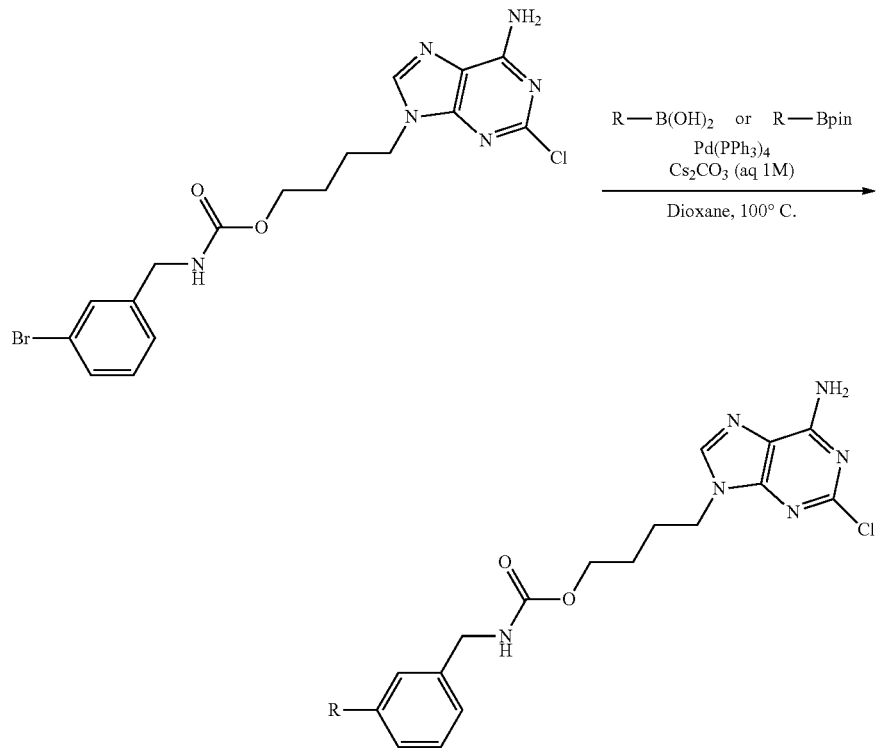

A (Hetero)aryl- or alkylenyl-boronic acid (R—B(OH)$_2$) or pinacol ester (R-Bpin) (0.275 mmol, 1.1 equiv.) and aqueous cesium carbonate (1M, 0.5 mmol, 2 equiv.) were added to a stirred solution of the 4-(6-amino-2-chloro-purin-9-yl)butyl-carbamate derivative (0.25 mmol, 1 equiv.) in dioxane (2.5 mL). The reaction mixture was purged three times with azote, then Pd(PPh$_3$)$_4$ (29 mg, 0.025 mmol, 0.1 equiv.) was introduced. The reaction mixture was warmed to 100° C. overnight. Evaporation of the solvent and purification of the crude mixture by flash column chromatography (0-5% MeOH in DCM) yielded the expected compound.

The following compounds are examples illustrating this procedure:

4-(6-amino-2-chloro-purin-9-yl)butyl-N-[[3-(3-furyl)phenyl]methyl]carbamate was prepared from 4-(6-amino-2-chloro-purin-9-yl)butyl N-[(3-bromophenyl)methyl]carbamate (91 mg, 0.20 mmol). Yield: 46 mg (52%) of the title compound as a white powder. $^1$H NMR (300 MHz, DMSO-$d_6$) δ 8.15-8.14 (m, 2H), 7.74-7.68 (m, 4H), 7.47 (bs, 2H), 7.35-7.29 (m, 1H), 7.17-7.11 (m, 1H), 6.90 (bs, 1H), 4.19 (d, J=5.8 Hz, 2H), 4.13 (t, J=7.2 Hz, 2H), 4.00 (t, J=6.3 Hz, 2H), 1.85-1.78 (m, 2H), 1.56-1.51 (m, 2H).

4-(6-amino-2-chloro-purin-9-yl)butyl-N-[[3-(1-methylpyrrol-2-yl)phenyl]methyl] carbamate was prepared from 4-(6-amino-2-chloro-purin-9-yl)butyl N-[(3-bromophenyl)

methyl]carbamate. Yield: 87 mg (77%) of the title compound as an orange powder. $^1$H NMR (300 MHz, DMSO-$d_6$) δ 8.15 (s, 1H), 7.74-7.68 (m, 3H), 7.41-7.29 (m, 3H), 7.15 (d, J=7.0 Hz, 1H), 6.82 (t, J=2.0 Hz, 1H), 6.12-6.11 (m, 1H), 6.05-6.03 (m, 1H), 4.20 (d, J=5.8 Hz, 2H), 4.12 (t, J=7.2 Hz, 2H), 4.00-3.97 (m, 2H), 3.61 (s, 3H), 1.84-1.78 (m, 2H), 1.57-1.50 (m, 2H).

4-(6-amino-2-chloro-purin-9-yl)butyl-N-[[3-(2-methylprop-1-enyl)phenyl]methyl] carbamate was prepared from 4-(6-amino-2-chloro-purin-9-yl)butyl N-[(3-bromophenyl)methyl]carbamate (226 mg, 0.5 mmol). Yield: 133 mg (62%) of the title compound as a white powder. ESI-MS: 429.0 (M+H)$^+$.

Example 9: General Procedure for the Preparation of Saturated 3-Alkylbenzylcarbamate Acyclic Purine Nucleoside Analogues

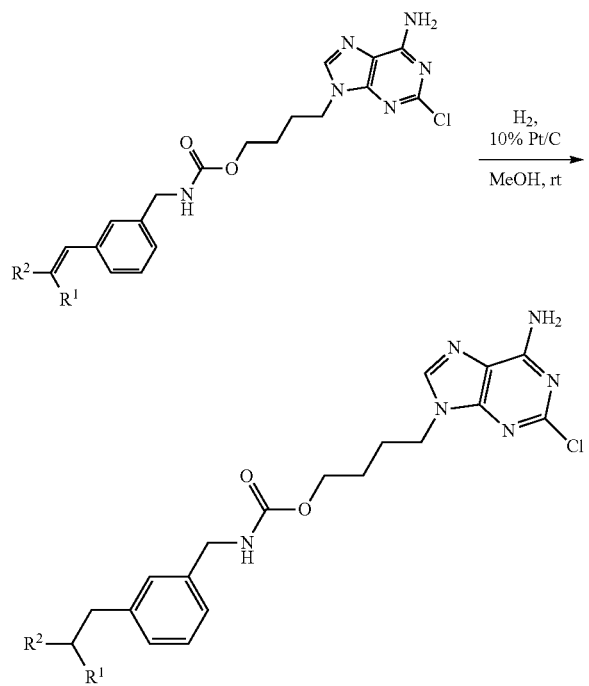

To a stirred solution of an unsaturated compound (1 equiv.) in dry methanol (10 mL/mmol), was added 10% platinum on carbon (~20 wt %) under azote atmosphere. Hydrogen gas was bubbled through the reaction mixture for 10 min and the mixture was stirred overnight under hydrogen atmosphere until completion. The mixture was passed through a plug of celite and the solvent was removed under reduced pressure. Purification by flash column chromatography (0-10% MeOH in DCM) and/or by reverse-phase chromatography (0-100% MeOH in water) resulted in the expected compound.

The following compounds are examples illustrating this procedure:

4-(6-amino-2-chloro-purin-9-yl)butyl N-[(3-propylphenyl)methyl]carbamate was prepared from 4-(6-amino-2-chloro-purin-9-yl)butyl N-[[3-[(Z)-prop-1-enyl]phenyl]methyl]carbamate (63 mg, 0.15 mmol). Yield: 30 mg (48%) of the title compound as a white powder. ESI-MS: 417.4 (M+H)$^+$.

4-(6-amino-2-chloro-purin-9-yl)butyl N-[(3-isobutylphenyl)methyl]carbamate was prepared 4-(6-amino-2-chloro-purin-9-yl)butyl N-[[3-(2-methylprop-1-enyl)phenyl]methyl]carbamate (90 mg, 0.21 mmol). Yield: 55 mg (61%) of the title compound as a white powder. $^1$H NMR (300 MHz, DMSO-$d_6$) δ 8.15 (s, 1H), 7.73 (bs, 2H), 7.63 (t, J=5.7 Hz, 1H), 7.20 (t, J=7.7 Hz, 1H), 7.05-6.99 (m, 3H), 4.15-4.10 (m, 4H), 3.99 (t, J=6.4 Hz, 2H), 2.40 (d, J=7.1 Hz, 2H), 1.84-1.76 (m, 3H), 1.58-1.48 (m, 2H), 0.85 (s, 3H), 0.82 (s, 3H).

4-(6-amino-2-chloro-purin-9-yl)butyl N-[(3-isopentylphenyl)methyl]carbamate was prepared 4-(6-amino-2-chloro-purin-9-yl)butyl N-[[3-(3-methylbut-1-ynyl)phenyl]methyl]carbamate (60 mg, 0.14 mmol). Yield: 31 mg (51%) of the title compound as a white powder. $^1$H NMR (300 MHz, DMSO-$d_6$) δ 8.15 (s, 1H), 7.73 (bs, 2H), 7.62 (t, J=6.1 Hz, 1H), 7.22-7.17 (m, 1H), 7.05-7.00 (m, 3H), 4.14-4.10 (m, 4H), 3.99 (t, J=6.3 Hz, 2H), 2.51-2.49 (m, 2H, overlapped with DMSO), 1.87-1.77 (m, 2H), 1.57-1.38 (m, 5H), 0.90 (s, 3H), 0.88 (s, 3H). ESI-MS: 445.4 (M+H)$^+$.

Example 10: General Procedure for the Preparation of Modified Alkyl Chain Acyclic Purine Nucleoside Analogues The following procedure illustrates the synthesis of cyclopropyl purine nucleoside analogues.

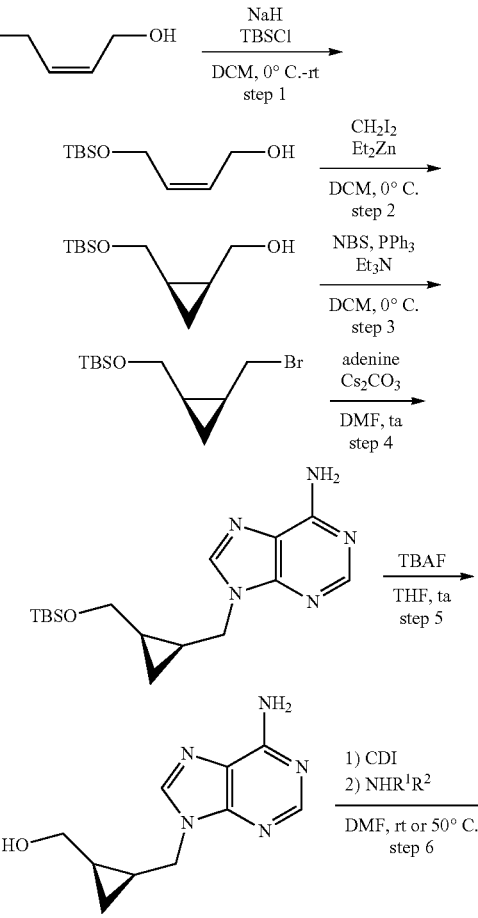

-continued

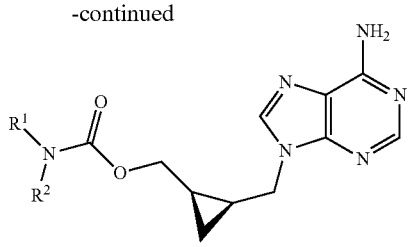

Step 1:

To a stirred solution of sodium hydride (60% wt in oil, 750 mg, 18.90 mmol, 1 equiv.) in dry THF (28 mL), was added cis-but-2-ene-1,4 diol (1.68 g, 18.90 mmol, 1 equiv.) dropwise over 50 minutes at 0° C. under azote atmosphere. The reaction mixture was warmed to room temperature and stirred for 1 hour. Then, tert-butyldimethylsilyl chloride (2.84 g, 18.90 mmol, 1 equiv.) in dry THF (28 mL) was added dropwise over 50 minutes and stirred for 1 hour. The reaction mixture was quenched by addition of a saturated solution of ammonium chloride (35 mL). After evaporation of THF, the aqueous layer was extracted twice with DCM and the combined organic layers were dried over $Na_2SO_4$, filtered and concentrated under vacuum. A purification of the residue by flash column chromatography (10-30% EtOAc in cyclohexane) provided (Z)-4-[tert-butyl(dimethyl)silyl]oxy-but-2-en-1-ol (3.14 g, 88%) as a yellow oil. $^1H$ NMR (300 MHz, $CDCl_3$) δ 5.70-5.68 (m, 2H), 4.26-4.25 (m, 2H), 4.20-4.18 (m, 2H), 0.90 (s, 6H), 0.09 (s, 9H).

Step 2:

To a stirred suspension of the previous intermediate (2.50 g, 12.35 mmol, 1 equiv.) in DCM (72 mL), were added dropwise diethyl zinc (3.25 g, 26.40 mmol, 2 equiv.) and diiodomethane (14.14 g, 52.80 mmol, 4 equiv.) at 0° C. under azote atmosphere. The reaction mixture was kept at 0° C. for 3 hours and then a saturated solution of ammonium chloride was added. The phases were separated and the aqueous layer was extracted once with DCM. The combined organic layers were dried over $Na_2SO_4$, filtered and concentrated under vacuum. The crude was then purified by flash column chromatography (10-30% EtOAc in cyclohexane) to provide [(1 S,2R)-2-[[tert-butyl(dimethyl)silyl] oxymethyl]cyclopropyl]methanol (1.86 g, 68%) as a yellow oil. $^1H$ NMR (300 MHz, $CDCl_3$) δ 4.14 (dd, J=11.5, 5.4 Hz, 1H), 3.96 (dd, J=12.2, 5.4 Hz, 1H), 3.28-3.21 (m, 2H), 1.43-1.30 (m, 1H), 1.28-1.15 (m, 1H), 0.90 (s, 9H), 0.76-0.74 (m, 1H), 0.19 (q, J=5.6 Hz, 1H), 0.10 (s, 6H).

Step 3:

To a stirred solution of the previous intermediate (1.47 g, 6.80 mmol, 1 equiv.) in dry DCM (87 mL), were added triphenylphosphine (3.56 g, 13.60 mmol, 2 equiv.) and triethylamine (1.83 mL, 13.60 mmol, 2 equiv.) under azote atmosphere. The mixture was cooled to 0° C. and N-bromosuccinimide (2.42 g, 13.60 mmol, 2 equiv.) was added portionwise. The reaction was then warmed to 40° C. for 1h30. The resulting solution was diluted with DCM and the aqueous phase was extracted once with DCM. The combined organic layers were dried over $Na_2SO_4$, filtered and concentrated under vacuum. A purification of the residue by flash column chromatography (10% EtOAc in cyclohexane) afforded [(1R,2S)-2-(bromomethyl)cyclopropyl]methoxy-tert-butyl-dimethyl-silane (1.89 g, 90%) as a colorless oil. $^1H$ NMR (300 MHz, $CDCl_3$) δ 3.82 (dd, J=11.2, 5.6 Hz, 1H), 3.69-3.40 (m, 3H), 1.47-1.25 (m, 2H), 0.88 (s, 9H), 0.40 (q, J=5.5 Hz, 2H), 0.06 (s, 6H).

Step 4:

To a stirred solution of the previous intermediate (1.72 g, 6.15 mmol, 1 equiv.) in dry DMF (15 mL), were added adenine (830 mg, 6.15 mmol, 1 equiv.) and cesium carbonate (2.40 g, 7.38 mmol, 1.2 equiv.) under azote atmosphere. The mixture was left at room temperature overnight, After evaporation of DMF, the residue was taken up with DCM and washed three times with water. The organic layer was then dried over $Na_2SO_4$, filtered and concentrated under vacuum. A purification of the residue by flash column chromatography (0-10% MeOH in DCM) yielded 9-[[(1S, 2R)-2-[[tert-butyl(dimethyl)silyl]oxymethyl]cyclopropyl] methyl]purin-6-amine (850 mg, 42%) as a white solid. $^1H$ NMR (300 MHz, $CDCl_3$) δ 8.33 (s, 1H), 8.29 (s, 1H), 7.04 (bs, 2H), 4.47 (dd, J=14.6, 6.5 Hz, 1H), 4.18-4.07 (m, 2H), 3.54 (dd, J=11.6, 8.7 Hz, 1H), 3.52 (d, J=11.6 Hz, 1H), 1.47-1.39 (m, 1H), 1.38-1.28 (m, 1H), 0.90 (s, 9H), 0.41 (q, J=11.1, 5.6 Hz, 2H), 0.07 (s, 6H).

Step 5:

To a stirred solution of the previous intermediate (850 mg, 2.56 mmol, 1 equiv.) in dry THF (13 mL), was added dropwise TBAF (1M in THF, 3.07 mmol, 1.2 equiv.) at 0° C. under azote atmosphere. The reaction was warmed to room temperature and stirred for 3 hours. The mixture was then concentrated under vacuum and the crude was purified by flash column chromatography (0-15% MeOH in DCM) to give [(1R,2S)-2-[(6-aminopurin-9-yl)methyl]cyclopropyl] methanol (550 mg, 95%) as a white solid. $^1H$ NMR (300 MHz, DMSO-$d_6$) δ 8.19 (s, 1H), 8.10 (s, 1H), 7.15 (s, 2H), 4.74 (t, J=5.2 Hz, 1H), 4.23-4.04 (m, 2H), 3.74-3.66 (m, 1H), 3.43-3.33 (m, 1H), 1.38-1.23 (m, 1H), 1.19.1.07 (m, 1H), 0.67-0.60 (m, 1H), 0.31-0.23 (q, J=5.5 Hz, 1H).

Step 6:

To a stirred solution of the previous intermediate (44 mg, 0.20 mmol, 1 equiv.) in dry DMF (2 mL), was added carbonydiimidazole (49 mg, 0.30 mmol, 1.5 equiv.) under azote atmosphere. After 2 hours of stirring at room temperature, the appropriate amine (3 equiv.) was added and the reaction mixture was stirred at room temperature or 50° C. until completion. The solvent was then removed under reduced pressure and the residue purified by flash column chromatography (0-10% MeOH in DCM) and by reverse-phase chromatography (0-100% MeOH in water) to give the carbamate derivative. The following compounds are examples illustrating this procedure. [(1R,2S)-2-[(6-aminopurin-9-yl)methyl]cyclopropyl]methyl N-(1,3-benzodioxol-5-ylmethyl)carbamate was prepared from [(1R,2S)-2-[(6-aminopurin-9-yl)methyl]cyclopropyl]methanol. Yield: 51 mg (64%) of the title compound as a white powder. $^1H$ NMR (300 MHz, DMSO-$d_6$) δ 8.16 (s, 1H), 8.14 (s, 1H), 7.64 (t, J=6.1 Hz, 1H), 7.16 (s, 2H), 6.83 (d, J=8.1 Hz, 2H), 6.72 (d, J=7.8 Hz, 1H), 5.96 (s, 2H), 4.34-4.21 (m, 2H), 4.12-3.91 (m, 4H), 1.56-1.40 (m, 1H), 1.37-1.24 (m, 1H), 0.81-0.69 (m, 1H), 0.50 (q, J=5.0 Hz, 1H).

[(1R,2S)-2-[(6-aminopurin-9-yl)methyl]cyclopropyl] methyl N-[2-(4-fluorophenyl)ethyl]carbamate was prepared from [(1R,2S)-2-[(6-aminopurin-9-yl)methyl]cyclopropyl] methanol. Yield: 46 mg (62%) of the title compound as a white powder. $^1H$ NMR (300 MHz, DMSO-$d_6$) δ 8.16 (s, 1H), 8.14 (s, 1H), 7.26-7.21 (m, 5H), 7.09 (t, J=9.0 Hz, 2H), 4.35-4.20 (m, 2H), 4.07-3.93 (m, 2H), 3.19 (q, J=6.5 Hz, 2H), 2.70 (t, J=7.7 Hz, 2H), 1.56-1.41 (m, 1H), 1.35-1.20 (m, 1H), 0.81-0.70 (m, 1H), 0.50 (q, J=5.3 Hz, 1H).

[(1R,2S)-2-[(6-aminopurin-9-yl)methyl]cyclopropyl] methyl-N-[(3-phenylphenyl) methylcarbamate was prepared from [(1R,2S)-2-[(6-aminopurin-9-yl)methyl]cyclopropyl] methanol. Yield: 66 mg (77%) of the title compound as a white powder. $^1$H NMR (300 MHz, DMSO-d$_6$) δ 8.17 (s, 1H), 8.14 (s, 1H), 7.78 (t, J=6.0 Hz, 1H), 7.63 (d, J=7.4 Hz, 2H), 7.58-7.22 (m, 9H), 4.39-4.24 (m, 4H), 4.11-3.98 (m, 2H), 1.56-1.42 (m, 1H), 1.40-1.25 (m, 1H), 0.82-0.72 (m, 1H), 0.53 (q, J=5.3 Hz, 1H).

The following procedure illustrates the synthesis of 1,3-cyclohexenyl and cyclohexanyl purine nucleoside analogues.

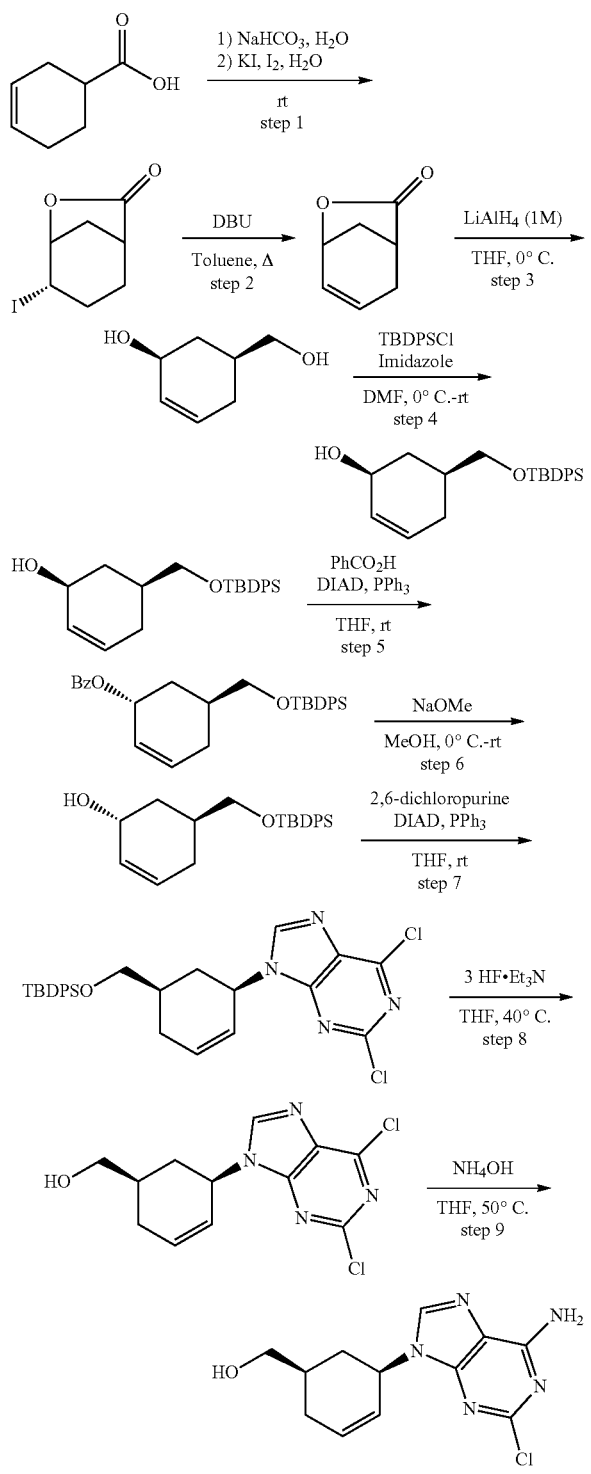

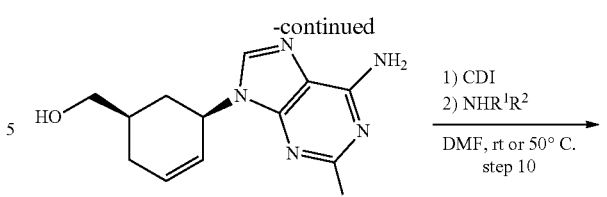

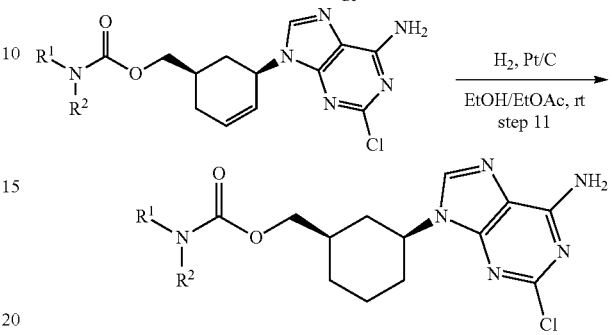

Step 1:

To a stirred solution of sodium hydrogencarbonate (7.50 g, 90 mmol, 3 equiv.) in water (73 mL), was added 3-cyclohexen-1-carboxylic acid (3.78 g, 30 mmol, 1 equiv.). The mixture was stirred at room temperature until it became clear. Then, a solution of potassium iodide (29.90 g, 180 mmol, 6 equiv.) and iodine (7.98 g, 31.50 mmol, 1.05 equiv.) in water (73 mL) was added in one portion and the reaction mixture was protected from light and stirred at room temperature overnight. Extraction with DCM was performed three times and the combined organic layers were washed successively with 10% aqueous of sodium thiosulfate; 10% aqueous sodium hydrogencarbonate and water, dried over Na$_2$SO$_4$, filtered and concentrated under vacuum to give (4S)-4-iodo-6-oxabicyclo[3.2.1]octan-7-one (7.21 g, 95%) as a yellow-white solid.

Step 2:

To a stirred suspension of the iodo intermediate (7.21 g, 28.60 mmol, 1 equiv.) in toluene (72 mL), was added dropwise DBU (6.40 mL, 42.91 mmol, 1.5 equiv.) under azote atmosphere. The mixture was warmed to reflux for 3 hours, and then concentrated under vacuum. The crude was purified by flash column chromatography (50% EtOAc in cyclohexane) to provide 6-oxabicyclo[3.2.1]oct-3-en-7-one (3.35 g, 94%) as a colorless oil. $^1$H NMR (300 MHz, CDCl$_3$) δ 6.26-6.19 (m, 1H), 5.87-5.81 (m, 1H), 4.75 (tt, J=5.5, 1.1 Hz, 1H), 2.93 (m, 1H), 2.57-2.39 (m, 3H), 2.10-2.07 (m, 1H).

Step 3:

To a stirred solution of alkene intermediate (1.68 g, 13.50 mmol, 1 equiv.) in dry THF (70 mL), was added dropwise lithium aluminum hydride (1M in THF, 20 mL, 20 mmol, 1.5 equiv.) at 0° C. under azote atmosphere. The reaction mixture was kept at 0° C. for 1 hours. Then, water (2 mL), 15% aqueous sodium hydroxide (2 mL) and water (5 mL) were successively added, and the mixture was allowed to warm to room temperature and stirred for 2h30. The salts were filtered through a pad of celite and the filtrate was dried over Na$_2$SO$_4$ and concentrated under vacuum to yield (1 S,5S)-5-(hydroxymethyl)cyclohex-2-en-1-ol (1.87 g, quant.) as a colorless oil.

Step 4:

To a stirred solution of the diol intermediate (1.87 g, 13.50 mmol, 1 equiv.) in dry DMF 67 mL), were added imidazole (1.84 g, 27 mmol, 2 equiv.) and tert-butyl(chloro)diphenylsilane (3.51 mL, 13.50 mmol, 1 equiv.) dropwise at 0° C. under azote atmosphere. The reaction mixture was allowed to warm to room temperature and stirred for 1 h30. The mixture was diluted with ethyl acetate and washed with brine. The organic layer was dried over $Na_2SO_4$, filtered and concentrated under vacuum. The residue was purified by flash column chromatography (0-30% EtOAc in cyclohexane) to afford (1 S,5S)-5-[[tert-butyl(diphenyl)silyl]oxymethyl]cyclohex-2-en-1-ol (2.77 g, 56%) as a colorless oil. $^1$H NMR (300 MHz, $CDCl_3$) δ 7.68-7.66 (m, 4H), 7.44-7.37 (m, 6H), 5.81-5.75 (m, 1H), 5.72-5.66 (m, 1H), 4.38-4.29 (m, 1H), 3.57 (d, J=5.8 Hz, 2H), 2.24-2.15 (m, 1H), 2.14-2.04 (m, 1H), 2.00-1.76 (m, 2H), 1.52 (d, J=6.6 Hz, 1H), 1.31-1.20 (m, 1H), 1.07 (s, 9H).

Step 5:

To a stirred solution of the previous intermediate (940 mg, 2.56 mmol, 1 equiv.) in dry THF (13 mL), were added triphenylphosphine (1.35 g, 5.13 mmol, 2 equiv.) and benzoic acid (626 mg, 5.13 mmol, 2 equiv.) under azote atmosphere. Then, DIAD (1 mL, 5.13 mmol, 2 equiv.) was added dropwise. The reaction mixture was left overnight at room temperature. The resulting solution was diluted with ethyl acetate and washed with a saturated solution of sodium hydrogencarbonate. The organic layer was dried over $Na_2SO_4$, filtered and concentrated under vacuum. The crude oil was purified by flash column chromatography (0-5% EtOAc in cyclohexane) to give [(1R,5S)-5-[[tert-butyl(diphenyl)silyl]oxymethyl]cyclohex-2-en-1-yl] benzoate (1.01 g, 84%) as a colorless oil.

Step 6:

The previous intermediate (1.0 g, 2.12 mmol, 1 equiv.) was treated with sodium methoxide (0.5 M in MeOH, 4.7 mL, 2.33 mmol, 1.1 equiv.) in methanol (20 mL) at 0° C. The reaction mixture was allowed to warm to room temperature overnight. Concentration of the crude followed by purification by flash column chromatography (0-30% EtOAc in cyclohexane) provided (1R, 5S)-5-[[tert-butyl(diphenyl)silyl]oxymethyl]cyclohex-2-en-1-ol (606 mg, 78%) as a colorless oil. $^1$H NMR (300 MHz, $CDCl_3$) δ 7.69-7.66 (m, 4H), 7.44-7.37 (m, 6H), 5.95-5.81 (m, 2H), 4.23 (bs, 1H), 3.65-3.54 (m, 2H), 2.26-2.17 (m, 1H), 2.11-1.97 (m, 1H), 1.89-1.77 (m, 2H), 1.59-1.40 (m, 1H), 1.40 (d, J=6.7 Hz, 1H), 1.07 (s, 9H).

Step 7:

To a stirred solution of the alcohol intermediate (600 mg, 1.64 mmol, 1 equiv.) in dry THF (16 mL), were added triphenylphosphine (859 mg, 3.28 mmol, 2 equiv.) and 2,6-dichloropurine (620 mg, 3.28 mmol, 2 equiv.) under azote atmosphere. Then, DIAD (645 µL, 3.28 mmol, 2 equiv.) was added dropwise over 40 minutes. The reaction mixture was stirred at room temperature for 2 hours and then concentrated under vacuum. The residue was purified by flash column chromatography (0-30% EtOAc in cyclohexane) to yield tert-butyl-[[(1R,5R)-5-(2,6-dichloropurin-9-yl)cyclohex-3-en-1-yl]methoxy]-diphenyl-silane (395 mg, 45%) as a white powder, contaminated with 25% of the trans derivative. $^1$H NMR (300 MHz, $CDCl_3$) δ 8.14 (s, cis, 0.75H), 8.12 (s, trans, 0.25H), 7.64-7.54 (m, 4H), 7.43-7.35 (m, 6H), 6.40-6.35 (m, trans, 0.25H), 6.21-6.15 (m, cis, 0.75H), 5.89-5.84 (m, trans, 0.25H), 5.72-5.69 (m, cis, 0.75H), 5.44-5.40 (m, cis, 0.75H), 5.33-5.29 (m, trans, 0.25H), 3.62 (d, J=5.2 Hz, cis, 1.5H), 3.54 (d, J=5.6 Hz, trans, 0.5H), 2.40-1.86 (m, 4H), 1.76-1.44 (m, 1H), 1.05 (s, cis, 6.4H), 0.99 (s, trans, 2.1H).

Step 8:

To a stirred solution of the previous intermediate (231 mg, 0.43 mmol, 1 equiv.) in dry THF (4.3 mL), was added dropwise triethylamine trihydrofluoride (350 µL, 2.15 mmol, 5 equiv.) under azote atmosphere. The reaction mixture was stirred at 40° C. for 24 hours. A saturated solution of sodium hydrogencarbonate was then slowly added until a neutral pH was achieved. The mixture was diluted with ethyl acetate and the aqueous layer was extracted twice with ethyl acetate. The combined organic layers were dried over $Na_2SO_4$, filtered and concentrated under vacuum. A purification of the residue by flash column chromatography (0-10% MeOH in DCM) provided [(1R, 5R)-5-(2,6-dichloropurin-9-yl)cyclohex-3-en-1-yl]methanol (125 mg, 97%) as a white, contaminated with 25% of trans derivative. $^1$H NMR (300 MHz, $CDCl_3$) δ 8.16 (s, 1H), 6.44-6.37 (m, trans, 0.25H), 6.23-6.16 (m, 1H, cis, 0.75H), 5.92-5.86 (m, trans, 0.25H), 5.75-5.72 (m, cis, 0.75H), 5.50-5.43 (m, cis, 0.75H), 5.38-5.34 (m, trans, 0.25H), 3.70-3.55 (m, 2H), 2.51-1.87 (m, 4H), 1.41-1.33 (m, 1H).

Step 9:

To a stirred solution of the previous intermediate (170 mg, 0.57 mmol, 1 equiv.) in dry THF (1.4 mL), was added an aqueous ammonia solution (28%, 1.4 mL). The reaction mixture was warmed to 50° C. overnight and then concentrated under vacuum. A purification of the residue by flash column chromatography (0-10% MeOH in DCM) provided [(1R, 5R)-5-(6-amino-2-chloro-purin-9-yl)cyclohex-3-en-1-yl]methanol (158 mg, 99%) as a white solid, contaminated with 25% of trans derivative. $^1$H NMR (300 MHz, DMSO-$d_6$) δ 8.10 (s, cis, 0.75H), 7.98 (s, trans, 0.25H), 7.75 (bs, 2H), 6.26-6.19 (m, trans, 0.25H), 6.04-5.99 (m, cis, 0.75H), 5.86-5.81 (m, trans, 0.25H), 5.73-5.68 (m, cis, 0.75H), 5.17-5.07 (m, 1H), 4.60 (t, J=4.8 Hz, cis, 0.75H), 4.51-4.48 (m, trans, 0.25H), 3.34-3.32 (m, 2H, overlapped with DMSO), 2.28-1.55 (m, 5H). ESI-MS: 280.2 $(M+H)^+$.

Step 10:

To a stirred solution of the previous intermediate (56 mg, 0.20 mmol, 1 equiv.) in DMF (2 mL), was added carbonyldiimidazole (49 mg, 0.30 mmol, 1.5 equiv.) under azote atmosphere. After 2 hours of stirring at room temperature, the appropriate amine (3 equiv.) was added and the reaction mixture was stirred at room temperature or 50° C. until completion. The solvent was then removed under reduced pressure and the residue purified by flash column chromatography (0-10% MeOH in DCM) and by reverse-phase chromatography (0-100% MeOH in water) to give the carbamate derivative.

The following compounds are examples illustrating this procedure. [(1R,5R)-5-(6-amino-2-chloro-purin-9-yl)cyclohex-3-en-1-yl]methyl N-(1,3-benzodioxol-5-ylmethyl)carbamate was prepared from [(1R,5R)-5-(6-amino-2-chloropurin-9-yl)cyclohex-3-en-1-yl]methanol. Yield: 67 mg (74%) of the title compound as a white powder, along with 25% of the trans derivative. ESI-MS: 457.4 $(M+H)^+$.

[(1R,5R)-5-(6-amino-2-chloro-purin-9-yl)cyclohex-3-en-1-yl]methyl N-[[3-(trifluoromethyl)phenyl]methyl]carbamate was prepared from [(1R,5R)-5-(6-amino-2-chloro-purin-9-yl)cyclohex-3-en-1-yl]methanol. Yield: 40 mg (41%) of the title compound as a white powder, along with 25% of the trans derivative. ESI-MS: 481.4 $(M+H)^+$.

Step 11: To a stirred solution of the previous compound (1 equiv.) in EtOH/EtOAc (30 mL/mmol each), was added 10% platinum on carbon under azote atmosphere. Hydrogen gas via balloon was bubbled for 10 min and the reaction mixture was stirred under hydrogen atmosphere until completion. The mixture was passed through a plug of celite and the solvent was removed under reduced pressure. Purification by flash column chromatography (0-10% MeOH in DCM) and/or by reverse-phase chromatography (0-100% MeOH in water) afforded the expected compound.

The following compound are example illustrating this procedure. [(1R,3S)-3-(6-amino-2-chloro-purin-9-yl)cyclohexyl]methyl-N-(1,3-benzodioxol-5-ylmethyl)carbamate was prepared from [(1R, 5R)-5-(6-amino-2-chloro-purin-9-yl)cyclohex-3-en-1-yl]methanol. Yield: 30 mg (81%) of the title compound as a white powder, along with 25% of the trans derivative. ESI-MS: 459.5 (M+H)$^+$.

The following procedure illustrates the synthesis of 1,4 cyclohexanyl purine nucleoside analogues.

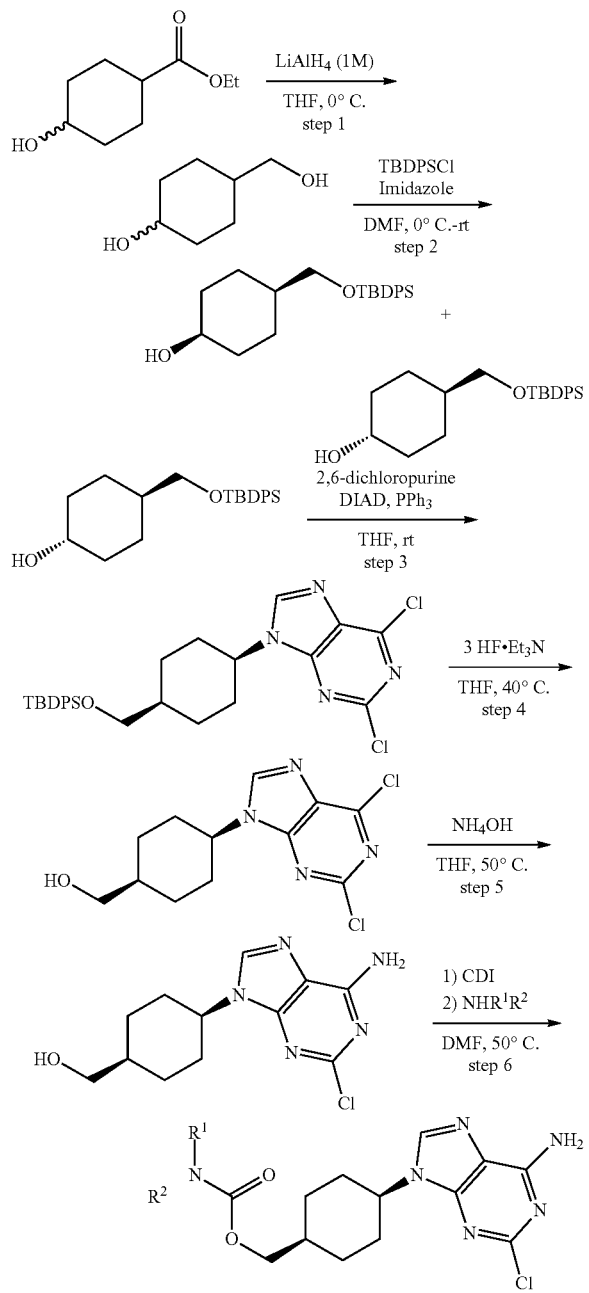

Step 1:
To a stirred solution ethyl 4-hydroxycyclohexanecarboxylate (2.78 g, 16.0 mmol, 1 equiv.) in dry THF (80 mL), was added dropwise lithium aluminum hydride (1M in THF, 24 mL, 24.0 mmol, 1.5 equiv.) at 0° C. under azote atmosphere. The reaction mixture was warmed to room temperature and stirred for 3h30. The mixture was then cooled to 0° C. and water (1 mL), 15% aqueous sodium hydroxide (1 mL) and water (3 mL) were successively added. The mixture was allowed to warm to room temperature and stirred overnight. The salts were filtered through a pad of celite and the filtrate was dried over Na$_2$SO$_4$ and concentrated under vacuum to yield 4-(hydroxymethyl)cyclohexanol (2.10 g, quant.) as a colorless oil.

Step 2:
To a stirred solution of the previous intermediate (755 mg, 5.80 mmol, 1 equiv.) in dry DMF (67 mL), were added imidazole (790 mg, 11.60 mmol, 2 equiv.) and tert-butyl (chloro)diphenylsilane (1.5 mL, 5.80 mmol, 1 equiv.) dropwise at 0° C. under azote atmosphere. The reaction mixture was allowed to warm to room temperature and stirred for 2 hours. The mixture was diluted with ethyl acetate and washed with brine. The organic layer was dried over Na$_2$SO$_4$, filtered and concentrated under vacuum. The residue was purified by flash column chromatography (10-30% EtOAc in cyclohexane) to afford the cis isomer (1 S,4S)-4-(((tert-butyldiphenylsilyl)oxy)methyl) cyclohexan-1-ol (first eluted product, 606 mg) and trans isomer (1R,4R)-4-(((tert-butyldiphenylsilyl)oxy)methyl)cyclohexan-1-ol (second eluted product, 754 mg). $^1$H NMR (300 MHz, CDCl$_3$) 5 cis compound: 7.71-7.69 (m, 4H), 7.47-7.38 (m, 6H), 4.01 (bs, 1H), 3.54 (d, J=6.4 Hz, 2H), 1.74-1.54 (m, 7H), 1.49-1.44 (m, 2H), 1.33-1.27 (m, 2H), 1.08 (s, 9H), trans compound: 7.69-7.67 (m, 4H), 7.47-7.38 (m, 6H), 3.57 (bs, 1H), 3.49 (d, J=6.2 Hz, 2H), 2.04-2.00 (m, 2H), 1.88-1.84 (m, 2H), 1.56-1.48 (m, 1H), 1.44 (bs, 1H), 1.30-1.23 (m, 2H), 1.10-1.03 (m, 10H).

Step 3:
To a stirred solution of the trans isomer (662 mg, 1.80 mmol, 1 equiv.) in dry THF (18 mL), were added triphenylphosphine (944 mg, 3.60 mmol, 2 equiv.) and 2,6-dichloropurine (680 mg, 3.60 mmol, 2 equiv.) under azote atmosphere. Then, DIAD (710 µL, 3.28 mmol, 2 equiv.) was added dropwise over 30 minutes. The reaction mixture was stirred at room temperature overnight and then concentrated under vacuum. The residue was purified by flash column chromatography (0-30% EtOAc in cyclohexane) to yield 9-((1S,4S)-4-(((tert-butyldiphenylsilyl)oxy)methyl)cyclohexyl)-2,6-dichloro-9H-purine (414 mg, 43%) as a colorless oil. $^1$H NMR (300 MHz, CDCl$_3$) δ 7.94 (s, 1H), 7.71-7.67 (m, 4H), 7.50-7.38 (m, 6H), 4.98 (q, J=6.1 Hz, 1H), 3.72 (d, J=7.4 Hz, 2H), 2.06-1.62 (m, 9H), 1.09 (s, 9H), Step 4:
To a stirred solution of the previous intermediate (1.10 g, 2.04 mmol, 1 equiv.) in dry THE (20 mL), was added dropwise triethylamine trihydrofluoride (1.70 mL, 10.20 mmol, 5 equiv.) under azote atmosphere. The reaction mixture was stirred at 40° C. for 24 hours. A saturated solution of sodium hydrogencarbonate was then slowly added until a neutral pH was achieved. The mixture was diluted with ethyl acetate and the aqueous layer was extracted twice with ethyl acetate. The combined organic layers were dried over Na$_2$SO$_4$, filtered and concentrated under vacuum. A purification of the residue by flash column chromatography (0-10% MeOH in DCM) provided ((1 S,4S)-4-(2,6-dichloropurin-9-yl)cyclohexyl)methanol (479 mg, 78%) as a white solid. $^1$H NMR (300 MHz, CDCl$_3$) δ 8.20 (s, 1H), 4.66-4.56 (m, 1H), 3.77 (d, J=7.3 Hz, 2H), 2.19-1.73 (m, 9H).

Step 5:

To a stirred solution of the previous intermediate (301 mg, 1 mmol, 1 equiv.) in dry THF (2.5 mL), was added an aqueous ammonia solution (28%, 2.5 mL). The reaction mixture was warmed to 50° C. overnight and then concentrated under vacuum. A purification of the residue by flash column chromatography (0-10% MeOH in DCM) provided (1 S,4S)-4-(6-amino-2-chloro-purin-9-yl)cyclohexyl)methanol (268 mg, 95%) as a white solid. $^1$H NMR (300 MHz, CDCl$_3$) δ 8.19 (s, 1H), 4.63-4.56 (m, 1H), 3.74 (d, J=7.3 Hz, 2H), 3.47 (s, 1H), 2.17-2.07 (m, 2H), 2.04-1.72 (m, 7H). ESI-MS: 282.3 (M+H).

Step 6:

To a stirred solution of the previous intermediate (56 mg, 0.20 mmol, 1 equiv.) in DMF (2 mL), was added carbonyldiimidazole (49 mg, 0.30 mmol, 1.5 equiv.) under azote atmosphere. After 2 hours of stirring at room temperature, the appropriate amine (3 equiv.) was added and the reaction mixture was stirred at room temperature or 50° C. until completion. The solvent was then removed under reduced pressure and the residue purified by flash column chromatography (0-10% MeOH in DCM) to give the carbamate derivative.

The following compounds are examples illustrating this procedure.

2-[(1 S,4S)-4-(6-amino-2-chloro-purin-9-yl)cyclohexyl] ethyl N-(1,3-benzodioxol-5-ylmethyl)carbamate was prepared from (1 S,4S)-4-(6-amino-2-chloro-purin-9-yl)cyclohexyl)methanol. Yield: 81 mg (89%) of the title compound as a white powder. $^1$H NMR (300 MHz, DMSO-d$_6$) δ 8.33 (s, 1H), 7.71 (bs, 2H), 7.64 (t, J=6.0 Hz, 1H), 6.86-6.80 (m, 2H), 6.74-6.71 (m, 1H), 5.97 (s, 2H), 4.36-4.29 (m, 1H), 4.15-4.07 (m, 4H), 2.09-1.67 (m, 9H).

2-[(1 S,4S)-4-(6-amino-2-chloro-purin-9-yl)cyclohexyl] ethyl-N-[[3-(trifluoromethyl)phenyl]methyl]carbamate was prepared from (1 S,4S)-4-(6-amino-2-chloro-purin-9-yl)cyclohexyl)methanol. Yield: 76 mg (78%) of the title compound as a white powder. $^1$H NMR (300 MHz, DMSO-d$_6$) δ 8.33 (s, 1H), 7.82 (t, J=6.0 Hz, 1H), 7.72 (bs, 2H), 7.62-7.56 (m, 4H), 4.37-4.27 (m, 3H), 4.16 (d, J=7.6 Hz, 2H), 2.08-1.99 (m, 3H), 1.81-1.72 (m, 6H).

Example 11: Preparation of Various Amine Intermediates

Preparation of 4-Benzylaminesulfonamide Derivatives

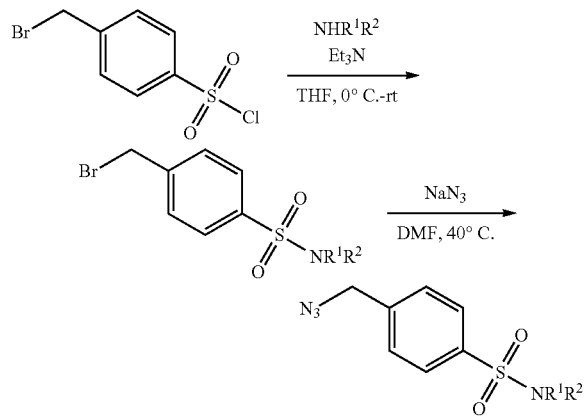

To a stirred solution of 4-(bromomethyl)benzenesulfonyl chloride (1.35 g, 5 mmol, 1 equiv.) in dry THF (20 mL), triethylamine (700 uL, 5 mmol, 1 equiv.) and the appropriate amine (1 equiv.) were added at 0° C. under azote atmosphere. The reaction mixture was allowed to warm to room temperature and stirred until completion. The mixture was then diluted with ethyl acetate and washed with water and brine. The organic layer was dried over Na$_2$SO$_4$, filtered and concentrated under vacuum.

The crude residue was dissolved in dry DMF (10 mL) and treated with sodium azide (390 mg, 6 mmol, 1.2 equiv.) under azote atmosphere. The reaction mixture was stirred at 40° C. overnight. The mixture was then diluted with ethyl acetate and washed with water and brine. The organic layer was dried over Na$_2$SO$_4$, filtered and concentrated under vacuum. Purification of the crude mixture resulted in the expected compound.

The following compounds are examples illustrating this procedure:

4-(azidomethyl)-N-benzyl-benzenesulfonamide was prepared from 4-(bromomethyl)benzenesulfonyl chloride. Yield: 1.18 g (78%) of the title compound as a yellow oil.

4-(azidomethyl)-N-[2-(4-fluorophenyl)ethyl]benzenesulfonamide was prepared from 4-(Bromomethyl)benzenesulfonyl chloride. Yield: 1.39 g (83%) of the title compound as a yellow oil.

4-(azidomethyl)-N-methyl-benzenesulfonamide was prepared from 4-(Bromomethyl)benzenesulfonyl chloride. Yield: 876 mg (78%) of the title compound as a colorless oil.

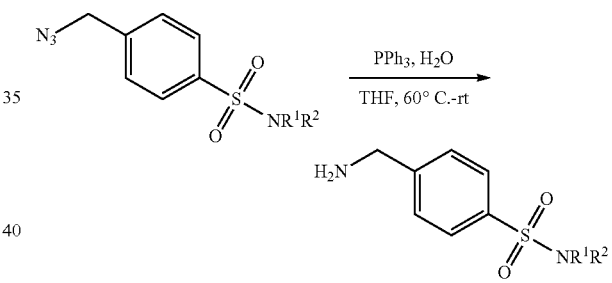

To a stirred solution of azide (1 equiv.) in THF (5 mL/mmol), triphenylphosphine (2 equiv.) was added under azote atmosphere. The reaction mixture was warmed to 60° C. for 1 hr. Water (20 equiv.) was added and the solution was stirred at room temperature overnight. Concentration of the crude mixture under vacuum and purification by flash column chromatography (0-10% MeOH in DCM+2% NH$_4$OH) provided the amino derivative.

The following compounds are examples illustrating this procedure:

4-(aminomethyl)-N-benzyl-benzenesulfonamide was prepared from 4-(azidomethyl)-N-benzyl-benzenesulfonamide (1.18 g, 3.90 mmol). Yield: 1.07 g (99%) of the title compound as a white powder. $^1$H NMR (300 MHz, DMSO-d$_6$) δ 7.77-7.73 (m, 2H), 7.54-7.52 (m, 2H), 7.32-7.20 (m, 5H), 3.94 (s, 2H), 3.79 (s, 2H).

4-(aminomethyl)-N-[2-(4-fluorophenyl)ethyl]benzenesulfonamide was prepared from 4-(azidomethyl)-N-[2-(4-fluorophenyl)ethyl]benzenesulfonamide (1.39 g, 4.16 mmol). Yield: 1.19 g (93%) of the title compound as a white powder. ESI-MS: 212.2 (M+H)$^+$.

4-(aminomethyl)-N-methyl-benzenesulfonamide was prepared from 4-(azidomethyl)-N-methyl-benzenesulfonamide (856 mg, 3.78 mmol). Yield: 546 mg (72%) of the title compound as a white powder. $^1$H NMR (300 MHz, DMSO-$d_6$) δ 7.71-7.68 (m, 2H), 7.56-7.53 (m, 2H), 3.80 (s, 2H), 2.39 (s, 3H).

Preparation of 3-Benzylaminesulfonamide Derivatives

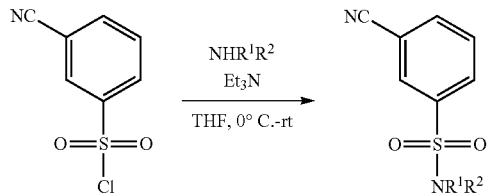

To a stirred solution of 3-cyanobenzenesulfonyl chloride (1 g, 5 mmol) in dry THF (10 mL), triethylamine (700 μL, 5 mmol, 1 equiv.) and the appropriate amine (1 equiv.) were added at 0° C. under azote atmosphere. The reaction mixture was stirred for 1 hr at room temperature, then diluted with ethyl acetate and washed with water and brine. The organic layer was dried over $Na_2SO_4$, filtered and concentrated under vacuum to provide the expected compound which was used without further purification.

The following compounds are examples illustrating this procedure:

N-benzyl-4-cyano-benzenesulfonamide was prepared from 3-cyanobenzene-sulfonyl chloride. Yield: 1.31 g (92%) of the title compound as a white powder.

N-methyl-4-cyano-benzenesulfonamide was prepared from 3-cyanobenzene-sulfonyl chloride. Yield: 899 mg (92%) of the title compound as a yellow oil. 4-morpholinosulfonylbenzonitrile was prepared from 3-cyanobenzene-sulfonyl chloride. Yield: 812 mg (64%) of the title compound as a colorless oil.

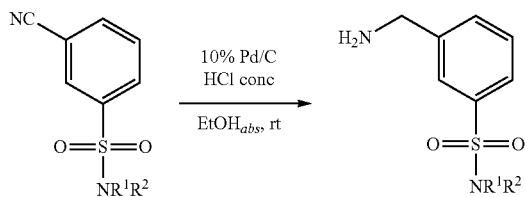

To a stirred solution of 3-cyanobenzenesulfonylamide derivative (1 equiv.) in absolute ethanol (4 mL/mmol) and conc. HCl (0.4 mL/mmol), 10% palladium on carbon (~20 wt %) was added under azote atmosphere. Hydrogen gas was bubbled through the reaction mixture for 10 min and the mixture was stirred overnight under hydrogen atmosphere until completion. The mixture was passed through a plug of celite and the solvent was removed under reduced pressure. Purification by flash column chromatography (0-10% MeOH in DCM+2% $NH_4OH$) yielded the expected compound.

The following compounds are examples illustrating this procedure:

N-benzyl-4-amino-benzenesulfonamide was prepared from N-benzyl-4-cyano-benzenesulfonamide (817 mg, 3 mmol). Yield: 602 mg (73%) of the title compound as a white powder. $^1$H NMR (300 MHz, DMSO-$d_6$) δ 8.49 (bs, 2H), 7.94-7.92 (m, 1H), 7.79-7.77 (m, 2H), 7.68-7.65 (m, 2H), 7.59-7.56 (m, 1H), 4.12 (s, 2H), 2.43 (d, J=4.8 Hz, 3H).

N-methyl-4-amino-benzenesulfonamide was prepared from N-methyl-4-cyano-benzenesulfonamide (450 mg, 2.29 mmol). Yield: 399 mg (87%) of the title compound as a white powder. $^1$H NMR (300 MHz, DMSO-$d_6$) δ 8.50 (bs, 2H), 8.25 (t, J=6.3 Hz, 1H), 7.97-7.96 (m, 1H), 7.82-7.75 (m, 2H), 7.63 (t, J=7.6 Hz, 1H), 7.33-7.20 (m, 5H), 4.11 (s, 2H), 4.00 (d, J=6.0 Hz, 2H).

(4-morpholinosulfonylphenyl)methanamine was prepared from 4-morpholinosulfonylbenzonitrile (812 mg, 3.13 mmol). Yield: 714 mg (89%) of the title compound as a colorless oil.

General Procedure for Boc Protection

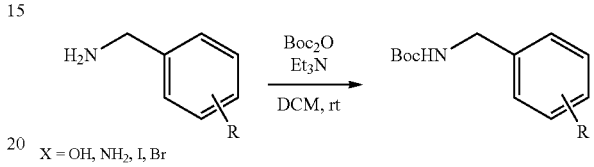

X = OH, $NH_2$, I, Br

To a stirred solution of benzylamine derivative (1 equiv.) in dry DCM, triethylamine (1.5 equiv.) and di-tert-butyl dicarbonate (1-1.2 equiv.) were added under azote atmosphere. The reaction mixture was stirred at room temperature until completion. Water was then added, the phases were separated and the aqueous phase was extracted once with DCM. The combined organic layers were washed with brine, dried over $Na_2SO_4$, filtered and concentrated under vacuum. The crude mixture was then purified by flash column chromatography (0-10% MeOH in DCM) to provide the expected compound.

The following compounds are examples illustrating this procedure:

Tert-butyl N-[(3-bromophenyl)methyl]carbamate was prepared from 3-bromobenzylamine (2 g, 10.75 mmol). Yield: 2.47 g (80%) of the title compound as a white powder.

Tert-butyl N-[(4-aminophenyl)methyl]carbamate was prepared from 4-aminobenzylamine (2 g, 16.37 mmol). Yield: 3.275 g (90%) of the title compound as a white powder. ESI-MS: 223.3 (M+H)$^+$.

Tert-butyl N-[(3-hydroyphenyl)methyl]carbamate was prepared from 3-(aminomethyl)phenol (1 g, 8.12 mmol), Yield: 1.281 g (70%) of the title compound as a yellow oil. $^1$H NMR (300 MHz, CDCl$_3$) δ 7.17 (t, J=7.8 Hz, 1H), 6.81-6.72 (m, 3H), 4.89 (bs, 1H), 4.25 (s, 2H), 1.46 (s, 9H).

Tert-butyl N-[(4-hydroyphenyl)methyl]carbamate was prepared from 4-hydroxybenzylamine (2 g, 16.24 mmol). Yield: 3.17 g (87%) of the title compound as a colorless oil. $^1$H NMR (300 MHz, CDCl$_3$) δ 7.08 (d, J=8.1 Hz, 2H), 6.89-6.74 (m, 2H), 4.87 (bs, 1H), 4.20 (s, 2H), 1.46 (s, 9H).

Tert-butyl N-[(3-iodophenyl)methyl]carbamate was prepared from 3-iodobenzylamine (1.18 g, 5.06 mmol). Yield: 1.42 g (84%) of the title compound as a white powder.

Tert-butyl N-[(4-iodophenyl)methyl]carbamate was prepared from 4-iodobenzylamine (967 mg, 4.15 mmol). Yield: 1.25 g (91%) of the title compound as a white powder.

Preparation of 4-benzylaminesulfonamide Derivatives "Inverse"

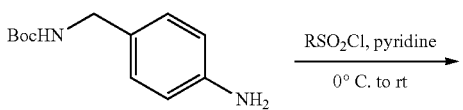

-continued

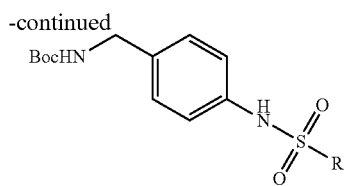

To a stirred solution of tert-butyl N-[(4-aminophenyl)methyl]carbamate (300 mg, 1.35 mmol) in dry pyridine (2.7 mL), the appropriate sulfonyl chloride (1.2 equiv.) was added dropwise at 0° C. under azote atmosphere. The reaction mixture was stirred at room temperature until completion. The mixture was then diluted with ethyl acetate and washed with saturated aqueous solution of ammonium chloride. The organic layer was dried over $Na_2SO_4$, filtered and concentrated under vacuum. The crude mixture was then purified by flash column chromatography (cyclohexane/EtOAc) to provide the expected compound.

The following compounds are examples illustrating this procedure:

Tert-butyl N-[[4-(methanesulfonamido)phenyl]methyl]carbamate was prepared from tert-butyl N-[(4-aminophenyl)methyl]carbamate, Yield: 405 mg (100%) of the title compound as a light brown powder. ESI-MS: 299.4 (M–H)⁻.

Tert-butyl N-[[4-(isobutylsulfonylamino)phenyl]methyl]carbamate was prepared from tert-butyl N-[(3-aminophenyl)methyl]carbamate. Yield: 446 mg (97%) of the title compound as a white powder. ESI-MS: 341.4 (M–H).

Tert-butyl N-[[4-(benzenesulfonamido)phenyl]methyl]carbamate was prepared from tert-butyl N-[(4-aminophenyl)methyl]carbamate. Yield: 450 mg (92%) of the title compound as a white powder. ESI-MS: 361.4 (M–H)⁻.

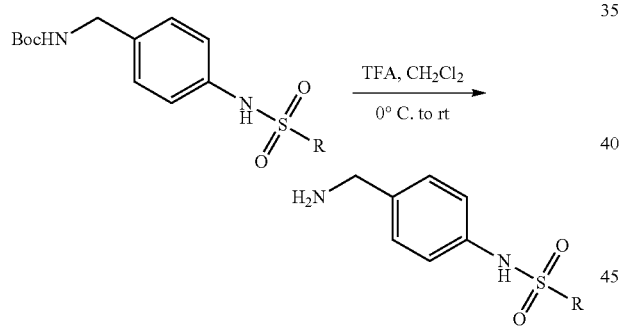

To a stirred solution of carbamate (1 equiv.) in dry DCM TFA (13 equiv.) was added at 0° C. The reaction mixture was stirred at room temperature for 2h. The mixture was quenched with a saturated aqueous solution of sodium bicarbonate and the product was extracted with DCM. The organic layers were dried over $Na_2SO_4$, filtered and concentrated under vacuum to provide the expected compound which was used without further purification.

The following compounds are examples illustrating this procedure:

N-[4-(aminomethyl)phenyl]methanesulfonamide was prepared from tert-butyl N-[[4-(methanesulfonamido)phenyl]methyl]carbamate (230 mg, 0.77 mmol)). Yield: 128 mg (84%) of the title compound as a yellow powder.

N-[4-(aminomethyl)phenyl]-2-methyl-propane-1-sulfonamide was prepared from tert-butyl N-[[4-(isobutylsulfonylamino)phenyl]methyl]carbamate (260 mg, 0.76 mmol)). Yield: 190 mg (100%) of the title compound as a white powder.

N-[4-(aminomethyl)phenyl]benzenesulfonamide was prepared from tert-butyl N-[[4-(benzenesulfonamido)phenyl]methyl]carbamate (275 mg, 0.76 mmol)). Yield: 170 mg (85%) of the title compound as a white powder.

Preparation of 3 and 4-alkoxybenzylamine Derivatives

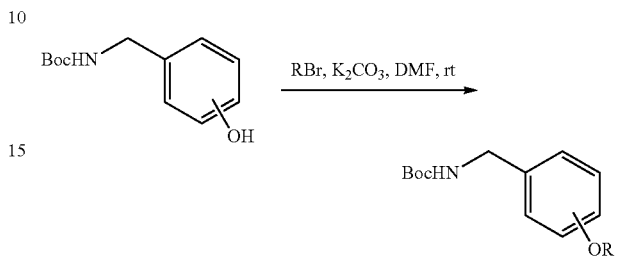

To a stirred solution of phenol (300 mg, 1.34 mmol) in DMF (13 mL), $K_2CO_3$ (557 mg, 4.03 mmol) was added under azote atmosphere. The appropriate alkyl bromide (1.1 equiv.) was then added and the reaction mixture was stirred at room temperature for 48h. The mixture was concentrated under vacuum. The crude mixture was then purified by flash column chromatography (cyclohexane/EtOAc) to provide the expected compound.

The following compounds are examples illustrating this procedure:

Tert-butyl N-[(3-isopentyloxyphenyl)methyl]carbamate was prepared from tert-butyl N-[(3-hydroyphenyl)methyl]carbamate (300 mg, 1.34 mmol). Yield: 346 mg (88%) of the title compound as a colorless oil. ESI-MS: 294.2 (M+H)⁺.

Tert-butyl N-[(4-isopentyloxyphenyl)methyl]carbamate was prepared from tert-butyl N-[(4-hydroyphenyl)methyl]carbamate (500 mg, 2.24 mmol). Yield: 565 mg (86%) of the title compound as a colorless oil.

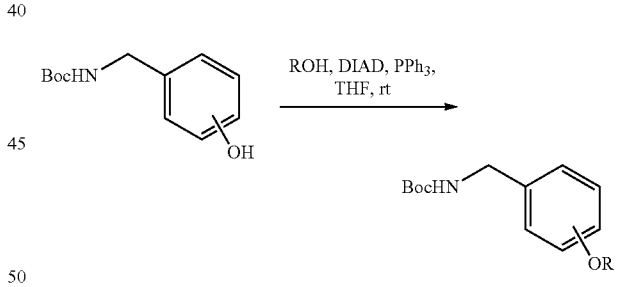

To a stirred solution of phenol (200 mg, 0.90 mmol) in dry THF (7 mL), triphenylphosphine (470 mg, 1.79 mmol) was added under azote atmosphere. The mixture was cooled and the corresponding alcohol (2 equiv.) was added. DIAD (0.353 mL, 1.79 mmol) was then added dropwise and the reaction mixture was stirred at room temperature overnight. The mixture was concentrated under vacuum. The crude mixture was then purified by flash column chromatography (cyclohexane/EtOAc) provide afford the expected compound.

The following compounds are examples illustrating this procedure:

Tert-butyl N-[(3-isobutoxyphenyl)methyl]carbamate was prepared from tert-butyl N-[(3-hydroyphenyl)methyl]carbamate (200 mg, 0.90 mmol). Yield: 145 mg (58%) of the title compound as a yellow oil. ESI-MS: 280.2 (M+H)⁺.

Tert-butyl N-[(4-isobutoxyphenyl)methyl]carbamate was prepared from tert-butyl N-[(4-hydroyphenyl)methyl]carbamate (500 mg, 2.24 mmol). Yield: 503 mg (80%) of the title compound as a white powder.

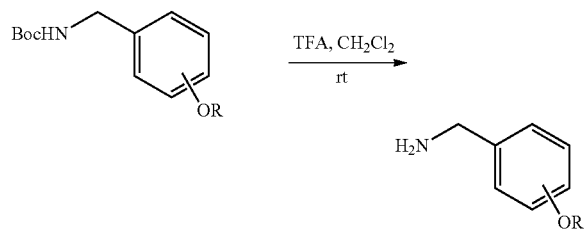

To a stirred solution of carbamate (1 equiv.) in dry DCM, TFA (10 equiv.) was added. The reaction mixture was stirred at room temperature for 2h. The mixture was quenched with a saturated aqueous solution of sodium bicarbonate and the product was extracted with DCM. The organic layers were dried over $Na_2SO_4$, filtered and concentrated under vacuum to provide the expected compound which was used without further purification.

The following compounds are examples illustrating this procedure:

(3-isopentyloxyphenyl)methanamine was prepared from tert-butyl N-[(3-isopentyloxyphenyl)methyl]carbamate (346 mg, 1.18 mmol). Yield: 228 mg (100%) of the title compound as a yellow oil.

(4-isopentyloxyphenyl)methanamine was prepared from tert-butyl N-[(4-isopentyloxyphenyl)methyl]carbamate (200 mg, 0.72 mmol). Yield: 120 mg (100%) of the title compound as a colorless oil.

Preparation of 3 and 4-alkylaminobenzylamine Derivatives

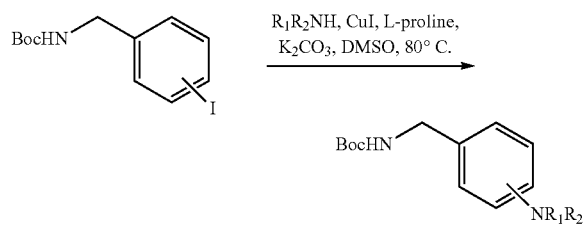

A mixture of a iodo derivative (300 mg, 0.90 mmol), CuI (26 mg, 0.14 mmol), L-proline (26 mg, 0.23 mmol), $K_2CO_3$ (498 mg, 3.60 mmol), the appropriate amine (4 equiv.) in DMSO (6 mL) under azote atmosphere was stirred at 80° C. until completion. Water was added and product was extracted with EtOAc. The organic layers were dried over $Na_2SO_4$, filtered and concentrated under vacuum. The crude was then purified by flash column chromatography (cyclohexane/EtOAc) to afford the expected compound.

The following compounds are examples illustrating this procedure:

Tert-butyl N-[(3-pyrrolidin-1-ylphenyl)methyl]carbamate was prepared from tert-butyl N-[(3-iodophenyl)methyl]carbamate (300 mg, 0.90 mmol). Yield: 205 mg (82%) of the title compound as a white powder. ESI-MS: 277.2 (M+H)+.

Tert-butyl N-[(4-pyrrolidin-1-ylphenyl)methyl]carbamate was prepared from tert-butyl N-[(4-iodophenyl)methyl]carbamate (300 mg, 0.90 mmol). Yield: 229 mg (92%) of the title compound as a white powder.

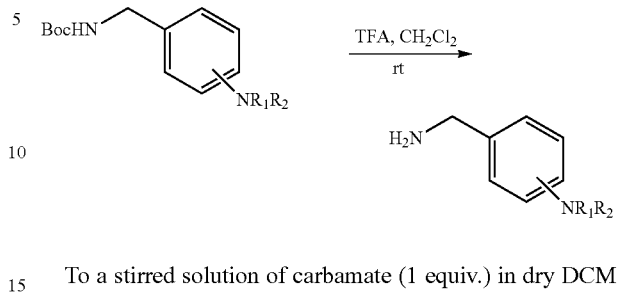

To a stirred solution of carbamate (1 equiv.) in dry DCM TFA (10 equiv.) was added. The reaction mixture was stirred at room temperature for 2h. The mixture was quenched with a saturated aqueous solution of sodium bicarbonate and the product was extracted with DCM. The organic layers were dried over $Na_2SO_4$, filtered and concentrated under vacuum to provide the expected compound which was used without further purification.

The following compounds are examples illustrating this procedure:

(3-pyrrolidin-1-ylphenyl)methanamine was prepared from tert-butyl N-[(3-pyrrolidin-1-ylphenyl)methyl]carbamate (203 mg, 0.74 mmol). Yield: 130 mg (100%) of the title compound as a brown oil.

(4-pyrrolidin-1-ylphenyl)methanamine was prepared from tert-butyl N-[(4-pyrrolidin-1-ylphenyl)methyl]carbamate (150 mg, 0.54 mmol). Yield: 100 mg (100%) of the title compound as a yellow oil.

Preparation of imidazo[1,2-a]pyridine Benzylamine Derivatives

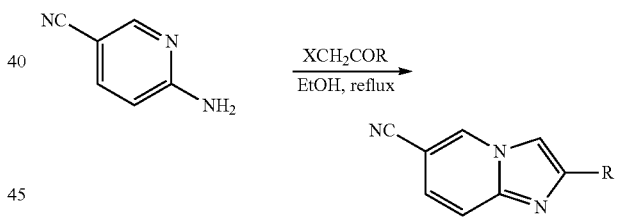

Imidazo[1,2-a]pyridine-6-carbonitrile: To a solution of 6-aminonicotinonitrile (2.38 g, 20 mmol) in absolute EtOH (50 mL), was added the chloroacetaldehyde (50% in water, 12.7 mL, 100 mmol). The reaction was refluxed for 5h and then concentrated. The resulting yellow solid was dissolved in water (20 mL) and saturated $NaHCO_3$ solution was added until precipitation (pH=8). The precipitate was then collected and dried over KOH to afford the title compound (1.56 g, 55%) as a yellow powder. ESI-MS: 144.2 (M+H)+.

2-phenylimidazo[1,2-a]pyridine-6-carbonitrile: To a solution of 6-aminonicotinonitrile (1.12 g, 10 mmol) in absolute EtOH (50 mL), was added the 2-bromoacetophenone (1.99 g, 10 mmol). The reaction was refluxed for 24h (conversion 50%) and then concentrated. The resulting yellow solid was dissolved in water and saturated $NaHCO_3$ solution was added until precipitation (pH=8). The precipitate was then collected and dried over KOH to afford a beige solid. The mother liquid was concentrated and purified by flash column chromatography (0-50% EtOAc in cyclohexane) to give the title compound (654 mg, 30%).

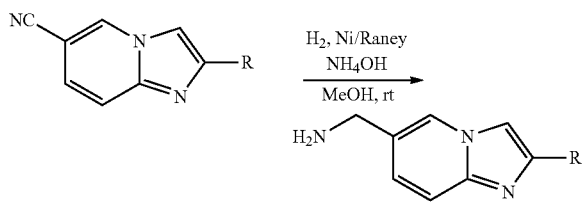

To a stirred solution of imidazo[1,2-a]pyridine-6-carbonitrile analogue (2 mmol) in MeOH (5 mL), Raney nickel (slurry in water, 1 g) and aqueous ammonia (2 mL) were added under azote atmosphere. Hydrogen gas was bubbled through the reaction mixture for 10 min and the mixture was stirred overnight under hydrogen atmosphere. The mixture was passed carefully through a plug of celite and concentrated to yield the expected compound in a quantitative yield.

Preparation of Benzofuran Derivatives

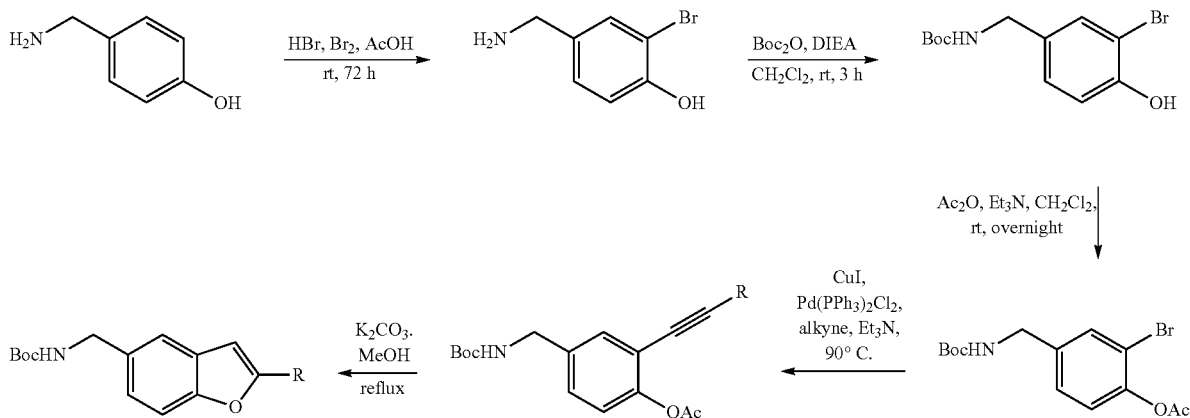

To a suspension of 4-hydroxybenzylamine (1 g, 8.12 mmol) in AcOH, HBr (33% in AcOH, 4 mL) and a solution of $Br_2$ (0.458 mL, 8.93 mmol) in AcOH (2.8 mL) were successively added over 1 h. The reaction mixture was stirred at room temperature for 48h. The precipitate was filtered and washed several times with AcOH and $Et_2O$ to obtain 4-(aminomethyl)-2-bromophenol.HBr as a white powder (1.785 g, 78%). $^1$H NMR (300 MHz, DMSO-$d_6$) δ 10.45 (s, 1H), 8.06 (bs, 3H), 7.63 (d, J=2.1 Hz, 1H), 7.26 (dd, J=8.4, 2.1 Hz, 1H), 6.97 (d, J=8.4 Hz, 1H), 3.93-3.89 (m, 2H).

To a stirred solution of the previous intermediate (1.755 g, 6.20 mmol) in dry DCM (20 mL) diisopropylethylamine (3.24 mL, 18.61 mmol) and di-tert-butyl dicarbonate (1.57 mL, 6.82 mmol) were added under azote atmosphere. The reaction mixture was stirred at room temperature for 3h. Water was added and the product was extracted with DCM. The organic layers were dried over $Na_2SO_4$, filtered and concentrated under vacuum. The crude mixture was then purified by flash column chromatography (cyclohexane/EtOAc) to provide tert-butyl N-[(3-bromo-4-hydroxyphenyl)methyl]-carbamate as a colorless oil (1.795 g, 95%). ESI-MS: 301.9-303.9 (M+H)$^+$.

To a stirred solution of the previous intermediate (1.795 g, 5.94 mmol) in dry DCM (35 mL) triethylamine (2.49 mL, 17.82 mmol) and acetic anhydride (0.62 mL, 6.53 mmol) were added under azote atmosphere. The reaction mixture was stirred overnight at room temperature. Water was added and the product was extracted with DCM. The organic layers were dried over $Na_2SO_4$, filtered and concentrated under vacuum. The crude mixture was then purified by flash column chromatography (cyclohexane/EtOAc) to afford [2-bromo-4-[(tert-butoxycarbonylamino)methyl]phenyl] acetate as a white powder (1.780 g, 87%). ESI-MS: 341.9-343.9 (M−H)$^-$.

To a mixture of the previous intermediate (1 g, 2.91 mmol), CuI (55 mg, 0.29 mmol), Pd(PPh$_3$)$_2$Cl$_2$ (102 mg, 0.15 mmol), the appropriate alkyne (1.5 equiv.) in Et$_3$N (10 mL) were added under azote atmosphere and stirred at 90° C. until completion. The mixture was concentrated under vacuum. The crude mixture was then purified by flash column chromatography (cyclohexane/EtOAc) to provide the expected compound. The coupling product was dissolved in MeOH (15 mL) and $K_2CO_3$ (1.5 equiv.) was added and the mixture was stirred under reflux until completion. Water was added and the product was extracted with DCM. The organic layers were dried over $Na_2SO_4$, filtered and concentrated under vacuum. The crude mixture was then purified by flash column chromatography (cyclohexane/EtOAc) to provide the expected compound.

The following compounds are examples illustrating this procedure:

Tert-butyl N-[(2-cyclopropylbenzofuran-5-yl)methyl]carbamate was prepared from [2-bromo-4-[(tert-butoxycarbonylamino)methyl]phenyl] acetate (1 g, 2.91 mmol). Yield: 238 mg (29%) of the title compound as a white powder. $^1$H NMR (300 MHz, CDCl$_3$) δ 7.35 (d, J=1.5 Hz, 1H), 7.30 (d, J=8.4 Hz, 1H), 7.09 (dd, J=8.4, 1.5 Hz, 1H), 6.31 (s, 1H), 4.81 (bs, 1H), 4.35 (s, 2H), 2.06-1.97 (m, 1H), 1.46 (s, 9H), 1.00-0.93 (m, 4H).

Tert-butyl N-[(2-phenylbenzofuran-5-yl)methyl]carbamate was prepared from [2-bromo-4-[(tert-butoxycarbonylamino)methyl]phenyl] acetate (1 g, 2.91 mmol). Yield: 226 mg (24%) of the title compound as a white powder. $^1$H NMR (300 MHz, CDCl$_3$) δ 7.88-7.85 (m, 2H), 7.50-7.42 (m, 4H), 7.38-7.33 (m, 1H), 7.20 (dd, J=8.4, 1.5 Hz, 1H), 6.99 (d, J=0.6 Hz, 1H), 4.86 (bs, 1H), 4.39 (s, 2H), 1.48 (s, 9H).

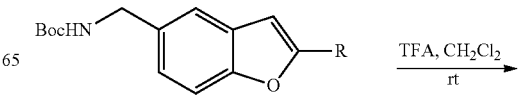

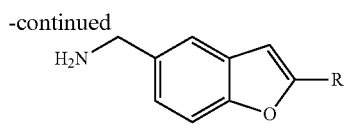

To a stirred solution of benzofuran (1 equiv.) in dry DCM, TFA (10 equiv.) was added. The reaction mixture was stirred at room temperature for 2h. The mixture was quenched with a saturated aqueous solution of sodium bicarbonate and the product was extracted with DCM. The organic layers were dried over $Na_2SO_4$, filtered and concentrated under vacuum to provide the expected compound which was used without further purification.

The following compounds are examples illustrating this procedure:

(2-cyclopropylbenzofuran-5-yl)methanamine was prepared from tert-butyl N-[(2-cyclopropylbenzofuran-5-yl) methyl]carbamate (185 mg, 0.64 mmol). Yield: 122 mg (100%) of the title compound as a yellow oil.

(2-phenylbenzofuran-5-yl)methanamine was prepared from tert-butyl N-[(2-phenylbenzofuran-5-yl)methyl]carbamate (150 mg, 0.46 mmol). Yield: 105 mg (100%) of the title compound as a white powder.

Preparation of Benzimidazole Derivatives centrated under vacuum. The crude mixture was then purified by flash column chromatography (cyclohexane/EtOAc) to provide the expected compound as an orange oil (745 mg, 74%, 2 steps). ESI-MS: 236.2 (M+H)$^+$.

To a mixture of the previous intermediate (733 mg, 3.12 mmol), $PPh_3$ (1.06 g, 4.05 mmol), $H_2O$ (0.43 mL) and THF (20 mL) was added and stirred at 60° C. for 2h. The mixture was concentrated under vacuum. The crude mixture was then purified by flash column chromatography (DCM/MeOH) to provide the expected compound as an orange oil (565 mg, 87%).

To a stirred solution of the previous intermediate (565 mg, 2.70 mmol) in dry DCM (18 mL) triethylamine (0.83 mL, 5.94 mmol) and di-tert-butyl dicarbonate (0.62 mL, 2.70 mmol) were added under azote atmosphere. The reaction mixture was stirred at room temperature for 2h. Water was added and the product was extracted with DCM. The organic layers were dried over $Na_2SO_4$, filtered and concentrated under vacuum. The crude mixture was then purified by flash column chromatography (cyclohexane/EtOAc) to provide the expected compound as an orange powder (800 mg, 96%).

To a mixture of the previous intermediate (800 mg, 2.59 mmol) in MeOH (20 mL), 10% Pd/C (80 mg) was added. After stirring under a hydrogen atmosphere for 3h, the reaction mixture was filtered through a pad of Celite, rinsed with MeOH, and concentrated under reduced pressure to

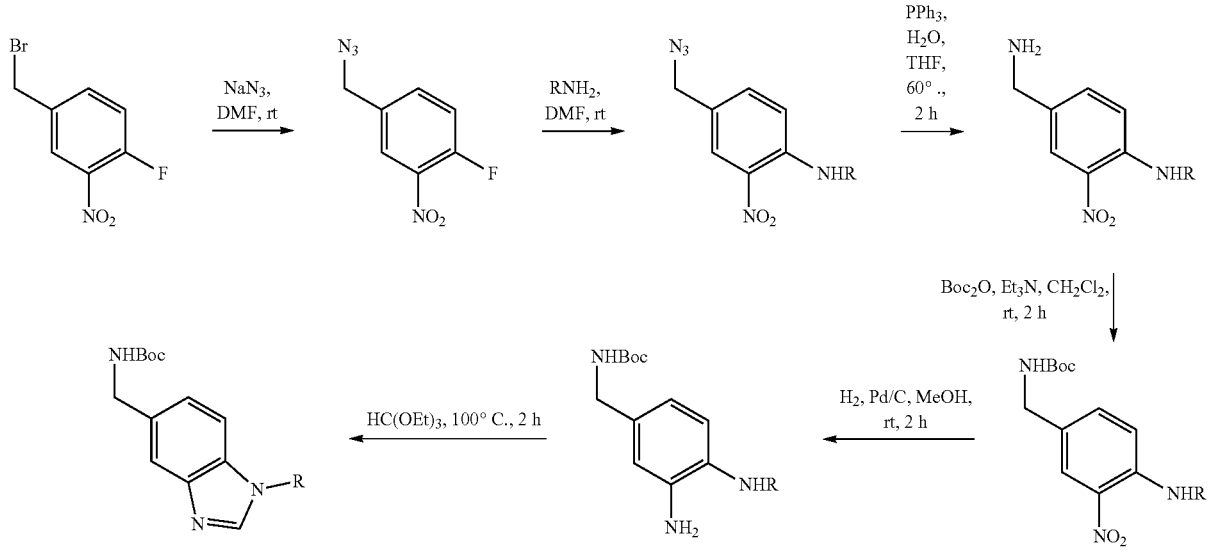

To a stirred solution of 4-fluoro-3-nitrobenzyl bromide (1 g, 4.27 mmol) in DMF (34 mL) sodium azide (333 mg, 5.13 mmol) was added under azote atmosphere. The reaction mixture was stirred overnight at room temperature. Water was added and the product was extracted with EtOAc. The organic layers were dried over $Na_2SO_4$, filtered and concentrated under vacuum to provide 4-(azidomethyl)-1-fluoro-2-nitrobenzene as an orange oil. The compound was used without further purification.

To a stirred solution of the previous intermediate (912 mg) in DMF (35 mL), isopropylamine (0.55 mL, 6.41 mmol) was added under azote atmosphere. The reaction mixture was stirred at room temperature until completion. Water was added and the product was extracted with EtOAc. The organic layers were dried over $Na_2SO_4$, filtered and con-provide the expected compound as purple oil which was used without further purification.

A mixture of the previous intermediate (753 mg) and triethyl orthoformate (13 mL) was stirred at 100° C. for 2h. The mixture was concentrated under vacuum. The crude mixture was then purified by flash column chromatography (DCM/MeOH) to provide tert-butyl N-[(1-isopropylbenzimidazol-5-yl)methyl]carbamate as white powder (653 mg, 87%, 2 steps). $^1$H NMR (300 MHz, CDCl$_3$) δ 8.19 (s, 1H), 7.74 (s, 1H), 7.42 (d, J=8.4 Hz, 1H), 7.30 (d, J=8.4 Hz, 1H), 4.67 (sept, J=6.6 Hz, 1H), 4.44 (d, J=5.7 Hz, 2H), 1.64 (d, J=6.6 Hz, 6H), 1.46 (s, 9H).

The following compound is an example illustrating this procedure:

Tert-butyl N-[(1-methylbenzimidazol-5-yl)methyl]carbamate: light brown powder. $^1$H NMR (300 MHz, CDCl$_3$) δ

8.03 (s, 1H), 7.70 (s, 1H), 7.36 (d, J=8.4 Hz, 1H), 7.29 (d, J=8.4 Hz, 1H), 4.43 (d, J=5.7 Hz, 2H), 3.86 (s, 3H), 1.46 (s, 9H).

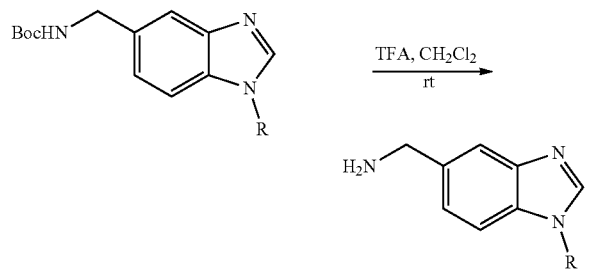

To a stirred solution of the protected benzimidazole (1 equiv.) in dry DCM TFA (10 equiv.) was added. The reaction mixture was stirred at room temperature for 2h. The mixture was quenched with a saturated aqueous solution of sodium bicarbonate and the product was extracted with DCM. The organic layers were dried over $Na_2SO_4$, filtered and concentrated under vacuum to provide the expected compound which was used without further purification.

The following compounds are examples illustrating this procedure:

(1-isopropylbenzimidazol-5-yl)methanamine was prepared from tert-butyl N-[(1-isopropylbenzimidazol-5-yl)methyl]carbamate (200 mg, 0.64 mmol). Yield: 131 mg (100%) of the title compound as a brown oil.

(1-methylbenzimidazol-5-yl)methanamine was prepared from tert-butyl N-[(1-methylbenzimidazol-5-yl)methyl]carbamate (150 mg, 0.57 mmol). Yield: 160 mg (87%) of the title compound as a light brown powder.

crude mixture was then purified by flash column chromatography (cyclohexane/EtOAc) to provide the expected compound.

The following compounds are examples illustrating this procedure:

5-bromo-N-isopentyl-2-nitroaniline was prepared from 5-bromo-2-nitroaniline (100 mg, 0.46 mmol). Yield: 126 mg (95%) of the title compound as a yellow oil. ESI-MS: 286.9-288.9 (M+H)$^+$.

5-bromo-N-isobutyl-2-nitroaniline was prepared from 5-bromo-2-nitroaniline (600 mg, 2.76 mmol). Yield: 426 mg (56%) of the title compound as a red oil. ESI-MS: 273.0-275.0 (M+H)$^+$.

To a stirred solution of the previous intermediate (426 mg, 1.56 mmol) in DMF (6.6 mL) zinc cyanide (238 mg, 2.03 mmol) was added under azote atmosphere. Pd(PPh$_3$)$_4$ (180 mg, 0.16 mmol) was added and the reaction mixture was stirred overnight at 90° C. The mixture was concentrated under vacuum. The crude mixture was then purified by flash column chromatography (cyclohexane/EtOAc) to provide the expected compound.

The following compounds are examples illustrating this procedure:

3-isopentylamino-4-nitrobenzonitrile was prepared from 5-bromo-N-isopentyl-2-nitroaniline (602 mg, 2.10 mmol). Yield: 440 mg (90%) of the title compound as an orange powder. ESI-MS: 234.1 (M+H)$^+$.

3-isobutylamino-4-nitrobenzonitrile was prepared from 5-bromo-N-isobutyl-2-nitroaniline (426 mg, 1.56 mmol). Yield: 315 mg (92%) of the title compound as red powder.

3-isopropylamino-4-nitrobenzonitrile: To a stirred solution of 3-fluoro-4-nitrobenzonitrile (500 mg, 3.01 mmol) in DMF (7 mL), isopropylamine (0.39 mL, 4.51 mmol) was added under azote atmosphere. The reaction mixture was stirred at room temperature until completion. Water was added and the product was extracted with EtOAc. The organic layers were dried over $Na_2SO_4$, filtered and concentrated under vacuum. The crude was then purified by flash column chromatography (cyclohexane/EtOAc) to provide the expected compound as a red powder. ESI-MS: 205.2 (M+H)$^+$.

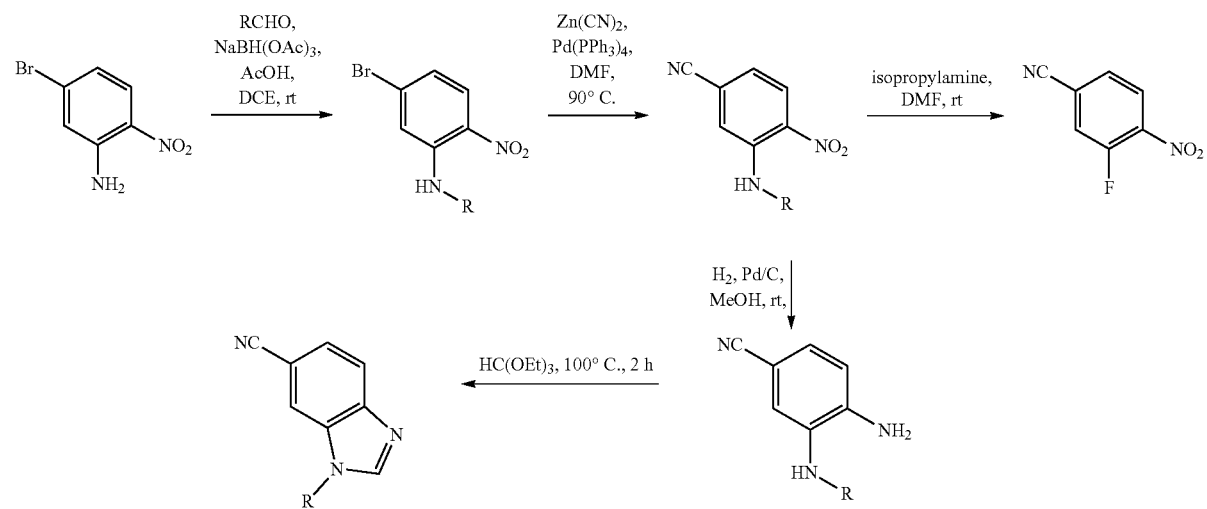

To a suspension of 5-bromo-2-nitroaniline (100 mg, 0.46 mmol) in DCE (1.2 mL) and AcOH (0.16 mL, 2.72 mmol) the appropriate aldehyde (1.9 equiv.) was added under azote atmosphere. NaBH(OAc)$_3$ (273 mg, 1.29 mmol) was added and the reaction mixture was stirred at room temperature until completion. The mixture was quenched with a saturated aqueous solution of sodium bicarbonate and the product was extracted with DCM. The organic layers were dried over $Na_2SO_4$, filtered and concentrated under vacuum. The To a mixture of nitrobenzonitrile (440 mg, 1.89 mmol) in MeOH (15 mL), 10% Pd/C (44 mg) was added. After stirring overnight under a hydrogen atmosphere, the reaction mixture was filtered through a pad of Celite, rinsed with MeOH, and concentrated under reduced pressure to afford the expected compound as a light brown powder which was used without further purification. This intermediate and triethyl orthoformate (9.5 mL) was stirred at 100° C. for 2h. The mixture was concentrated under vacuum. The crude mixture was then purified by flash column chromatography (DCM/MeOH) to provide the expected compound.

The following compounds are examples illustrating this procedure:

3-isopentylbenzimidazole-5-carbonitrile was prepared from 3-isopentylamino-4-nitrobenzonitrile (440 mg, 1.44 mmol). Yield: 266 mg (93% 2 steps) of the title compound as light brown powder. ESI-MS: 214.2 (M+H)$^+$.

3-isobutylbenzimidazole-5-carbonitrile was prepared from 3-isobutylamino-4-nitrobenzonitrile (315 mg, 1.89 mmol). Yield: 341 mg (85% 2 steps) of the title compound as light brown powder. ESI-MS: 200.2 (M+H)$^+$.

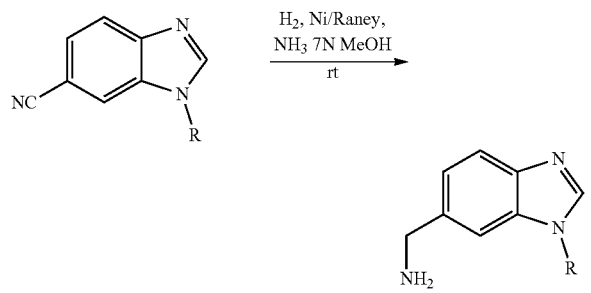

To a mixture of benzimidazole (190 mg, 0.89 mmol) in ammonia (solution 7N in MeOH, 9 mL) Raney nickel (slurry in water, 1 g) was added. After stirring overnight under a hydrogen atmosphere, the reaction mixture was filtered through a pad of Celite, rinsed with MeOH, and concentrated under reduced pressure to provide the expected compound which was used without further purification.

The following compounds are examples illustrating this procedure:

(3-isopentylbenzimidazol-5-yl)methanamine was prepared from 3-isopentylbenzimidazole-5-carbonitrile (190 mg, 0.89 mmol). Yield: 195 mg (100%) of the title compound as a green oil.

(3-isobutylbenzimidazol-5-yl)methanamine was prepared from 3-isobutylbenzimidazole-5-carbonitrile (175 mg, 0.88 mmol). Yield: 180 mg (100%) of the title compound as an orange oil.

Preparation of Indole Derivatives

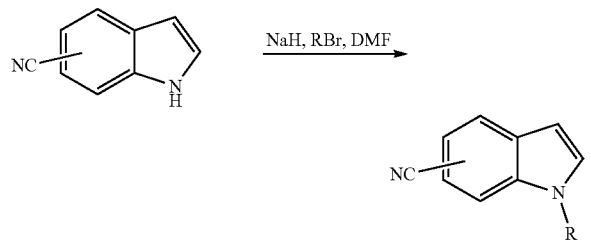

To a stirred solution of indole (500 mg, 3.52 mmol) in DMF (8.7 mL), NaH (60% in mineral oil, 211 mg, 5.28 mmol) was added under azote atmosphere. The reaction mixture was stirred at 50° C. for 1 h. The mixture was cooled to room temperature and the appropriate alkyl bromide (1.5 equiv.) was added. The reaction mixture was stirred at room temperature overnight. Water was added and the product was extracted with EtOAc. The organic layers were dried over Na$_2$SO$_4$, filtered and concentrated under vacuum. The crude mixture was then purified by flash column chromatography (cyclohexane/EtOAc) to provide the expected compound.

The following compounds are examples illustrating this procedure:

1-isobutylindole-5-carbonitrile was prepared from 5-cyanoindole (500 mg, 3.52 mmol). Yield: 680 mg (98%) of the title compound as a colorless oil. ESI-MS: 199.2 (M+H)$^+$.

1-isobutylindole-6-carbonitrile was prepared from 6-cyanoindole (500 mg, 3.52 mmol). Yield: 645 mg (92%) of the title compound as a colorless oil. $^1$H NMR (300 MHz, CDCl$_3$) δ 7.68-7.65 (m, 2H), 7.31 (dd, J=8.4, 1.2 Hz, 1H), 7.26 (m, 1H), 6.55 (dd, J=3.3, 0.9 Hz, 1H), 3.94 (d, J=7.2 Hz, 2H), 2.19 (sept, J=6.6 Hz, 1H), 0.93 (d, J=6.6 Hz, 6H).

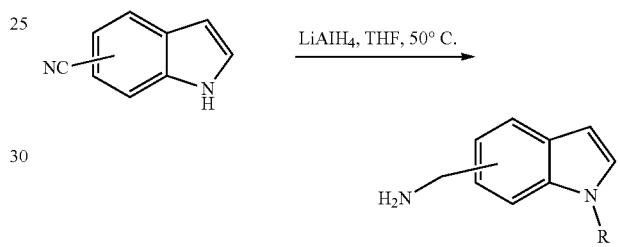

To a stirred solution of indole (120 mg, 0.61 mmol) in dry THF (1 mL), LiAlH$_4$ (1M THF, 1.21 mL, 1.21 mmol) was added under azote atmosphere. The reaction mixture was stirred overnight at 50° C. The mixture was quenched with a 10% aqueous solution of sodium hydroxide and the product was extracted with EtOAc. The organic layers were dried over Na$_2$SO$_4$, filtered and concentrated under vacuum to provide the expected compound which was used without further purification.

The following compounds are examples illustrating this procedure:

(1-isobutylindol-5-yl)methanamine was prepared from 1-isobutylindole-5-carbonitrile (120 mg, 0.61 mmol). Yield: 122 mg (100%) of the title compound as a green oil.

(1-isobutylindol-6-yl)methanamine was prepared from 1-isobutylindole-6-carbonitrile (200 mg, 1.01 mmol). Yield: 204 mg (100%) of the title compound as a green oil.

Preparation of 2-chloro-3-isopropylbenzylamine and 2-chloro-5-isopropylbenzylamine

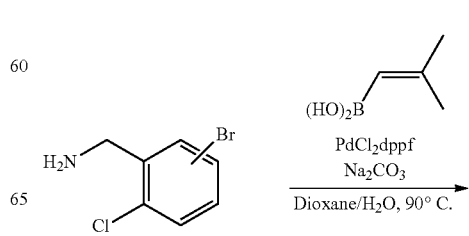

-continued

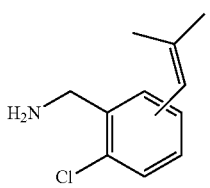

To a stirred solution of 2-chloro-X-bromobenzylamine derivative (1 equiv.) in dioxane/water (6/1, 5 mL/mmol) under azote atmosphere, were added sodium carbonate (2 equiv.), 2,2-dimethylethenylboronic acid (1.1 equiv.) and 1,1'-bis(diphenylphosphino)ferrocene-palladium(II)dichloride dichloromethane complex (0.1 equiv.). The reaction mixture was warmed to 90° C. overnight. Then, the reaction mixture was partitioned between EtOAc and H₂O. The layers were separated and the aqueous layer was extracted twice with EtOAc. The combined organic layers were dried over Na₂SO₄ and concentrated. Purification of the crude was achieved by flash column chromatography (0-10% MeOH in DCM) to give the expected compound.

[2-chloro-5-(2-methylprop-1-enyl)phenyl]methanamine was prepared from (5-bromo-2-chloro-phenyl)methanamine (500 mg, 2.27 mmol). Yield: 248 mg (56%) of the title compound as a dark oil. ESI-MS: 196.2 (M+H)$^+$.

[2-chloro-3-(2-methylprop-1-enyl)phenyl]methanamine was prepared from (3-bromo-2-chloro-phenyl)methanamine (500 mg, 2.27 mmol). Yield: 326 mg (73%) of the title compound as a dark oil. ESI-MS: 196.2 (M+H)$^+$.

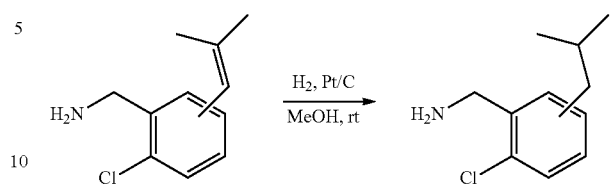

To a stirred solution of the alkene derivative (1 equiv.) in MeOH (10 mL/mmol), was added 10% platinum on carbon (~30 wt %) under azote atmosphere. Hydrogen gas was bubbled through the reaction mixture for 10 min and the mixture was stirred under hydrogen atmosphere over weekend. The mixture was passed through a plug of celite and the solvent was removed under reduced pressure to afford the saturated compound which was used without further purification.

(2-chloro-5-isobutyl-phenyl)methanamine was prepared from [2-chloro-5-(2-methylprop-1-enyl)phenyl]methanamine (248 mg, 1.27 mmol). Yield: 205 mg (82%) of the title compound as a yellow oil. ESI-MS: 198.2 (M+H)$^+$.

(2-chloro-3-isobutyl-phenyl)methanamine was prepared from [2-chloro-3-(2-methylprop-1-enyl)phenyl]methanamine (326 mg, 1.67 mmol). Yield: 275 mg (83%) of the title compound as a brown oil. ESI-MS: 198.2 (M+H)$^+$.

TABLE 1

Examples of compounds

| No | Structure | Substituent R$^1$ | Substituent R$^2$ |
|---|---|---|---|
| 1 | 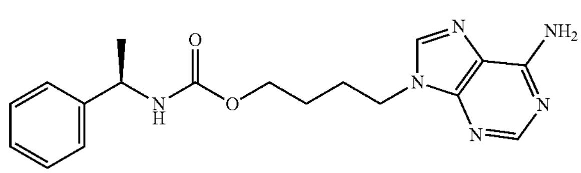 [SMILES: C[C@@H](NC(=O)OCCCCn1cnc2c(N)ncnc21)c1ccccc1] | (1R)-1-(4-chlorophenyl)ethanamine | H |
| 2 | 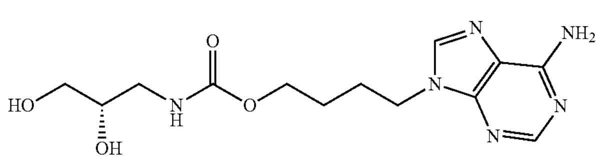 [SMILES: Nc1ncnc2c1ncn2CCCCOC(=O)NC[C@H](O)CO] | (2S)-3-aminopropane-1,2-diol | H |
| 3 | 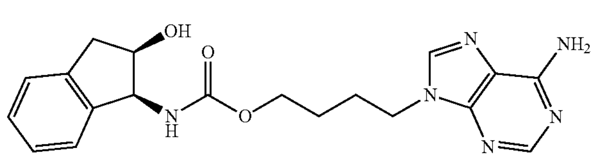 [SMILES: Nc1ncnc2c1ncn2CCCCOC(=O)N[C@H]1c2ccccc2C[C@H]1O] | (1S,2R)-1-aminoindan-2-ol | H |

TABLE 1-continued

Examples of compounds

| | | | |
|---|---|---|---|
| 4 | | (3R)-1-benzylpyrrolidin-3-amine | H |
| 5 | | 1-methylsulfonylspiro[indoline-3,4'-piperidine] | H |
| 6 | | 3-(1H-benzimidazol-2-yl)propan-1-amine | H |
| 7 | | (1S)-1-(4-chlorophenyl)ethanamine | H |
| 8 | | (4-chlorophenyl)methanamine | H |
| 9 | | (1R)-1-phenylethanamine | H |
| 10 | | phenylmethanamine | H |
| 11 | | 2-(2-pyridyl)ethanamine | H |

TABLE 1-continued

Examples of compounds

| | Structure | Name | R |
|---|---|---|---|
| 12 | | 2-(4-fluorophenyl) ethanamine | H |
| 13 | | 1-[4-(1-piperidyl)phenyl] ethanamine | H |
| 14 | | (1R)-1-(4-methoxyphenyl) ethanamine | H |
| 15 | | (4-phenylphenyl) methanamine | H |
| 16 | | 1,3-benzodioxol-5-yl methanamine | H |
| 17 | | (1R)-1-phenylbutan-1-amine | H |
| 18 | | (1R)-1-(p-tolyl) ethanamine | H |
| 19 | | (1R)-1-(3-chlorophenyl) Ethanamine | H |

TABLE 1-continued
Examples of compounds
| | | | |
|---|---|---|---|
| 20 | 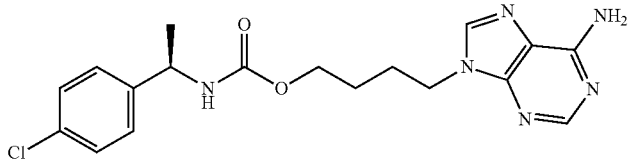 [SMILES: C[C@@H](NC(=O)OCCCCn1cnc2c(N)ncnc21)c1ccc(Cl)cc1] | (1R)-1-(4-chlorophenyl)ethanamine | H |
| 21 | 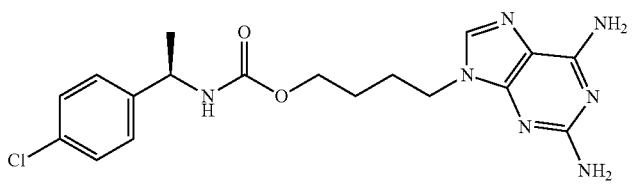 [SMILES: C[C@@H](NC(=O)OCCCCn1cnc2c(N)nc(N)nc21)c1ccc(Cl)cc1] | (1R)-1-(4-chlorophenyl)ethanamine | NH$_2$ |
| 22 | 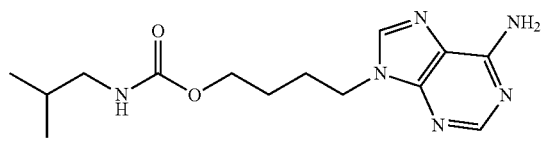 [SMILES: CC(C)CNC(=O)OCCCCn1cnc2c(N)ncnc21] | 2-methylpropan-1-amine | H |
| 23 | 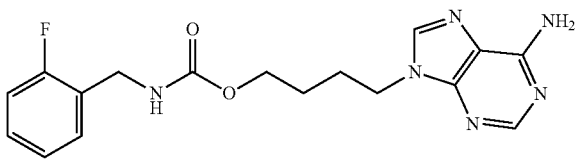 [SMILES: Nc1ncnc2c1ncn2CCCCOC(=O)NCc1ccccc1F] | (2-fluorophenyl)methanamine | H |
| 24 | 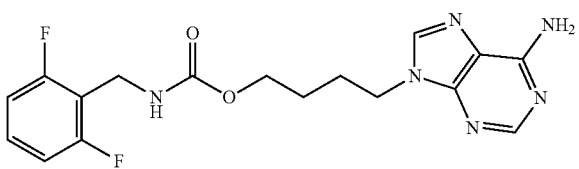 [SMILES: Nc1ncnc2c1ncn2CCCCOC(=O)NCc1c(F)cccc1F] | (2,6-difluorophenyl)methanamine | H |
| 25 | 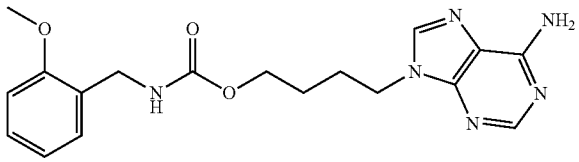 [SMILES: COc1ccccc1CNC(=O)OCCCCn1cnc2c(N)ncnc21] | (2-methoxyphenyl)methanamine | H |
| 26 | 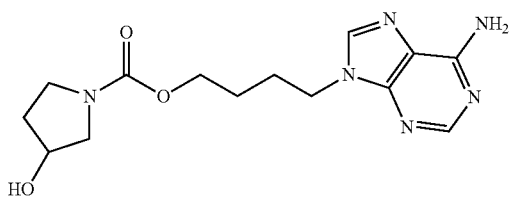 [SMILES: Nc1ncnc2c1ncn2CCCCOC(=O)N1CCC(O)C1] | pyrrolidin-3-ol | H |
| 27 | 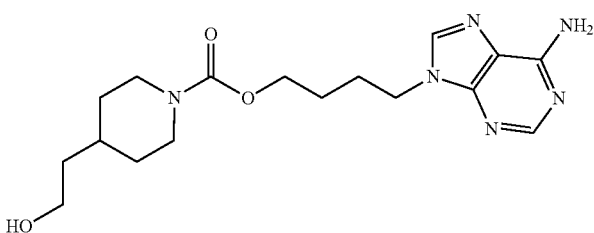 [SMILES: Nc1ncnc2c1ncn2CCCCOC(=O)N1CCC(CCO)CC1] | 2-(4-piperidyl)ethanol | H |

TABLE 1-continued

Examples of compounds

| 28 | | 3-piperidylmethanol | H |
| 29 | | 1-(2-methoxyethyl)piperazine | H |
| 30 | | azetidine | H |
| 31 | | 1,2,3,4,4a,5,6,7,8,8a-Decahydroisoquinoline | H |
| 32 | | 1-butylpiperazine | H |
| 33 | | 1-piperazin-1-ylethanone | H |
| 34 | | 1-methyl-1,4-diazepane | H |

TABLE 1-continued

Examples of compounds

| 35 | | 1,2,3,6-tetrahydropyridine | H |
| 36 | | 1-(cyclopropylmethyl) piperazine | H |
| 37 | | 4-fluoropiperidine | H |
| 38 | | (3S)-3-fluoropyrrolidine | H |
| 39 | | (3R)-3-fluoropyrrolidine | H |
| 40 | | 4-phenylpiperidine-4-carbonitrile | H |
| 41 | | 1,3-benzodioxol-5-yl methanamine | NH₂ |
| 42 | | (4-chlorophenyl) methanamine | NH₂ |

… 141 142 …
TABLE 1-continued
Examples of compounds
| 43 | 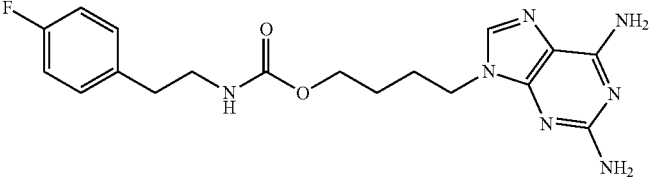 [SMILES: Nc1nc(N)c2ncn(CCCCOC(=O)NCCc3ccc(F)cc3)c2n1] | 2-(4-fluorophenyl)ethanamine | NH$_2$ |
| 44 | 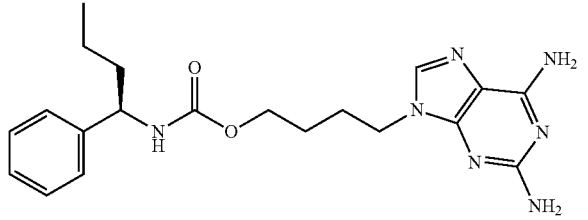 [SMILES: CCC[C@@H](NC(=O)OCCCCn1cnc2c(N)nc(N)nc21)c1ccccc1] | (1R)-1-phenylbutan-1-amine | NH$_2$ |
| 45 | 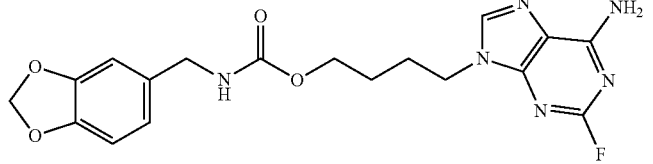 | 1,3-benzodioxol-5-ylmethanamine | F |
| 46 | 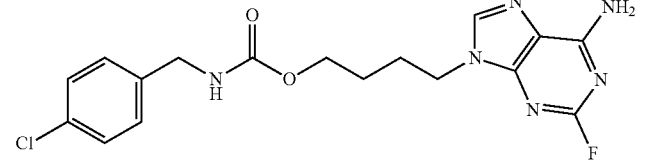 | (4-chlorophenyl)methanamine | F |
| 47 | 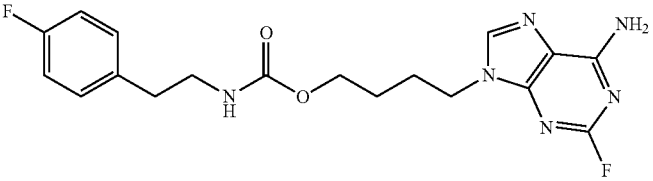 | 2-(4-fluorophenyl)ethanamine | F |
| 48 | 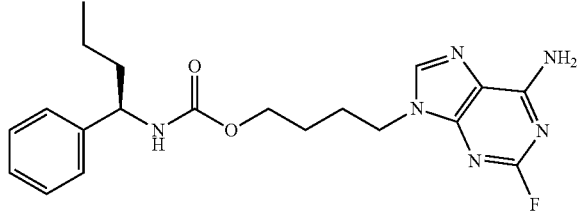 | (1R)-1-phenylbutan-1-amine | F |
| 49 | 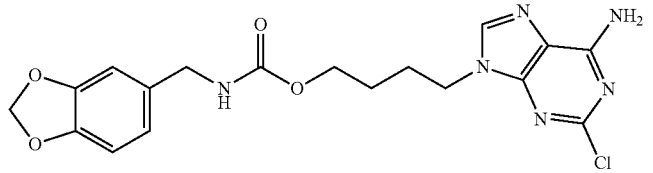 [SMILES: Nc1nc(F)nc2c1ncn2CCCCOC(=O)NCc1ccc2c(c1)OCO2] | 1,3-benzodioxol-5-yl methanamine | Cl |
| 50 | 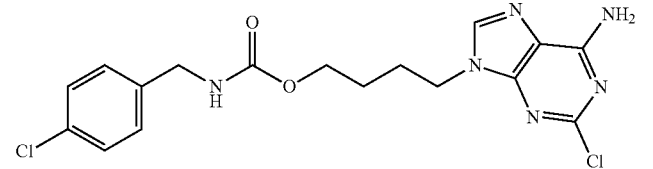 [SMILES: Nc1nc(Cl)nc2c1ncn2CCCCOC(=O)NCc1ccc(Cl)cc1] | (4-chlorophenyl)methanamine | Cl |

TABLE 1-continued

Examples of compounds

| | | | |
|---|---|---|---|
| 51 | (4-fluorobenzyl carbamate structure with purine, 2-Cl) | 2-(4-fluorophenyl)ethanamine | Cl |
| 52 | ((1R)-1-phenylbutyl carbamate structure with purine, 2-Cl) | (1R)-1-phenylbutan-1-amine | Cl |
| 53 | (2-chlorobenzyl carbamate structure with adenine) | (2-chlorophenyl)ethanamine | H |
| 54 | (2,6-dichlorobenzyl carbamate structure with adenine) | (2,6-dichlorophenyl)methanamine | H |
| 55 | (3-methoxybenzyl carbamate structure with adenine) | (3-methoxyphenyl)methanamine | H |
| 56 | (1,3-benzodioxol-5-ylmethyl carbamate structure with 2-(furan-3-yl)adenine) | 1,3-benzodioxol-5-ylmethanamine | furan-3-yl |
| 57 | (1,3-benzodioxol-5-ylmethyl carbamate structure with 2-(furan-2-yl)adenine) | 1,3-benzodioxol-5-ylmethanamine | furan-2-yl |

TABLE 1-continued

Examples of compounds

| 58 | [structure] | 1,3-benzodioxol-5-ylmethanamine | 2-methyl pyrazol-3-yl |
| 59 | [structure] | 1,3-benzodioxol-5-ylmethanamine | 1-methyl pyrrol-2-yl |
| 60 | [structure] | 1,3-benzodioxol-5-ylmethanamine | 3,5-dimethyl isoxazol-4-yl |
| 61 | [structure] | 1,3-benzodioxol-5-ylmethanamine | methyl amine |
| 62 | [structure] | 1,3-benzodioxol-5-ylmethanamine | cyclopropyl amine |
| 63 | [structure] | 1,3-benzodioxol-5-ylmethanamine | isobutyl amine |

TABLE 1-continued

Examples of compounds

| | Structure | Amine | R |
|---|---|---|---|
| 64 | | (3-bromophenyl)methanamine | Cl |
| 65 | | [3-(3-furyl)phenyl]methanamine | Cl |
| 66 | | 3-(2-furyl)phenyl]methanamine | Cl |
| 67 | | [3-(1-methylpyrrol-2-yl)phenyl]methanamine | Cl |
| 68 | | [3-(2-methylpyrazol-3-yl)phenyl]methanamine | Cl |
| 69 | | [3-(3,5-dimethylisoxazol-4-yl)phenyl]methanamine | Cl |

TABLE 1-continued
Examples of compounds
| | | | |
|---|---|---|---|
| 70 | 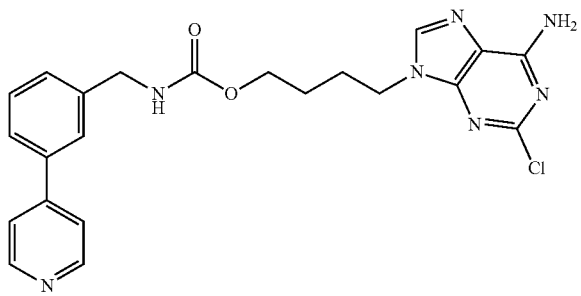 [SMILES: Nc1nc(Cl)nc2c1ncn2CCCCOC(=O)NCc1cccc(-c2ccncc2)c1] | [3-(4-pyridyl)phenyl]methanamine | Cl |
| 71 | 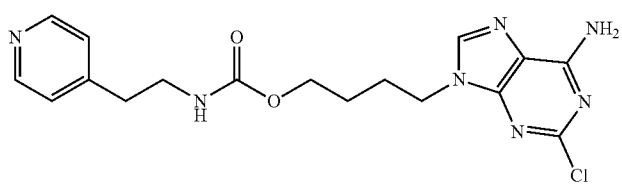 [SMILES: Nc1nc(Cl)nc2c1ncn2CCCCOC(=O)NCCc1ccncc1] | 2-(4-pyridyl)ethanamine | Cl |
| 72 | 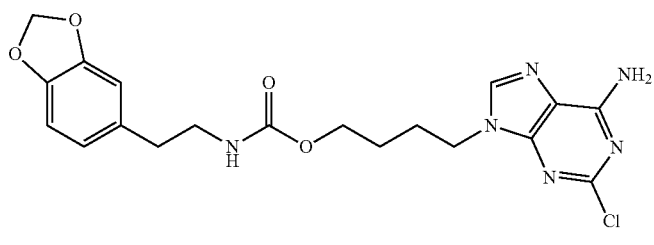 [SMILES: Nc1nc(Cl)nc2c1ncn2CCCCOC(=O)NCCc1ccc2c(c1)OCO2] | 2-(1,3-benzodioxol-5-yl)ethanamine | Cl |
| 73 | 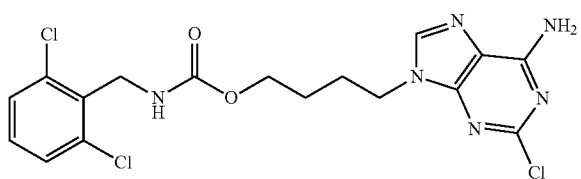 [SMILES: Nc1nc(Cl)nc2c1ncn2CCCCOC(=O)NCc1c(Cl)cccc1Cl] | (2,6-dichlorophenyl)methanamine | Cl |
| 74 | 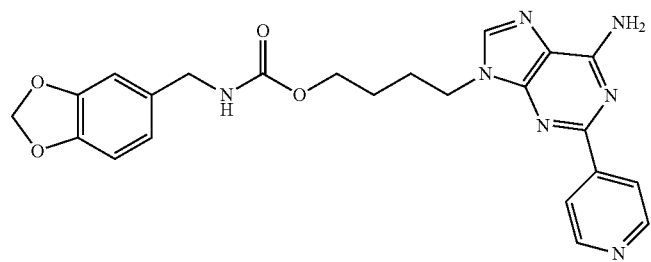 [SMILES: Nc1nc(-c2ccncc2)nc2c1ncn2CCCCOC(=O)NCc1ccc2c(c1)OCO2] | 1,3-benzodioxol-5-ylmethanamine | 4-pyridinyl |
| 75 | 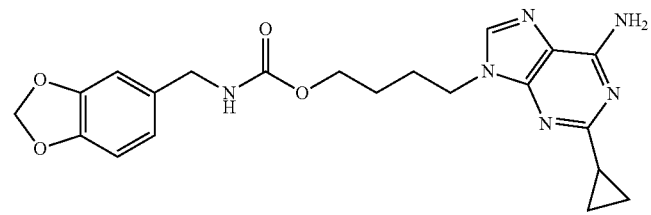 [SMILES: Nc1nc(C2CC2)nc2c1ncn2CCCCOC(=O)NCc1ccc2c(c1)OCO2] | 1,3-benzodioxol-5-ylmethanamine | cyclopropyl |
| 76 | 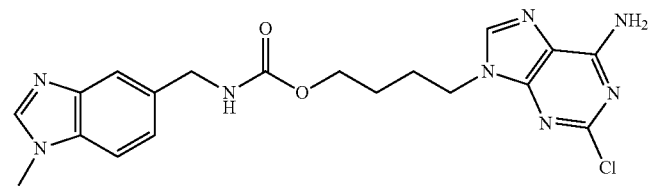 [SMILES: Cn1cnc2cc(CNC(=O)OCCCCn3cnc4c(N)nc(Cl)nc43)ccc21] | (1-methylbenzimidazol-5-yl)methanamine | Cl |

TABLE 1-continued
Examples of compounds
| | | | |
|---|---|---|---|
| 77 | 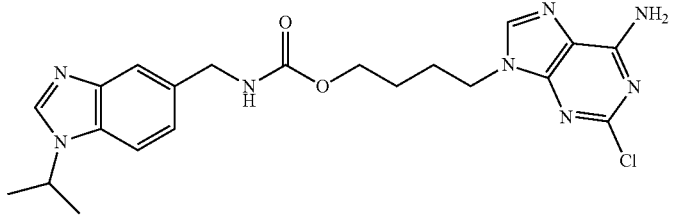 [SMILES: CC(C)n1cnc2cc(CNC(=O)OCCCCn3cnc4c(N)nc(Cl)nc43)ccc21] | (1-isopropyl-benzimidazol-5-yl)methanamine | Cl |
| 78 | 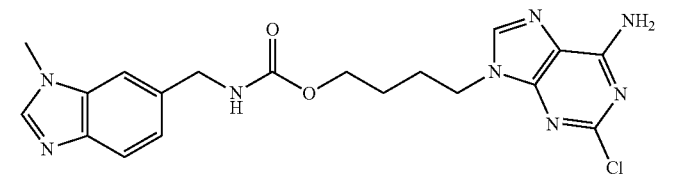 [SMILES: Cn1cnc2ccc(CNC(=O)OCCCCn3cnc4c(N)nc(Cl)nc43)cc21] | (3-methylbenzimidazol-5-yl)methanamine | Cl |
| 79 | 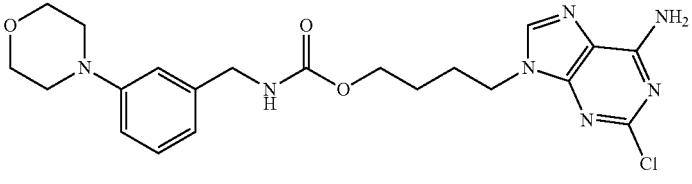 [SMILES: Nc1nc(Cl)nc2c1ncn2CCCCOC(=O)NCc1cccc(N2CCOCC2)c1] | (3-morpholinophenyl)Methanamine | Cl |
| 80 | 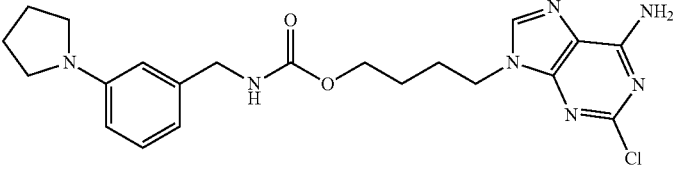 [SMILES: Nc1nc(Cl)nc2c1ncn2CCCCOC(=O)NCc1cccc(N2CCCC2)c1] | (3-pyrrolidin-1-yl-phenyl)methanamine | Cl |
| 81 | 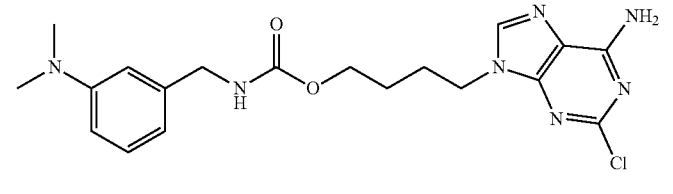 [SMILES: CN(C)c1cccc(CNC(=O)OCCCCn2cnc3c(N)nc(Cl)nc32)c1] | 3-(aminomethyl)-N,N-dimethyl-aniline | Cl |
| 82 | 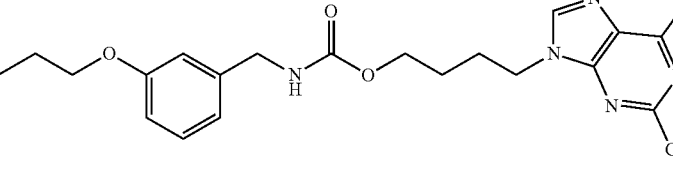 | (3-isopentyloxyphenyl)methanamine | Cl |
| 83 | 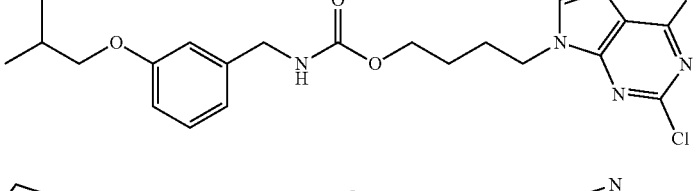 | (3-isobutoxyphenyl)methanamine | Cl |
| 84 | 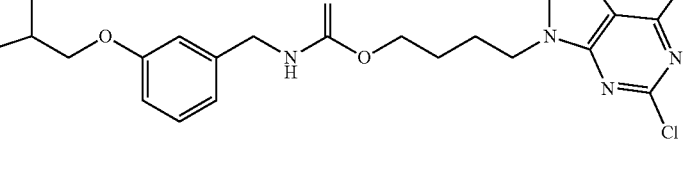 | [3-(cyclopentylmethoxy)phenyl]methanamine | Cl |

TABLE 1-continued

Examples of compounds

| 85 | | (3-isopropyl-benzimidazol-5-yl) methanamine | Cl |
|---|---|---|---|
| 86 | | 1H-indol-6-ylmethanamine | Cl |
| 87 | | 1,3-benzoxazol-6-ylmethanamine | Cl |
| 88 | | (4-isobutoxyphenyl) methanamine | Cl |
| 89 | | (4-isopentyloxyphenyl) Methanamine | Cl |
| 90 | | (4-pyrrolidin-1-ylphenyl)methanamine | Cl |
| 91 | | 4-(aminomethyl)-N,N-dimethyl-aniline | Cl |
| 92 | | (2,6-difluorophenyl) methanamine | Cl |

TABLE 1-continued
Examples of compounds
| | | | |
|---|---|---|---|
| 93 | 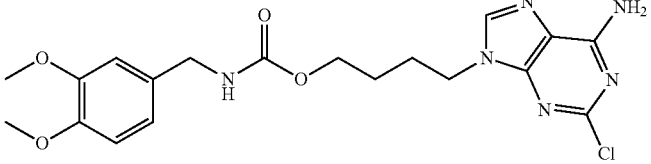 | (3,4-dimethoxyphenyl)methanamine | Cl |
| 94 | 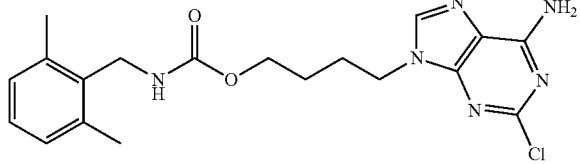 | (2,6-dimethylphenyl)methanamine | Cl |
| 95 | 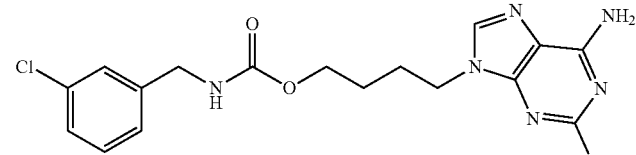 | (3-chlorophenyl)methanamine | Cl |
| 96 | 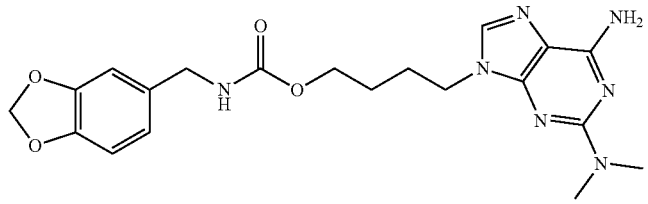 [SMILES: CN(C)c1nc(N)c2ncn(CCCCOC(=O)NCc3ccc4c(c3)OCO4)c2n1] | 1,3-benzodioxol-5-ylmethanamine | dimethylamine |
| 97 | 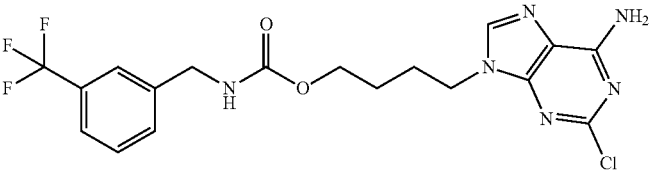 [SMILES: Nc1nc(Cl)nc2c1ncn2CCCCOC(=O)NCc1cccc(C(F)(F)F)c1] | [3-(trifluoromethyl)phenyl]methanamine | Cl |
| 98 | 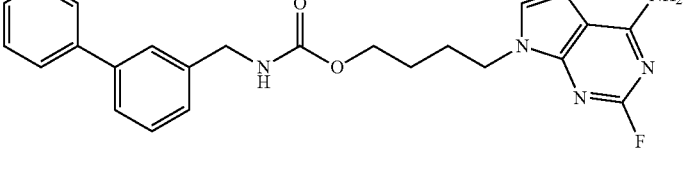 | (3-phenylphenyl)methanamine | F |
| 99 | 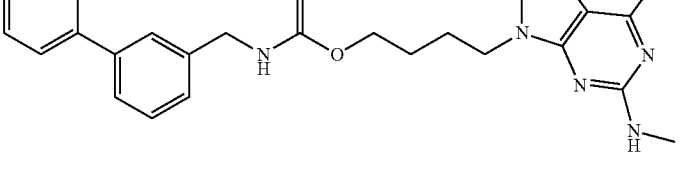 | (3-phenylphenyl)methanamine | methylamine |
| 100 | 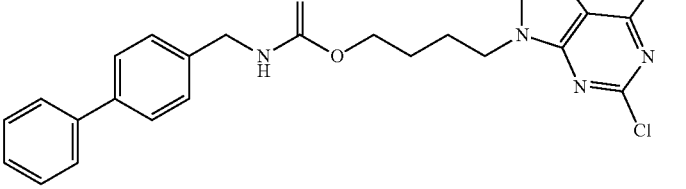 | (4-phenylphenyl)methanamine | Cl |

TABLE 1-continued
Examples of compounds
| | | | |
|---|---|---|---|
| 101 | 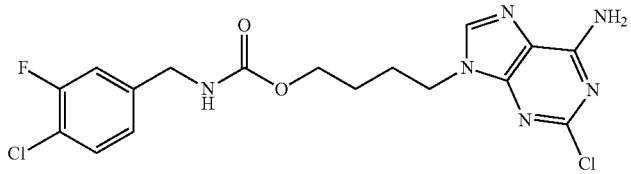 [SMILES: Nc1nc(Cl)nc2c1ncn2CCCCOC(=O)NCc1ccc(Cl)c(F)c1] | (4-chloro-3-fluoro-phenyl)methanamine | Cl |
| 102 | 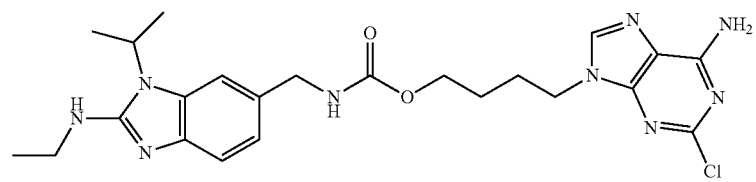 [SMILES: CCNc1nc2ccc(CNC(=O)OCCCCn3cnc4c(N)nc(Cl)nc43)cc2n1C(C)C] | 6-(aminomethyl)-N-ethyl-1-isopropyl-benzimidazol-2-amine | Cl |
| 103 | 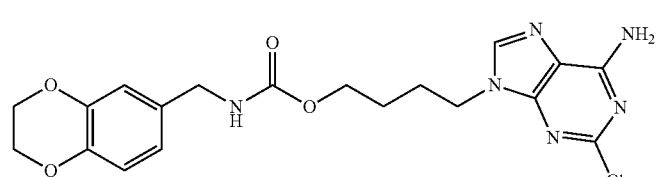 | 2,3-dihydro-1,4-benzodioxin-6-ylmethanamine | Cl |
| 104 | 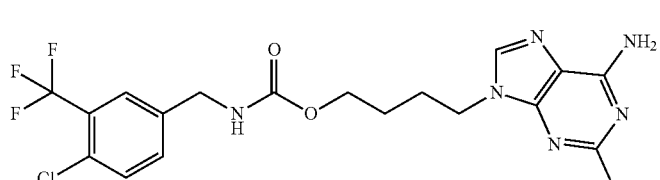 | [4-chloro-3-(trifluoromethyl)phenyl]methanamine | Cl |
| 105 | 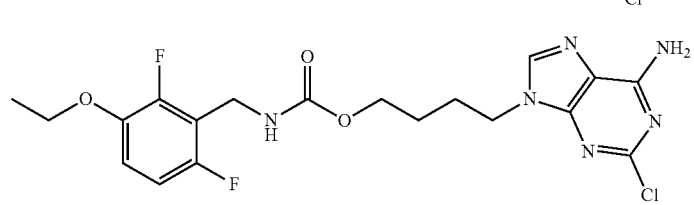 | (3-ethoxy-2,6-difluoro-phenyl)methanamine | Cl |
| 106 | 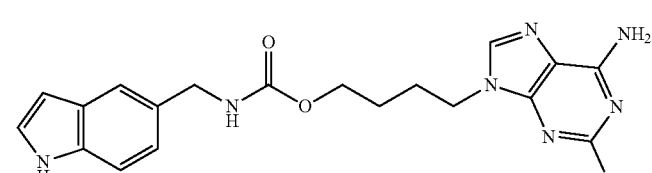 | 1H-indol-5-yl methanamine | Cl |
| 107 | 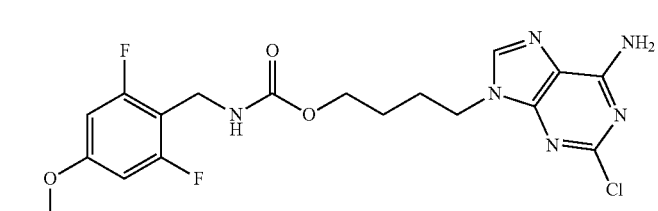 | (4-ethoxy-2,6-difluoro-phenyl)methanamine | Cl |
| 108 | 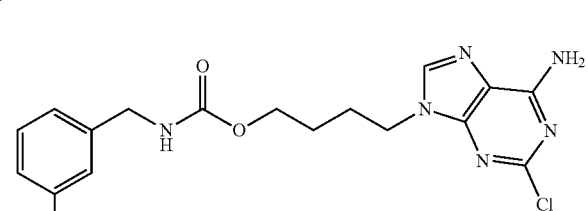 | m-tolylmethanamine | Cl |

TABLE 1-continued

Examples of compounds

| | | | |
|---|---|---|---|
| 109 | | [3-(trifluoromethoxy) phenyl]methanamine | Cl |
| 110 | | (3-fluorophenyl) methanamine | Cl |
| 111 | | 4-(aminomethyl)-N-[2-(4-fluorophenyl)ethyl] benzenesulfonamide | Cl |
| 112 | | (4-morpholinosulfonyl phenyl)methanamine | Cl |
| 113 | | [3-(trifluoromethyl) phenyl]methanamine | methylamine |

TABLE 1-continued

Examples of compounds

| 114 | | (3-cyclopropylphenyl) methanamine | Cl |
| --- | --- | --- | --- |
| 115 | | (3-chloro-1-methyl-indol-6-yl) methanamine | Cl |
| 116 | | 3-(aminomethyl) benzonitrile | Cl |
| 117 | | (2-phenylbenzofuran-5-yl)methanamine | Cl |
| 118 | | imidazo[1,2-a]pyridin-6-ylmethanamine | Cl |
| 119 | | (1-isobutylindol-6-yl)methanamine | Cl |
| 120 | | (2-cyclopropyl-benzofuran-5-yl) methanamine | Cl |

TABLE 1-continued

Examples of compounds

| 121 | (1-isopentylindol-6-yl)methanamine | Cl |
| 122 | benzofuran-5-ylmethanamine | Cl |
| 123 | (1-isopropylindol-6-yl)methanamine | Cl |
| 124 | 4-(aminomethyl)-N-isobutyl-benzene-sulfonamide | Cl |
| 125 | (2-phenylimidazo[1,2-a]pyridin-6-yl)methanamine | Cl |
| 126 | 5-(aminomethyl)pyridin-2-amine | Cl |
| 127 | [3-(2-methylprop-1-enyl)phenyl]methanamine | Cl |

TABLE 1-continued
Examples of compounds
| | | | |
|---|---|---|---|
| 128 | 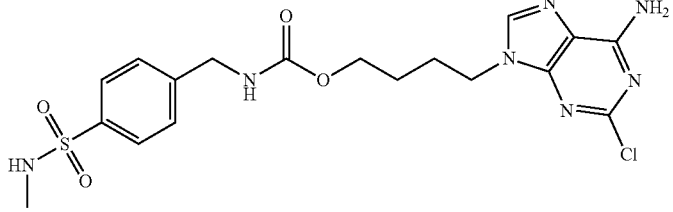 | 4-(aminomethyl)-N-methyl-benzene-sulfonamide | Cl |
| 129 | 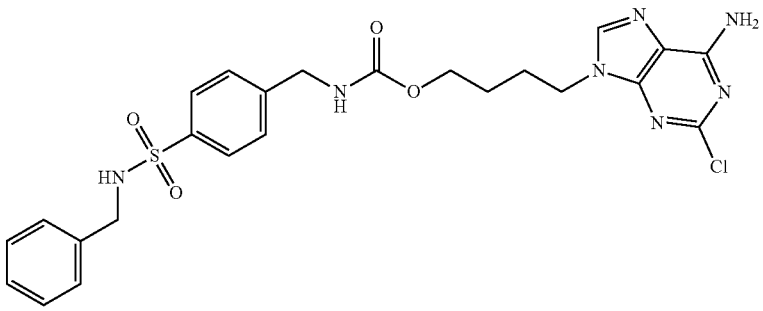 | 4-(aminomethyl)-N-benzyl-benzene-sulfonamide | Cl |
| 130 | 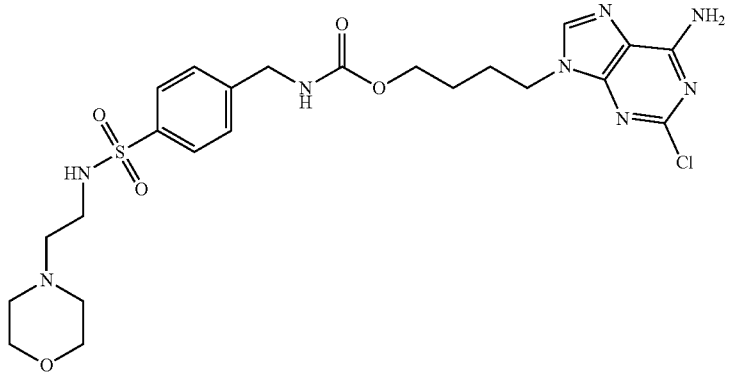 [SMILES: Nc1nc(Cl)nc2c1ncn2CCCCOC(=O)NCc1ccc(S(=O)(=O)NCCN2CCOCC2)cc1] | 4-(aminomethyl)-N-(2-morpholinoethyl)benzenesulfonamide | Cl |
| 131 | 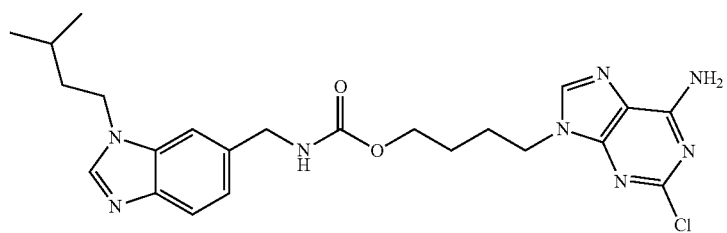 [SMILES: CC(C)CCn1cnc2ccc(CNC(=O)OCCCCn3cnc4c(N)nc(Cl)nc43)cc21] | (3-isopentyl-benzimidazol-5-yl)methanamine | Cl |
| 132 | 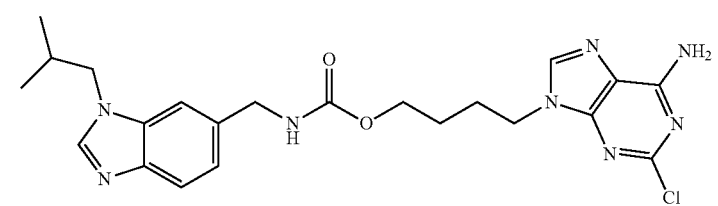 [SMILES: CC(C)Cn1cnc2ccc(CNC(=O)OCCCCn3cnc4c(N)nc(Cl)nc43)cc21] | (3-isobutyl-benzimidazol-5-yl)methanamine | Cl |

TABLE 1-continued

Examples of compounds

| 133 | [structure] | (3-isobutylphenyl)methanamine | Cl |
| 134 | [structure] | 4-(aminomethyl)-N-phenyl-benzene-sulfonamide | Cl |
| 135 | [structure] | 2-[3-(aminomethyl)phenyl]benzamide | Cl |
| 136 | [structure] | 2-[3-(aminomethyl)phenyl]benzonitrile | Cl |
| 137 | [structure] | 4-[3-(aminomethyl)phenyl]benzonitrile | Cl |

TABLE 1-continued

Examples of compounds

| 138 | | 3-[3-(aminomethyl)phenyl]benzonitrile | Cl |
| --- | --- | --- | --- |
| 139 | | N-[4-(aminomethyl)phenyl]methane-sulfonamide | Cl |
| 140 | | N-[4-(aminomethyl)phenyl]cyclohexane-sulfonamide | Cl |
| 141 | | [3-(3-pyridyl)phenyl]methanamine | Cl |
| 142 | | N-[4-(aminomethyl)phenyl]benzene-sulfonamide | Cl |

TABLE 1-continued

Examples of compounds

| | | | |
|---|---|---|---|
| 143 | | N-[4-(aminomethyl)phenyl]cyclopropane-sulfonamide | Cl |
| 144 | | N-[4-(aminomethyl)phenyl]-2-methyl-propane-1-sulfonamide | Cl |
| 145 | | [3-(3-thienyl)phenyl]methanamine | Cl |
| 146 | | 3-[3-(aminomethyl)phenyl]aniline | Cl |
| 147 | | (3-imidazol-1-ylphenyl)methanamine | Cl |

TABLE 1-continued

Examples of compounds

| 148 | (structure) | (1-isopropylindol-5-yl) methanamine | Cl |
| 149 | (structure) | (3-isopropyl-1H-indol-5-yl)methanamine | Cl |
| 150 | (structure) | (4-pyrrolidin-1-yl sulfonylphenyl) methanamine | Cl |
| 151 | (structure) | 4-(aminomethyl)-N-cyclohexyl-benzenesulfonamide | Cl |
| 152 | (structure) | (3-propylphenyl) methanamine | Cl |
| 153 | (structure) | [4-[4-(cyclopropyl-methyl)piperazin-1-yl] sulfonylphenyl] methanamine | Cl |

TABLE 1-continued
Examples of compounds
| | | | | |
|---|---|---|---|---|
| 154 | 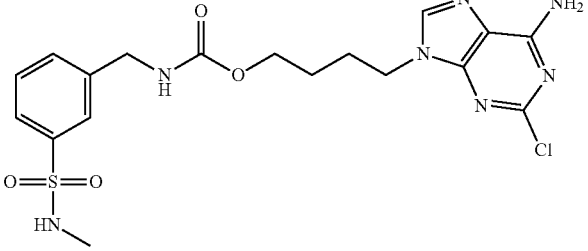 | | 3-(aminomethyl)-N-methyl-benzene-sulfonamide | Cl |
| 155 | 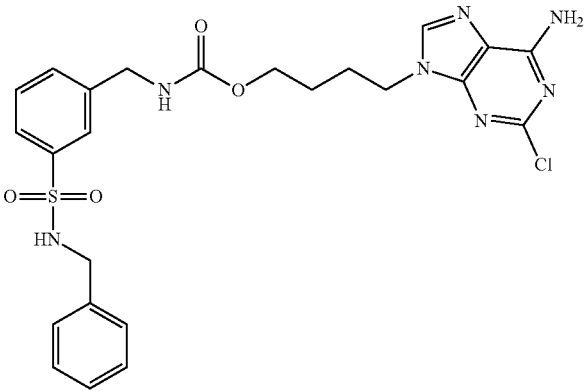 [SMILES: Nc1nc(Cl)nc2c1ncn2CCCCOC(=O)NCc1cccc(S(=O)(=O)NCc2ccccc2)c1] | | 3-(aminomethyl)-N-benzyl-benzene-sulfonamide | Cl |
| 156 | 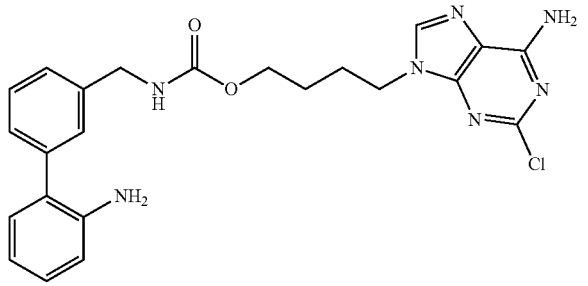 [SMILES: Nc1ccccc1-c1cccc(CNC(=O)OCCCCn2cnc3c(N)nc(Cl)nc32)c1] | | 2-[3-(aminomethyl)phenyl]aniline | Cl |
| 157 | 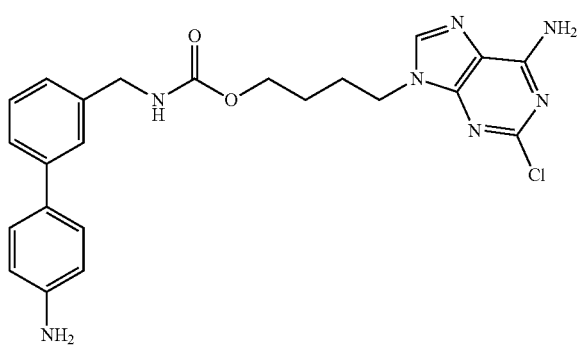 [SMILES: Nc1ccc(-c2cccc(CNC(=O)OCCCCn3cnc4c(N)nc(Cl)nc43)c2)cc1] | | 4-[3-(aminomethyl)phenyl]aniline | Cl |
| 158 | 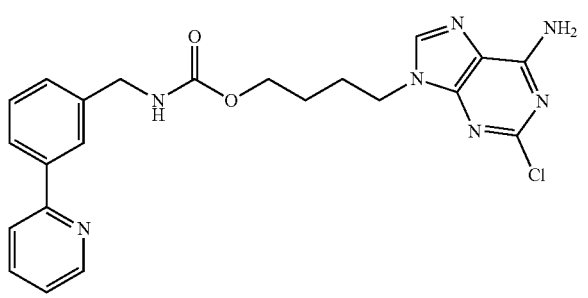 [SMILES: Nc1nc(Cl)nc2c1ncn2CCCCOC(=O)NCc1cccc(-c2ccccn2)c1] | | [3-(2-pyridyl)phenyl]methanamine | Cl |

TABLE 1-continued

Examples of compounds

| | | | | |
|---|---|---|---|---|
| 159 | | (3-phenylphenyl)methanamine | Cl |
| 160 | | (1-isobutyl-benzimidazol-5-yl)methanamine | Cl |
| 161 | | (3-pyrrol-1-ylphenyl)methanamine | Cl |
| 162 | | (1-isobutylindol-5-yl)methanamine | Cl |
| 171 | | 4-(aminomethyl)-N-(2-furylmethyl)benzenesulfonamide | Cl |

TABLE 1-continued
Examples of compounds
| 172 | 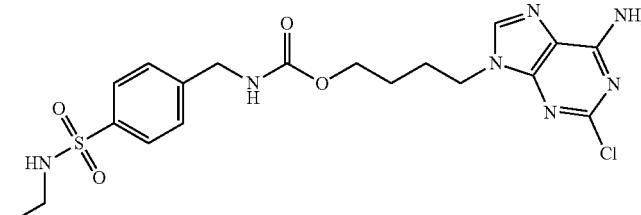 | 4-(aminomethyl)-N-[(4-chlorophenyl)methyl]benzenesulfonamide | Cl |
| 173 | 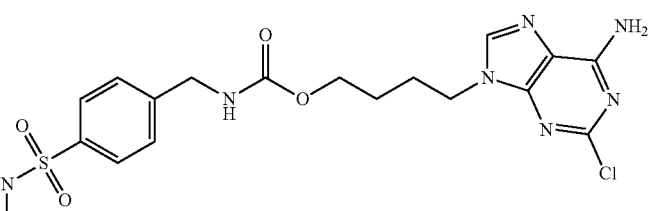 | 4-(aminomethyl)-N-[(3-fluorophenyl)methyl]benzenesulfonamide | Cl |
| 174 | 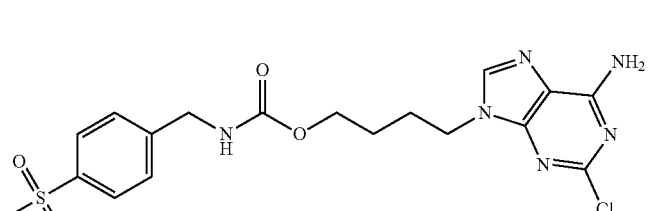 | 4-(aminomethyl)-N-[(2-fluorophenyl)methyl]benzenesulfonamide | Cl |
| 175 | 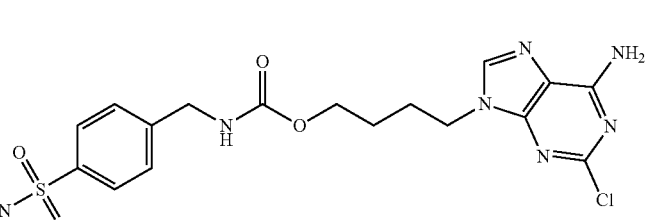 | 4-(aminomethyl)-N-[(2,6-difluorophenyl)methyl]benzenesulfonamide | Cl |

TABLE 1-continued

Examples of compounds

| | | | |
|---|---|---|---|
| 176 | | 4-(aminomethyl)-N-[[3-(trifluoromethyl)phenyl]methyl]benzenesulfonamide | Cl |
| 177 | | 4-(aminomethyl)-N-[(3-methoxyphenyl)methyl]benzenesulfonamide | Cl |
| 178 | | 4-(aminomethyl)-N-benzyl-benzenesulfonamide | F |
| 179 | | 4-(aminomethyl)-N-[(4-chlorophenyl)methyl]benzenesulfonamide | dimethyl-amine |

TABLE 1-continued

Examples of compounds

| | | | |
|---|---|---|---|
| 180 | | 4-(aminomethyl)-N-[(1S)-1-(4-chlorophenyl)ethyl]benzenesulfonamide | Cl |
| 181 | | 4-(aminomethyl)-N-[(1R)-1-(4-chlorophenyl)ethyl]benzenesulfonamide | Cl |
| 182 | | 4-(aminomethyl)-N-[(4-fluorophenyl)methyl]benzenesulfonamide | Cl |
| 183 | | 4-(aminomethyl)-N-[[4-(trifluoromethyl)phenyl]methyl]benzenesulfonamide | Cl |
| 184 | | 4-(aminomethyl)-N-[(4-chlorophenyl)methyl]benzenesulfonamide | F |

TABLE 1-continued
Examples of compounds
| | | | |
|---|---|---|---|
| 185 | 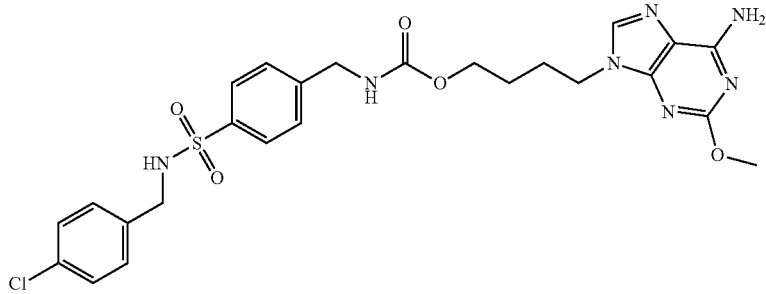 [SMILES: COc1nc(N)c2ncn(CCCCOC(=O)NCc3ccc(S(=O)(=O)NCc4ccc(Cl)cc4)cc3)c2n1] | 4-(aminomethyl)-N-[(4-chlorophenyl)methyl]benzenesulfonamide | methoxy |
| 186 | 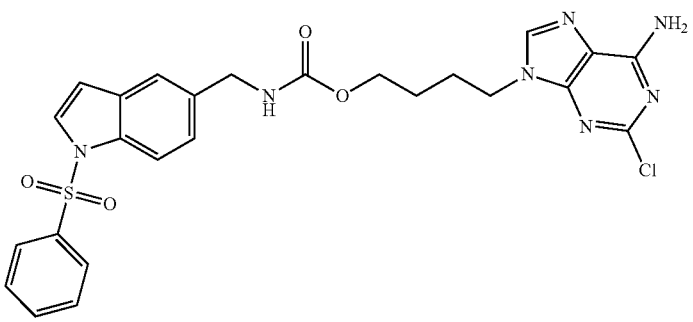 [SMILES: Nc1nc(Cl)nc2c1ncn2CCCCOC(=O)NCc1ccc2c(ccn2S(=O)(=O)c2ccccc2)c1] | [1-(benzenesulfonyl)indol-5-yl]methanamine | Cl |
| 187 | 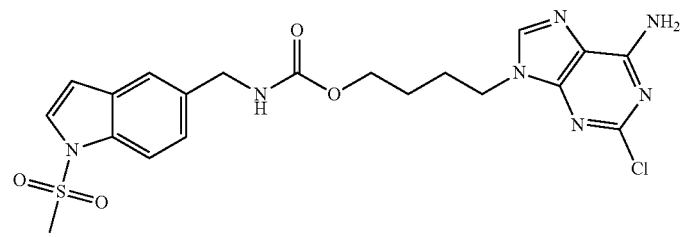 [SMILES: CS(=O)(=O)n1ccc2cc(CNC(=O)OCCCCn3cnc4c(N)nc(Cl)nc43)ccc21] | (1-methylsulfonylindol-5-yl)methanamine | Cl |
| 188 | 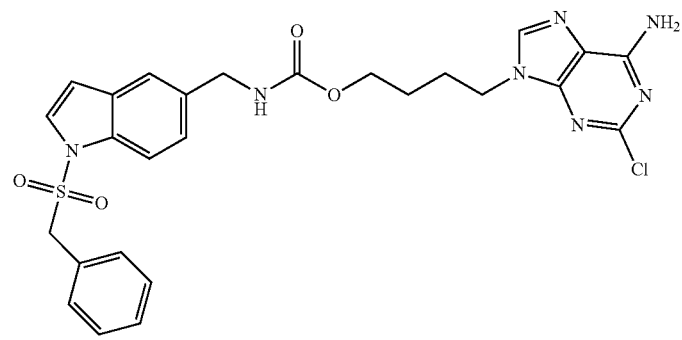 [SMILES: Nc1nc(Cl)nc2c1ncn2CCCCOC(=O)NCc1ccc2c(ccn2S(=O)(=O)Cc2ccccc2)c1] | (1-benzylsulfonylindol-5-yl)methanamine | Cl |
| 189 | 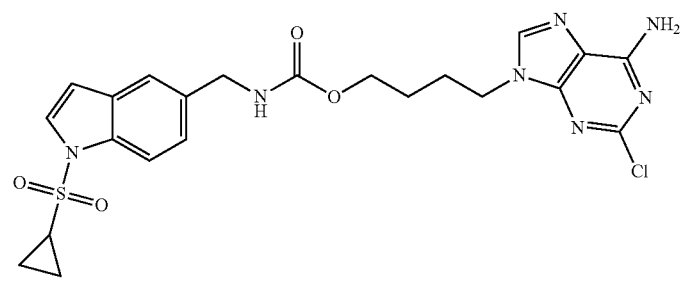 [SMILES: Nc1nc(Cl)nc2c1ncn2CCCCOC(=O)NCc1ccc2c(ccn2S(=O)(=O)C2CC2)c1] | (1-cyclopropylsulfonylindol-5-yl)methanamine | Cl |

TABLE 1-continued

Examples of compounds

| | | | |
|---|---|---|---|
| 190 | (structure) | 4-(aminomethyl)-N-[(4-chlorophenyl)methyl]benzenesulfonamide | diethoxy |
| 191 | (structure) | 4-(aminomethyl)-N-((4-chlorophenyl)methyl]benzenesulfonamide | propoxy |
| 192 | (structure) | 4-(aminomethyl)-N-[(4-chlorophenyl)methyl]benzenesulfonamide | iso-propoxy |
| 193 | (structure) | 4-(aminomethyl)-N-[(4-chlorophenyl)methyl]benzenesulfonamide | iso-butoxy |
| 194 | (structure) | 4-(aminomethyl)-N-[(4-chlorophenyl)methyl]benzenesulfonamide | cyclo-pentyl-methoxy |

TABLE 1-continued

Examples of compounds

| 195 | 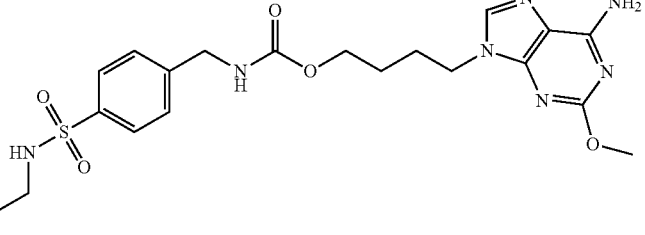 | 4-(aminomethyl)-N-[(4-chlorophenyl)methyl]benzenesulfonamide | methyl-sulfanyl |
| 196 | 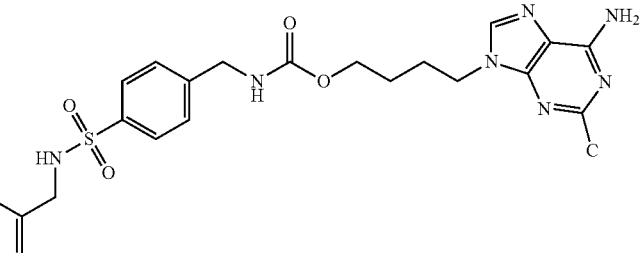 | 4-(aminomethyl)-N-[(4-cyanophenyl)methyl]benzenesulfonamide | Cl |
| 197 | 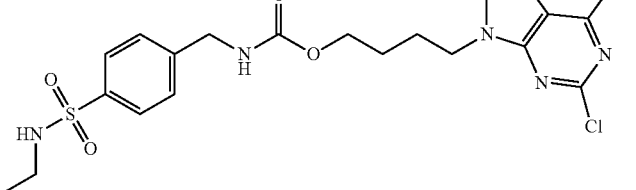 | 4-(aminomethyl)-N-[(4-bromophenyl)methyl]benzenesulfonamide | Cl |
| 198 | 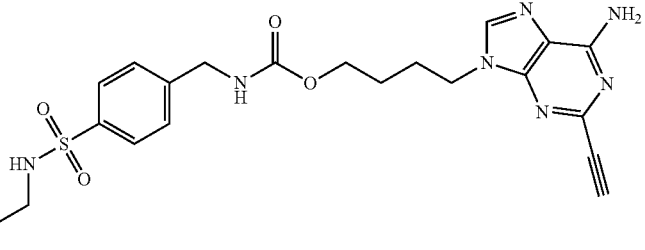 | 4-(aminomethyl)-N-[(4-chlorophenyl)methyl]benzenesulfonamide | ethyne |
| 199 | 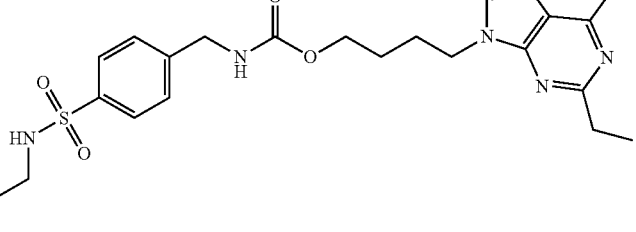 | 4-(aminomethyl)-N-[(4-chlorophenyl)methyl]benzenesulfonamide | ethyl |

TABLE 1-continued

Examples of compounds

| | | | |
|---|---|---|---|
| 200 | 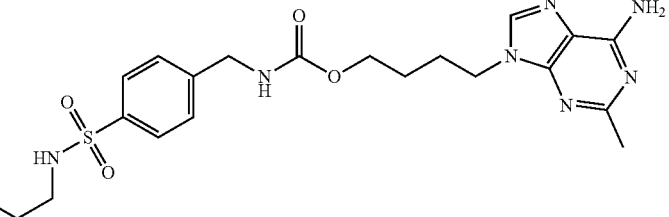 | 4-(aminomethyl)-N-[(4-chlorophenyl)methyl]benzenesulfonamide | methyl |
| 201 | 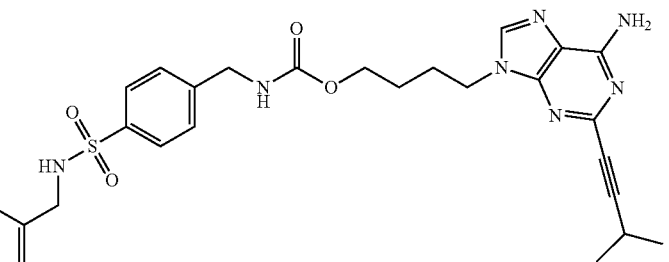 | 4-(aminomethyl)-N-[(4-chlorophenyl)methyl]benzenesulfonamide | iso-propyl-ethyne |
| 202 | 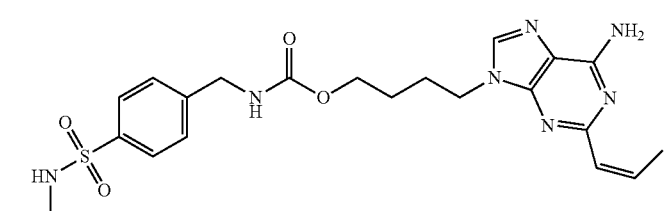 | 4-(aminomethyl)-N-[(4-chlorophenyl)methyl]benzenesulfonamide | (Z)-prop-1-enyl |
| 203 | 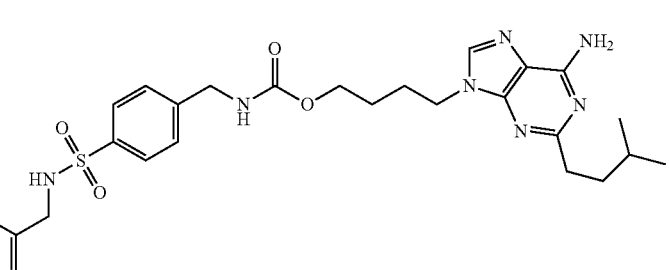 | 4-(aminomethyl)-N-[(4-chlorophenyl)methyl]benzenesulfonamide | isopentyl |
| 204 | 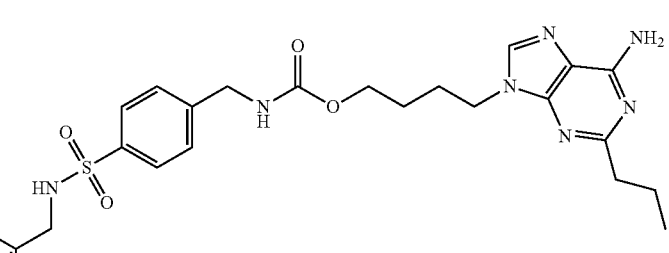 | 4-(aminomethyl)-N-[(4-chlorophenyl)methyl]benzenesulfonamide | propyl |

TABLE 1-continued

Examples of compounds

| | | | |
|---|---|---|---|
| 205 | | 4-(aminomethyl)-N-[[4-(trifluoromethyl)phenyl]methyl]benzenesulfonamide | F |
| 206 | | 4-(aminomethyl)-N-methyl-benzenesulfonamide | dimethly-amine |
| 207 | | (4-methylsulfonylphenyl)methanamine | dimethyl-amine |
| 208 | | (1-methylsulfonylindol-5-yl)methanamine | dimethyl-amine |
| 209 | | (3-bromophenyl)methanamine | dimethyl-amine |
| 210 | | (4-chlorophenyl)methanamine | dimethyl-amine |

TABLE 1-continued

Examples of compounds

| | | | |
|---|---|---|---|
| 211 | 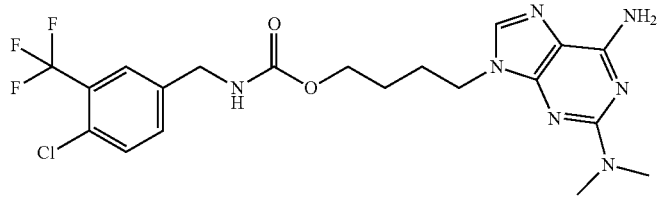 [SMILES: CN(C)c1nc(N)c2ncn(CCCCOC(=O)NCc3ccc(Cl)c(C(F)(F)F)c3)c2n1] | [4-chloro-3-(trifluoromethyl)phenyl]methanamine | dimethyl-amine |
| 212 | 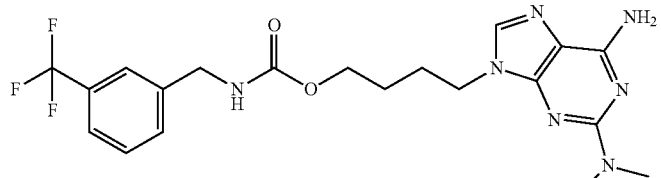 | [3-(trifluoromethyl)phenyl]methanamine | dimethyl-amine |
| 213 | 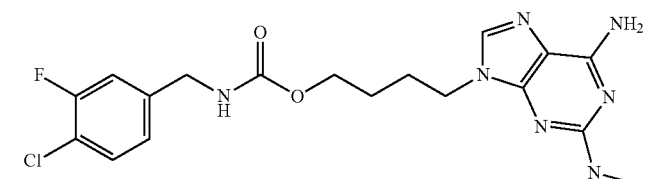 | (4-chloro-3-fluoro-phenyl)methanamine | dimethyl-amine |
| 214 | 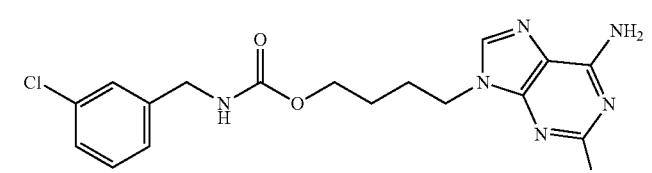 | (3-chlorophenyl)methanamine | dimethyl-amine |
| 215 | 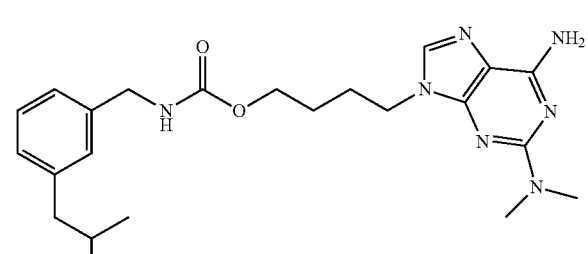 | (3-isobutylphenyl)methanamine | dimethyl-amine |
| 216 | 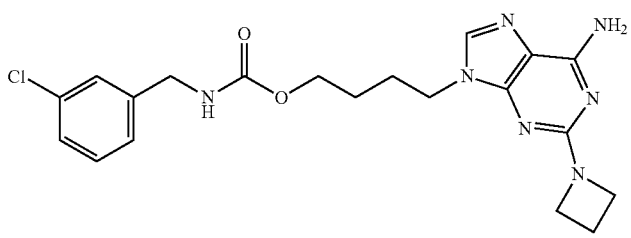 [SMILES: Nc1nc(N2CCC2)nc2c1ncn2CCCCOC(=O)NCc1cccc(Cl)c1] | (3-chlorophenyl)methanamine | azetidine |
| 217 | 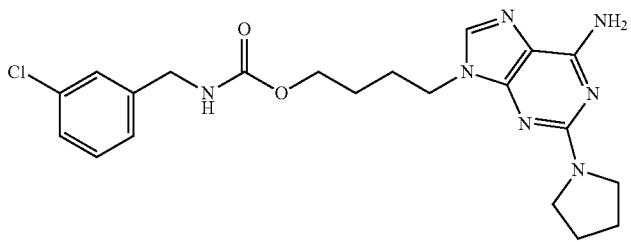 [SMILES: Nc1nc(N2CCCC2)nc2c1ncn2CCCCOC(=O)NCc1cccc(Cl)c1] | (3-chlorophenyl)methanamine | pyrro-lidine |

TABLE 1-continued

Examples of compounds

| | | | |
|---|---|---|---|
| 218 | [structure] | (3-chloro-2,6-difluorophenyl)methanamine | dimethlyamine |
| 219 | [structure] | (3-chloro-2,4-difluorophenyl)methanamine | dimethylamine |
| 220 | [structure] | 4-(aminomethyl)-N,N-dimethyl-benzenesulfonamide | dimethylamine |
| 221 | [structure] | (4-chloro-2,6-difluorophenyl)methanamine | dimethylamine |
| 222 | [structure] | imidazo[1,2-a]pyridin-6-ylmethanamine | dimethylamine |
| 223 | [structure] | [2,6-dichloro-3-(trifluoromethyl)phenyl]methanamine | dimethylamine |
| 224 | [structure] | 3-(trifluoromethyl)aniline | Cl |

TABLE 1-continued

Examples of compounds

| | | | |
|---|---|---|---|
| 225 | | [2,6-dichloro-3-(trifluoromethyl)phenyl]methanamine | Cl |
| 226 | | [2,6-dichloro-3-(trifluoromethyl)phenyl]methanamine | F |
| 227 | | [2,6-dichloro-3-(trifluoromethyl)phenyl]methanamine | methyl-amine |
| 228 | | [4-(trifluoromethyl)phenyl]methanamine | Cl |
| 229 | | [2-chloro-5-(trifluoromethyl)phenyl]methanamine | Cl |
| 230 | | [3,5-bis(trifluoromethyl)phenyl]methanamine | Cl |
| 231 | | [2-chloro-3-(trifluoromethyl)phenyl]methanamine | Cl |
| 232 | | (3,6-dichloro-2-fluorophenyl)methanamine | Cl |

US 11,236,093 B2

TABLE 1-continued

Examples of compounds

| 233 | 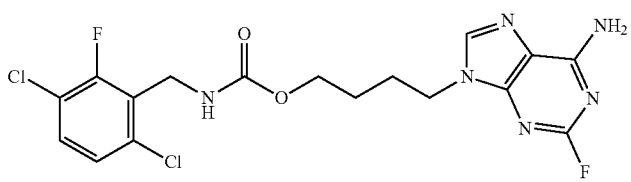 [SMILES: Nc1nc(F)nc2c1ncn2CCCCOC(=O)NCc1c(Cl)ccc(Cl)c1F] | (3,6-dichloro-2-fluoro-phenyl)methanamine | F |
| 234 | 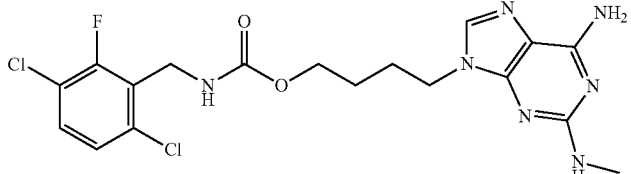 | (3,6-dichloro-2-fluoro-phenyl)methanamine | methyl-amine |
| 235 | 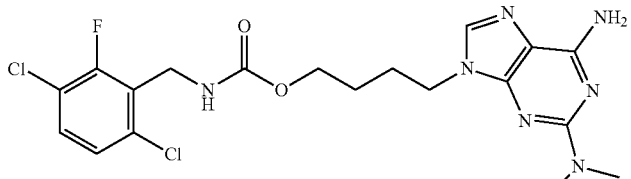 | (3,6-dichloro-2-fluoro-phenyl)methanamine | dimethyl-amine |
| 236 | 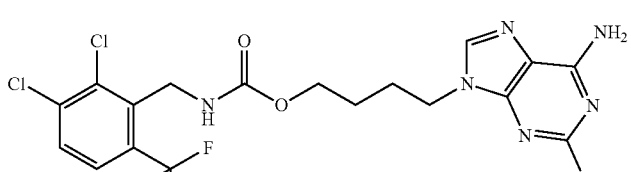 | [2,3-dichloro-6-(trifluoromethyl)phenyl]methanamine | Cl |
| 237 | 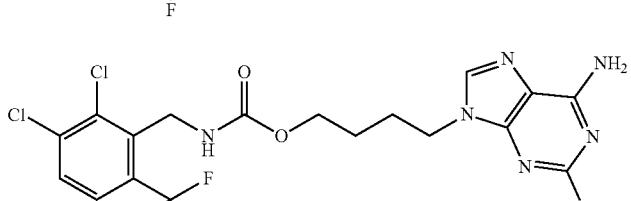 | [2,3-dichloro-6-(trifluoromethyl)phenyl]methanamine | F |
| 238 | 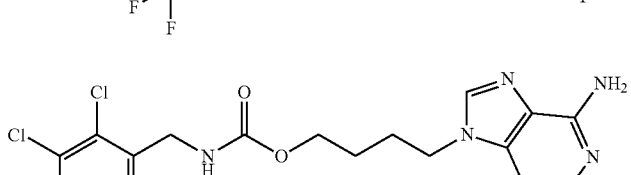 | [2,3-dichloro-6-(trifluoromethyl)phenyl]methanamine | dimethyl-amine |
| 239 | 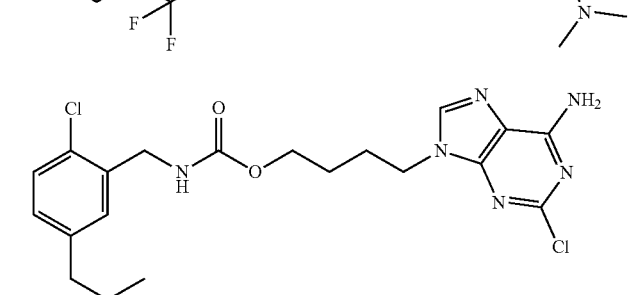 | (2-chloro-5-isobutyl-phenyl)methanamine | Cl |

TABLE 1-continued

Examples of compounds

| | | | |
|---|---|---|---|
| 240 | | (2-chloro-5-isobutyl-phenyl)methanamine | F |
| 241 | | (2-chloro-5-isobutyl-phenyl)methanamine | dimethyl-amine |
| 242 | | (3-isopropylbenzimidazol-5-yl)methanamine | azetidine |
| 243 | | (3-isopropylbenzimidazol-5-yl)methanamine | phenyl |
| 244 | | [3-(trifluoromethyl)phenyl]methanamine | azetidine |
| 245 | | [3-(trifluoromethyl)phenyl]methanamine | pyrro-lidine |

TABLE 1-continued
Examples of compounds
| | | | |
|---|---|---|---|
| 246 | 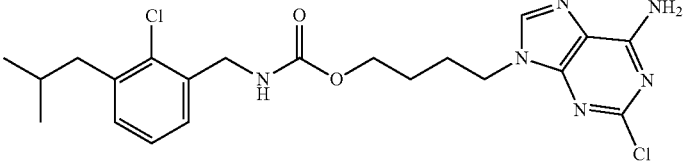 | (2-chloro-3-isobutyl-phenyl)methanamine | Cl |
| 247 | 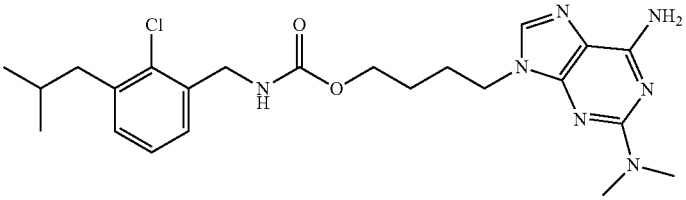 [SMILES: CC(C)Cc1cccc(CNC(=O)OCCCCn2cnc3c(N)nc(N(C)C)nc32)c1Cl] | (2-chloro-3-isobutyl-phenyl)methanamine | dimethyl-amine |
| 248 | 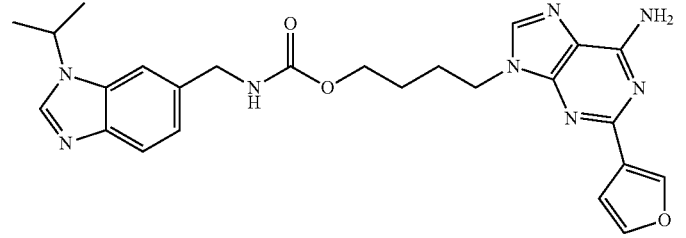 [SMILES: CC(C)n1cnc2ccc(CNC(=O)OCCCCn3cnc4c(N)nc(-c5ccoc5)nc43)cc21] | (3-isopropylbenzimidazol-5-yl)methanamine | furan-3-yl |
| 249 | 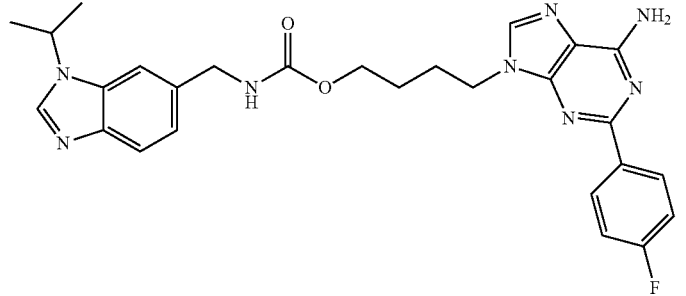 [SMILES: CC(C)n1cnc2ccc(CNC(=O)OCCCCn3cnc4c(N)nc(-c5ccc(F)cc5)nc43)cc21] | (3-isopropylbenzimidazol-5-yl)methanamine | 4-fluoro-phenyl |
| 250 | 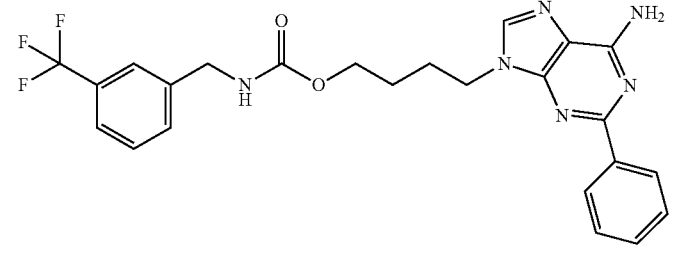 [SMILES: Nc1nc(-c2ccccc2)nc2c1ncn2CCCCOC(=O)NCc1cccc(C(F)(F)F)c1] | [3-(trifluoromethyl)phenyl]methanamine | phenyl |
| 251 | 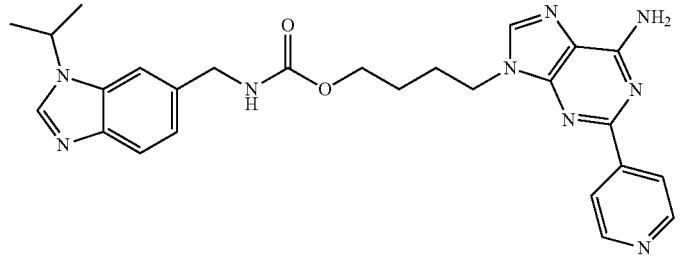 [SMILES: CC(C)n1cnc2ccc(CNC(=O)OCCCCn3cnc4c(N)nc(-c5ccncc5)nc43)cc21] | (3-isopropylbenzimidazol-5-yl)methanamine | 4-pyridinyl |

TABLE 1-continued

Examples of compounds

| | | | |
|---|---|---|---|
| 252 | | 1,3-benzodioxol-5-ylmethanamine | phenyl |
| 253 | | (3-isopropylbenzimidazol-5-yl)methanamine | 3-fluoro-phenyl |
| 254 | | (3-isopropylbenzimidazol-5-yl)methanamine | 3-cyano-phenyl |
| 255 | | (3-isopropylbenzimidazol-5-yl)methanamine | 4-cyano-phenyl |
| 256 | | [3-(trifluoromethyl)phenyl]methanamine | 2-fluoro-phenyl |

TABLE 1-continued
Examples of compounds
| | | | |
|---|---|---|---|
| 257 | 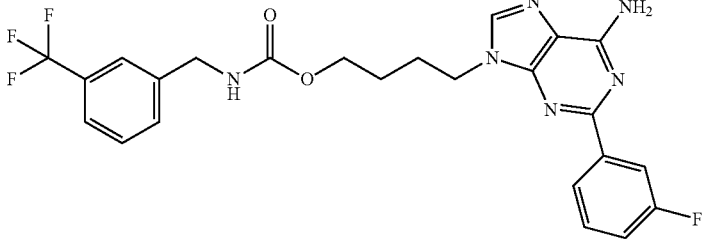 | [3-(trifluoromethyl)phenyl]methanamine | 3-fluoro-phenyl |
| 258 | 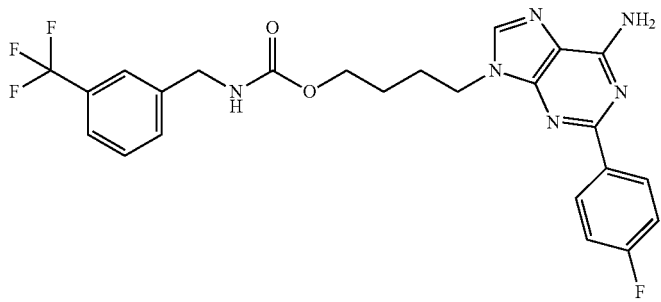 [SMILES: Nc1nc(-c2ccc(F)cc2)nc2c1ncn2CCCCOC(=O)NCc1cccc(C(F)(F)F)c1] | [3-(trifluoromethyl)phenyl]methanamine | 4-fluoro-phenyl |
| 259 | 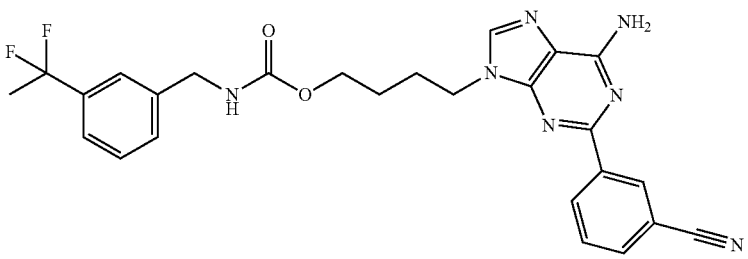 [SMILES: CC(F)(F)c1cccc(CNC(=O)OCCCCn2cnc3c(N)nc(-c4cccc(C#N)c4)nc32)c1] | [3-(trifluoromethyl)phenyl)methanamine | 3-cyano-phenyl |
| 260 | 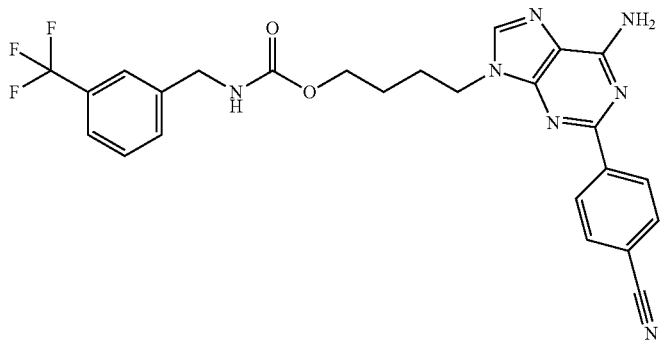 [SMILES: N#Cc1ccc(-c2nc(N)c3ncn(CCCCOC(=O)NCc4cccc(C(F)(F)F)c4)c3n2)cc1] | [3-(trifluoromethyl)phenyl]methanamine | 4-cyano-phenyl |
| 261 | 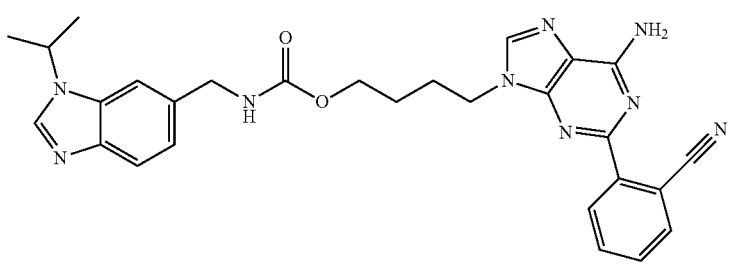 [SMILES: CC(C)n1cnc2ccc(CNC(=O)OCCCCn3cnc4c(N)nc(-c5ccccc5C#N)nc43)cc21] | (3-isopropylbenzimidazol-5-yl)methanamine | 2-cyano-phenyl |

TABLE 1-continued

Examples of compounds

| | | | |
|---|---|---|---|
| 262 | | [3-(trifluoromethyl)phenyl]methanamine | furan-3-yl |
| 263 | | [3-(trifluoromethyl)phenyl]methanamine | 4-pyridyl |
| 264 | | (3-isopropylbenzimidazol-5-yl)methanamine | o-tolyl |
| 265 | | (3-isopropylbenzimidazol-5-yl)methanamine | m-tolyl |
| 266 | | (3-isopropylbenzimidazol-5-yl)methanamine | p-tolyl |
| 267 | | (3-isopropylbenzimidazol-5-yl)methanamine | 2-fluorophenyl |

TABLE 1-continued
Examples of compounds
| | | | |
|---|---|---|---|
| 268 | 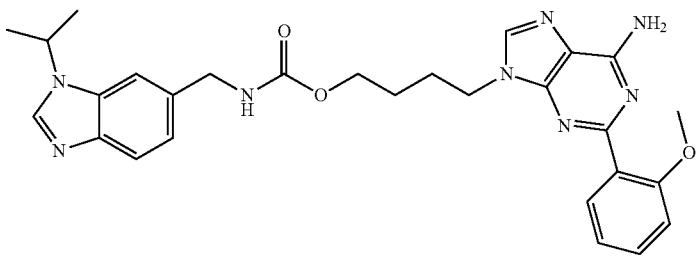 [SMILES: COc1ccccc1-c1nc(N)c2ncn(CCCCOC(=O)NCc3ccc4ncn(C(C)C)c4c3)c2n1] | (3-isopropylbenzimidazol-5-yl)methanamine | 2-methoxy-phenyl |
| 269 | 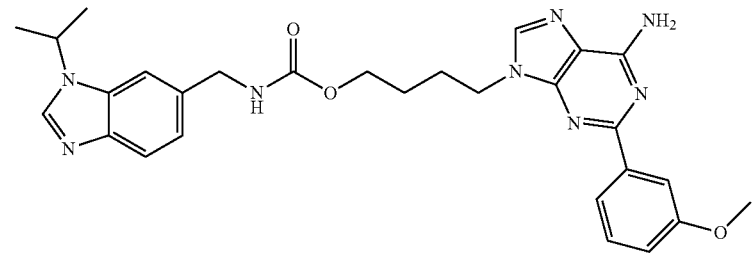 [SMILES: COc1cccc(-c2nc(N)c3ncn(CCCCOC(=O)NCc4ccc5ncn(C(C)C)c5c4)c3n2)c1] | (3-isopropylbenzimidazol-5-yl)methanamine | 3-methoxy-phenyl |
| 270 | 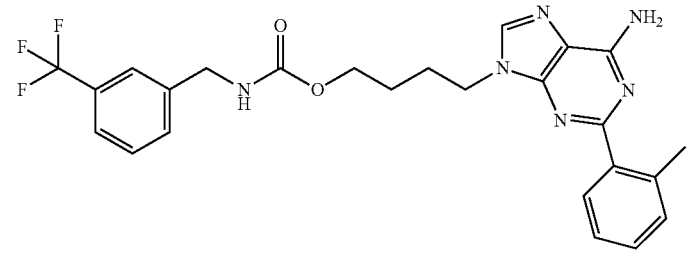 [SMILES: Cc1ccccc1-c1nc(N)c2ncn(CCCCOC(=O)NCc3cccc(C(F)(F)F)c3)c2n1] | [3-(trifluoromethyl)phenyl]methanamine | o-tolyl |
| 271 | 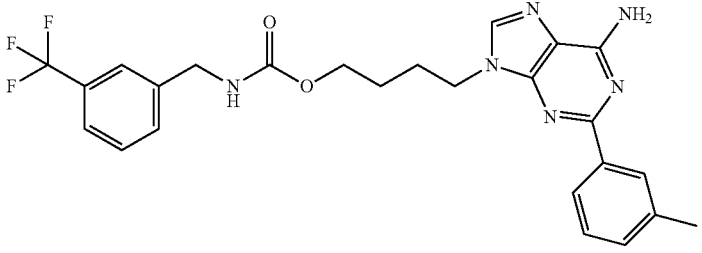 [SMILES: Cc1cccc(-c2nc(N)c3ncn(CCCCOC(=O)NCc4cccc(C(F)(F)F)c4)c3n2)c1] | [3-(trifluoromethyl)phenyl]methanamine | m-tolyl |
| 272 | 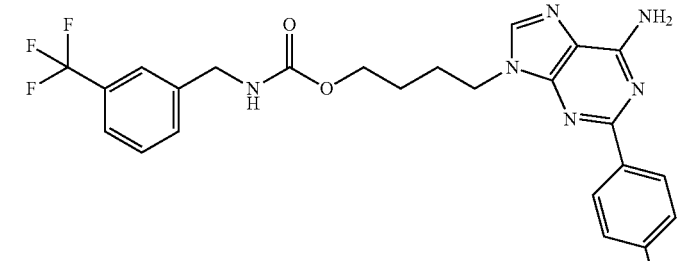 | [3-(trifluoromethyl)phenyl]methanamine | p-tolyl |

TABLE 1-continued

Examples of compounds

| | | | |
|---|---|---|---|
| 273 | | [3-(trifluoromethyl)phenyl]methanamine | 2-methoxyphenyl |
| 274 | | [3-(trifluoromethyl)phenyl]methanamine | 3-methoxyphenyl |
| 275 | | [3-(trifluoromethyl)phenyl]methanamine | 4-methoxyphenyl |
| 276 | | (3-isopropylbenzimidazol-5-yl)methanamine | 4-methoxyphenyl |
| 277 | | [3-(trifluoromethyl)-phenyl]methanamine | 3-pyridinyl |

TABLE 1-continued
Examples of compounds
| No | Structure | Substituent Linker | R¹ | R² |
|---|---|---|---|---|
| 278 | 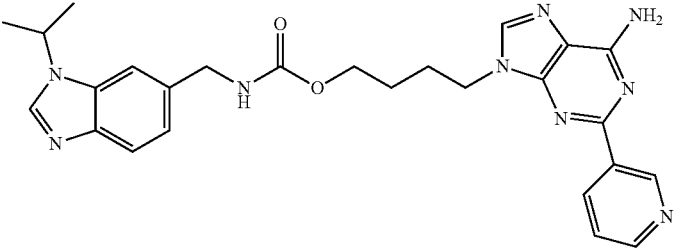 [SMILES: CC(C)n1cnc2ccc(CNC(=O)OCCCCn3cnc4c(N)nc(-c5cccnc5)nc43)cc21] | | (3-isopropylbenzimidazol-5-yl)methanamine | 3-pyridinyl |
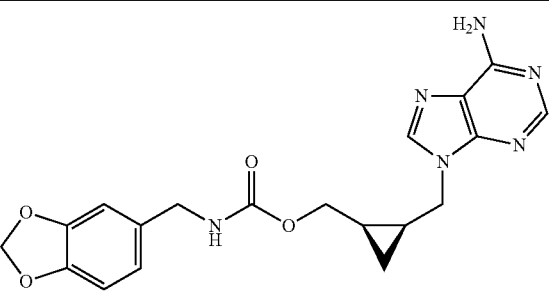
| No | Structure | Substituent Linker | R¹ | R² |
|---|---|---|---|---|
| 163 | 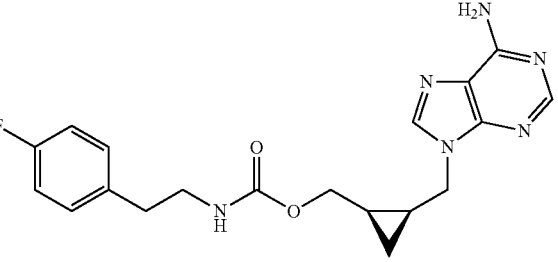 | cyclopropyl methyl | 1,3-benzo-dioxol-5-yl-methan-amine | H |
| 164 | 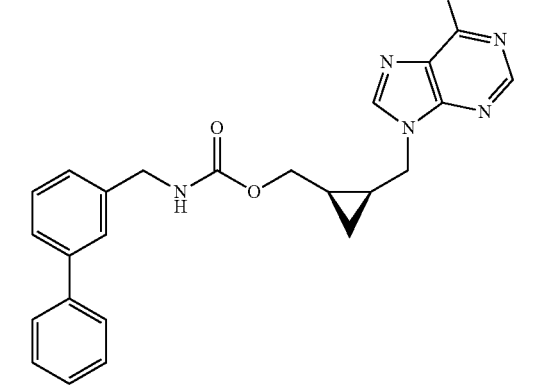 | cyclopropyl methyl | 2-(4-fluoro phenyl)ethanamine | H |
| 165 | | cyclopropyl methyl | (3-phenyl phenyl)methan-amine | H |

TABLE 1-continued

Examples of compounds

| | | | | |
|---|---|---|---|---|
| 166 | | (1R,5R)-cyclohex-3-en-1-yl | 1,3-benzodioxol-5-yl methanamine | Cl |
| 167 | | (1R,5R)-cyclohex-3-en-1-yl | [3-(trifluoromethyl)phenyl] methanamine | Cl |
| 168 | | (1R,3S)-cyclohexyl | 1,3-benzodioxol-5-yl methanamine | Cl |
| 169 | | (1S,4S)-cyclohexyl | 1,3-benzodioxol-5-yl methanamine | Cl |
| 170 | | (1S,4S)-cyclohexyl | [3-(trifluoromethyl)phenyl] methanamine | Cl |

Example 12: Biological Assay Measuring the Protein Kinase Inhibition

A biochemical assay was performed in order to measure the protein kinase inhibition. The kinase binding assays were performed against different kinases using the SelectScreen Biochemical Kinase Profiling Service®. For all kinases, the Z'-Lyte® biochemical kinase assay technology was used except for FLT3-ITD where the LanthaScreen® kinase assay technology was used.

Figure 1B:
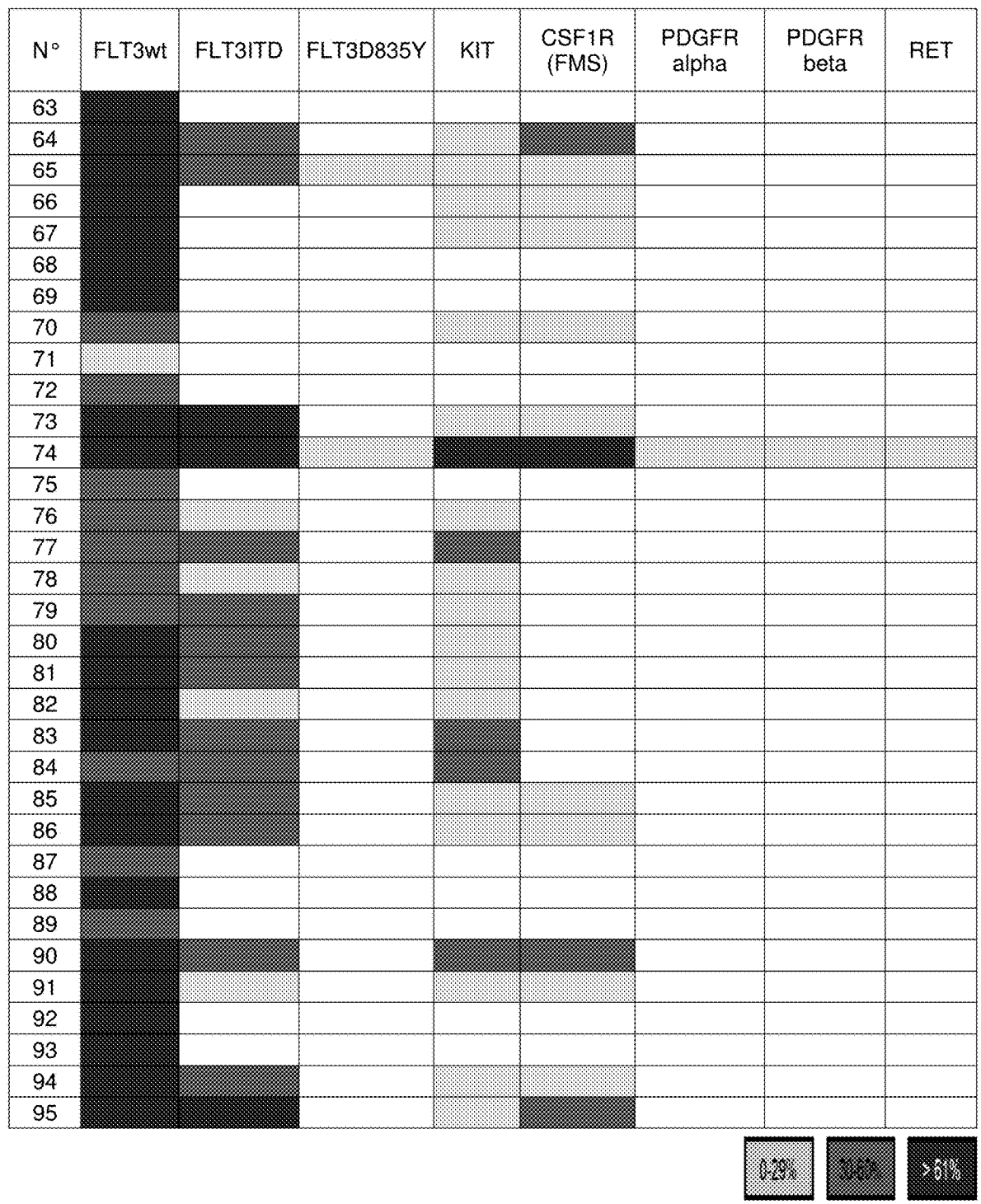
Figure 1C:
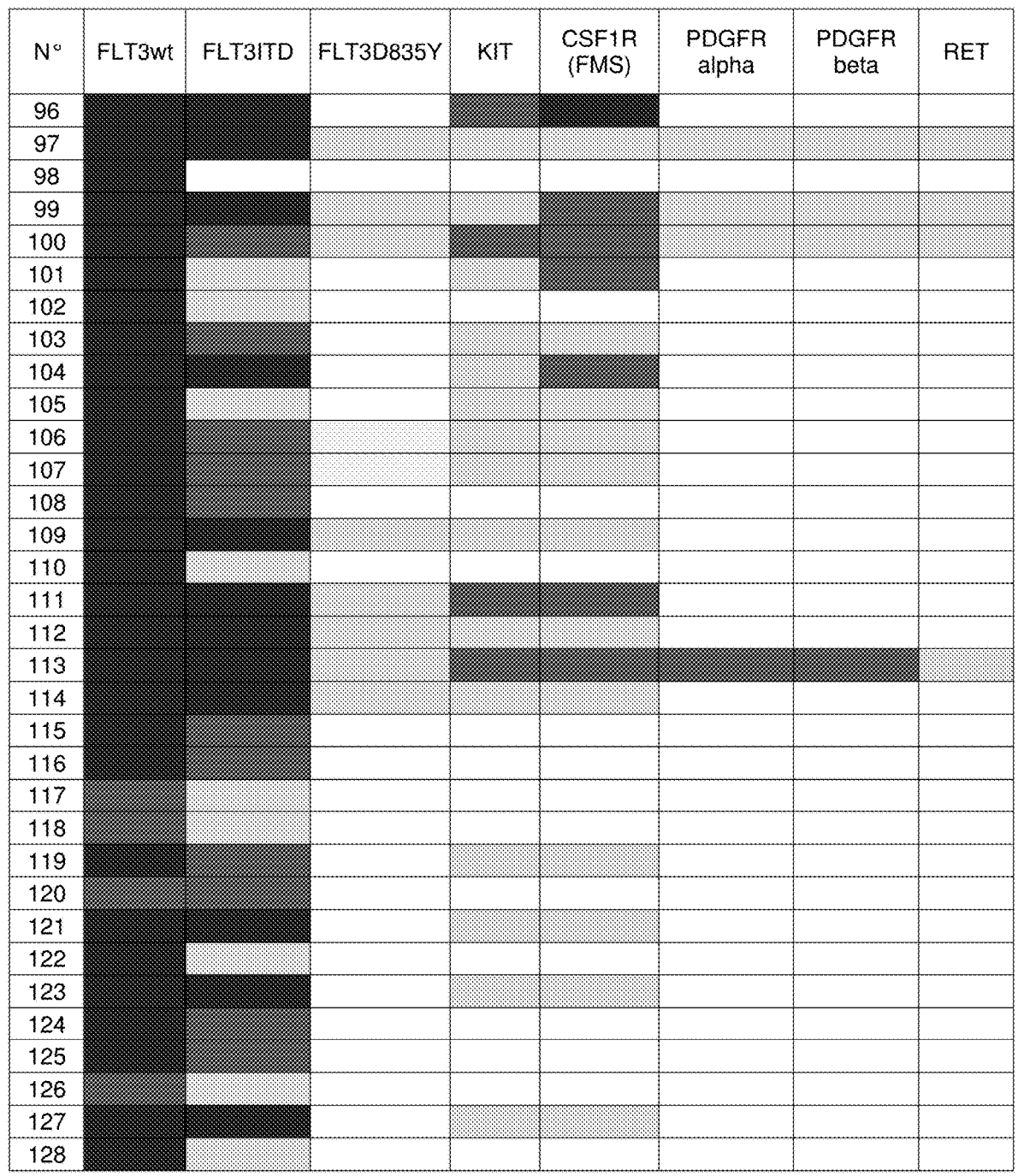
Figure 1D:
Figure 1E:
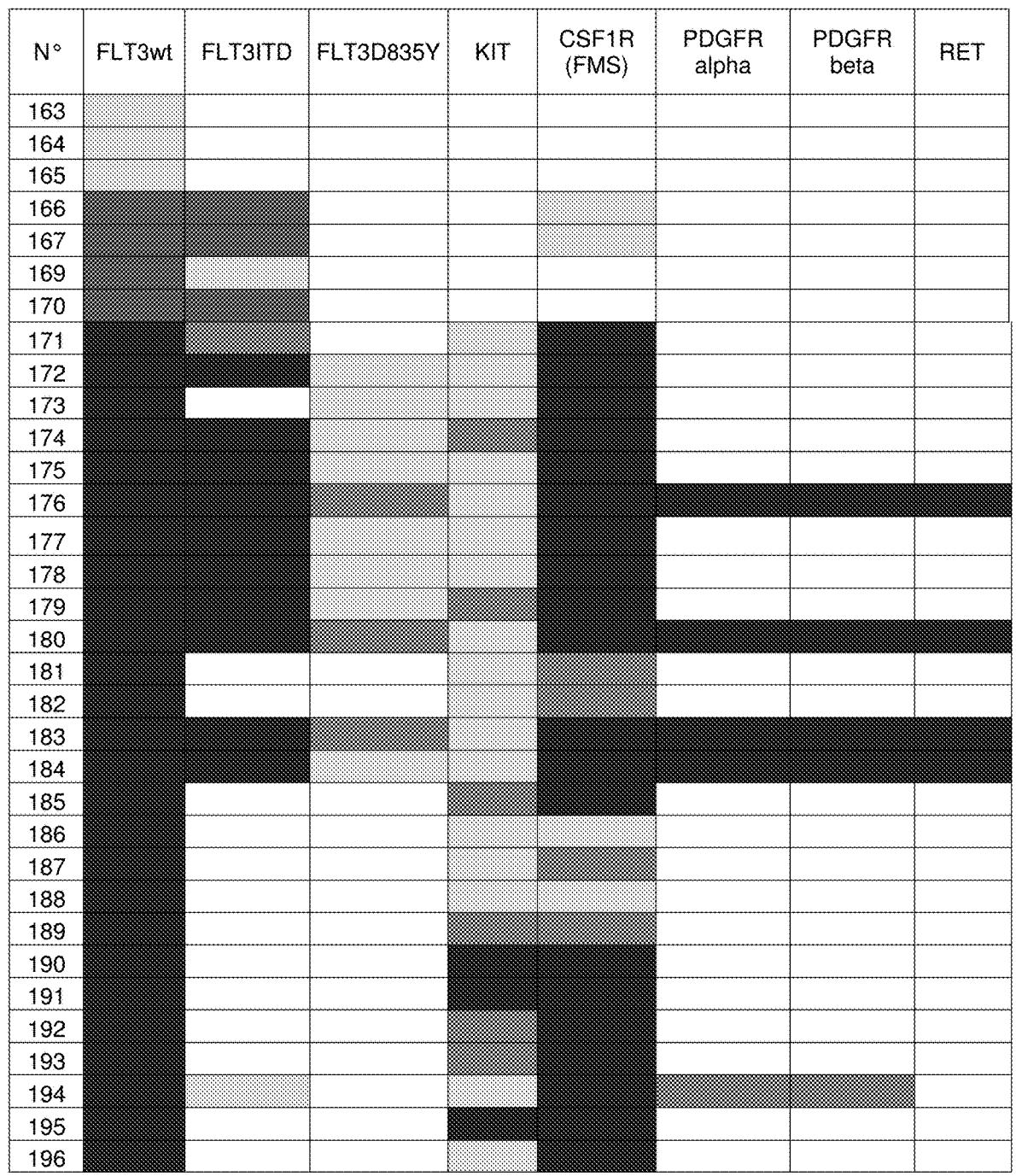
Figure 1F:
Figure 1G:
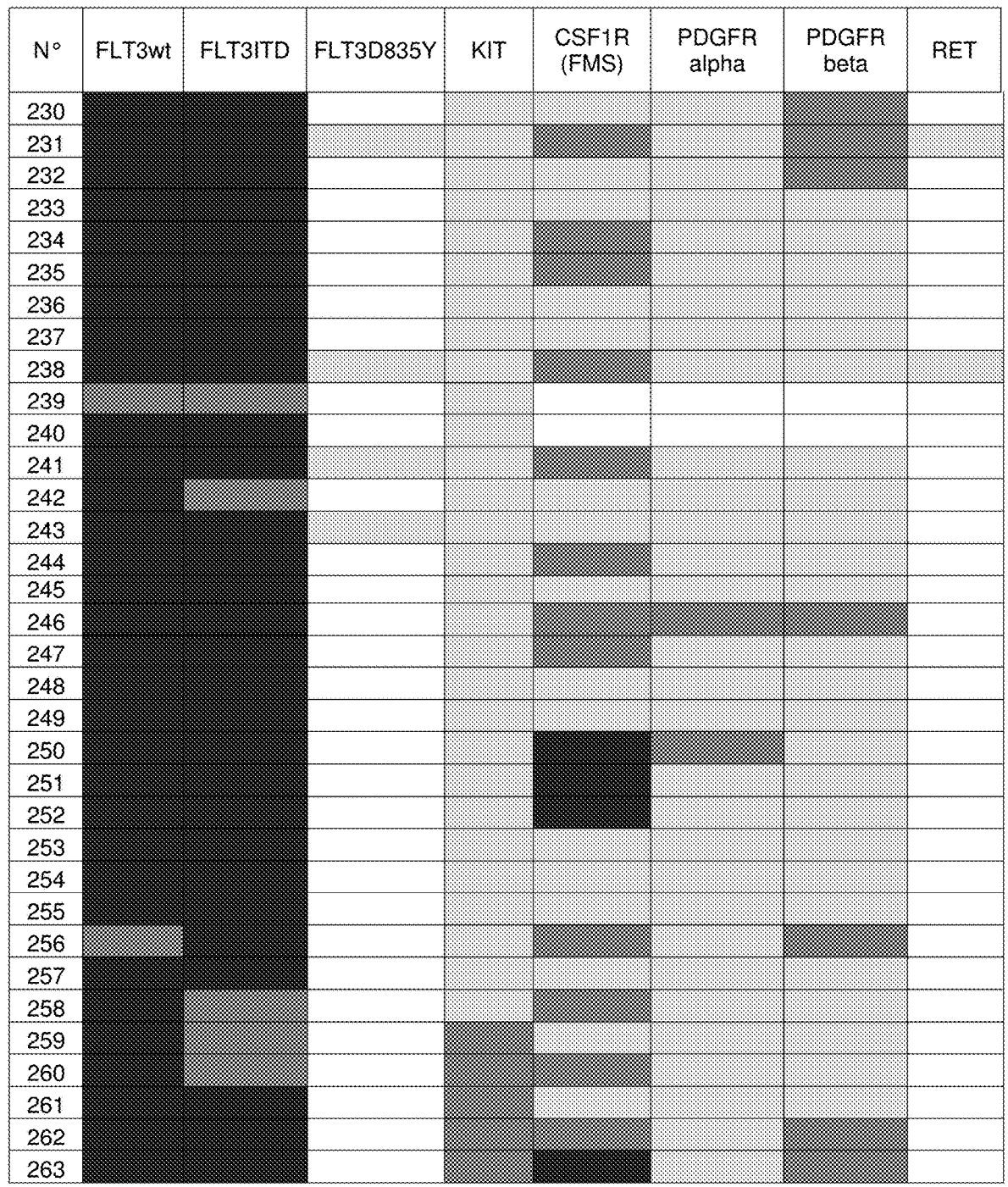
Figure 1H:

Inhibitions were measured at 50 nM in duplicate for each compound and are reported in percentage. Some data are presented in FIGS. 1A-1H.

The invention claimed is:

1. A compound according to general formula (I), or the N-oxide, pharmaceutically acceptable salt, pharmaceutically acceptable solvate, or stereoisomer thereof:

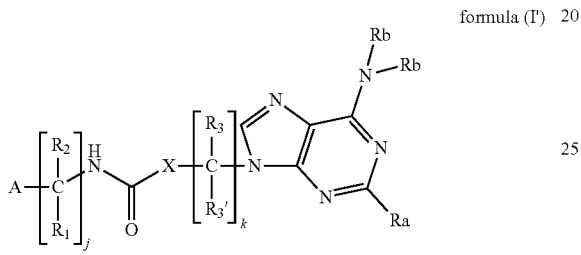

formula (I')

wherein:
A is selected from the group consisting of phenyl, heteroaryl being a monocyclic ring structure containing 5 or 6 ring atoms, or a bicyclic aromatic group having 8 to 10 atoms, containing 1-3 heteroatoms independently selected from O or N, and heterocyclyl containing 3 to 12 carbon atoms and 1 or 2 heteroatoms independently selected from O or N, wherein each A is optionally substituted with 1, 2, or 3 substituents independently selected from the group consisting of halo, $C_{1-6}$ alkyl, $C_{2-4}$ alkenyl, $C_{3-6}$ cycloalkyl, $CF_3$, CN, $OR_{11}$, $N(R_{11})_2$, $-OC(R_{11})_2O-$, $-OC(R_{11})_2C(R_{11})_2O-$, $SO_2R_{12}$, $SO_2N(R_{11})_2$, $NHSO_2R_{11}$, optionally substituted phenyl, heteroaryl being a monocyclic ring structure containing 5 or 6 ring atoms, or a bicyclic aromatic group having 8 to 10 atoms, containing 1 to 3 heteroatoms independently selected from O or N, cycloalkyl containing 3 to 6 carbon atoms, and heterocyclyl containing 3 to 12 carbon atoms and 1 or 2 heteroatoms independently selected from O or N, and each optional phenyl, heteroaryl, cycloalkyl and heterocyclyl is further optionally substituted with alkyl, $N(R_{11})_2$, or CN, and wherein each of $R_{11}$ and $R_{12}$, independently from each other and at each occurrence, are selected from the group consisting of hydrogen, $C_{1-5}$ alkyl, heterocyclyl containing 3 to 6 carbon atoms and 1 or 2 heteroatoms each independently selected from O or N, phenyl, benzyl, and $CF_3$ wherein said alkyl, heterocyclyl, phenyl and benzyl are optionally substituted with halo or heterocyclyl containing 3 to 6 carbon atoms and 1 or 2 heteroatoms each independently selected from O or N;

X is O;

$R_1$ and $R_2$, independently from each other and at each occurrence, are selected from the group consisting of hydrogen and $C_{1-4}$ alkyl;

j is an integer in the range from 0 to 2;

$R_3$ and $R_{3'}$, independently from each other and at each occurrence, are selected from the group consisting of hydrogen and $C_{1-4}$ alkyl;

k is an integer in the range from 2 to 5;

$R_a$ is hydrogen, halo, $N(R_{14})_2$, $C_{1-15}$ alkyl, $C_{2-15}$ alkenyl, or $C_{2-15}$ alkynyl, or $R_a$ is phenyl, heteroaryl being a monocyclic ring structure containing 5 or 6 ring atoms, or a bicyclic aromatic group having 8 to 10 atoms, containing 1-3 heteroatoms independently selected from O or N, cycloalkyl containing 3 to 6 carbon atoms, or heterocyclyl containing 3 to 12 carbon atoms and 1 or 2 heteroatoms independently selected from O or N, each of which are optionally substituted with 1, 2, or 3 substituents selected from halo, $C_{1-15}$ alkyl, and $O-C_{1-6}$ alkyl; and wherein each of $R_{14}$, independent from each other, is hydrogen, $C_{1-15}$ alkyl, or $C_{3-6}$ cycloalkyl; and $R_b$ is hydrogen or a methyl.

2. A compound of formulae (II), (IV), or (V) or the N-oxide, pharmaceutically acceptable salt, pharmaceutically acceptable solvate, or stereoisomer thereof:

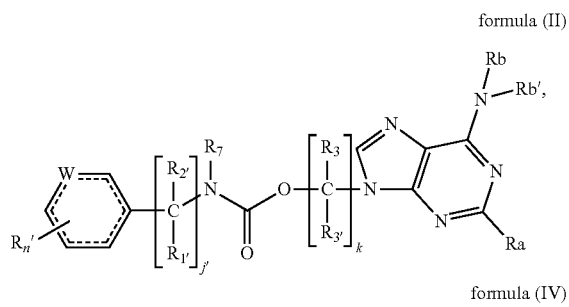

formula (II)

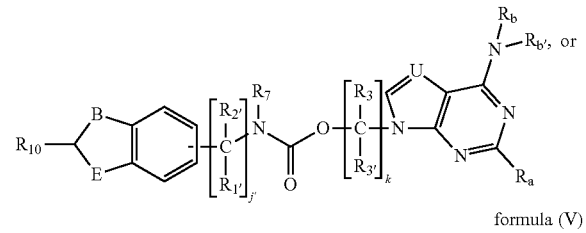

formula (IV)

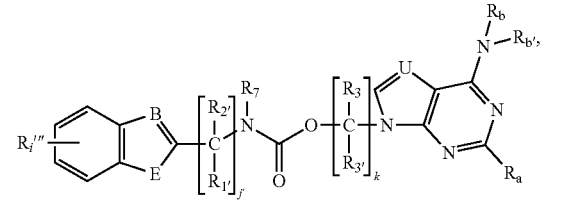

formula (V)

wherein:
each of $R_a$ is independently hydrogen, halo, $N(R_{14})_2$, $C_{1-15}$ alkyl, $C_{2-15}$ alkenyl, $C_{2-15}$ alkynyl, phenyl, heteroaryl being a monocyclic ring structure containing 5 or 6 ring atoms, or a bicyclic aromatic group having 8 to 10 atoms, containing 1-3 heteroatoms independently selected from O or N, cycloalkyl containing 3 to 6 carbon atoms, or heterocyclyl containing 3 to 12 carbon atoms and 1 or 2 heteroatoms independently selected from O or N, wherein said alkyl, cycloalkyl, heterocyclyl, phenyl, and heteroaryl are optionally substituted with one or more substituents selected from halo, $C_{1-15}$ alkyl, and O—$C_{1-6}$ alkyl; and wherein each of $R_{14}$, independent from each other, is selected from hydrogen, $C_{1-15}$ alkyl, and $C_{3-6}$ cycloalkyl;

each of U is N;

each of R' and R''', independently from each other and at each occurrence, are halo, $C_{1-6}$ alkyl, $C_{2-6}$ alkenyl, $CF_3$, CN, $OR_{21}$, $N(R_{21})_2$, —$OC(R_{21})_2O$—, —$OC(R_{21})_2C(R_{21})_2O$—, $SO_2R_{22}$, or $SO_2N(R_{21})_2$, phenyl, heteroaryl being a monocyclic ring structure containing 5 or 6 ring atoms, or a bicyclic aromatic group having 8 to 10 atoms, containing 1-3 heteroatoms independently selected from O or N, cycloalkyl containing 3 to 6 carbon atoms, or heterocyclyl containing 3 to 12 carbon atoms and 1 or 2 heteroatoms independently selected from O or N, wherein said alkyl, alkenyl, cycloalkyl, phenyl, heterocyclyl, and heteroaryl group is optionally substituted with one or more substituents selected from alkyl, $N(R_{21})_2$, $CON(R_{21})_2$, and CN; wherein each of $R_{21}$ and $R_{22}$ are independently hydrogen, $C_{1-5}$ alkyl, $CF_3$, phenyl, or heterocyclyl containing 3 to 12 carbon atoms and 1 or 2 heteroatoms independently selected from O or N, wherein said alkyl, heterocyclyl, and phenyl substituents are optionally substituted with halo or heterocyclyl containing 3 to 12 carbon atoms and 1 or 2 heteroatoms independently selected from O or N; and wherein when W is a nitrogen, R' may be attached to one carbon atom and the nitrogen atom of the phenyl group thereby forming an imidazo[1,2-a]pyridine ring system;

each dotted line denotes a bond or an absence of a bond with the proviso that the cycle is aromatic;

n is an integer in the range from 0 to 4;

$R_{1'}$ and $R_{2'}$, independently from each other and at each occurrence, are selected from the group consisting of hydrogen and $C_{1-4}$ alkyl;

each of $R_3$ and $R_{3'}$ is hydrogen each of $R_b$ and $R_{b'}$, independent from each other and at each occurrence, are hydrogen or methyl;

each of $R_7$ is independently hydrogen or methyl;

each of k is an integer in the range from 4 to 5;

each of W is, independently and at each occurrence, C-halo, C—$R_{24}$, or N; wherein $R_{24}$ is hydrogen or an $C_{1-10}$ alkyl which is optionally substituted by a halogen atom or a phenyl;

each of E is independently $CH_2$, CH-halo, or $NR_{25}$, wherein $R_{25}$ is hydrogen or $C_{1-10}$ alkyl which is optionally substituted by a halogen atom, or a phenyl;

each of B is, independently and at each occurrence, C-halo, C—$R_{26}$, or N, wherein $R_{26}$ is hydrogen or $C_{1-10}$ alkyl which is optionally substituted by a halogen atom, or a phenyl;

each of j' is an integer in the range from 0 to 3;

each of $R_{10}$ is independently hydrogen, halo, $C_{1-6}$ alkyl, $C_{2-6}$ alkenyl, $C_{3-6}$ cycloalkyl, or $N(R_{27})_2$, wherein $R_{27}$ is independently hydrogen or an $C_{1-10}$ alkyl which is optionally substituted by a phenyl.

3. The compound according to claim 1, wherein compound is a compound of formulae (XXVI) to (LIX); (LXIV) to (CXIII) or (CLVIII), or the N-oxide, pharmaceutically acceptable salt, pharmaceutically acceptable solvate, or stereoisomer thereof:

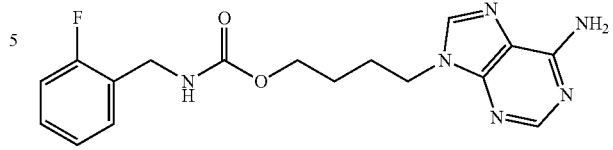

formula (XXVI)

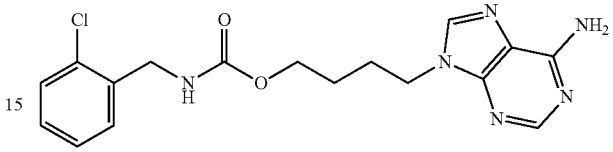

formula (XXVII)

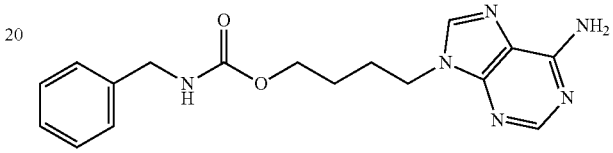

formula (XXVIII)

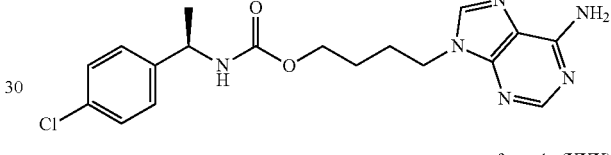

formula (XXIX)

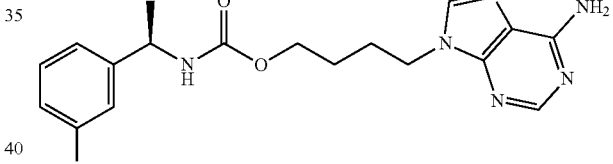

formula (XXX)

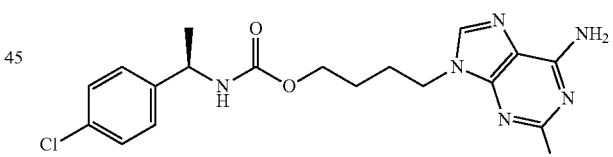

formula (XXXI)

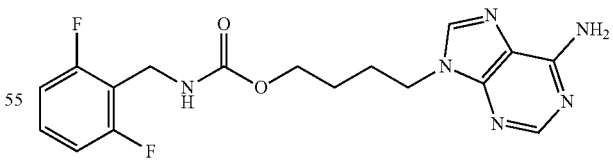

formula (XXXII)

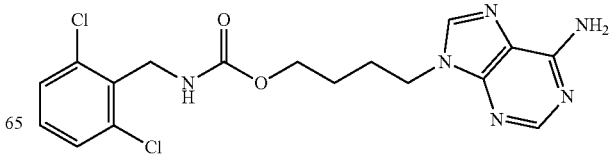

formula (XXXIII)

formula (XXXIV)
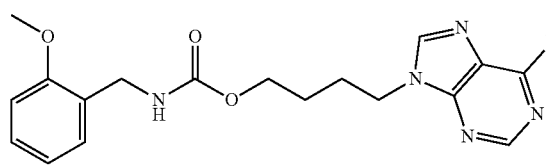
formula (XXXV)
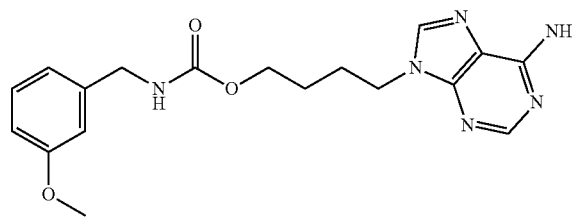
formula (XXXVI)
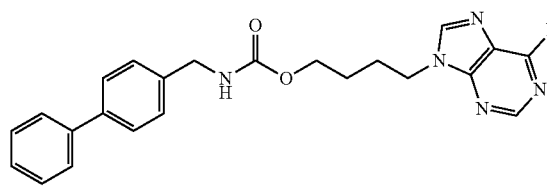
formula (XXXVI-1)
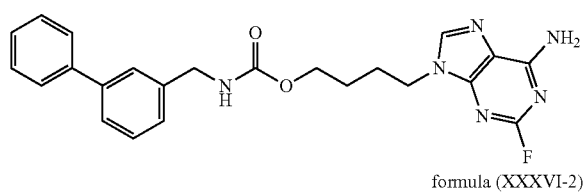
formula (XXXVI-2)
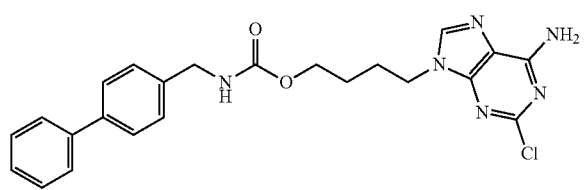
formula (XXXVII)
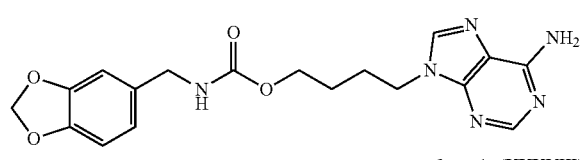
formula (XXXVIII)
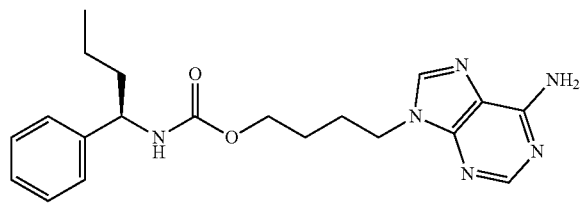
formula (XXXIX)
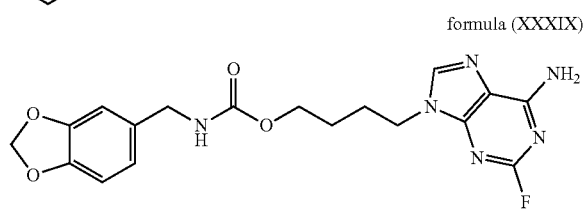
formula (XL)
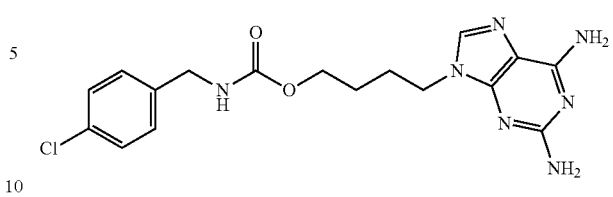
formula (XLI)
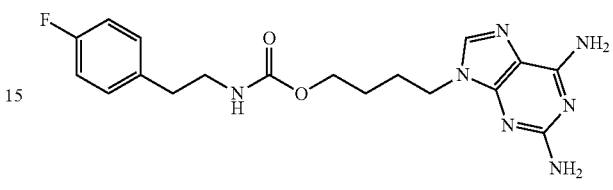
formula (XLII)
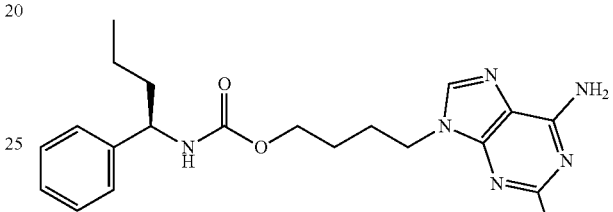
formula (XLIII)
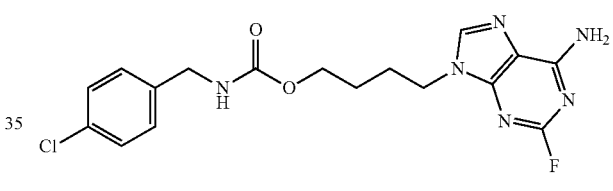
formula (XLIV)
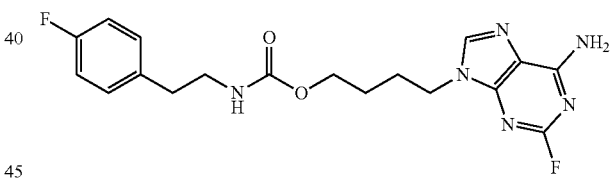
formula (XLV)
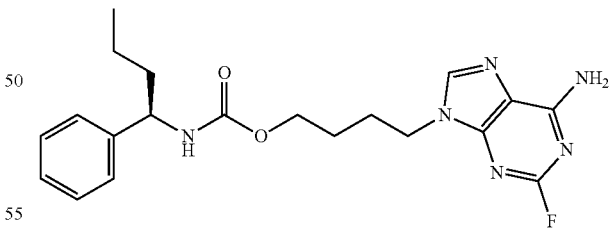
formula (XLVI)
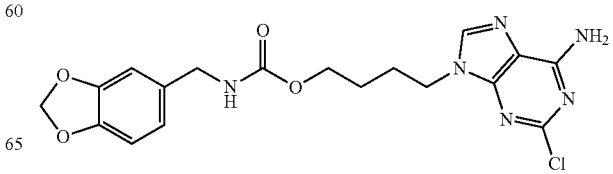

formula (XLVI-1)
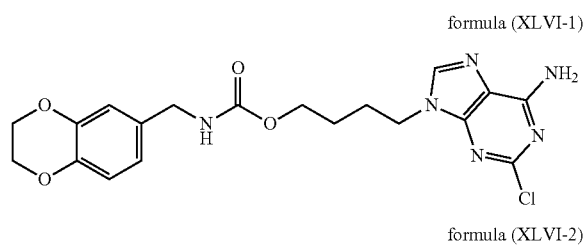
formula (XLVI-2)
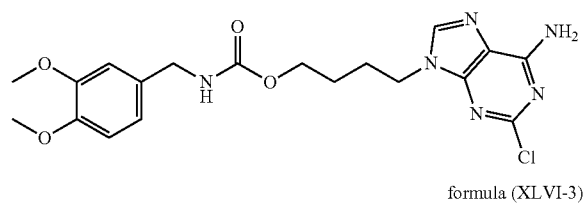
formula (XLVI-3)
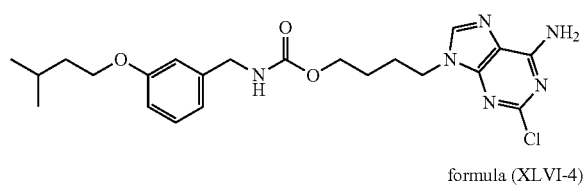
formula (XLVI-4)
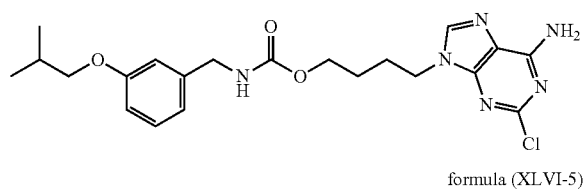
formula (XLVI-5)
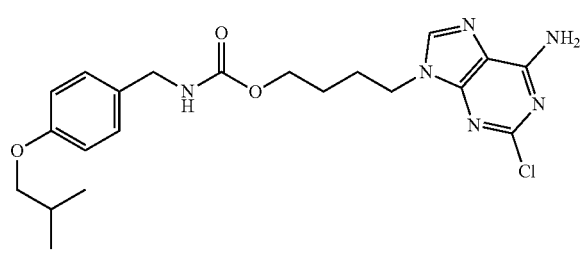
formula (XLVI-7)
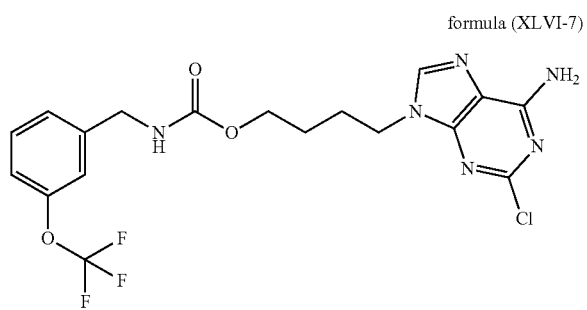
formula (XLVI-8)
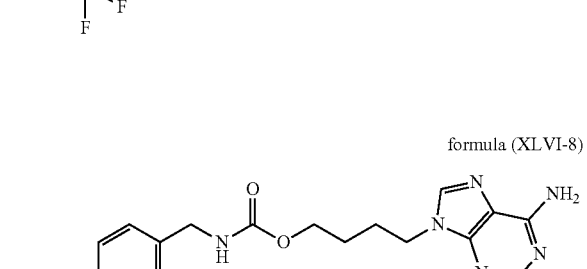
formula (XLVI-9)
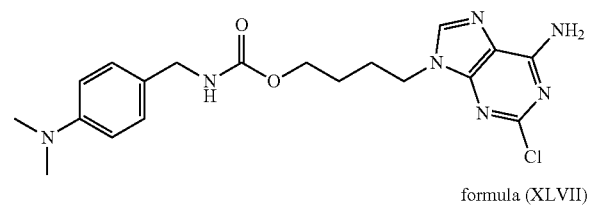
formula (XLVII)
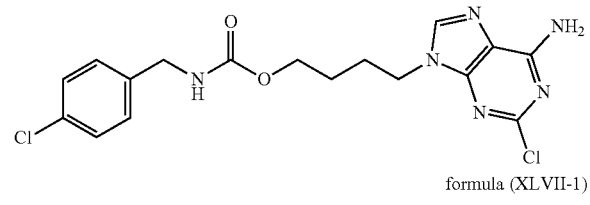
formula (XLVII-1)
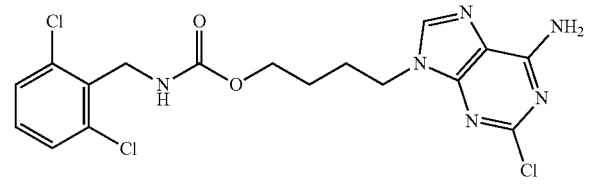
formula (XLVIII)
formula (XLIX)
formula (XLIX-1)
formula (L)
formula (LI)
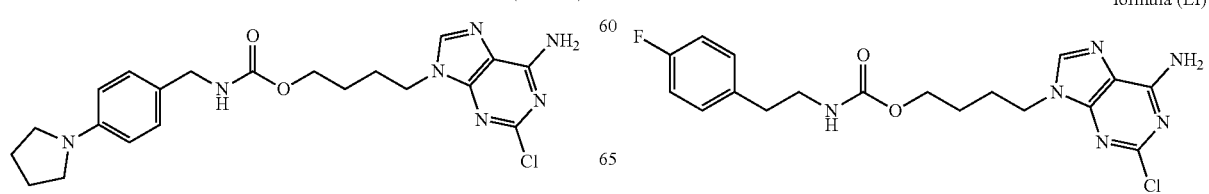

formula (LI-1)
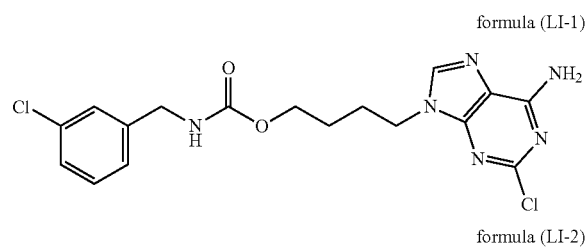
formula (LI-2)
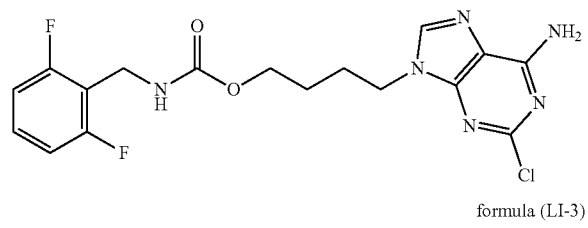
formula (LI-3)
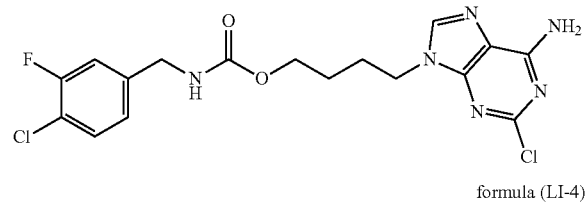
formula (LI-4)
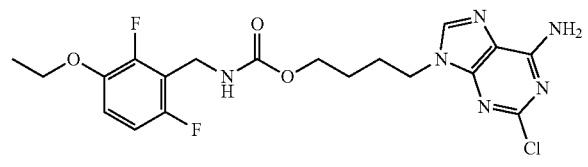
formula (LI-5)
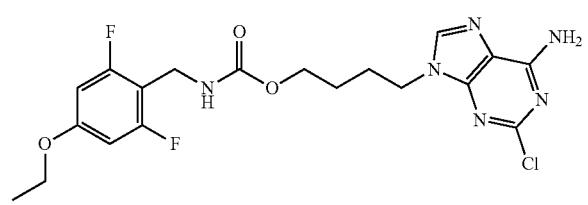
formula (LI-6)
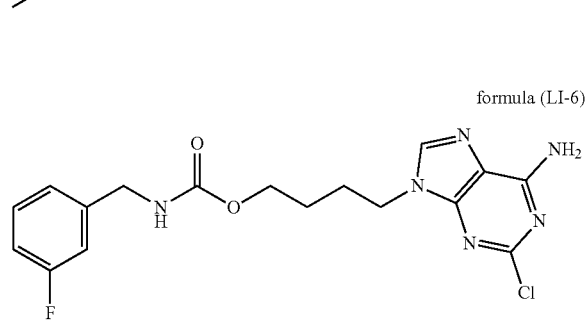
formula (LI-7)
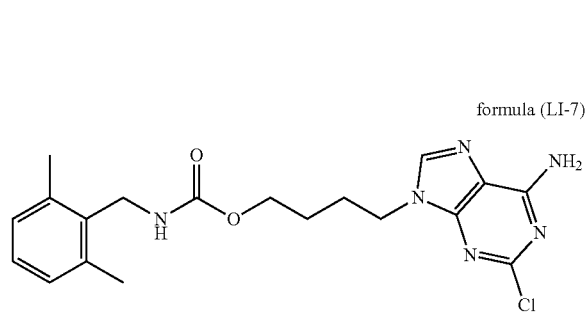
formula (LII)
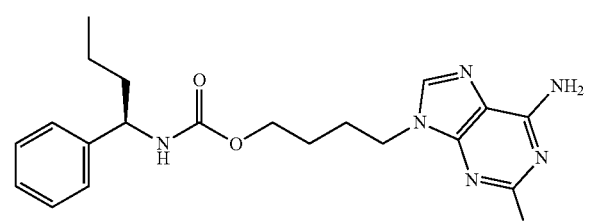
formula (LIII)
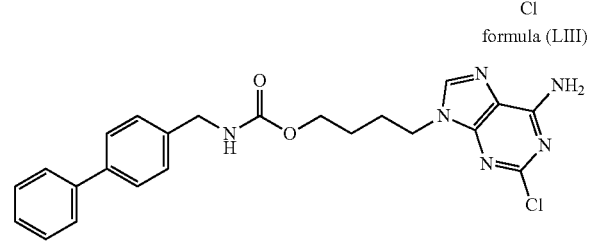
formula (LIII-1)
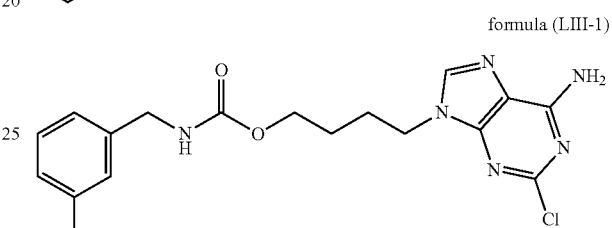
formula (LIII-2)
formula (LIII-3)
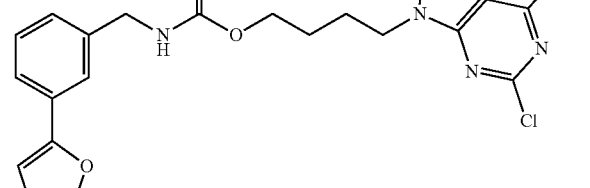
formula (LIII-4)
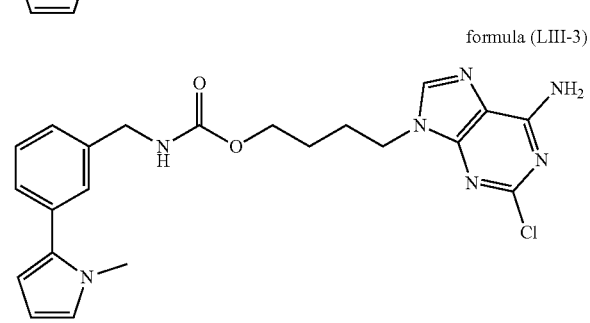
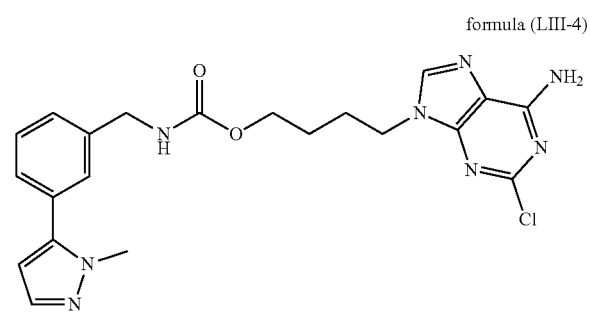

-continued
formula (LIII-5)
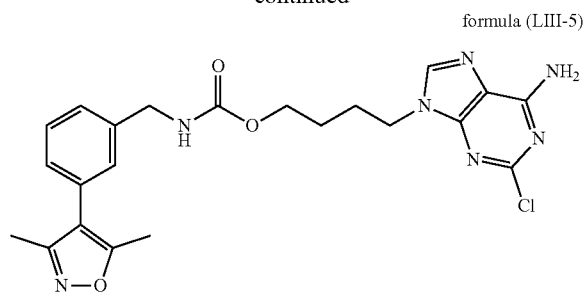
formula (LIII-6)
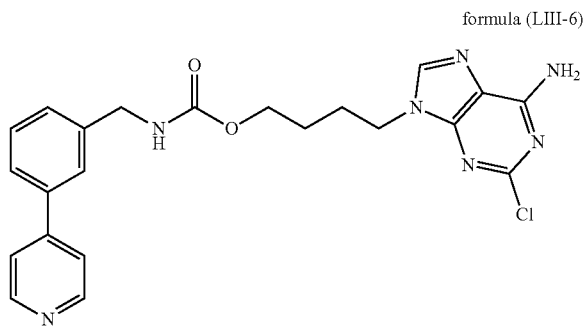
formula (LIII-7)
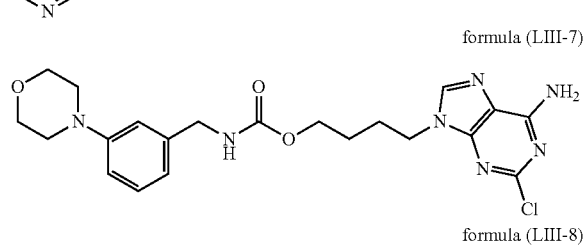
formula (LIII-8)
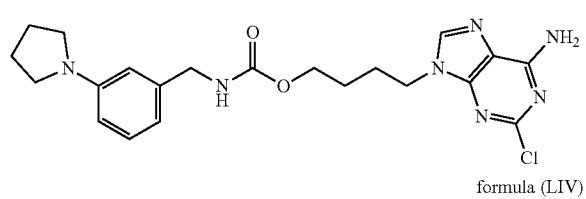
formula (LIV)
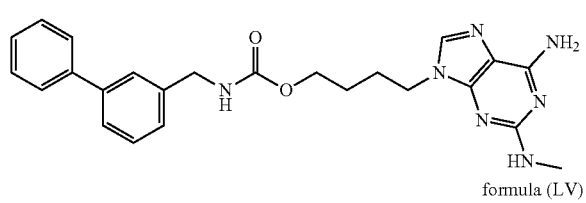
formula (LV)
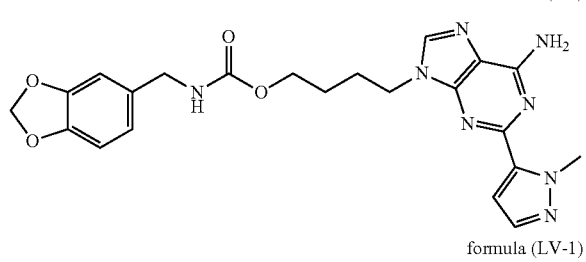
formula (LV-1)
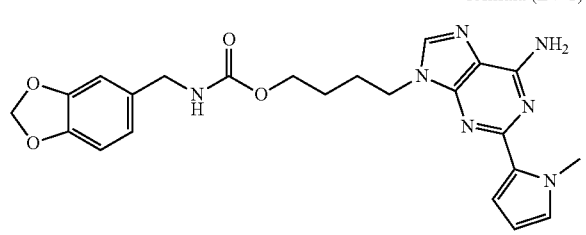
-continued
formula (LV-2)
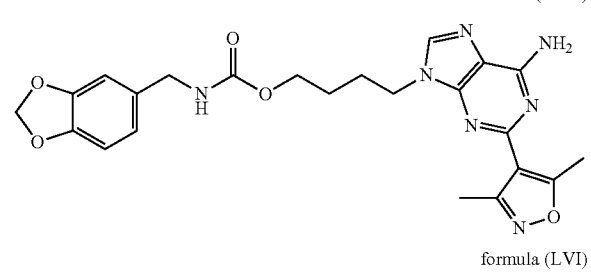
formula (LVI)
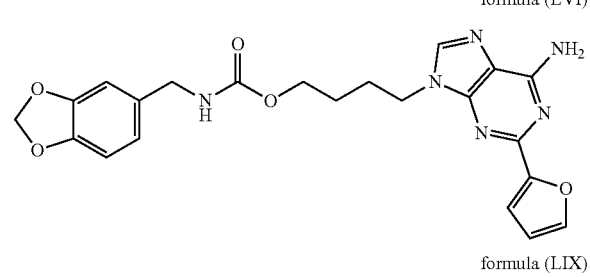
formula (LIX)
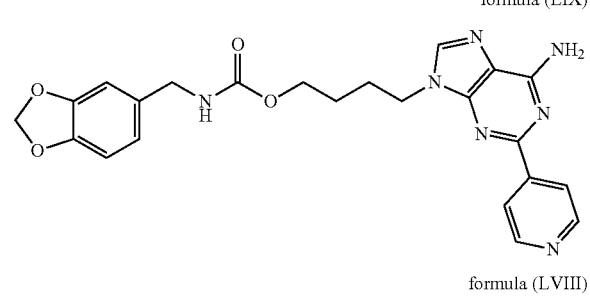
formula (LVIII)
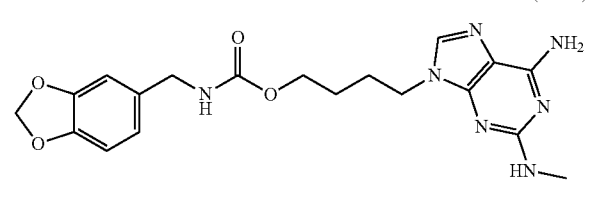
formula (LVIII-1)
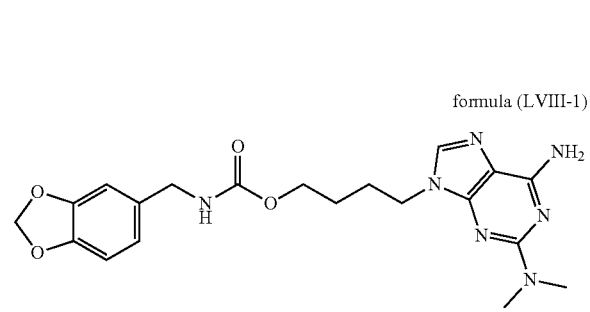
formula (CLVIII)
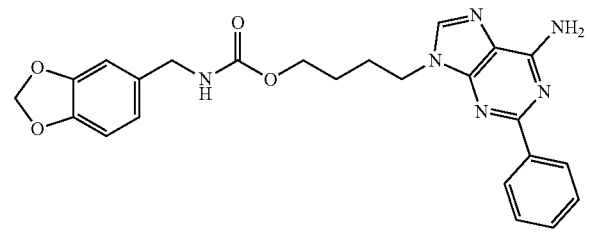

formula (LXIV)
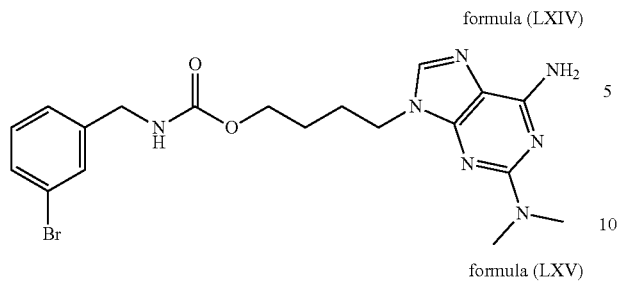
formula (LXV)
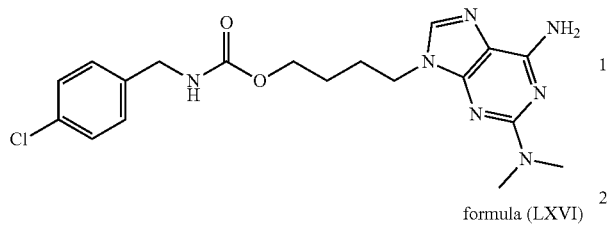
formula (LXVI)
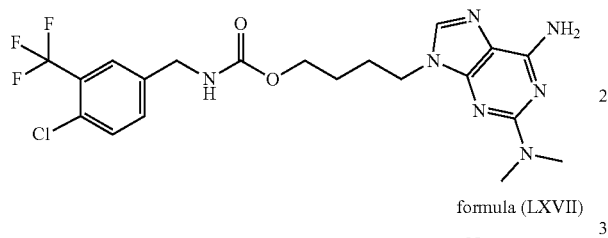
formula (LXVII)
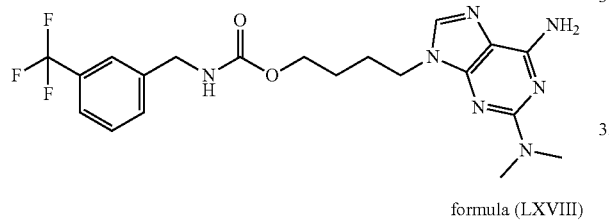
formula (LXVIII)
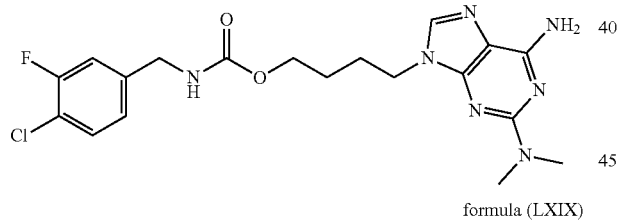
formula (LXIX)
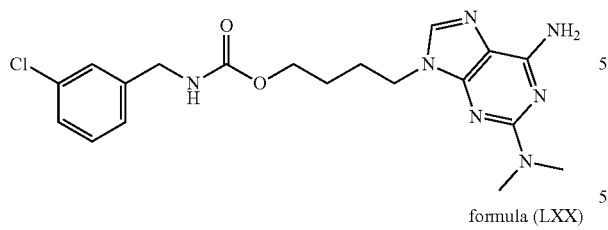
formula (LXX)
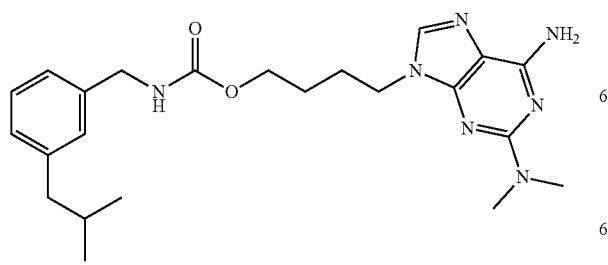
formula (LXXI)
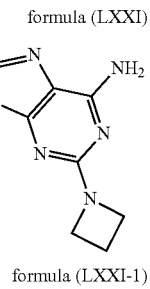
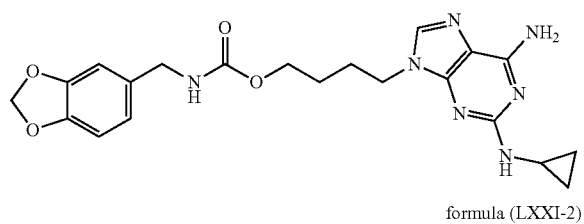
formula (LXXI-1)
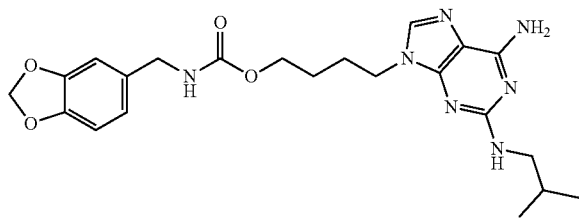
formula (LXXI-2)
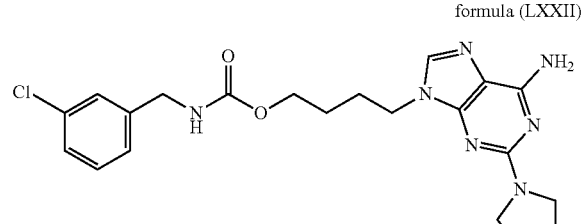
formula (LXXII)
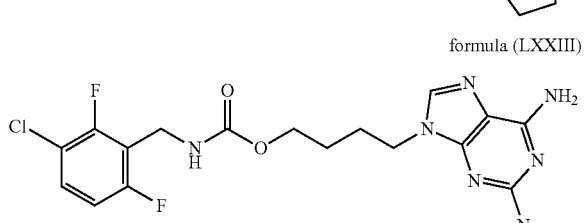
formula (LXXIII)
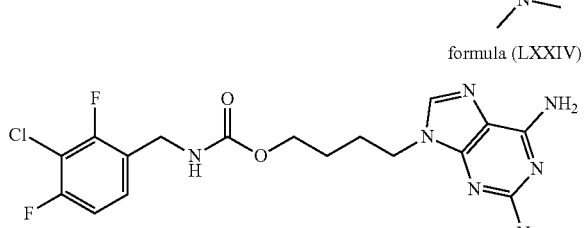
formula (LXXIV)
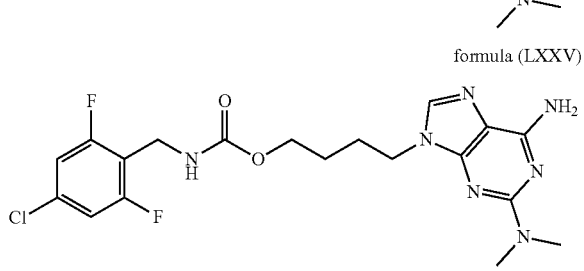
formula (LXXV)

formula (LXXVI)
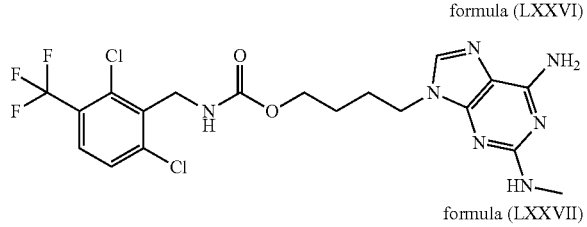
formula (LXXVII)
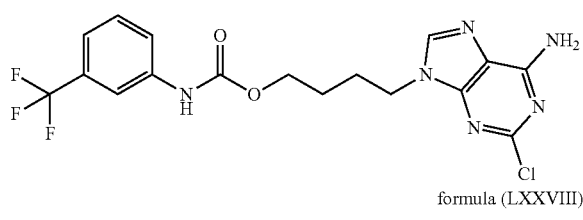
formula (LXXVIII)
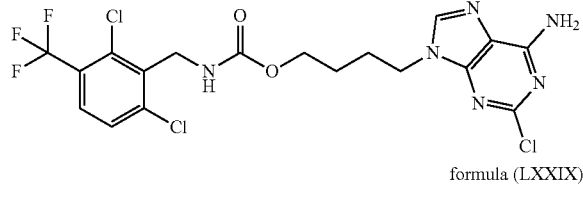
formula (LXXIX)
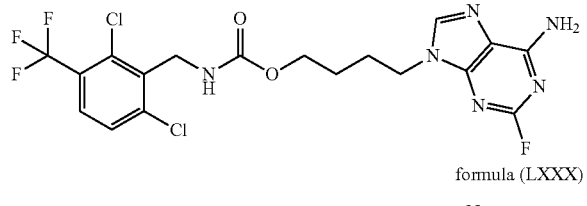
formula (LXXX)
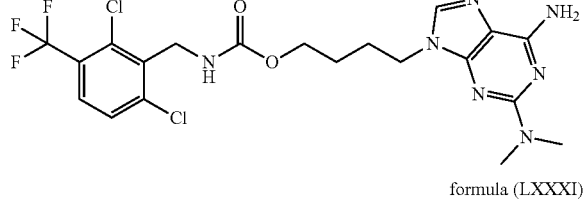
formula (LXXXI)
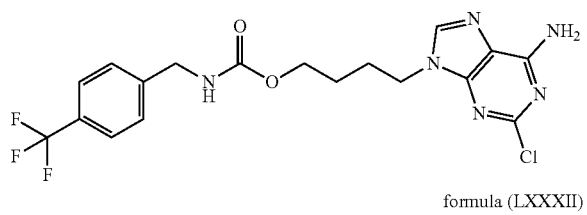
formula (LXXXII)
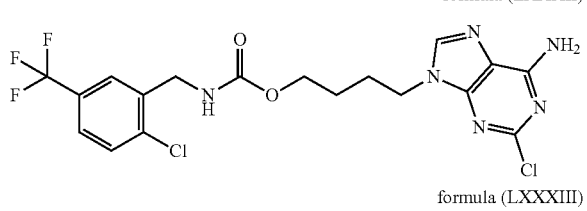
formula (LXXXIII)
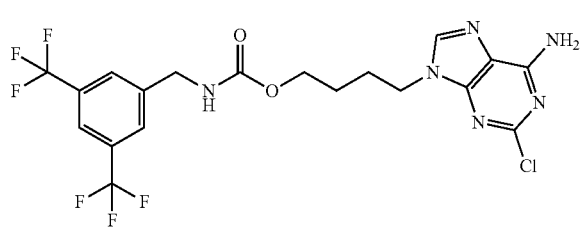
formula (LXXXIV)
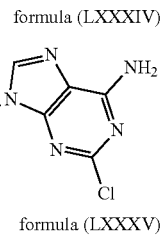
formula (LXXXV)
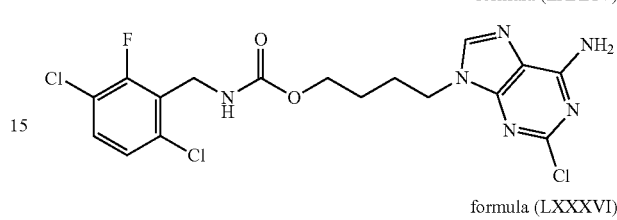
formula (LXXXVI)
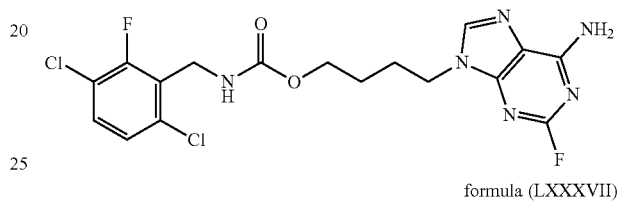
formula (LXXXVII)
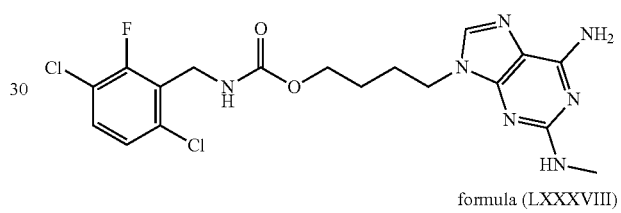
formula (LXXXVIII)
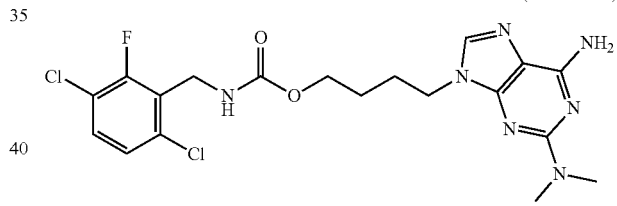
formula (LXXXIX)
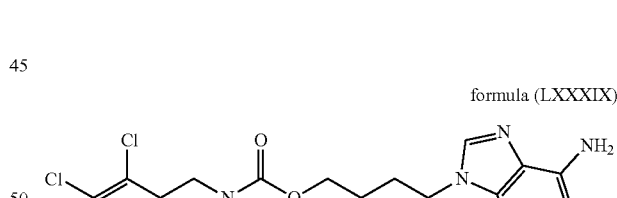
formula (XC)
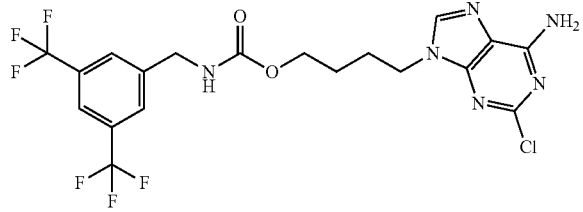

237
-continued
formula (XCI)
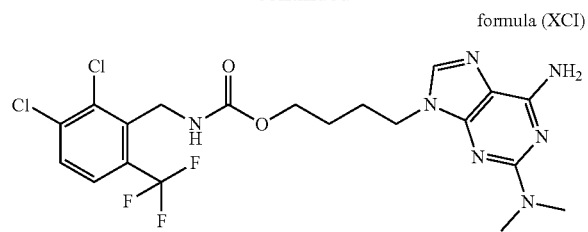
formula (XCII)
formula (XCII-1)
formula (XCII-2)
formula (XCII-3)
238
-continued
formula (XCII-4)
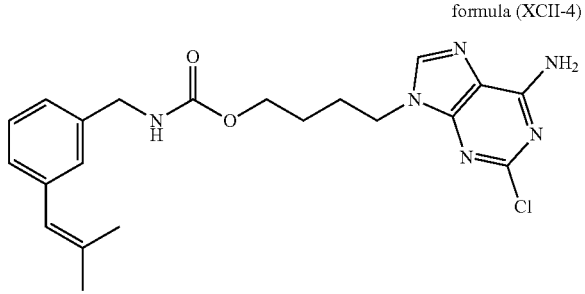
formula (XCII-5)
formula (XCII-6)
formula (XCII-7)
formula (XCIV)
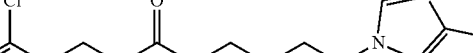

formula (XCV)
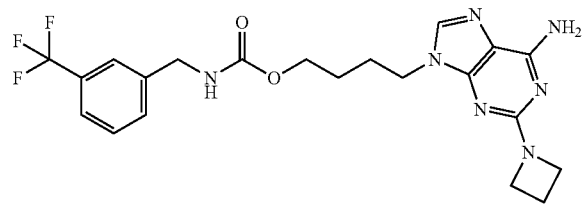
formula (C)
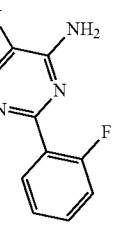
formula (XCVI)
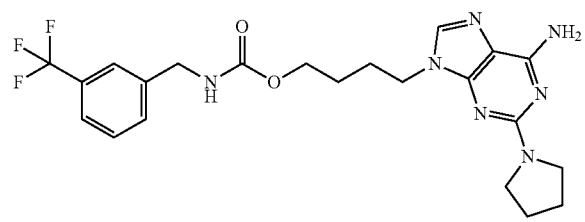
formula (CI)
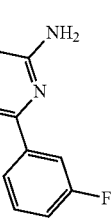
formula (XCVII)
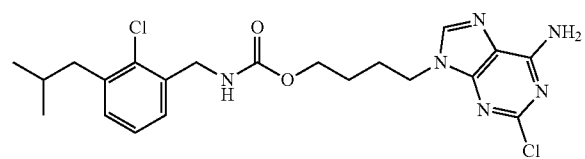
formula (CII)
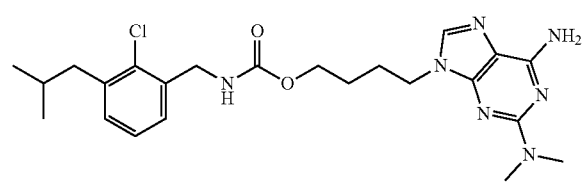
formula (XCVIII)
formula (XCIX)
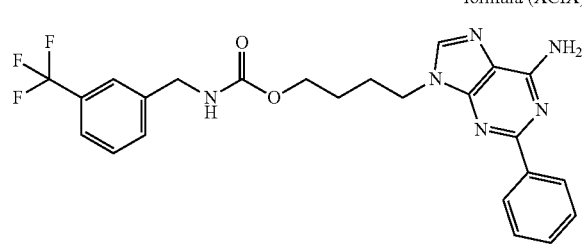
formula (CV)
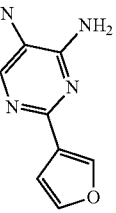

formula (CVI)
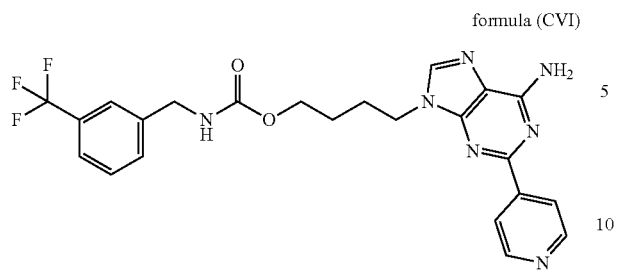
formula (CVII)
formula (CVIII)
formula (CIX)
formula (CX)
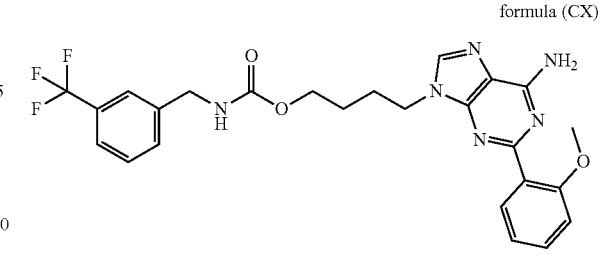
formula (CXI)
formula (CXII)
formula (CXIII)
4. The compound according to claim 1, wherein the compound a is a compound of formulae (CXV) to (CXLVII), or the N-oxide, pharmaceutically acceptable salt, pharmaceutically acceptable solvate, or stereoisomer thereof:
formula (CXV)
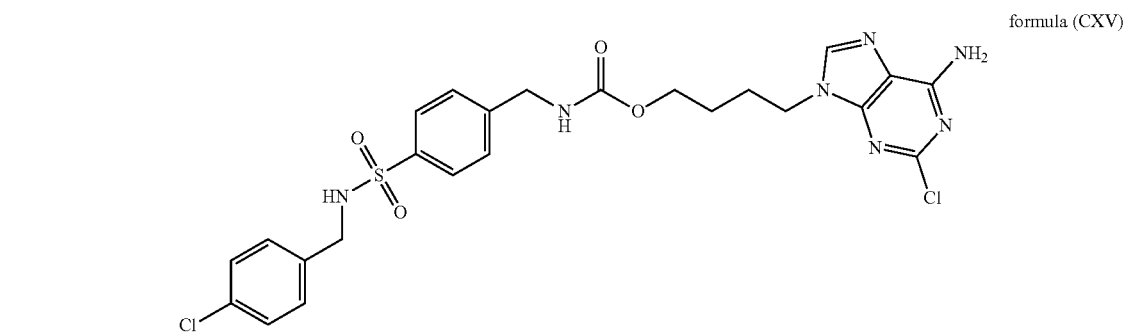

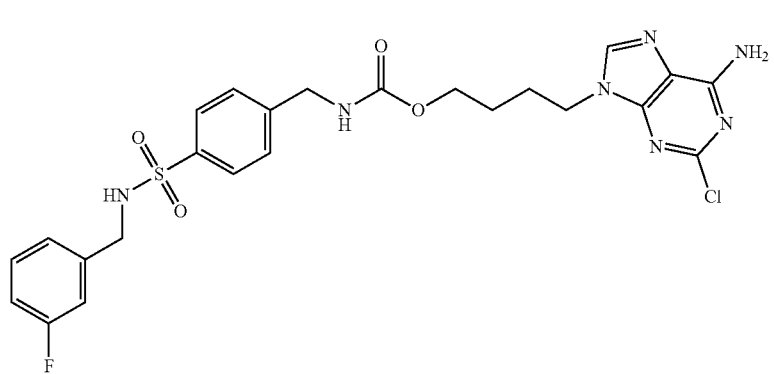
formula (CXVI)
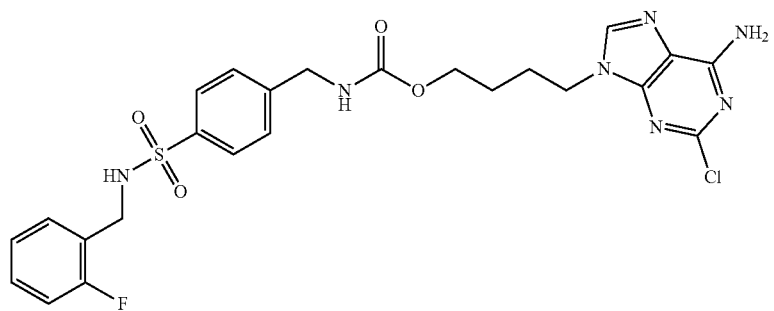
formula (CXVII)
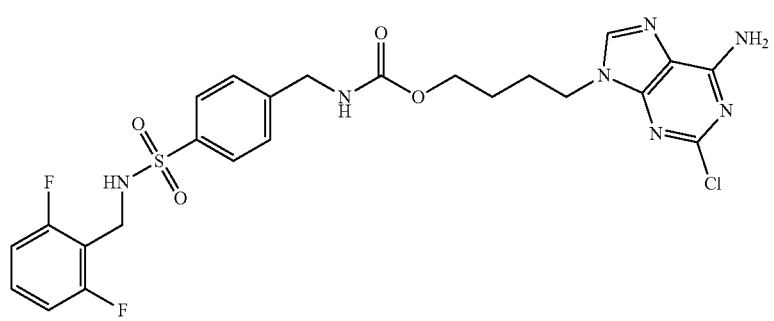
formula (CXVIII)
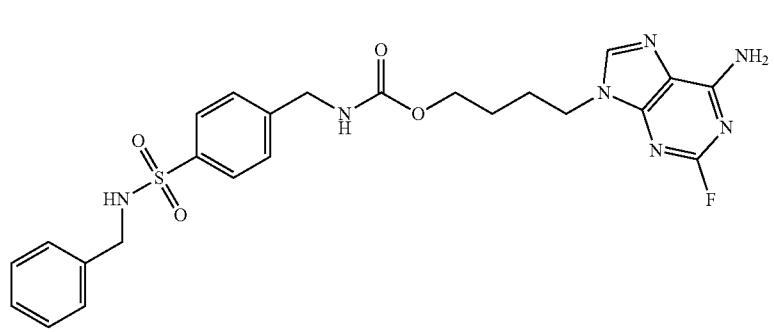
formula (CXXI)
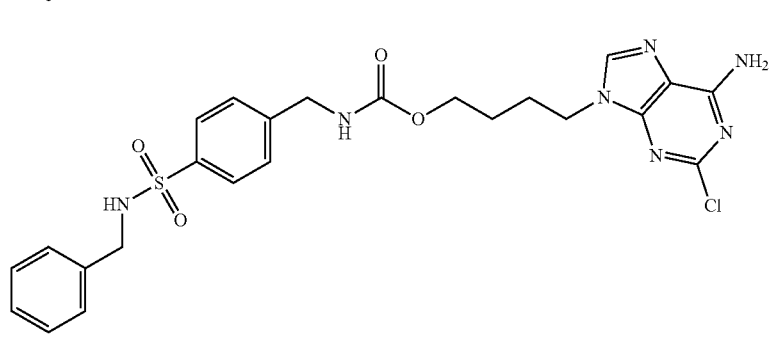
formula (CXXI-1)

-continued
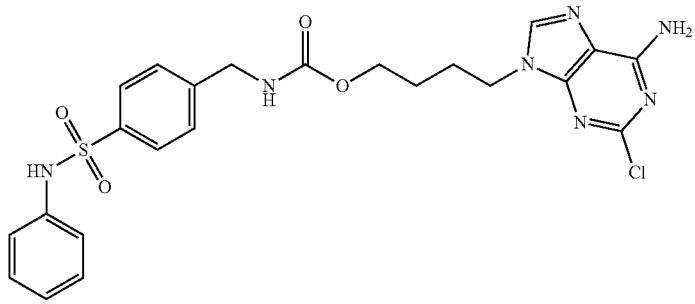
formula(CXXI-2)
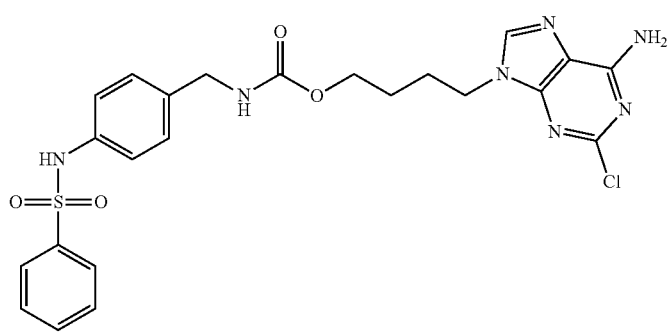
formula (CXXI-3)
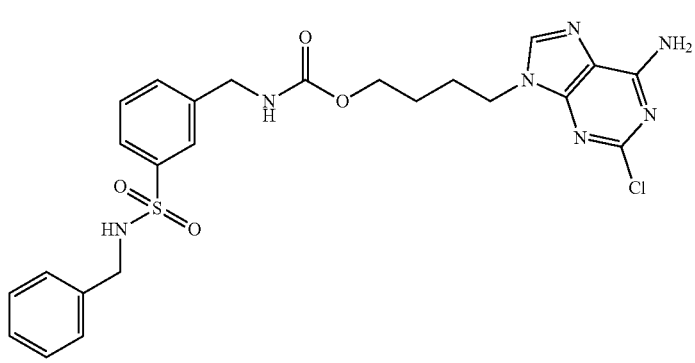
formula (CXXI-4)
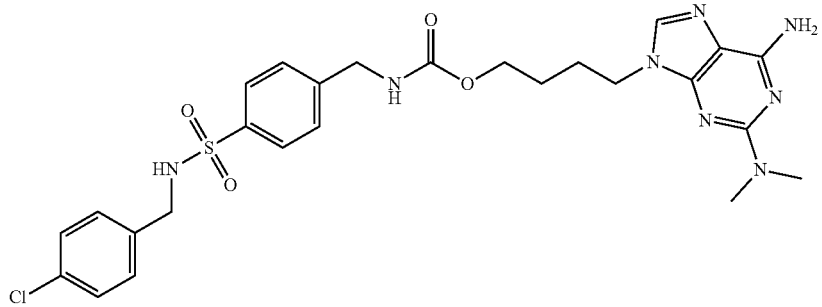
formula (CXXII)
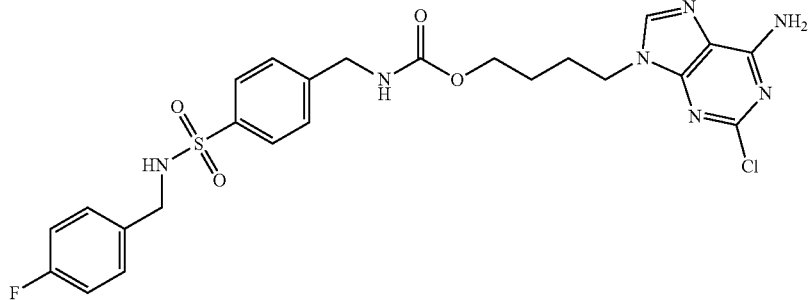
formula (CXXV)

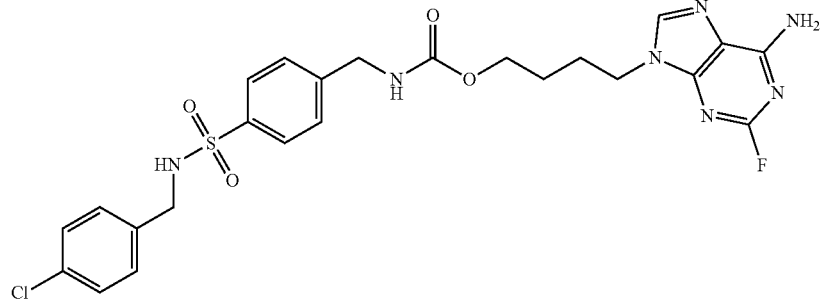
formula (CXXVII)
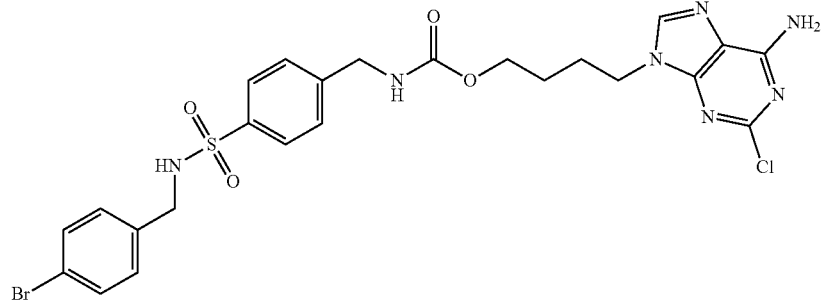
formula (CXXXVI)
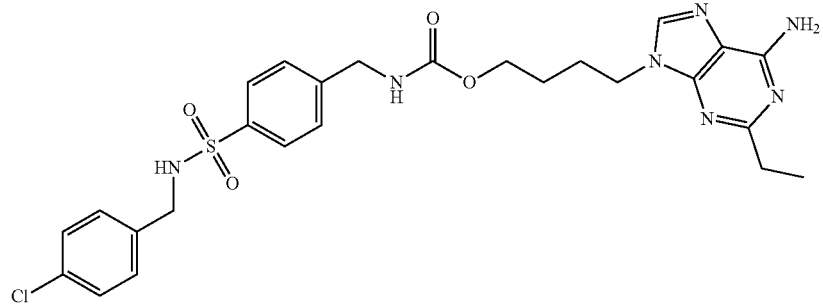
formula (CXXXVIII)
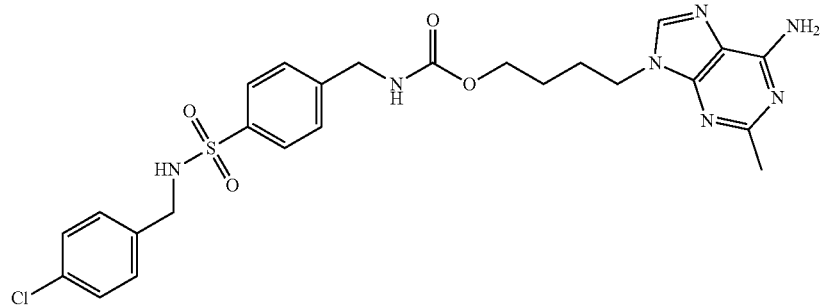
formula (CXXXIX)
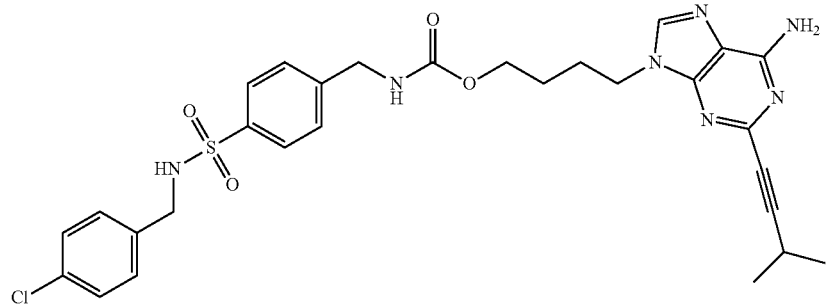
formula (CXL)

-continued
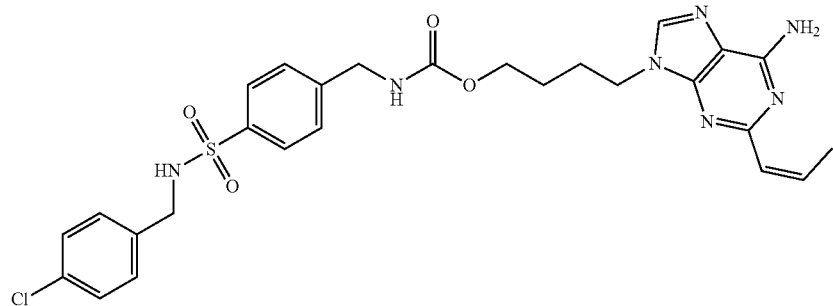
formula (CXLI)
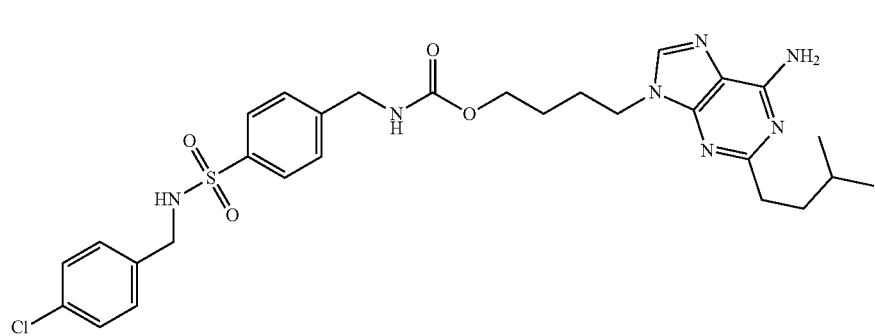
formula (CXLII)
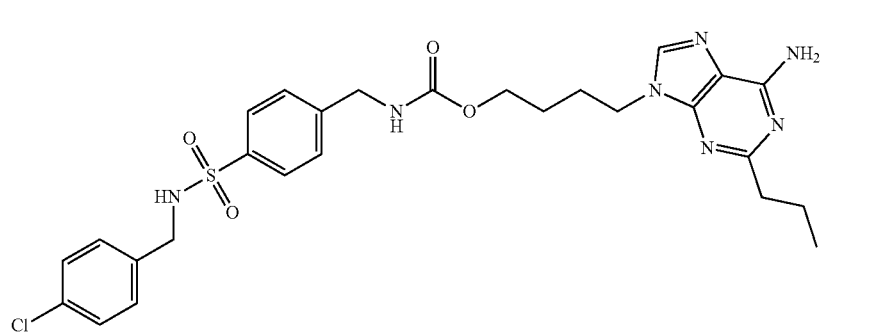
formula (CXLIII)
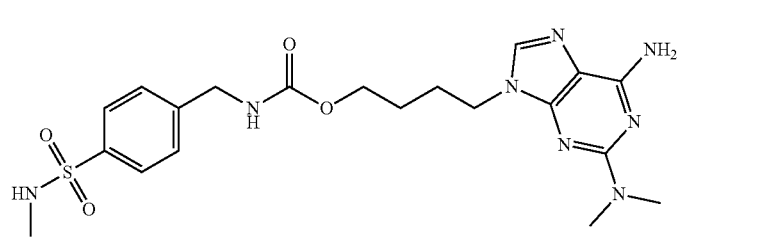
formula (CXLV)
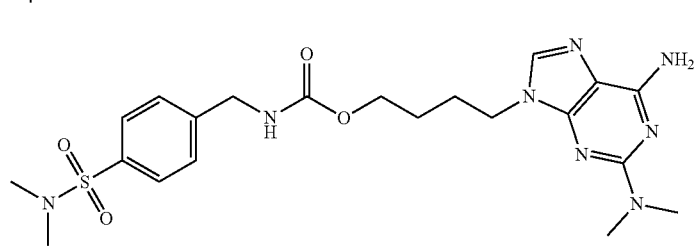
formula (CXLVI)
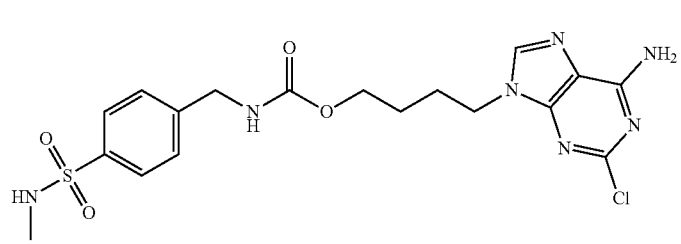
formula (CXLVI-1)

-continued
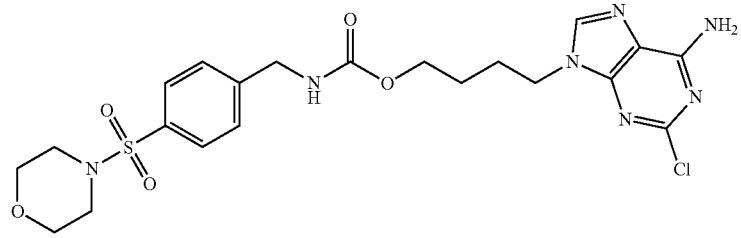
formula (CXLVI-2)
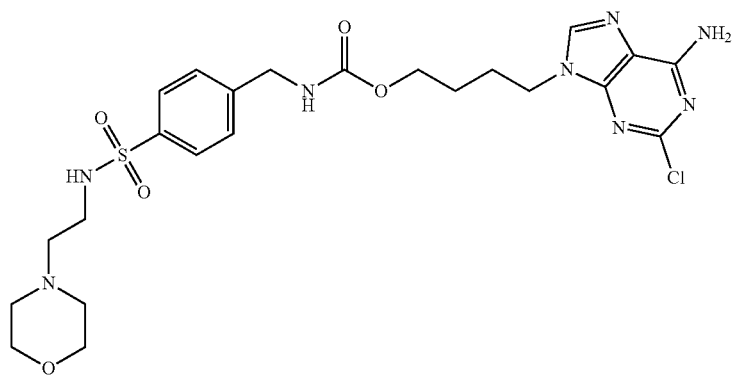
formula (CXLVI-3)
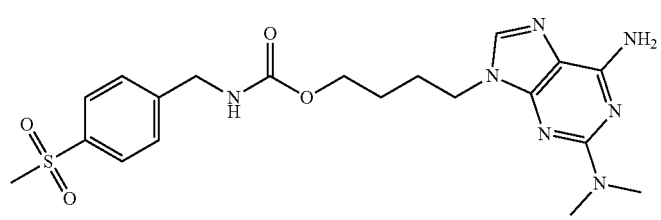
formula (CXLVII)
5. The compound according to claim 1, wherein the compound is a compound of formulae (CXLVIII) to (CLVII), (CLIX) to (CLXX), or (XXV) to (XXV-13), or the N-oxide, pharmaceutically acceptable salt, pharmaceutically acceptable solvate, or stereoisomer thereof:
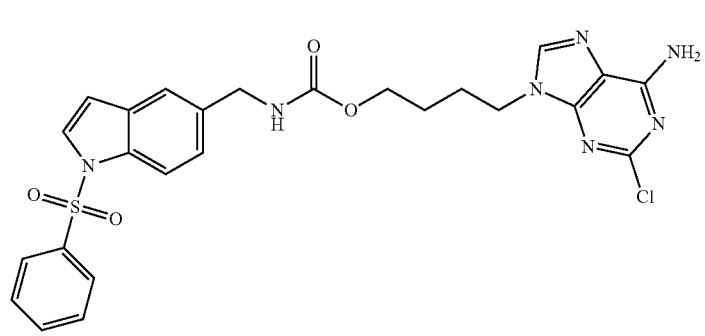
formula (CXLVIII)
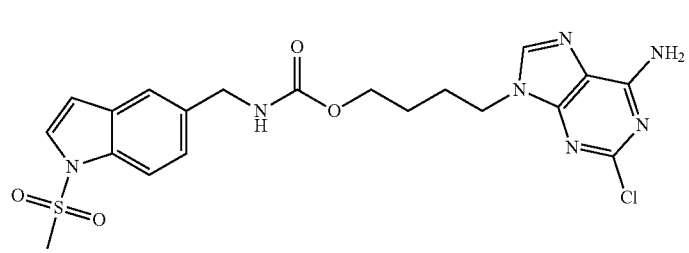
formula (CXLIX)

-continued
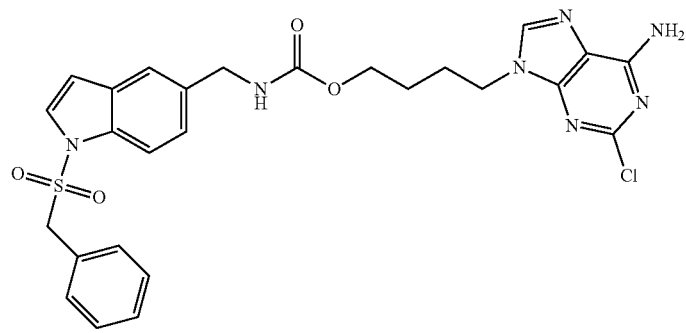
formula (CL)
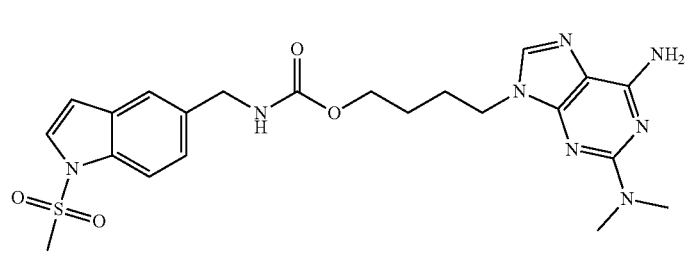
formula (CLII)
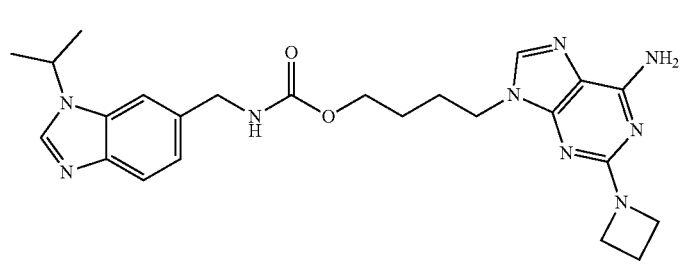
formula (CLIII)
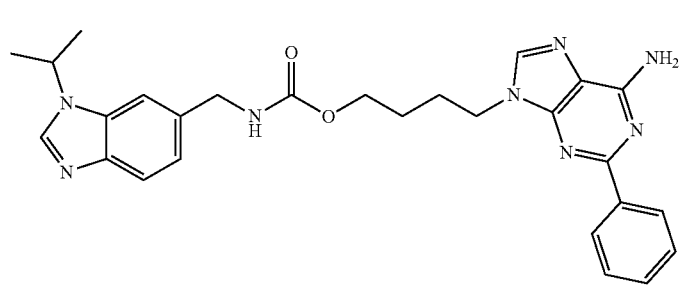
formula (CLIV)
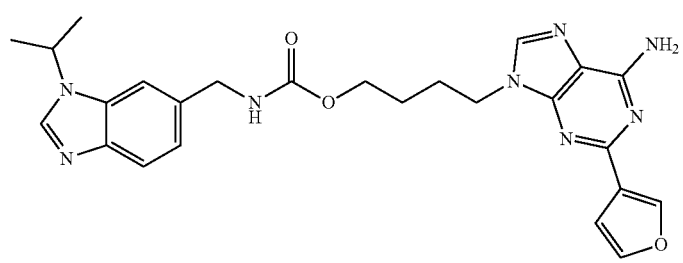
formula (CLV)

-continued
formula (CLVI)
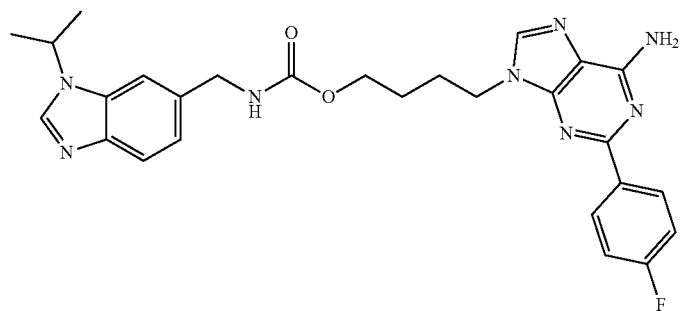
formula (CLVI-1)
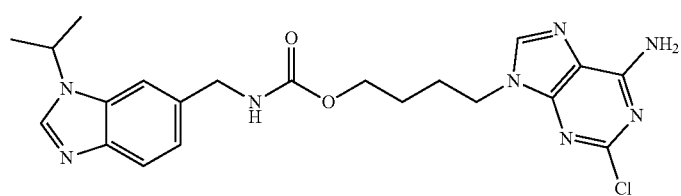
formula (CLVI-2)
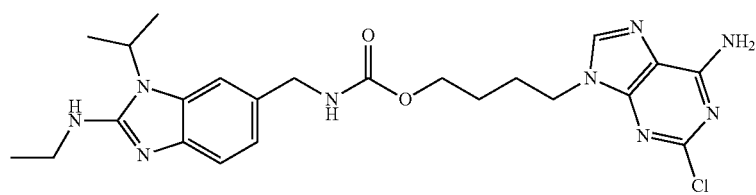
formula (CLVII)
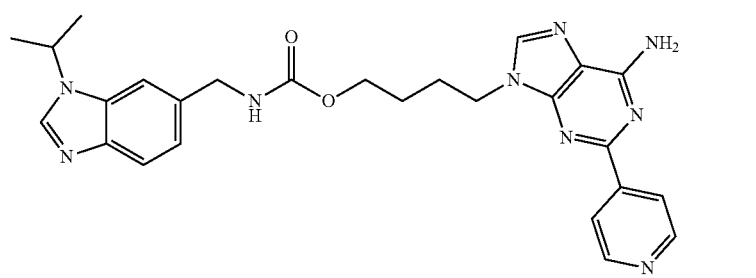
formula (CLIX)
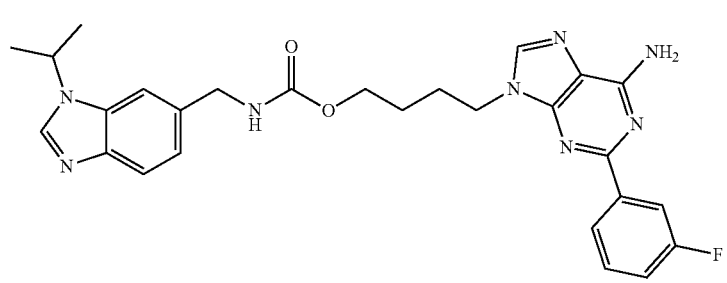
formula (CLXIII)
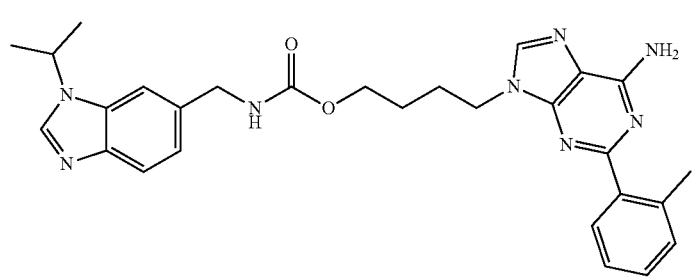

-continued
formula (CLXIV)
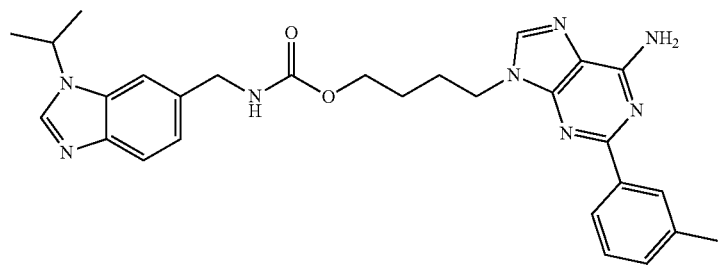
formula (CLXV)
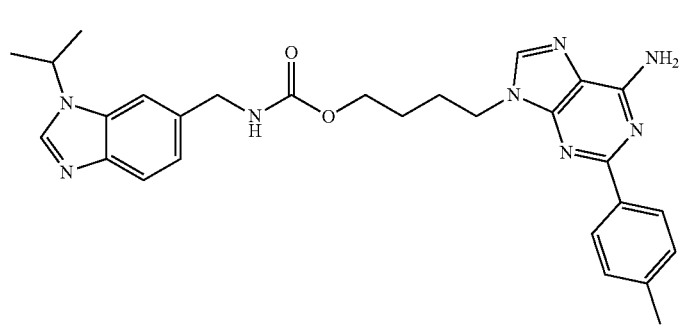
formula (CLXVI)
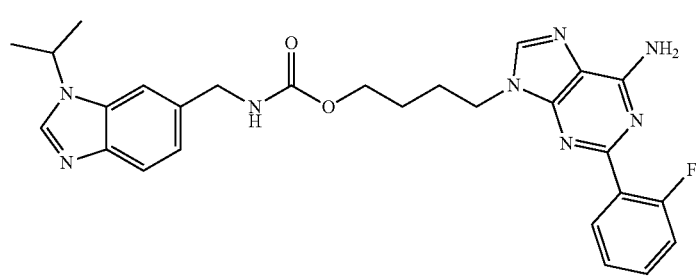
formula (CLXVII)
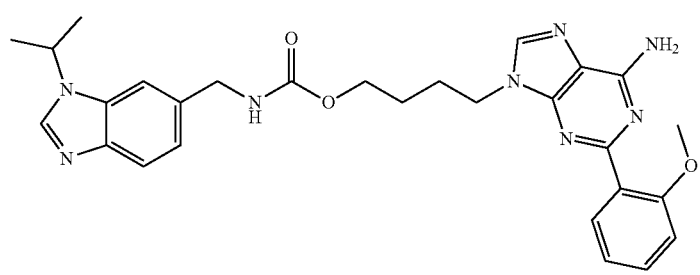
formula (CLXVIII)
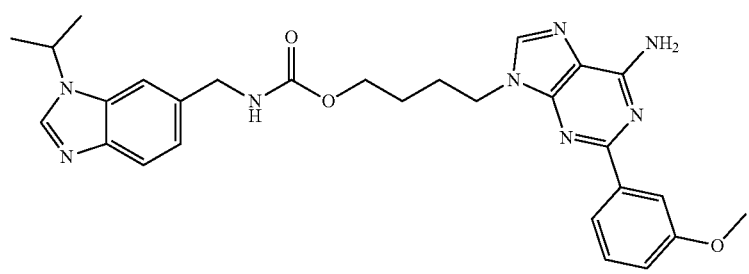

-continued
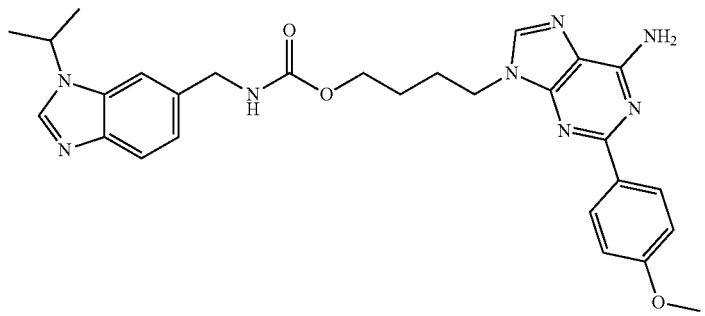
formula (CLXIX)
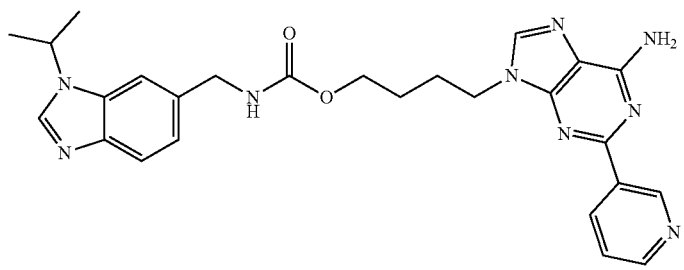
formula (CLXX)
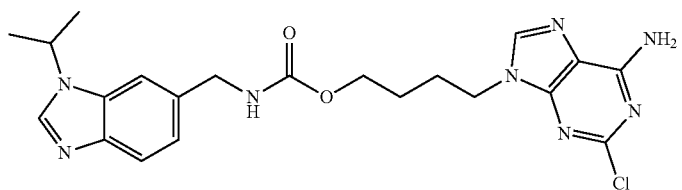
formula (XXV)
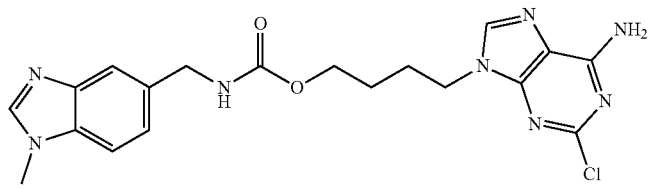
formula (XXV-1)
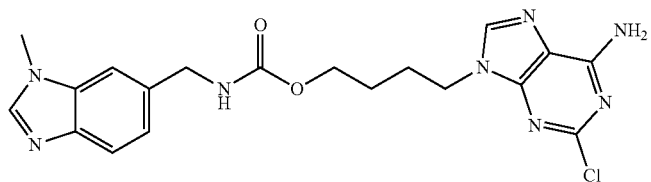
formula (XXV-2)
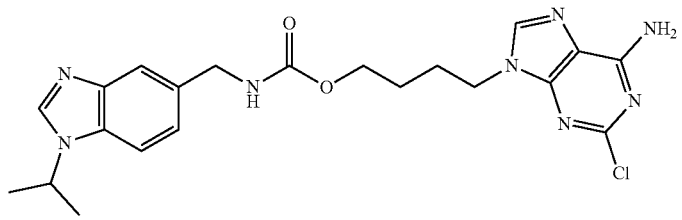
formula (XXV-3)
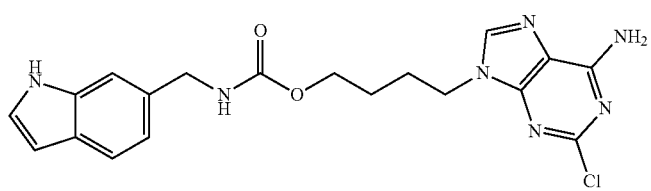
formula (XXV-4)

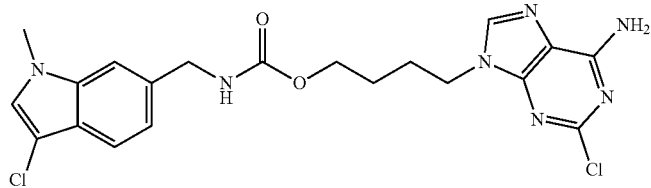
formula (XXV-5)
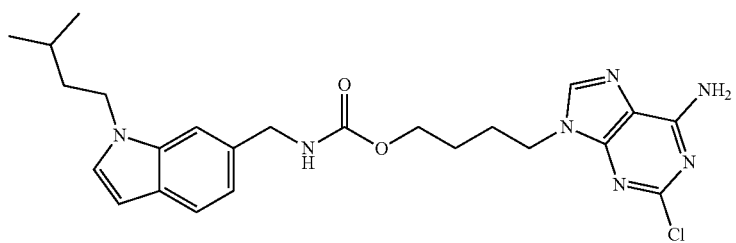
formula (XXV-6)
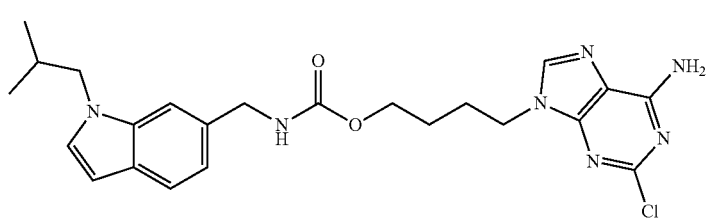
formula (XXV-7)
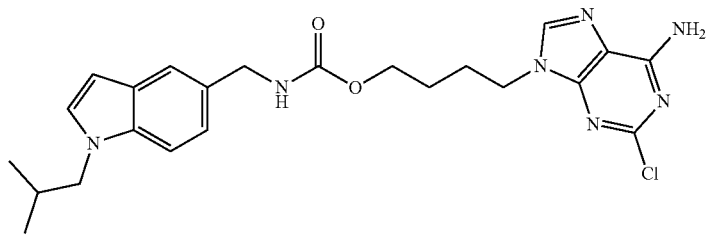
formula (XXV-8)
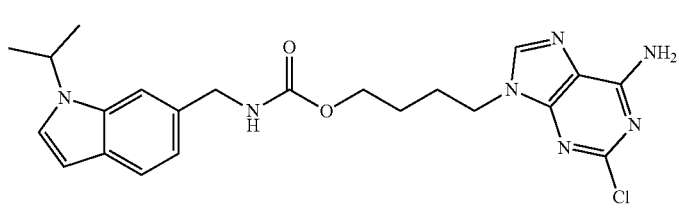
formula (XXV-9)
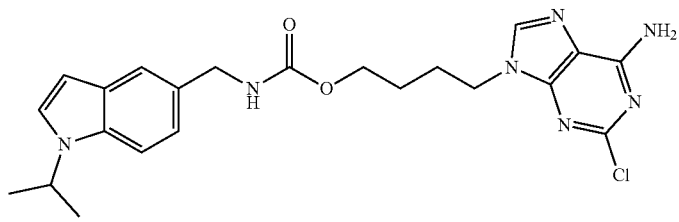
formula (XXV-10)
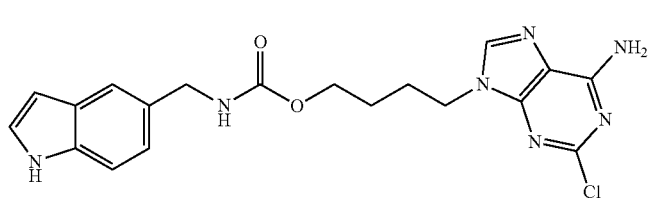
formula (XXV-11)

-continued formula (XXV-12)

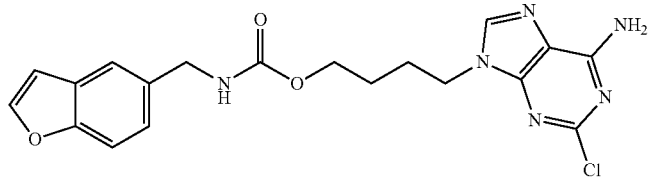

formula (XXV-13)

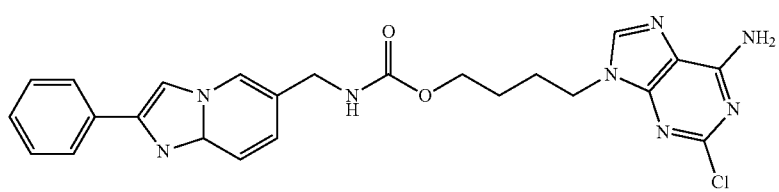

6. The compound of claim 1, wherein the compound is:

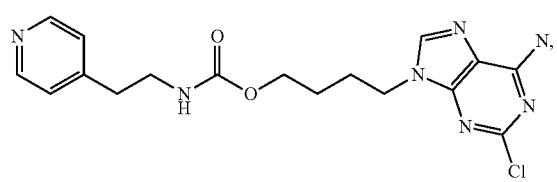

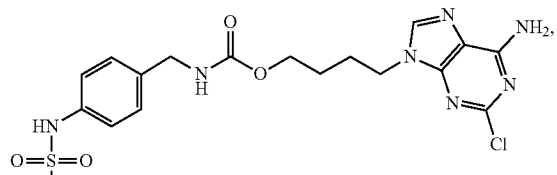

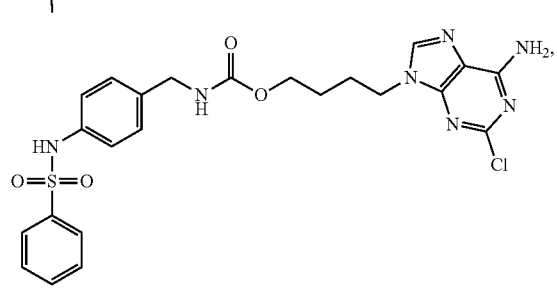

or

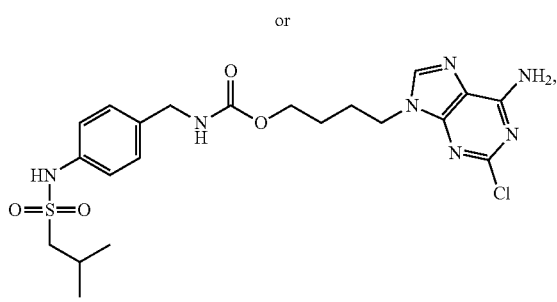

7. A pharmaceutical composition comprising a carrier, and as active ingredient compound according to claim 1.

8. The compound of claim 1, wherein the compound is a compound of formula (II-a-1), or the N-oxide, pharmaceutically acceptable salt, pharmaceutically acceptable solvate, or stereoisomer thereof:

formula (II-a-1)

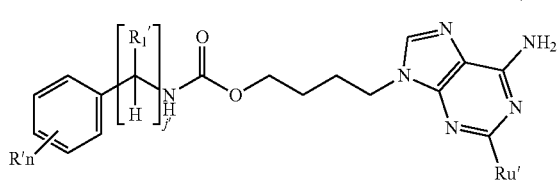

wherein:
Ru' is hydrogen; heteroaryl selected from the group consisting of furanyl, pyrrolyl, isoxazolyl, pyrazolyl, and pyridinyl, wherein said heteroaryl is optionally further substituted with methyl; phenyl and wherein said phenyl is optionally further substituted with —$CH_3$;

and each of R' is selected from the group consisting of $CF_3$; hydrogen; halo; heterocyclyl containing 3 to 12 carbon atoms and 1 or 2 heteroatoms independently selected from O or N;

$OCH_3$; $CH_3$; heteroaryl selected from the group consisting of furanyl, pyrrolyl, isoxazolyl, pyrazolyl, and pyridinyl and wherein said heteroaryl is optionally further substituted with methyl; and phenyl wherein said phenyl is optionally substituted with CN;

n is an integer in the range from 0 to 3;

each of $R'_1$ is hydrogen or a linear or branched $C_zH_{2z+1}$ wherein z is an integer from 1 to 4 and j' is an integer in the range from 1 to 2.

9. The compound of claim 1, wherein the compound is a compound of formula (II-a-2), or the N-oxide, pharmaceutically acceptable salt, pharmaceutically acceptable solvate, or stereoisomer thereof:

formula (II-a-2)

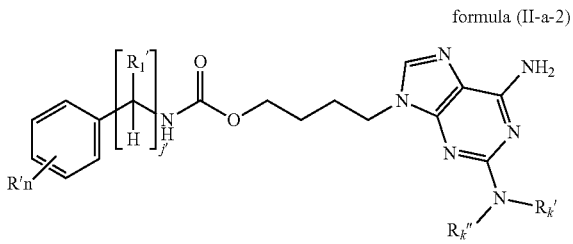

wherein:
  each of R' is selected from the group consisting of hydrogen, halo, $CF_3$, heterocyclyl containing 3 to 6 carbon atoms and 1 or 2 heteroatoms independently selected from O or N, phenyl, and a linear or branched $C_wH_{2w+1}$ wherein w is an integer from 1 to 5, and n is an integer in the range from 0 to 3 and each of $R'_1$ is an hydrogen or a linear or branched $C_zH_{2z+1}$ wherein z is an integer from 1 to 4;
  j' is an integer in the range from 1 to 2;
  $R_{k'}$ and $R_{k''}$ are independently from each other and at each occurrence selected from H, $C_{1-4}$ alkyl and $C_{3-4}$ cycloalkyl, $R_{k'}$ and $R_{k''}$ may also form together with the nitrogen N an azetidine or pyrrolidine.

10. The compound of claim 1, wherein the compound is a compound of formula (II-a-3), or the N-oxide, pharmaceutically acceptable salt, pharmaceutically acceptable solvate, or stereoisomer thereof:

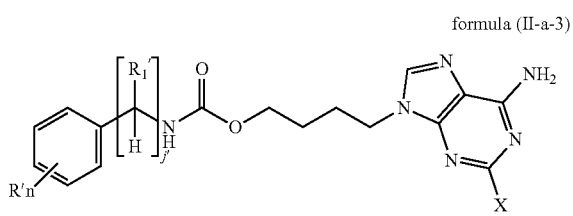

formula (II-a-3)

wherein:
  each of R' is selected from the group consisting of hydrogen; halo; heterocyclyl containing 3 to 6 carbon atoms and 1 or 2 heteroatoms independently selected from O or N; $C_{3-5}$ cycloalkyl; $C_{2-3}$ alkenyl; $C_6H_5$; $CF_3$; $CH_3$; CN; heteroaryl selected from the group consisting of furanyl, pyrrolyl, isoxazolyl, pyrazolyl, and pyridinyl and wherein said heteroaryl is optionally further substituted with methyl; phenyl wherein said phenyl is optionally substituted with CN; $OR_{21}$; $N(R_{21})_2$ wherein each of $R_{21}$ is independently selected from the group consisting of hydrogen, $C_{1-5}$ alkyl, heterocyclyl containing 3 to 6 carbon atoms and 1 or 2 heteroatoms independently selected from O or N, phenyl, benzyl, and $CF_3$; and a linear or branched $C_wH_{2w+1}$ wherein w is an integer from 1 to 5, and n is an integer in the range from 0 to 3, and $R'_1$ is an hydrogen or a linear or branched $C_zH_{2z+1}$;
  z is an integer from 1 to 4;
  j' is an integer in the range from 1 to 2; and
  X is Cl or F.

11. The compound of claim 1, wherein the compound is a compound of formula (II-a-4), or the N-oxide, pharmaceutically acceptable salt, pharmaceutically acceptable solvate, or stereoisomer thereof:

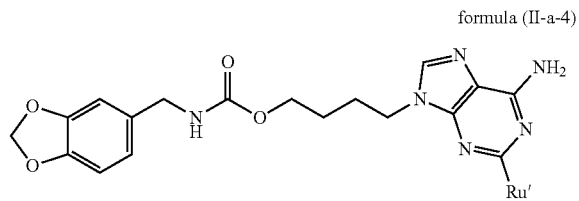

formula (II-a-4)

wherein:
  Ru' is hydrogen; halo; cyclopropyl; heteroaryl selected from the group consisting of furanyl, pyrrolyl, isoxazolyl, pyrazolyl, and pyridinyl; or $C_6H_5$,
  wherein said heteroaryl is optionally further substituted with methyl.

12. The compound of claim 1, wherein the compound is a compound of formula (II-a-5), or the N-oxide, pharmaceutically acceptable salt, pharmaceutically acceptable solvate, or stereoisomer thereof:

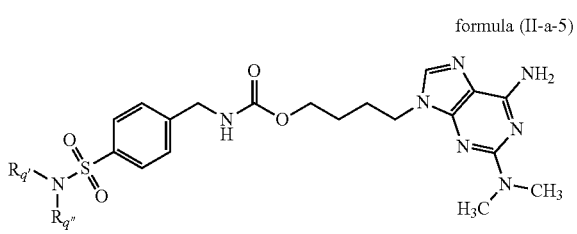

formula (II-a-5)

wherein:
  each of $R_{q'}$ and $R_{q''}$ are independently from each other and at each occurrence selected from H, $C_{1-5}$ alkyl, heterocyclyl containing 3 to 6 carbon atoms and 1 or 2 heteroatoms independently selected from O or N, phenyl, and benzyl, wherein said phenyl is optionally further substituted with a halo.

13. The compound of claim 1, wherein the compound is a compound of formula (II-a-6), or the N-oxide, pharmaceutically acceptable salt, pharmaceutically acceptable solvate, or stereoisomer thereof:

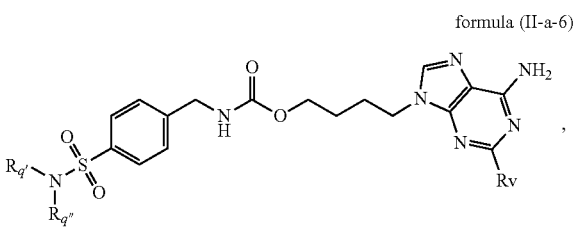

formula (II-a-6)

wherein:
  each of $R_{q'}$ and $R_{q''}$ are independently from each other and at each occurrence selected from H, $C_{1-5}$ alkyl, heterocyclyl containing 3 to 6 carbon atoms and 1 or 2 heteroatoms independently selected from O or N, phenyl, and benzyl, wherein said phenyl is optionally further substituted with halo; and
  Rv is halo.

14. The compound of claim 1, wherein the compound is a compound of formula (II-a-7), or the N-oxide, pharmaceutically acceptable salt, pharmaceutically acceptable solvate, or stereoisomer thereof:

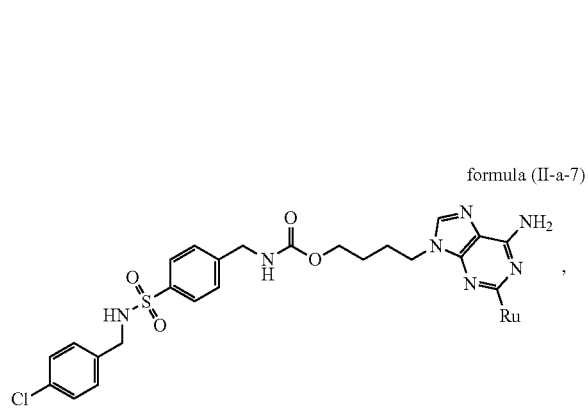

formula (II-a-7)

wherein $R_u$ is selected from the group consisting of $C_{1-5}$ alkyl, $C_{2-3}$ alkenyl and $C_{2-3}$ alkynyl.

15. The compound of claim 1, wherein the compound is a compound of formulae (IV-a-1) or (IV-a-2), or the N-oxide, pharmaceutically acceptable salt, pharmaceutically acceptable solvate, or stereoisomer thereof:

formula (IV-a-1)

formula (IV-a-2)

Ru''' is selected from the group consisting of halo, azetidine, phenyl, heteroaryl selected from the group consisting of furanyl, pyrrolyl, isoxazolyl, pyrazolyl, and pyridinyl, and wherein said phenyl is optionally further substituted with —CH₃, F, or —OCH₃;

Ru' is selected from the group consisting of halo; heteroaryl selected from the group consisting of furanyl, pyrrolyl, isoxazolyl, pyrazolyl, and pyridinyl; and phenyl, and wherein said phenyl is optionally further substituted with —CH₃, F, or —OCH₃; and R' is hydrogen or $C_{1-5}$ alkyl.

* * * * *

UNITED STATES PATENT AND TRADEMARK OFFICE
CERTIFICATE OF CORRECTION

PATENT NO. : 11,236,093 B2
APPLICATION NO. : 16/097805
DATED : February 1, 2022
INVENTOR(S) : D. Surleraux et al.

Page 1 of 1

It is certified that error appears in the above-identified patent and that said Letters Patent is hereby corrected as shown below:

In the Claims

| Column | Line | |
|---|---|---|
| 268 | 21 | Change "Ru" to -- wherein: Ru --. |

Signed and Sealed this
Twelfth Day of July, 2022

Katherine Kelly Vidal
*Director of the United States Patent and Trademark Office*